(12) United States Patent
Lee et al.

(10) Patent No.: US 10,149,462 B2
(45) Date of Patent: Dec. 11, 2018

(54) ANIMAL MODELS AND THERAPEUTIC MOLECULES

(71) Applicant: Kymab Limited, Cambridge (GB)

(72) Inventors: E-Chiang Lee, Cambridge (GB); Jasper Clube, Cambridge (GB); Allan Bradley, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 15/088,805

(22) Filed: Apr. 1, 2016

(65) Prior Publication Data

US 2017/0135327 A1 May 18, 2017

Related U.S. Application Data

(63) Continuation of application No. PCT/GB2014/052971, filed on Oct. 1, 2014.

(30) Foreign Application Priority Data

| Oct. 1, 2013 | (FR) | ................................ | 13 59518 |
| Oct. 1, 2013 | (GB) | ................................ | 1317410.7 |

(51) Int. Cl.

| *A01K 67/027* | (2006.01) |
| *C07K 16/46* | (2006.01) |
| *C12N 15/85* | (2006.01) |
| *C07K 16/00* | (2006.01) |
| *C12P 21/02* | (2006.01) |

(52) U.S. Cl.
CPC .......... *A01K 67/0278* (2013.01); *C07K 16/00* (2013.01); *C07K 16/462* (2013.01); *C12N 15/85* (2013.01); *C12N 15/8509* (2013.01); *C12P 21/02* (2013.01); *A01K 2207/15* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/14* (2013.01); *C07K 2317/21* (2013.01); *C07K 2317/24* (2013.01); *C07K 2317/92* (2013.01); *C12N 2800/204* (2013.01)

(58) Field of Classification Search
CPC ............................ A01K 67/0278; C07K 16/00
See application file for complete search history.

(56) References Cited

U.S. PATENT DOCUMENTS

| 4,720,449 A | 1/1988 | Borror et al. |
| 5,169,939 A | 12/1992 | Gefter et al. |
| 5,545,806 A | 8/1996 | Lonberg et al. |
| 5,545,807 A | 8/1996 | Surani et al. |
| 5,565,321 A | 10/1996 | Spriggs et al. |
| 5,633,425 A | 5/1997 | Lonberg et al. |
| 5,770,429 A | 6/1998 | Lonberg et al. |
| 5,789,215 A | 8/1998 | Berns et al. |
| 5,939,598 A | 8/1999 | Kucherlapati et al. |
| 5,948,600 A | 9/1999 | Roschger et al. |
| 6,130,364 A | 10/2000 | Jakobovits et al. |
| 6,162,963 A | 12/2000 | Kucherlapati et al. |
| 6,319,906 B1 | 11/2001 | Bennett et al. |
| 6,395,487 B1 | 5/2002 | Bradley et al. |
| 6,461,818 B1 | 10/2002 | Bradley et al. |
| 6,596,541 B2 | 7/2003 | Murphy et al. |
| 6,673,986 B1 | 1/2004 | Kucherlapati et al. |
| 6,713,610 B1 | 3/2004 | Kucherlapati et al. |
| 6,833,268 B1 | 12/2004 | Green et al. |
| 6,914,128 B1 | 7/2005 | Salfeld et al. |
| 6,992,235 B2 | 1/2006 | Bode et al. |
| 6,998,514 B2 | 2/2006 | Bruggemann |
| 7,105,348 B2 | 9/2006 | Murphy et al. |
| 7,119,248 B1 | 10/2006 | Rajewsky et al. |
| 7,205,140 B2 | 4/2007 | Gottschalk et al. |
| 7,205,148 B2 | 4/2007 | Economides et al. |
| 7,294,754 B2 | 11/2007 | Poueymirou et al. |
| 7,435,871 B2 | 10/2008 | Green et al. |
| 7,501,552 B2 | 3/2009 | Lonberg et al. |
| 7,605,237 B2 | 10/2009 | Stevens et al. |
| 7,605,238 B2 | 10/2009 | Korman et al. |
| 7,910,798 B2 | 3/2011 | Tanamachi et al. |
| 7,932,431 B2 | 4/2011 | Bruggemann |
| 8,158,419 B2 | 4/2012 | Lonberg et al. |
| 8,502,018 B2 | 8/2013 | Murphy et al. |
| 8,592,644 B2 | 11/2013 | Harriman et al. |
| 8,642,835 B2 | 2/2014 | MacDonald et al. |

(Continued)

FOREIGN PATENT DOCUMENTS

| CA | 2307503 A1 | 11/2001 |
| CA | 2747534 | 6/2010 |

(Continued)

OTHER PUBLICATIONS

U.S. Appl. No. 09/552,219, filed Apr. 19, 2000, issued May 28, 2002 as U.S. Pat. No. 6,395,487.
U.S. Appl. No. 09/552,626, filed Apr. 19, 2000, issued Oct. 8, 2002 as U.S. Pat. No. 6,461,818.
U.S. Appl. No. 13/310,431, filed Dec. 2, 2011.
U.S. Appl. No. 13/416,684, filed Mar. 9, 2012, issued Sep. 20, 2016 as U.S. Pat. No. 9,447,177.
U.S. Appl. No. 13/433,084, filed Mar. 28, 2012, issued Sep. 20, 2016 as U.S. Pat. No. 9,445,581.
U.S. Appl. No. 13/434,361, filed Mar. 29, 2012, issued Feb. 9, 2016 as U.S. Pat. No. 9,253,965.

(Continued)

*Primary Examiner* — Scott Long
(74) *Attorney, Agent, or Firm* — Nutter McClennen & Fish LLP

(57) ABSTRACT

The invention discloses methods for the generation of chimaeric human—non-human antibodies and chimaeric antibody chains, antibodies and antibody chains so produced, and derivatives thereof including fully humanized antibodies; compositions comprising said antibodies, antibody chains and derivatives, as well as cells, non-human mammals and vectors, suitable for use in said methods.

24 Claims, 18 Drawing Sheets

Specification includes a Sequence Listing.

(56) References Cited

U.S. PATENT DOCUMENTS

| | | | |
|---|---|---|---|
| 8,697,940 B2 | 4/2014 | MacDonald et al. |
| 8,754,287 B2 | 6/2014 | MacDonald et al. |
| 8,791,323 B2 | 7/2014 | Murphy et al. |
| 8,877,901 B2 | 11/2014 | Govindan |
| 9,253,965 B2 | 2/2016 | Liang et al. |
| 9,434,782 B2 | 9/2016 | Bradley et al. |
| 9,445,581 B2 | 9/2016 | Bradley et al. |
| 9,447,177 B2 | 9/2016 | Bradley et al. |
| 9,504,236 B2 | 11/2016 | Bradley et al. |
| 9,505,827 B2 | 11/2016 | Bradley et al. |
| 2002/0088016 A1 | 7/2002 | Bruggemann |
| 2002/0183275 A1 | 12/2002 | Murphy et al. |
| 2003/0108925 A1 | 6/2003 | Dix et al. |
| 2003/0217373 A1 | 11/2003 | Green et al. |
| 2004/0128703 A1 | 7/2004 | Shizuya |
| 2004/0231012 A1 | 11/2004 | Bruggemann |
| 2005/0048621 A1 | 3/2005 | Grasso et al. |
| 2006/0015949 A1 | 1/2006 | Lonberg et al. |
| 2006/0015957 A1 | 1/2006 | Lonberg et al. |
| 2006/0021074 A1 | 1/2006 | Kellermann et al. |
| 2006/0199204 A1 | 9/2006 | Dix et al. |
| 2007/0280945 A1 | 12/2007 | Stevens et al. |
| 2008/0098490 A1 | 4/2008 | Jakobovits et al. |
| 2009/0083870 A1 | 3/2009 | Horn et al. |
| 2009/0083879 A1 | 3/2009 | Dhugga |
| 2009/0093059 A1 | 4/2009 | Baszczynski et al. |
| 2009/0209036 A1 | 8/2009 | Reynaud et al. |
| 2009/0307787 A1 | 12/2009 | Grosveld et al. |
| 2010/0011450 A1 | 1/2010 | Garcia et al. |
| 2010/0069614 A1 | 3/2010 | Houtzager et al. |
| 2010/0146647 A1 | 6/2010 | Logtenberg et al. |
| 2010/0196367 A1 | 8/2010 | Day |
| 2010/0330676 A1 | 12/2010 | Horowitz et al. |
| 2011/0119779 A1 | 5/2011 | Shizuya et al. |
| 2011/0138489 A1 | 6/2011 | Tanamachi et al. |
| 2011/0145937 A1 | 6/2011 | MacDonald et al. |
| 2011/0195454 A1† | 8/2011 | McWhirter |
| 2011/0236378 A1 | 9/2011 | Green et al. |
| 2011/0283376 A1 | 11/2011 | Murphy et al. |
| 2012/0070861 A1 | 3/2012 | MacDonald et al. |
| 2012/0073004 A1 | 3/2012 | MacDonald et al. |
| 2012/0096572 A1 | 4/2012 | MacDonald et al. |
| 2012/0195910 A1† | 8/2012 | Wu |
| 2012/0204278 A1† | 8/2012 | Bradley |
| 2012/0233715 A1 | 9/2012 | Kuroiwa et al. |
| 2012/0322108 A1 | 12/2012 | MacDonald et al. |
| 2013/0039850 A1 | 2/2013 | Lonberg et al. |
| 2013/0096287 A1 | 4/2013 | MacDonald et al. |
| 2013/0102031 A1 | 4/2013 | King et al. |
| 2013/0160153 A1 | 6/2013 | MacDonald et al. |
| 2013/0198879 A1 | 8/2013 | McWhirter et al. |
| 2013/0212719 A1 | 8/2013 | MacDonald et al. |
| 2013/0247235 A1 | 9/2013 | McWhirter et al. |
| 2013/0254911 A1 | 9/2013 | MacDonald et al. |
| 2013/0323790 A1 | 12/2013 | MacDonald et al. |
| 2013/0323791 A1 | 12/2013 | MacDonald et al. |
| 2013/0326647 A1 | 12/2013 | MacDonald et al. |
| 2013/0333057 A1 | 12/2013 | MacDonald et al. |
| 2014/0017228 A1 | 1/2014 | MacDonald et al. |
| 2014/0041067 A1 | 2/2014 | Bradley et al. |
| 2014/0120582 A1 | 5/2014 | Bradley et al. |
| 2014/0130193 A1 | 5/2014 | MacDonald et al. |
| 2014/0130194 A1 | 5/2014 | MacDonald et al. |
| 2014/0137275 A1 | 5/2014 | MacDonald et al. |
| 2014/0150125 A1 | 5/2014 | Bradley et al. |
| 2014/0150126 A1 | 5/2014 | Bradley et al. |
| 2014/0182003 A1 | 6/2014 | Bradley et al. |
| 2014/0201854 A1 | 7/2014 | Bradley et al. |
| 2014/0201856 A1 | 7/2014 | Bradley et al. |
| 2014/0212416 A1 | 7/2014 | Friedrich et al. |
| 2014/0213773 A1 | 7/2014 | MacDonald et al. |
| 2014/0283150 A1 | 9/2014 | Bradley et al. |
| 2014/0325690 A1 | 10/2014 | Bradley et al. |
| 2014/0331339 A1 | 11/2014 | Bradley et al. |
| 2014/0331343 A1 | 11/2014 | Bradley et al. |
| 2014/0331344 A1 | 11/2014 | Friedrich et al. |
| 2014/0359797 A1 | 12/2014 | Bradley et al. |
| 2015/0033369 A1 | 1/2015 | Bradley et al. |
| 2015/0033372 A1 | 1/2015 | Bradley et al. |
| 2015/0037337 A1 | 2/2015 | Friedrich et al. |
| 2015/0040250 A1 | 2/2015 | Bradley et al. |
| 2015/0082466 A1 | 3/2015 | Clube |
| 2015/0113669 A1 | 4/2015 | Bradley et al. |
| 2015/0133641 A1 | 5/2015 | Germaschewski et al. |
| 2015/0196015 A1 | 7/2015 | MacDonald et al. |
| 2015/0334998 A1 | 11/2015 | Bradley et al. |
| 2016/0044900 A1 | 2/2016 | Bradley et al. |
| 2016/0150768 A1 | 6/2016 | Bradley et al. |
| 2016/0219846 A1 | 8/2016 | Liang |
| 2016/0249592 A1 | 9/2016 | Bradley et al. |
| 2016/0345551 A1 | 12/2016 | Bradley et al. |
| 2016/0345552 A1 | 12/2016 | Bradley et al. |
| 2016/0353719 A1 | 12/2016 | Friedrich et al. |
| 2017/0051045 A1 | 2/2017 | Bradley et al. |
| 2017/0071174 A1 | 3/2017 | Bradley et al. |
| 2017/0081423 A1 | 3/2017 | Bradley et al. |
| 2017/0094956 A1 | 4/2017 | Bradley et al. |
| 2017/0096498 A1 | 4/2017 | Bradley et al. |
| 2017/0099815 A1 | 4/2017 | Bradley et al. |
| 2017/0099816 A1 | 4/2017 | Bradley et al. |
| 2017/0099817 A1 | 4/2017 | Bradley et al. |
| 2017/0101482 A1 | 4/2017 | Bradley et al. |
| 2017/0101483 A1 | 4/2017 | Bradley et al. |
| 2017/0105396 A1 | 4/2017 | Bradley et al. |
| 2017/0135327 A1 | 5/2017 | Lee et al. |
| 2017/0320936 A1 | 11/2017 | Bradley et al. |
| 2017/0354131 A1 | 12/2017 | Bradley et al. |
| 2018/0030121 A1 | 2/2018 | Bradley et al. |

FOREIGN PATENT DOCUMENTS

| | | |
|---|---|---|
| DE | 10251918 A1 | 5/2004 |
| EP | 1780272 A1 | 5/2007 |
| EP | 0937140 B1 | 9/2007 |
| EP | 2517557 A2 | 10/2012 |
| EP | 2480676 B1 | 4/2016 |
| GB | 2398784 A | 9/2004 |
| GB | 2403475 A | 1/2005 |
| JP | 2004524841 A | 8/2004 |
| JP | 2005510253 A | 4/2005 |
| JP | 2008507257 A | 3/2008 |
| JP | 2012521211 A | 9/2012 |
| KR | 20050042792 A | 5/2005 |
| WO | WO-9004036 A1 | 4/1990 |
| WO | WO-9100906 A1 | 1/1991 |
| WO | WO-9110741 A1 | 7/1991 |
| WO | WO-9312227 A1 | 6/1993 |
| WO | WO-9402602 A1 | 2/1994 |
| WO | WO-9404667 A1 | 3/1994 |
| WO | WO-9425585 A1 | 11/1994 |
| WO | WO-9630498 A1 | 10/1996 |
| WO | WO-9824884 A1 | 6/1998 |
| WO | WO-9824893 A2 | 6/1998 |
| WO | WO-9945962 A1 | 9/1999 |
| WO | WO-0026373 A1 | 5/2000 |
| WO | WO-0208409 A2 | 1/2002 |
| WO | WO-0236789 A2 | 5/2002 |
| WO | WO-0243478 A2 | 6/2002 |
| WO | WO-02053596 A2 | 7/2002 |
| WO | WO-02059263 A2 | 8/2002 |
| WO | WO-02066630 A1 | 8/2002 |
| WO | WO-02070648 A2 | 9/2002 |
| WO | WO 03006639 A1 | 1/2003 |
| WO | WO-03047336 A2 | 6/2003 |
| WO | WO-03061363 A2 | 7/2003 |
| WO | WO-2004050838 A2 | 6/2004 |
| WO | WO-2005003364 A2 | 1/2005 |
| WO | WO-2005004592 A2 | 1/2005 |
| WO | WO-2005019463 A1 | 3/2005 |
| WO | WO-2005058815 A2 | 6/2005 |
| WO | WO-2005092926 A2 | 10/2005 |
| WO | WO-2006008548 A2 | 1/2006 |
| WO | WO-2006044492 A2 | 4/2006 |
| WO | WO-2006055704 A2 | 5/2006 |

(56) References Cited

FOREIGN PATENT DOCUMENTS

| | | |
|---|---|---|
| WO | WO-2006068953 A2 | 6/2006 |
| WO | WO-2006122442 A1 | 11/2006 |
| WO | WO-2007085837 A1 | 8/2007 |
| WO | WO-2007096779 A2 | 8/2007 |
| WO | 2007117410 A2 † | 10/2007 |
| WO | WO-2007117410 A2 | 10/2007 |
| WO | WO-2007143168 A2 | 12/2007 |
| WO | WO-2008022391 A1 | 2/2008 |
| WO | WO-2008054606 A2 | 5/2008 |
| WO | WO-2008070367 A2 | 6/2008 |
| WO | WO-2008076379 A2 | 6/2008 |
| WO | WO-2008081197 A1 | 7/2008 |
| WO | WO-2008094178 A2 | 8/2008 |
| WO | WO-2008103474 A1 | 8/2008 |
| WO | WO-2008118970 A2 | 10/2008 |
| WO | WO-2008122886 A2 | 10/2008 |
| WO | WO-2008151081 A1 | 12/2008 |
| WO | 2009013620 A2 † | 1/2009 |
| WO | WO-2009013620 A2 | 1/2009 |
| WO | WO-2009018411 A1 | 2/2009 |
| WO | WO-2009023540 A1 | 2/2009 |
| WO | WO-2009076464 A2 | 6/2009 |
| WO | WO-2009080254 A1 | 7/2009 |
| WO | WO-2009097006 A2 | 8/2009 |
| WO | WO-2009118524 A2 | 10/2009 |
| WO | WO-2009129247 A2 | 10/2009 |
| WO | WO-2009143472 A2 | 11/2009 |
| WO | WO-2009157771 A2 | 12/2009 |
| WO | WO-2010039900 A2 | 4/2010 |
| WO | WO-2010070263 A1 | 6/2010 |
| WO | WO-2010077854 A1 | 7/2010 |
| WO | WO-2010097385 A1 | 9/2010 |
| WO | WO-2010109165 A2 | 9/2010 |
| WO | WO-2010113039 A1 | 10/2010 |
| WO | WO-2011004192 A1 | 1/2011 |
| WO | WO-2011008093 A1 | 1/2011 |
| WO | WO-2011014469 A1 | 2/2011 |
| WO | WO-2011056864 A1 | 5/2011 |
| WO | WO-2011062206 A1 | 5/2011 |
| WO | WO-2011062207 A1 | 5/2011 |
| WO | WO-2011071957 A1 | 6/2011 |
| WO | WO-2011072204 A1 | 6/2011 |
| WO | WO-2011097603 A1 | 8/2011 |
| WO | WO-2011146121 A1 | 11/2011 |
| WO | WO-2011158009 A1 | 12/2011 |
| WO | WO-2011163311 A1 | 12/2011 |
| WO | WO-2011163314 A1 | 12/2011 |
| WO | WO-2012018764 A1 | 2/2012 |
| WO | WO-2012023053 A2 | 2/2012 |
| WO | WO-2012064682 A1 | 5/2012 |
| WO | WO-2012141798 A1 | 10/2012 |
| WO | WO-2012148873 A2 | 11/2012 |
| WO | WO-2013022782 A1 | 2/2013 |
| WO | 2013041844 A2 † | 3/2013 |
| WO | WO-2013041844 A2 | 3/2013 |
| WO | WO-2013041845 A2 | 3/2013 |
| WO | WO-2013041846 A2 | 3/2013 |
| WO | WO-2013059230 A1 | 4/2013 |
| WO | 2013061098 A2 † | 5/2013 |
| WO | WO-2013061098 A2 | 5/2013 |
| WO | WO-2013096142 A1 | 6/2013 |
| WO | WO-2013116609 A1 | 8/2013 |
| WO | WO-2013134263 A1 | 9/2013 |
| WO | WO-2013166236 A1 | 11/2013 |
| WO | WO-2013176772 A1 | 11/2013 |
| WO | WO-2014093622 A2 | 6/2014 |

OTHER PUBLICATIONS

U.S. Appl. No. 13/740,727, filed Jan. 14, 2013, issued Nov. 29, 2016 as U.S. Pat. No. 9,505,827.
U.S. Appl. No. 13/846,672, filed Mar. 18, 2013.
U.S. Appl. No. 13/875,892, filed May 2, 2013.
U.S. Appl. No. 13/886,511, filed May 3, 2013.
U.S. Appl. No. 14/040,405, filed Sep. 27, 2013.
U.S. Appl. No. 14/040,427, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013.
U.S. Appl. No. 14/137,902, filed Dec. 20, 2013, issued Sep. 6, 2016 as U.S. Pat. No. 9,434,782.
U.S. Appl. No. 14/220,074, filed Mar. 19, 2014.
U.S. Appl. No. 14/220,080, filed Mar. 19, 2014.
U.S. Appl. No. 14/220,095, filed Mar. 19, 2014.
U.S. Appl. No. 14/220,099, filed Mar. 19, 2014.
U.S. Appl. No. 14/226,698, filed Mar. 26, 2014.
U.S. Appl. No. 14/226,706, filed Mar. 26, 2014.
U.S. Appl. No. 14/263,158, filed Apr. 28, 2014.
U.S. Appl. No. 15/088,805, filed Apr. 1, 2016.
Baxendale H.E., et al., "Natural human antibodies to pneumococcus have distinctive molecular characteristics and protect against pneumococcal disease," *Clinical and Experimental Immunology*, 2007, vol. 151, pp. 51-60.
D'Eustachio P., et al., "Mouse Chromosome 12," *Mammalian Genome*, 1998, vol. 8, pp. S241-S257.
Forsman A., et al., "Llama Antibody Fragments with Cross-Subtype Human Immunodeficiency Virus Type I (HIV-1)-Neutralizing Properties and High Affinity for HIV-1 gp120," *Journal of Virology*, Dec. 2008, vol. 82 (24), pp. 12069-12081.
Grund M., European Patent Attorney, Grund Intellectual Property Group, Third-Party Observations according to Article 115 EPC regarding 12762377.5, dated Jun. 20, 2017, 4 pages.
Jones B.T., Attorney for Applicant, Third-Party Pre-Issuance Submission Under 37 CFR Sec. 1.290 in U.S. Appl. No. 15/251,969, filed May 4, 2017, 22 pages.
Jones B.T., Attorney for Applicant, Third-Party Pre-Issuance Submission Under 37 CFR Sec. 1.290 in U.S. Appl. No. 15/383,101, filed May 30, 2017, 32 pages.
Jones B.T., Attorney for Applicant, Third-Party Pre-Issuance Submission Under 37 CFR Sec. 1.290 in U.S. Appl. No. 15/383,188, filed May 30, 2017, 33 pages.
Suárez E. et al., "Human monoclonal antibodies produced in transgenic BABκ,λ mice recognising idiotypic immunoglobulins of human lymphoma cells," *Molecular Immunology*, 2004, vol. 41, pp. 519-526.
Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.
1st International MUGEN Conference on Animal Models for Human Immunological Disease, Sep. 10-13, 2006—Athens Greece (Abstracts 1-52), 52 pages.
Adams D.J., et al., "A Genome-Wide, End-Sequenced 129Sv BAC Library Resource for Targeting Vector Construction," *Genomics*, 2005, vol. 86 (6), pp. 753-758.
Adams D.J. et al., "Contemporary approaches for modifying the mouse genome," *Physiological Genomics*, vol. 34, 2008, pp. 225-238.
Adams D.J. et al., "Mutagenic Insertion and Chromosome Engineering Resource (MICER)," *Nature Genetics*, vol. 36 (8), Aug. 2004, pp. 867-871.
Affidavits Evidencing Murphy Slides as Printed Publication, dated Jun. 20, 2016, 84 pages.
Aguilera R.J. et al., "Characterization of immunoglobulin enhancer deletions in murine plasmacytomas," *The EMBO Journal*, 1985, vol. 4 (13B), pp. 3689-3693.
Ahmed T., "Sanofi-aventis and Regeneron Extend Therapeutic Antibody Agreement," *PharmaDeals Review*, Nov. 2009, vol. 11, p. 115.
Arnaout R., et al., "High-Resolution Description of Antibody Heavy-Chain Repertoires in Humans," *PLoS One*, Aug. 2011, vol. 6 (8), pp. e22365-1-e22365-8.
Arthur J.S.C. et al., "Gene-Targeting Vectors," *Transgenesis Techniques, Principles and Protocols*, Third edition, Chapter 9, 2009 (24 pages, including cover sheet, copyright and preface pages and table of contents), pp. 127-144.

(56) References Cited

OTHER PUBLICATIONS

Asenbauer H. et al., "The immunoglobulin lambda light chain enhancer consists of three modules which synergize in activation of transcription," *European Journal of Immunology*, 1999, vol. 29, pp. 713-724.
Askew G.R., et al., "Site-Directed Point Mutations in Embryonic Stem Cells: A Gene-Targeting Tag-and-Exchange Strategy," *Molecular and Cellular Biology*, Jul. 1993, vol. 13 (7), pp. 4115-4124.
Atlas of Genetics and Cytogenetics in Oncology and Haematology, VPREB1 (pre-B lymphocyte 1), 5 pages. [Retrieved online at http://atlasgeneticsoncolgy.org/Genes/GC_VPREB1.html on May 25, 2015].
Auerbach W., et al., "Establishment and Chimera Analysis of 129/SvEv- and C57BL/6-Derived Mouse Embryonic Stem Cell Lines," BioTechniques, 2000, vol. 29 (5), pp. 1024-1032.
Avery S., Attorney for Applicant, Third-Party Pre-Issuance Submission Under 37 CFR Section 1.290 in U.S. Appl. No. 14/517,755, dated Jun. 26, 2015, 16 pages.
Baer A. et al., "Coping with kinetic and thermodynamic barriers: RMCE, an efficient strategy for the targeted integration of transgenes," *Current Opinions in Biotechnology*, Oct. 2001, vol. 12 (5), pp. 473-480.
Baker A.M., et al., "Adaptation of TCR Expression Vectors for the Construction of Mouse-Human Chimeric MBP-Specific TCR Transgenes," *Journal of Neuroscience Research*, 1996, vol. 45 (4), pp. 487-491.
Baker M.D., et al., "Homologous Recombination Between Transferred and Chromosomal Immunoglobulin κ Genes," *Molecular and Cellular Biology*, Oct. 1988, vol. 8 (10), pp. 4041-4047.
Barreto V.M., et al., "AID from bony fish catalyzes class switch recombination," *Journal of Experimental Medicine*, 2005, vol. 202 (6), pp. 733-738.
Bates J.G., et al., "Chromosomal Position of a $V_H$ Gene Segment Determines its Activation and Inactivation as a Substrate for V(D)J Recombination," *Journal of Experimental Medicine*, 2007, vol. 204 (13), pp. 3247-3256.
Beard C., et al., "Efficient Method to Generate Single-Copy Transgenic Mice by Site-Specific Integration in Embryonic Stem Cells," *Genesis*, 2006, vol. 44 (1), pp. 23-28.
Beck E., et al., "Nucleotide Sequence and Exact Localization of the Neomycin Phosphotransferase Gene From Transposon Tn5," *Genesis*, 1982, vol. 19 (3), pp. 327-336.
Beck J.A., et al., "Genealogies of mouse inbred strains," *Nature Genetics*, 2000, vol. 24, pp. 23-25 (with supporting table and chart).
Beerli R.R., et al., "Mining Human Antibody Repertoires," *mAbs*, Jul./Aug. 2010, vol. 2 (4), pp. 365-378.
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Berg D.E., et al., "Inverted Repeats of Tn5 are Transposable Elements," *Proceedings of the National Academy of Sciences U.S.A*, 1982, vol. 79 (8), pp. 2632-2635.
Bethke B., et al., "Segmental Genomic Replacement by Cre-Mediated Recombination: Genotoxic Stress Activation of the p53 Promoter in Single-Copy Transformants," *Nucleic Acids Research*, 1997, vol. 25 (14), pp. 2828-2834.
Bhattacharya P., et al., "Switch Region Identity Plays an Important Role in Ig Class Switch Recombination," *Journal of Immunology*, 2010, vol. 184 (11), pp. 6242-6248.
Billiard F., et al., "Ongoing Dll4-Notch Signaling is Required for T-Cell Homeostasis in the Adult Thymus," *European Journal of Immunology*, 2011, vol. 41 (8), pp. 2207-2216.
Birling M.C. et al., "Site-Specific Recombinases for Manipulation of the Mouse Genome," *Transgenesis Techniques, Principles and Protocols*, Third edition, Chapter 16, 2009 (25 pages, including cover sheet, copyright and preface pages and table of contents), pp. 245-263.
Blankenstein T. et al., "Immunoglobulin $V_H$ Region Genes of the Mouse are Organized in Overlapping Clusters," *European Journal of Immunology*, 1987, vol. 17 (9), pp. 1351-1357.

Board of Appeal of the European Patent Office, Datasheet for the Decision of Nov. 9, 2015 for Application No. 02709544.7, Case T 2220/14-3.3.08, 83 pages.
Bode J., et al., "The Transgeneticist's Toolbox: Novel Methods for the Targeted Modification of Eukaryotic Genomes," *Biological Chemistry*, Sep./Oct. 2000, vol. 381 (9-10), pp. 801-813.
Bogen B., et al., "A Rearranged $\lambda_2$ Light Gene Chain Retards but does not Exclude x and $\lambda_1$ Expression," *European Journal of Immunology*, 1991, vol. 21 (10), pp. 2391-2395.
Bolland D.J., et al., "Antisense Intergenic Transcription Precedes Igh D-To-J Recombination and is Controlled by the Intronic Enhancer Eμ," *Molecular and Cellular Biology*, 2007, vol. 27 (15), pp. 5523-5533.
Bonin A., et al., "Isolation, Microinjection, and Transfer of Mouse Blastocysts," *Methods in Molecular Biology*, Chapter 9, 2001, vol. 158, pp. 121-134.
Bornstein, G.G. et al., "Development of a new fully human anti-CD20 monoclonal antibody for the treatment of B-cell malignancies", 2010, vol. 28, pp. 561-574.
Bottaro A., et al., "Deletion of the IgH Intronic Enhancer and Associated Matrix-Attachment Regions Decreases, but does not Abolish, Class Switching at the μ Locus," *International Immunology*, 1998, vol. 10 (6), pp. 799-806.
Bradley A., et al., "Formation of Germ-Line Chimaeras from Embryo-Derived Teratocarcinoma Cell Lines," *Nature*, 1984, vol. 309 (5965), pp. 255-256.
Branstetter R., et al., "Activation-Induced Cytidine Deaminase Deaminates Deoxycytidine on Single-Stranded DNA but Requires the Action of RNase," *Proceedings of the National Academy of Sciences of the U.S.A*, Apr. 2003, vol. 100 (7), pp. 4102-4107.
Brault V., et al., "Modeling Chromosomes in Mouse to Explore the Function of Genes, Genomic Disorders, and Chromosonal Organization," *PLoS Genetics*, Jul. 2006, vol. 2 (7), pp. e86-1-e86-9.
Breden F., et al., "Comparison of Antibody Repertoires Produced by HIV-1 Infection, Other Chronic and Acute Infections, and Systemic Autoimmune Disease," PLoS One, 2011, vol. 6 (3), pp. e16857.
Brezinschek H.P., et al., "Analysis of the Human $V_H$ Gene Repertoire," *Journal of Clinical Investigation*, 1997, vol. 99 (10), pp. 2488-2501.
Brüggemann M. et al., "A Repertoire of Monoclonal Antibodies with Human Heavy Chains from Transgenic Mice," *Proceedings of the National Academy of Sciences U.S.A*, 1989, vol. 86 (17), pp. 6709-6713.
Brüggemann M., "Human Antibody Expression in Transgenic Mice," *Archivum Immunologiae et Therapia Experimentalis*, 2001, vol. 49 (3), pp. 203-208.
Brüggemann M., et al., "Human Antibody Production in Transgenic Mice: Expression from 100 Kb of the Human IgH Locus," *European Journal of Immunology*, May 1991, vol. 21 (5), pp. 1323-1326.
Brüggemann M., et al., "Immunoglobulin Heavy Chain Locus of the Rat: Striking Homology to Mouse Antibody Genes," *Proceedings of the National Academy of Sciences U.S.A*, 1986, vol. 83 (16), pp. 6075-6079.
Brüggemann M., et al., "The Immunogenicity of Chimeric Antibodies," *The Journal of Experimental Medicine*, Dec. 1989, vol. 170 (6), pp. 2153-2157.
Brüggemann M., et al., "Strategies for Expressing Human Antibody Repertoires in Transgenic Mice," *Immunology Today*, Aug. 1996, vol. 17 (8), pp. 391-397.
Briney B.S., et al., "Human Peripheral Blood Antibodies with Long HCDR3s are Established Primarily at Original Recombination using a Limited Subset of Germline Genes," *PLoS One*, 2012, vol. 7 (5), pp. e36750-1-e36750-13.
Brocker C.N., et al., "Evolutionary Divergence and Functions of the ADAM and ADAMTS Gene Families," *Human Genomics*, 2009, vol. 4 (1), pp. 43-55.
Brüggemann M., "Human Monoclonal Antibodies from Translocus Mice," *Molecular Biology of B Cells*, Chapter 34, 2003, pp. 547-561.
Buehr M., et al., "Capture of Authentic Embryonic Stem Cells from Rat Blastocysts," *Cell*, 2008, vol. 135 (7), pp. 1287-1298.

(56) References Cited

OTHER PUBLICATIONS

Butler J.E., "Immunoglobulin Diversity, B-Cell and Antibody Repertoire Development in Large Farm Animals," *Revue scientifique et technique (International Office of Epizootics)*, 1998, vol. 17 (7), pp. 43-70.
Cadiñanos J., et al., "Generation of an Inducible and Optimized PiggyBac Transposon System," *Nucleic Acids Research*, 2007, vol. 35 (12), pp. e87.
Call L.M., et al., "A Cre-lox recombination system for the targeted integration of circular yeast artificial chromosomes into embryonic stem cells," *Human Molecular Genetics*, 2000, vol. 9 (12), pp. 1745-1751.
Carstea A.C., et al., "Germline Competence of Mouse ES and iPS Cell Lines: Chimera Technologies and Genetic Background," *World Journal of Stem Cells*, 2009, vol. 1 (1), pp. 22-29.
Carter T.C., et al., "Standardized Nomenclature for Inbred Strains of Mice," *Cancer Research*, 1952, vol. 12 (8), pp. 602-613.
Casrouge A., et al., "Size Estimate of the $\alpha\beta$ TCR Repertoire of Naive Mouse Splenocytes," *The Journal of Immunology*, 2000, vol. 164 (11), pp. 5782-5787.
Chan A.C., et al., "Therapeutic Antibodies for Autoimmunity and Inflammation," *Nature Reviews Immunology*, 2010, vol. 10 (5), pp. 301-316.
Chen C., et al., "Immunoglobulin Heavy Chain Gene Replacement: A Mechanism of Receptor Editing," *Immunity*, 1995, vol. 3 (6), pp. 747-755.
Chen J., et al., "B Cell Development in Mice that Lack One or Both Immunoglobulin κ Light Chain Genes," *The EMBO Journal*, 1993, vol. 12 (3), pp. 821-830.
Chen Y., "PiggyBac Transposon-Mediated, Reversible Gene Transfer in Human Embryonic Stem Cells," *Stem Cells and Development*, Nov. 2010, vol. 19 (6), 9 pages.
Chia R., et al., "The origins and uses of mouse outbred stocks," *Nature Genetics*, 2005, vol. 37 (11), pp. 1181-1186.
Chinese Patent Office, First Office Action (English Translation) for Chinese Application No. 201180039668.1, dated Jan. 3, 2014, 6 pages.
Chinese Patent Office, First Office Action for Chinese Patent Application No. 201180039668.1, dated Jan. 3, 2014, 6 pages.
Chinese Patent Office, Office Action (English Translation) for Chinese Patent Application No. 201380029744.1, dated Nov. 10, 2016, 2 pages.
Chinese Patent Office, Office Action for Chinese Patent Application No. 201380027944.1, dated Nov. 10, 2016, 5 pages.
Chinese Patent Office, Search Report (English Translation), Chinese Patent Application No. 201180039668.1, dated Jan. 3, 2014, 2 pages.
Chinese Patent Office, Search Report, Chinese Patent Application No. 201180039668.1, dated Jan. 3, 2014, 1 page.
Cho C., "Testicular and Epididymal ADAMs: Expression and Function During Fertilization," *Nature Reviews Urology*, 2012, vol. 9 (10), pp. 550-560.
Choi I., et al., "Characterization and Comparative Genomic Analysis of Intronless Adams with Testicular Gene Expression," *Genomics*, 2004, vol. 83 (4), pp. 636-646.
Clark J., et al., "A Future for Transgenic Livestock," *Nature Reviews Genetics*, 2003, vol. 4 (10), pp. 825-833.
Clark L.A., et al., "Trends in Antibody Sequence Changes During the Somatic Hypermutation Process," *The Journal of Immunology*, 2006, vol. 177 (1), pp. 333-340.
Clark M.R., "IgG Effector Mechanisms," *Chemical Immunology*, 1997, vol. 65, pp. 88-110.
Colbère-Garapin F., et al., "A New Dominant Hybrid Selective Marker for Higher Eukaryotic Cells," *Journal of Molecular Biology*, 1981, vol. 150 (1), pp. 1-14.
Collins F.S., et al., "A Mouse for All Reasons," *Cell*, 2007, vol. 128 (1), pp. 9-13.
Combriato G., et al., "Regulation of Human Igλ Light Chain Gene Expression by NF-κB1," *The Journal of Immunology*, 2002, vol. 168 (3), pp. 1259-1266.
Conrath K., et al., "Camel Single-domain Antibodies as Modular Building Units in Bispecific and Bivalent Antibody Constructs," *The Journal of Biological Chemistry*, 2001, vol. 276 (10), pp. 7346-7350.
Copeland N.G., et al., "Recombineering: A Powerful New Tool for Mouse Functional Genomics," *Nature Reviews Genetics*, 2001, vol. 2 (10), pp. 769-779.
Corbett S.J., et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," *Journal of Molecular Biology*, 1997, vol. 270 (4), pp. 587-597.
Corti D., et al., "A Neutralizing Antibody Selected from Plasma Cells that Binds to Group 1 and Group 2 Influenza A Hemagglutinins," *Science*, 2011, vol. 333 (6044), pp. 850-856.
Crouch E.E., et al., "Regulation of AID expression in the Immune Response," *Journal of Experimental Medicine*, May 2007, vol. 204 (5), pp. 1145-1156.
Cuesta A.M., et al., "Multivalent Antibodies: When Design Surpasses Evolution," *Trends in Biotechnology*, 2010, vol. 28 (7), pp. 355-362.
Davies N.P., et al., "Creation of Mice Expressing Human Antibody Light Chains by Introduction of a Yeast Artificial Chromosome Containing the Core Region of the Human Immunoglobulin κ Locus," *Nature Biotechnology*, Aug. 1993, vol. 11 (8), pp. 911-914.
De Bono B., et al., "$V_H$ Gene Segments in the Mouse and Human Genomes," *Journal of Molecular Biology*, 2004, vol. 342 (1), pp. 131-143.
De Kruif J., et al., "Human Immunoglobulin Repertoires Against Tetanus Toxoid Contain a Large and Diverse Fraction of High-Affinity Promiscuous $V_H$ Genes," *Journal of Molecular Biology*, 2009, vol. 387 (3), pp. 548-558.
De Saint Vincent B.R., et al., "Homologous Recombination in Mammalian Cells Mediates Formation of a Functional Gene from Two Overlapping Gene Fragments," *Proceedings of the National Academy of Sciences of the U.S.A*, 1983, vol. 80 (7), pp. 2002-2006.
De Wildt R.M.T., et al., "Analysis of Heavy and Light Chain Pairings Indicates that Receptor Editing Shapes the Human Antibody Repertoire," *Journal of Molecular Biology*, 1999, vol. 285, pp. 895-901.
Dechiara T.M., et al., "Producing Fully ES Cell-Derived Mice from Eight-Cell Stage Embryo Injections," *Methods in Enzymology*, Chapter 16, 2010, vol. 476, pp. 285-294.
Dechiara T.M., et al., "VelociMouse: Fully ES Cell-Derived F0-Generation Mice Obtained from the Injection of ES Cells into Eight-Cell-Stage Embryos," *Methods in Molecular Biology*, Chapter 16, 2009, vol. 530, pp. 311-324.
Declerck P.J., et al., "Generation of Monoclonal Antibodies against autologous Proteins in Gene-inactivated Mice," *The Journal of Biological Chemistry*, Apr. 1995, vol. 270 (15), pp. 8397-8400.
Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.
Deng C., et al., "Reexamination of Gene Targeting Frequency as a Function of the Extent of Homology Between the Targeting Vector and the Target Locus," *Molecular and Cellular Biology*, Aug. 1992, vol. 12 (8), pp. 3365-3371.
Denome R.M., et al., "Patterns of Polyadenylation Site Selection in Gene Constructs Containing Multiple Polyadenylation Signals," *Molecular and Cellular Biology*, 1988, vol. 8 (11), pp. 4829-4839.
Di Noia, J.M., et al., "Molecular Mechanisms of Antibody Somatic Hypermutation," *Annual Review of Biochemistry*, 2007, vol. 76, pp. 1-22.
Diez-Roux G., et al., "A High-Resolution Anatomical Atlas of the Transcriptome in the Mouse Embryo," *PLoS Biology*, 2011, vol. 9 (1), pp. 1-13.
Ding L., et al., "Generation of High-Affinity Fully Human Anti-Interleukin-8 Antibodies from its cDNA by Two-Hybrid Screening and Affinity Maturation in Yeast," *Protein Science*, 2010, vol. 19 (10), pp. 1957-1966.
Doetschman T., et al., "Establishment of Hamster Blastocyst-Derived Embryonic Stem (ES) Cells," *Developmental Biology*, 1988, vol. 127 (1), pp. 224-227.

(56) References Cited

OTHER PUBLICATIONS

Doetschman T., et al., "Targeted Mutation of the Hprt Gene in Mouse Embryonic Stem Cells," *Proceedings of the National Academy of Sciences of the U.S.A*, 1988, vol. 85 (22), pp. 8583-8587.
Donohoe M.E., et al., "Transgenic Human λ5 Rescues the Murine λ5 Nullizygous Phenotype," *Journal of Immunology*, 2000, vol. 164, pp. 5269-5276.
Doyle A., et al., "The Construction of Transgenic and Gene Knockout/Knockin Mouse Models of Human Disease," *Transgenic Research*, 2012, vol. 21 (2), pp. 327-349.
Durbin R., et al., "A Map of Human Genome Variation from Population-Scale Sequencing," *Nature*, 1000 Genomes Project Consortium, 2010, vol. 467 (7319), pp. 1061-1073.
Durdik J., et al., "Isotype Switching by a Microinjected μ Immunoglobulin Heavy Chain Gene in Transgenic Mice," *Proceedings of the National Academy of Sciences of the U.S.A*, 1989, vol. 86 (7), pp. 2346-2350.
Ebert A., et al., "The Distal $V_H$ Gene Cluster of the Igh Locus Contains Distinct Regulatory Elements with Pax5 Transcription Factor-Dependent Activity in Pro-B Cells," *Immunity*, Feb. 2011, vol. 34 (2), pp. 175-187.
Edwards D.R., et al., "The ADAM Metalloproteinases," *Molecular Aspects of Medicine*, 2008, vol. 29 (5), pp. 258-289.
Eisener-Dorman A.F., "Cautionary Insights on Knockout Mouse Studies: The Gene or not the Gene?," *Brain, Behavior, and Immunity*, 2009, vol. 23 (3), pp. 318-324.
Ekiert D.C., et al., "A Highly Conserved Neutralizing Epitope on Group 2 Influenza A Viruses," *Science*, 2011, vol. 333 (6044), pp. 843-850.
Engel H., et al., "Expression level of a transgenic λ2 chain results in isotype exclusion and commitment to B1 cells," *European Journal of Immunology*, 1998, vol. 28, pp. 2289-2299.
European Patent Office, Alessandro Brero, Authorized officer, International Search Report for Application No. PCT/GB2012/052296, dated May 17, 2013, 30 pages, together with the Written Opinion of the International Searching Authority.
European Patent Office, Alessandro Brero, Authorized officer, International Search Report for Application No. PCT/GB2012/052297, dated Jun. 19, 2013, 24 pages, together with the Written Opinion of the International Searching Authority.
European Patent Office, Alessandro Brero, Authorized Officer, International Search Report for Application No. PCT/GB2012/052298, dated Jun. 13, 2013, 21 pages, together with the Written Opinion of the International Searching Authority.
European Patent Office, Examination Report for Application No. 12762378.3, dated Jun. 8, 2016, 5 pages.
European Patent Office, Extended European Search Report for Application No. 16189625.3, dated Nov. 23, 2016, 8 pages.
European Patent Office, Communication pursuant to Rule 114(2) EPC regarding 14772198.9, dated Mar. 30, 2016, 16 pages.
European Patent Office, European Search Report for Application No. 12194977.0, dated Jul. 5, 2013, 4 pages.
European Patent Office, Extended European Search Report for Application No. 12171791.2, dated Jun. 18, 2013, 5 pages.
European Patent Office, Extended European Search Report for Application No. 12195041.4, dated Nov. 18, 2013, 8 pages.
European Patent Office, Extended European Search Report for Application No. 14176740.0, dated Oct. 15, 2014, 7 pages.
European Patent Office, Extended European Search Report for Application No. 16151215.7, dated Mar. 16, 2016, 11 pages.
European Patent Office, F. Chambonnet, Authorized officer, International Search Report for Application No. PCT/GB2012/052380, dated Jan. 3, 2013, 17 pages, together with the Written Opinion of the International Searching Authority.
European Patent Office, Gaby Brouns, Authorized officer, International Search Report for Application No. PCT/GB2012/052956, dated Mar. 1, 2013, 14 pages, together with the Written Opinion of the International Searching Authority.
European Patent Office, Gaby Brouns, Authorized officer, International Search Report for Application No. PCT/GB2012/052960, dated Apr. 29, 2013, 19 pages, together with the Written Opinion of the International Searching Authority.
European Patent Office, Gaby Brouns, Authorized officer, International Search Report for Application No. PCT/GB2013/050682, dated Sep. 25, 2013, 16 pages, together with the Written Opinion of the International Searching Authority.
European Patent Office, Gaby Brouns, Authorized officer, International Search Report for Application No. PCT/GB2013/050683, dated Jul. 9, 2013, 11 pages, together with the Written Opinion of the International Searching Authority.
European Patent Office, Gaby Brouns, Authorized officer, International Search Report for Application No. PCT/GB2013/051280, dated Nov. 15, 2013, 19 pages, together with the Written Opinion of the International Searching Authority.
European Patent Office, Extended European Search Report for Application No. 15188522.5 dated Feb. 2, 2016, 15 pages.
European Patent Office, Examination Report for Application No. 12795841.1, dated Feb. 12, 2016, 5 pages.
European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, International Searching Authority, Examiners Report on Allowable Claims for Application No. PCT/GB2010/051122, dated Jan. 2004, 1 page.
European Patent Office, Examination Report for Application No. 12778780.2, dated Oct. 14, 2016, 3 pages.
European Patent Office, Extended European Search Report for Application No. 14196645.7, dated Jun. 26, 2015, 12 pages.
European Patent Office, Julien Landre, Authorized officer, International Search Report for Application No. PCT/GB2012/052670, dated Feb. 14, 2013, 12 pages, together with the Written Opinion of the International Searching Authority.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, dated Sep. 29, 2010, 9 pages, together with the Written Opinion of the International Searching Authority.
European Patent Office, Laurent Deleu, Authorized officer, International Search Report for Application No. PCT/GB2011/050019, dated May 16, 2011, 12 pages, together with the Written Opinion of the International Searching Authority.
European Patent Office, Examination Report for Application No. 12194970.5, dated Sep. 23, 2013, 6 pages.
European Patent Office, Examination Report for Application No. 14176740.0, dated Jun. 6, 2016, 5 pages.
European Patent Office, Examination Report for Application No. 14176740.0, dated Oct. 23, 2015, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 14170196.1, dated Oct. 8, 2014, 8 pages.
European Patent Office, Notice of opposition to a European patent, pertaining to Application No. 10734546.4, dated Jan. 23, 2013, 41 pages.
European Patent Office, Opposition against EP2421357 Animal Models and Therapeutic Molecules in the name of Kymab Limited pertaining to Application No. 10734546.4, dated Oct. 23, 2013, 44 pages.
European Patent Office, Opposition against EP2517557 Animal Models and Therapeutic Molecules in the name of Kymab Limited pertaining to Application No. 12171793.8, dated Jan. 17, 2017, 39 pages.
European Patent Office, Statement of Fact and Arguments in Support of Opposition pertaining to Application No. 10734546.4, dated Oct. 22, 2013, 41 pages.

(56) References Cited

OTHER PUBLICATIONS

European Patent Office, Invitation to Pay Additional Fees and, Where Applicable, Protest Fee, Application No. PCT/GB2012/052296, mailed on Jan. 24, 2013, 9 pages.
Evans J.P., "Fertilin β and Other ADAMs as Integrin Ligands: Insights into Cell Adhesion and Fertilization," *Bioessays*, 2001, vol. 23 (7), pp. 628-639.
Featherstone K., et al., "The Mouse Immunoglobulin Heavy Chain V-D Intergenic Sequence Contains Insulators that May Regulate Ordered V(D)J Recombination," *Journal of Biological Chemistry*, 2010, vol. 285 (13), pp. 9327-9338.
Feeney A.J., "Genetic and Epigenetic Control of V Gene Rearrangement Frequency," *Advances in Experimental Medicine and Biology*, Chapter 6, 2009, vol. 650, pp. 73-81.
Fell H.P., "Homologous Recombination in Hybridoma Cells: Heavy Chain Chimeric Antibody Produced by Gene Targeting," *Proceedings of the National Academy of Sciences of the U.S.A*, 1989, vol. 86 (21), pp. 8507-8511.
Feng Y.Q., et al., "Site-Specific Chromosomal Integration in Mammalian Cells: Highly Efficient CRE Recombinase-Mediated Cassette Exchange," *Journal of Molecular Biology*, 1999, vol. 292 (4), pp. 779-785.
Feschotte C., et al., "DNA Transposons and the Evolution of Eukaryotic Genomes," *Annual Review of Genetics*, 2007, vol. 41, pp. 331-368.
Festing, M.F.W., et al., "Revised nomenclature for strain 129 mice," *Mammalian Genome*, 1999, vol. 10, p. 836.
Fleischer B., et al., "Reactivity of Mouse T-Cell Hybridomas Expressing Human Vβ Gene Segments With Staphylococcal and Streptococcal Superantigens," *Infection and Immunity*, Mar. 1996, vol. 64 (3), pp. 987-994.
Folger K.R., et al., "Patterns of Integration of DNA Microinjected into Cultured Mammalian Cells: Evidence for Homologous Recombination Between Injected Plasmid DNA Molecules," *Molecular and Cellular Biology*, 1982, vol. 2 (11), pp. 1372-1387.
Forconi F., et al., "The Normal IGHV1-69-Derived B-Cell Repertoire Contains Stereotypic Patterns Characteristic of Unmutated CLL," *Blood*, 2010, vol. 115 (1), pp. 71-77.
French Patent Office, INPI, Laurent Deleu, Authorized officer, International Search Report for Patent Application No. 1359518, dated Aug. 20, 2014, 3 pages.
Friedrich G., Statement of Dr. Glenn Friedrich, dated Mar. 3, 2016, 4 pages.
Fujieda S., et al., "Multiple Types of Chimeric Germ-Line Ig Heavy Chain Transcripts in Human B Cells: Evidence for Trans-Splicing of Human Ig RNA," *Journal of Immunology*, 1996, vol. 157 (8), pp. 3450-3459.
Fukita Y., et al., "Somatic Hypermutation in the Heavy Chain Locus Correlates with Transcription," *Immunity*, 1998, vol. 9 (1), pp. 105-114.
Gallo M.L., et al., "The Human Immunoglobulin Loci Introduced into Mice: V (D) and J Gene Segment Usage Similar to that of Adult Humans," *European Journal of Immunology*, 2000, vol. 30 (2), pp. 534-540.
Gama Sosa M.A., et al., "Animal Transgenesis: An Overview," *Brain Structure and Function*, 2010, vol. 214 (2-3), pp. 91-109.
Gavilondo J.V., et al., "Antibody Engineering at the Millennium," *BioTechniques*, Jul. 2000, vol. 29 (1), pp. 128-145.
Genbank (D. Muzny et al.), "Rattus norvegicus clone CH230-30N12, * Sequencing in Progress *, 6 unordered pieces," Accession No. AC111740, Nov. 9, 2002, 42 pages. [Retrieved from the Internet: http://www.ncbi.nlm.nih.gov/nuccore/AC111740 on Feb. 28, 2013].
Genbank, "DNA Sequence of the Human Immunoglobulin D Segment Locus," Accession No. x97051.1 S64822, Aug. 6, 2014, 29 pages. [Retrieved from the Internet: http://www.ncbi.nlm.nih.gov/nuccore/X97051].
Genbank, "DNA Sequence of the Human Immunoglobulin D Segment Locus," Accession No. x97051.1 S64822, updated Mar. 3, 2015, 26 pages.
Genbank, "*Homo sapiens* immunoglobulin heavy-chain (IGHV2-5) gene, IGHV2-5*10 allele, partial sequence," Accession No. KF698731.1, dated Nov. 18, 2013, 1 page.
Genbank, "Mus musculus strain 129S1/SvlmJ chromosome 12 genomic sca locus group 129S1/SvlmJ 129S1/SVIMJ_MMCHR12_CTG1," NCBI Reference Sequence No. NT_114985.3, dated May 5, 2014, 1 page.
Gerdes T., et al., "Physical Map of the Mouse λ Light Chain and Related Loci," *Immunogenetics*, 2002, vol. 54 (1), pp. 62-65.
Gerstein R.M., et al., "Isotype Switching of an Immunoglobulin Heavy Chain Transgene Occurs by DNA Recombination Between Different Chromosomes," *Cell*, 1990, vol. 63 (3), pp. 537-548.
Geurts A.M., et al., "Knockout Rats via Embryo Microinjection of Zinc-Finger Nucleases," *Science*, 2009, vol. 325 (5939), p. 433.
Giallourakis C.C., et al., "Elements Between the IgH Variable (V) and Diversity (D) Clusters Influence Antisense Transcription and Lineage-Specific V(D)J Recombination," *Proceedings of the National Academy of Sciences of the U.S.A.*, 2010, vol. 107 (51), pp. 22207-22212.
Giraldo P., et al., "Size Matters: Use of YACs, BACs and PACs in Transgenic Animals," *Transgenic Research*, 2001, vol. 10 (2), pp. 83-103.
Giusti A.M., et al., "Hypermutation is Observed only in Antibody H Chain V Region Transgenes that have Recombined with Endogenous Immunoglobulin H DNA: Implications for the Location of cis-acting Elements Required for Somatic Mutation," *The Journal of Experimental Medicine*, Mar. 1993, vol. 177 (3), pp. 797-809.
Glanville J., et al., "Naive Antibody Gene-Segment Frequencies are Heritable and Unaltered by Chronic Lymphocyte Ablation," *Proceedings of the National Academy of Sciences of the U.S.A*, Dec. 2011, vol. 108 (50), pp. 20066-20071.
Glaser S. et al., "Current issues in mouse genome engineering," *Nature Genetics*, Nov. 2005, Vo. 37 (11), pp. 1187-1193.
Gluzman Y., "SV40-Transformed Simian Cells Support the Replication of Early SV40 Mutants," *Cell*, 1981, vol. 23 (1), pp. 175-182.
Goldman I.L., et al., "Transgenic Animals in Medicine: Integration and Expression of Foreign Genes, Theoretical and Applied Aspects," *Medical Science Monitor*, 2004, vol. 10 (11), pp. RA274-RA285.
Goodhardt M., et al., "Rearrangement and Expression of Rabbit Immunoglobulin κ Light Chain Gene in Transgenic Mice," *Proceedings of the National Academy of Sciences of the U.S.A.*, 1987, vol. 84 (12), pp. 4229-4233.
Gorman Jr., et al., "The Igκ 3' Enhancer Influences the Ratio of Igκ Versus Igλ B Lymphocytes," *Immunity*, 1996, vol. 5 (3), pp. 241-252.
Gorny M.K., et al., "Human Anti-V3 HIV-1 Monoclonal Antibodies Encoded by the VH5-51/VL Lambda Genes Define a Conserved Antigenic Structure," *PLoS One*, 2011, vol. 6 (12), pp. e27780-1-e27780-10.
Goyenechea B., et al., "Cells Strongly Expressing Igκ Transgenes Show Clonal Recruitment of Hypermutation: A Role for Both MAR and the Enhancers," *EMBO Journal*, 1997, vol. 16 (13), pp. 3987-3994.
Gratz S. et al., "Genome Engineering of *Drosophila* with the CRISPR RNA-Guided Cas9 Nuclease," *Genetics*, Aug. 2013, vol. 194, pp. 1029-1035.
Green L.L., "Antibody Engineering via Genetic Engineering of the Mouse: XenoMouse Strains are a Vehicle for the Facile Generation of Therapeutic Human Monoclonal Antibodies," *Journal of Immunological Methods*, Dec. 1999, vol. 231 (1-2), pp. 11-23.
Green L.L., et al., "Antigen-Specific Human Monoclonal Antibodies from Mice Engineered with Human Ig Heavy and Light Chain YACs," *Nature Genetics*, May 1994, vol. 7 (1), pp. 13-21.
Green L.L., et al., "Regulation of B Cell Development by Variable Gene Complexity in Mice Reconstituted with Human Immunoglobulin Yeast Artificial Chromosomes," *The Journal of Experimental Medicine*, Aug. 1998, vol. 188 (3), pp. 483-495.
Grippo V., et al., "The Heavy Chain Variable Segment Gene Repertoire in Chronic Chagas' Heart Disease," *The Journal of Immunology*, Dec. 2009, vol. 182 (12), pp. 8015-8025.
Grund M., European Patent Attorney, Grund Intellectual Property Group, Third-Party Observations according to Article 115 EPC regarding 11705964.2, dated Apr. 30, 2014, 4 pages.

(56) References Cited

OTHER PUBLICATIONS

Grund M., European Patent Attorney, Grund Intellectual Property Group, Third-Party Observations according to Article 115 EPC regarding 11705964.2, dated Aug. 5, 2016, 11 pages.
Grund M., European Patent Attorney, Grund Intellectual Property Group, Third-Party Observations according to Article 115 EPC regarding 11705964.2, dated Oct. 9, 2013, 8 pages.
Grund M., European Patent Attorney, Grund Intellectual Property Group, Third-Party Observations according to Article 115 EPC regarding 12171791.2, dated Aug. 4, 2014, 6 pages.
Grund M., European Patent Attorney, Grund Intellectual Property Group, Third-Party Observations according to Article 115 EPC regarding 12171791.2, dated Dec. 19, 2014, 7 pages.
Grund M., European Patent Attorney, Grund Intellectual Property Group, Third-Party Observations according to Article 115 EPC regarding 12171791.2, dated Feb. 26, 2014, 9 pages.
Grund M., European Patent Attorney, Grund Intellectual Property Group, Third-Party Observations according to Article 115 EPC regarding 12171793.8, dated Jun. 25, 2014, 7 pages.
Grund M., European Patent Attorney, Grund Intellectual Property Group, Third-Party Observations according to Article 115 EPC regarding 12194970.5, dated Apr. 25, 2014, 6 pages.
Grund M., European Patent Attorney, Grund Intellectual Property Group, Third-Party Observations according to Article 115 EPC regarding 12194970.5, dated Aug. 12, 2014, 5 pages.
Grund M., European Patent Attorney, Grund Intellectual Property Group, Third-Party Observations according to Article 115 EPC regarding 12194970.5, dated Mar. 5, 2014, 9 pages.
Grund M., European Patent Attorney, Grund Intellectual Property Group, Third-Party Observations according to Article 115 EPC regarding 12194970.5, dated Nov. 15, 2013, 6 pages.
Grund M., European Patent Attorney, Grund Intellectual Property Group, Third-Party Observations according to Article 115 EPC regarding 12194970.5, dated Sep. 9, 2013, 11 pages.
Grund M., European Patent Attorney, Grund Intellectual Property Group, Third-Party Observations according to Article 115 EPC regarding 12194977.0, dated Mar. 26, 2014, 4 pages.
Grund M., European Patent Attorney, Grund Intellectual Property Group, Third-Party Observations according to Article 115 EPC regarding 12194977.0, dated May 12, 2015, 5 pages.
Grund M., European Patent Attorney, Grund Intellectual Property Group, Third-Party Observations according to Article 115 EPC regarding 12195041.4, dated Jul. 30, 2014, 5 pages.
Grund M., European Patent Attorney, Grund Intellectual Property Group, Third-Party Observations according to Article 115 EPC regarding 12762377.5, dated Feb. 12, 2016, 8 pages.
Grund M., European Patent Attorney, Grund Intellectual Property Group, Third-Party Observations according to Article 115 EPC regarding 12762377.5, dated May 22, 2015, 7 pages.
Grund M., European Patent Attorney, Grund Intellectual Property Group, Third-Party Observations according to Article 115 EPC regarding 12762378.3, dated Feb. 15, 2017, 6 pages.
Grund M., European Patent Attorney, Grund Intellectual Property Group, Third-Party Observations according to Article 115 EPC regarding 12772122.3, dated Mar. 12, 2015, 5 pages.
Grund M., European Patent Attorney, Grund Intellectual Property Group, Third-Party Observations according to Article 115 EPC regarding 12772122.3, dated May 17, 2016, 7 pages.
Grund M., European Patent Attorney, Grund Intellectual Property Group, Third-Party Observations according to Article 115 EPC regarding 12795606.8, dated Aug. 22, 2014, 8 pages.
Grund M., European Patent Attorney, Grund Intellectual Property Group, Third-Party Observations according to Article 115 EPC regarding 12795606.8, dated Feb. 26, 2014, 6 pages.
Grund M., European Patent Attorney, Grund Intellectual Property Group, Third-Party Observations according to Article 115 EPC regarding 12795606.8, dated Mar. 26, 2015, 4 pages.
Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding 16151215.7, dated Mar. 1, 2017, 4 pages.
Grund M., European Patent Attorney, Grund Intellectual Property Group, Third-Party Observations according to Article 115 EPC regarding 16189625.3, dated Mar. 23, 2017, 5 pages.
Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/GB2013/050683, dated Jul. 28, 2014, 2 pages.
Grund M., European Patent Attorney, Grund Intellectual Property Group, Third-Party Observations regarding Application No. PCT/US2012/026416, dated Jun. 6, 2013, 2 pages.
Grund M., European Patent Attorney, Grund Intellectual Property Group, Third-Party Observations according to Article 115 EPC regarding 11705964.2, dated Feb. 26, 2015, 5 pages.
Gu H., et al., "Independent Control of Immunoglobulin Switch Recombination at Individual Switch Regions Evidenced Through Cre-loxP-Mediated Gene Targeting," *Cell*, 1993, vol. 73 (6), pp. 1155-1164.
Guan C. et al., "A Review of Current Large-Scale Mouse Knockout Efforts," *Genesis*, vol. 48, 2010, pp. 73-85.
Guerrero C., et al., "The Bleomycin Resistance Gene of Transposon Tn5 is an Excellent Marker for Transformation of Corynebacteria," *Applied Microbiology and Biotechnology*, 1992, vol. 36 (6), pp. 759-762.
Guirouilh-Barbat J. et al., "Is homologous recombination really an error-free process?", *Frontiers in Genetics*, Jun. 2014, vol. 5 (175), 15 pages.
Guntaka R.V., "Transcription Termination and Polyadenylation in Retroviruses," *Microbiological Reviews*, 1993, vol. 57 (3), pp. 511-521.
Guo, Y., et al., "A Preliminary Analysis of the Immunoglobulin Genes in the African Elephant (*Loxodonta africana*)," *PLoS ONE*, Feb. 2011, vol. 6 (2), pp. e16889-1-e16889-14.
Hagiwara S., "Transgenic Expression of VpreB-3 Under the Control of the Immunoglobulin Heavy Chain Enhancer and SV40 Promoter," *Kobe Journal of Medical Sciences*, 1996, vol. 42 (1), pp. 43-59 (abstract only).
Hamers-Caterman C. et al., "Naturally occurring antibodies devoid of light chains," *Nature*, Jun. 1993, vol. 363, pp. 446-448.

(56) References Cited

OTHER PUBLICATIONS

Han C., et al., "Comprehensive Analysis of Reproductive ADAMs: Relationship of ADAM4 and ADAM6 with an ADAM Complex Required for Fertilization in Mice," *Biology of Reproduction*, 2009, vol. 80 (5), pp. 1001-1008.
Harding F.A., et al., "Class Switching in Human Immunoglobulin Transgenic Mice," *Annals of the New York Academy of Sciences*, 1995, vol. 764, pp. 536-546.
Hasty P., et al., "Target Frequency and Integration Pattern for Insertion and Replacement Vectors in Embryonic Stem Cells," *Molecular and Cellular Biology*, 1991, vol. 11 (9), pp. 4509-4517.
Hendricks J., et al., "Organization of the Variable Region of the Immunoglobulin Heavy-Chain Gene Locus of the Rat," *Immunogenetics*, 2010, vol. 62 (7), pp. 479-486.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association between the Igk and Igh immunoglobulin loci mediated by the 3' Igk enhancer Induces 'decontraction' of the Igh locus in pre-B cells," *Nature Immunology*, Apr. 2008, vol. 9 (4), pp. 396-404.
Hong J. et al., "Derivation and Characterization of Embryonic Stem Cells Lines Derived from Transgenic Fischer 344 and Dark Agouti Rats," *Stem Cells and Development*, 2012, vol. 21 (6), pp. 1571-1586.
Houdebine L.M., "The Methods to Generate Transgenic Animals and to Control Transgene Expression," *Journal of Biotechnology*, 2002, vol. 98 (2-3), pp. 145-160.
Houdebine L.M., "Transgenic Animal Models in Biomedical Research," *Methods in Molecular Biology*, Chapter 10, 2007, vol. 360, pp. 163-202.
Houldsworth J., et al., "Comparative Genomic Hybridization: An Overview," *The American Journal of Pathology*, Dec. 1994, vol. 145 (6), pp. 1253-1260.
Hsu E., et al., "The plasticity of immunoglobulin gene systems in evolution," *Immunology Reviews*, vol. 210, Apr. 2006, pp. 8-26.
Huang C.C., et al., "Structural Basis of Tyrosine Sulfation and $V_H$-Gene Usage in Antibodies that Recognize the HIV Type 1 Coreceptor-Binding Site on gp120," *Proceedings of the National Academy of Sciences of the U.S.A.*, 2004, vol. 101 (9), pp. 2706-2711.
Huang, D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Huber V.C. et al., "Distinct Contributions of Vaccine-Induced Immunoglobulin G1 (IgG1) and IgG2a Antibodies to Protective Immunity Against Influenza," *Clinical and Vaccine Immunology*, 2006, vol. 13 (9), pp. 981-990.
Hudziak R.M., et al., "Establishment of Mammalian Cell Lines Containing Multiple Nonsense Mutations and Functional Suppressor tRNA Genes," *Cell*, 1982, vol. 31 (1), pp. 137-146.
Huovila A.J., et al., "Shedding Light on ADAM Metalloproteinases," *Trends in Biochemical Sciences*, 2005, vol. 30 (7), pp. 413-422.
Iglesias-Ussel MD., et al., "Forced Expression of AID Facilitates the Isolation of Class Switch Variants from Hybridoma Cells," *Journal of Immunological Methods*, 2006, vol. 316 (1-2), pp. 59-66.
Ivics Z., et al., "The Expanding Universe of Transposon Technologies for Gene and Cell Engineering," *Mobile DNA*, 2010, vol. 1 (1), 15 pages.
Ivics Z., et al., "The Sleeping Beauty Transposable Element: Evolution, Regulation and Genetic Applications," *Current Issues in Molecular Biology*, 2004, vol. 6 (1), pp. 43-55.
Izsvák Z., et al., "Sleeping Beauty Transposition: Biology and Applications for Molecular Therapy," *Molecular Therapy*, 2004, vol. 9 (2), pp. 147-156.
Jacob H.J., et al., "Gene Targeting in the Rat: Advances and Opportunities," *Trends in Genetics*, 2010, vol. 26 (12), pp. 510-518.
Jakobovits A., et al., "From XenoMouse Technology to Panitumumab, the First Fully Human Antibody Product from Transgenic Mice," *Nature Biotechnology*, 2007, vol. 25 (10), pp. 1134-1143.
Jakobovits A., "Production of Fully Human Antibodies by Transgenic Mice," *Current Opinion in Biotechnology*, 1995, vol. 6 (5), pp. 561-566.
Jakobovits A., "The Long-Awaited Magic Bullets: Therapeutic Human Monoclonal Antibodies from Transgenic Mice," *Expert Opinion Investigational Drugs*, 1998, vol. 7 (4), pp. 607-614.
Janeway C.A. et al., "The rearrangement of antigen-receptor gene segments controls lymphocyte development," Immunobiology: The Immune System in Health and Disease, 5th Edition, Aug. 2015, 13 pages. [Retrieved from the Internet: http://www.ncbi.nlm.nih.gov/books/NBK27113/].
Janeway et al., "Structural Variation in Immunoglobulin Constant Regions," *Immunobiology: The Immune System in Health and Disease*, 5th Edition, 2001, 5 pages.
Janssens R., et al., "Generation of Heavy-Chain-only Antibodies in Mice," *Proceedings of the National Academy of Sciences of the U.S.A.*, 2006, vol. 103 (41), pp. 15130-15135.
Jasper, P.J., et al., "B lymphocyte deficiency in IgH-transgenic rabbits," *European Journal of Immunology*, 2007, vol. 37, pp. 2290-2299.
Jendreyko N., et al., "Intradiabodies, Bispecific, Tetravalent Antibodies for the Simultaneous Functional Knockout of Two Cell Surface Receptors," *The Journal of Biological Chemistry*, 2003, vol. 278 (48), pp. 47812-47819.
Jessen K.A., et al., "Molecular Analysis of Metastasis in a Polyomavirus Middle T Mouse Model: the Role of Osteopontin," *Breast Cancer Research*, 2004, vol. 6 (3), pp. R157-R169.
Johnston C.M., et al., "Complete Sequence Assembly and Characterization of the C57BL/6 Mouse Ig Heavy Chain V Region," *The Journal of Immunology*, 2006, vol. 176 (7), pp. 4221-4234.
Jones, B.T., Attorney for Applicant, Third-Party Pre-Issuance Submission Under 37 CFR Sec. 1.290 in U.S. Appl. No. 15/016,211, dated Oct. 4, 2016, 59 pages.
Jones, B.T., Attorney for Applicant, Third-Party Pre-Issuance Submission Under 37 CFR Sec. 1.290 in U.S. Appl. No. 15/018,670, dated Aug. 12, 2016, 26 pages.
Jones, B.T., Attorney for Applicant, Third-Party Pre-Issuance Submission Under 37 CFR Sec. 1.290 in U.S. Appl. No. 15/095,315, dated Sep. 16, 2016, 26 pages.
Jones, B.T., Attorney for Applicant, Third-Party Pre-Issuance Submission Under 37 CFR Sec. 1.290 in U.S. Appl. No. 15/232,122, filed Mar. 13, 2017, 32 pages.
Jones, B.T., Attorney for Applicant, Third-Party Pre-Issuance Submission Under 37 CFR Sec. 1.290 in U.S. Appl. No. 15/214,963, filed Mar. 2, 2017, 42 pages.
Jones, B.T., Attorney for Applicant, Third-Party Pre-Issuance Submission Under 37 CFR Section 1.290 in U.S. Appl. No. 15/360,502, dated May 8, 2017, 40 pages.
Jones B.T., Attorney for Applicant, Third-Party Pre-Issuance Submission Under 37 CFR Section 1.290 in U.S. Appl. No. 15/383,196, dated May 8, 2017, 25 pages.
Jones B.T., Attorney for Applicant, Third-Party Pre-Issuance Submission Under 37 CFR Section 1.290 in U.S. Appl. No. 15/383,202, dated May 3, 2017, 23 pages.
Jung D., et al., "Mechanism and Control of V(D)J Recombination at the Immunoglobulin Heavy Chain Locus," *Annual Review of Immunology*, 2006, vol. 24, pp. 541-570.
Kaminski D.A., et al., "Antibody Class Switching differs among SJL, C57BL/6 and 129 Mice," *International Immunology*, 2007, vol. 19 (4), pp. 545-556.
Karu A.E., et al., "Recombinant Antibody Technology," *ILAR Journal / National Research Council, Institute of Laboratory Animal Resources*, 1995, vol. 37 (3), pp. 132-141.
Kaushik A., et al., "Novel Insight into Antibody Diversification from Cattle," *Veterinary Immunology and Immunopathology*, 2002, vol. 87 (3-4), pp. 347-350.
Kawasaki, K., et al., "One-Megabase Sequence Analysis of the Human Immunoglobulin λ Gene Locus," *Genome Research*, 1997, vol. 7, pp. 250-261.

(56) References Cited

OTHER PUBLICATIONS

Kellermann, et al., "Developing the Xenomouse® Technology for Evaluating Immunogenicity," AntibOZ 2: An International Forum to Predict the Next Wave of Protein-based Therapies and Immuno Diagnostics, 2004, *AntibOZ 2 Conference*, Australia, 1 page (abstract only).

Kenter A.L., et al., "Three-Dimensional Architecture of the IgH Locus Facilitates Class Switch Recombination," *Annals of the New York Academy of Sciences*, 2012, vol. 1267, pp. 86-94.

Köhrer C., et al., "Import of Amber and Ochre Suppressor tRNAs into Mammalian Cells: a General Approach to Site-Specific Insertion of Amino Acid Analogues into Proteins," *Proceedings of the National Academy of Sciences of the U.S.A.*, 2001, vol. 98 (25), pp. 14310-14315.

Kim J.Y., et al., "CHO Cells in Biotechnology for Production of Recombinant Proteins: Current State and Further Potential," *Applied Microbiology Biotechnology*, 2012, vol. 93 (3), pp. 917-930.

Kim T., et al., "Expression and Relationship of Male Reproductive ADAMs in Mouse," *Biology of Reproduction*, 2006, vol. 74 (4), pp. 744-750.

Kindt T.J. et al., "Organization and Expression of Immunoglobulin Genes," *Immunology*, Sixth edition, Chapter 5, 2007 (36 pages, including cover sheet and copyright page), pp. 111-144.

Kingzette M., et al., "Trans-Chromosomal Recombination within the Ig Heavy Chain Switch Region in B Lymphocytes," *Proceedings of the National Academy of Sciences of the U.S.A.*, 1998, vol. 95 (20), pp. 11840-11845.

Kitamura D., et al., "A B Cell-Deficient Mouse by Targeted Disruption of the Membrane Exon of the Immunoglobulin µ Chain Gene," *Nature*, 1991, vol. 350 (6317), pp. 423-426.

Kondo S., et al., "Highly improved Gene Targeting by Germline-Specific Cas9 Expression in *Drosophila*," *Genetics*, vol. 195, Nov. 2013, pp. 715-721 (Abstract).

Kondo S., et al., "Highly improved Gene Targeting by Germline-Specific Cas9 Expression in *Drosophila*," *Genetics*, vol. 195, Nov. 2013, pp. 715-721.

Kostenuik P.J., et al., "Denosumab, a Fully Human Monoclonal Antibody to RANKL, Inhibits Bone Resorption and Increases BMD in Knock-in Mice that Express Chimeric (Murine/Human) RANKL," *Journal of Bone and Mineral Research*, 2009, vol. 24 (2), pp. 182-195.

Kotzamanis G., et al., "Recombining Overlapping BACs into a Single Larger BAC," *BMC Biotechnology*, 2004, vol. 4 (1), 10 pages.

Kouskoff V., et al., "Cassette Vectors Directing Expression of T Cell Receptor Genes in Transgenic Mice," *Journal of Immunological Methods*, 1995, vol. 180 (2), pp. 273-280.

Krause J.C., et al., "Epitope-Specific Human Influenza Antibody Repertoires Diversify by B Cell Intraclonal Sequence Divergence and Interclonal Convergence," *Journal of Immunology*, 2011, vol. 187 (7), pp. 3704-3711.

Krutskikh A., et al., "Epididymal Protein Rnase10 is Required for Post-Testicular Sperm Maturation and Male Fertility," *The FASEB Journal*, 2012, vol. 26 (10), pp. 4198-4209.

Kucherlapati R.S., et al., "Homologous Recombination Between Plasmids in Mammalian Cells can be Enhanced by Treatment of Input DNA," *Proceedings of the National Academy of Sciences of the U.S.A.*, 1984, vol. 81 (10), pp. 3153-3157.

Kuraoka M., et al., "AID Expression During B-Cell Development: Searching for Answers," *Immunologic Research*, 2011, vol. 49 (1-3), pp. 3-13.

Kuroiwa Y., et al., "Sequential Targeting of the Genes Encoding Immunoglobulin-µ and Prion Protein in Cattle," *Nature Genetics*, 2004, vol. 36 (7), pp. 775-780.

Kuzin I.I., et al, "Requirement for enhancer specificity in immunoglobulin heavy chain locus regulation," *Journal of Immunology*, Jun. 2008, vol. 180 (11), pp. 7443-7450.

Laffleur B., et al., "Production of Human or Humanized Antibodies in Mice," *Methods in Molecular Biology*, Chapter 9, 2012, vol. 901, pp. 149-159.

Largaespada D.A., "Transposon Mutagenesis in Mice," *Methods in Molecular Biology*, vol. 530, 2009, pp. 379-390.

Laventie B., et al., "Heavy Chain-Only Antibodies and Tetravalent Bispecific Antibody Neutralizing *Staphylococcus aureus* Leukotoxins," *Proceedings of the National Academy of Sciences of the U.S.A.*, 2011, vol. 108 (39), pp. 16404-16409.

Le Mouellic H., et al., "Pattern of Transcription of the Homeo Gene Hox-3.1 in the Mouse Embryo," *Genes & Development*, 1988, vol. 2 (1), pp. 125-135.

Lee E., et al., "Complete Humanization of the Mouse Immunoglobulin Loci Enables Efficient Therapeutic Antibody Discovery," *Nature Biotechnology*, 2014, vol. 32 (4), pp. 356-363.

Lee E., et al., "The Application of Transgenic Mice for Therapeutic Antibody Discovery," *Methods in Molecular Biology*, Chapter 8, 2012, vol. 901, pp. 137-148.

Lee H., et al., "Human C5aR Knock-in Mice Facilitate the Production and Assessment of Anti-Inflammatory Monoclonal Antibodies," *Nature Biotechnology*, 2006, vol. 24 (10), pp. 1279-1284.

Lefranc M., Appendix 1P, Abbreviations and Useful Data, "Nomenclature of the Human Immunoglobulin Genes," *Current Protocols in Immunology*, 2000, Supp. 40, pp. A.1P.1-A.1P.37.

Lefranc M.P., et al., "IGHJ group," The Immunoglobulin FactsBook, IMGT, the international ImMunoGeneTics database, May 2001, 4 pages (including cover sheet and copyright pages).

Lefranc M.P., et al., Excerpts from "The Immunoglobulin FactsBook," *IMGT*, the international ImMunoGeneTics database, May 2001, 455 pages.

Lefranc M.P., et al., "Immunoglobulin Lambda (IGL) Genes of Human and Mouse," *Molecular Biology of B Cells*, Chapter 4, p. 47, 2004 (Edtrs. Honjo et al.).

Lefranc M.P., "Nomenclature of the Human Immunoglobulin Heavy (IGH) Genes," *Experimental and Clinical Immunogenetics*, 2001, vol. 18 (2), pp. 100-116.

Lefranc M.P., "Nomenclature of the Human Immunoglobulin Kappa (IGK) Genes," *Experimental and Clinical Immunogenetics*, 2001, vol. 18 (3), pp. 161-174.

Lefranc M.P., "Nomenclature of the Human Immunoglobulin Lambda (IGL) Genes," *Experimental and Clinical Immunogenetics*, 2001, vol. 18 (4), pp. 242-254.

Levin A.M., et al., "Optimizing the affinity and specificity of proteins with molecular display," *Molecular Biosystems*, 2006, vol. 2, pp. 49-57.

Li H., et al., "Genetic Diversity of the Human Immunoglobulin Heavy Chain $V_H$ Region," *Immunological Reviews*, Dec. 2002, vol. 190, pp. 53-68.

Li L., et al., "Transgenic Mice with a Diverse Human T Cell Antigen Receptor Repertoire," *Nature Medicine*, 2010, vol. 16 (9), pp. 1029-1034.

Li M., Second Declaration of Dr. Meng (Amy) Li, dated Sep. 5, 2016, 2 pages.

Li M.A., et al., "Crafting Rat Genomes with Zinc Fingers," *Nature Biotechnology*, 2011, vol. 29 (1), pp. 39-41.

Li P., et al., "Germline Competent Embryonic Stem Cells Derived from Rat Blastocysts," *Cell*, 2008, vol. 135 (7), pp. 1299-1310.

Li X., et al., "The Minimum Internal and External Sequence Requirements for Transposition of the Eukaryotic Transformation Vector PiggyBac," *Molecular Genetics & Genomics*, 2001, vol. 266 (2), pp. 190-198.

Liang Q., et al., "Extensive genomic copy number variation in embryonic stem cells," *Proceedings of the National Academy of Sciences of the U.S.A.*, Nov. 2008, vol. 105 (45), pp. 17453-17456.

Liao J., et al., "Generation of Induced Pluripotent Stem Cell Lines from Adult Rat Cells," *Cell Stem Cell*, 2009, vol. 4 (1), pp. 11-15.

Little M., et al., "Generation of a Large Complex Antibody Library from Multiple Donors," *Journal of Immunological Methods*, 1999, vol. 231 (1-2), pp. 3-9.

Liu L., et al., "Potent and Broad Anti-HIV-1 Activity Exhibited by a Glycosyl-Phosphatidylinositol-Anchored Peptide derived from the CDR H3 of Broadly Neutralizing Antibody PG16," *Journal of Virology*, 2011, vol. 85 (17), pp. 8467-8476.

Lonberg N., "Human Antibodies from Transgenic Animals," *Nature Biotechnology*, 2005, vol. 23 (9), pp. 1117-1125.

(56) References Cited

OTHER PUBLICATIONS

Lonberg N., "Fully Human Antibodies from Transgenic Mouse and Phage Display Platforms," *Current Opinion in Immunology*, 2008, vol. 20 (4), pp. 450-459.

Loveslati B.Y., et al., "A Study of Gm Allotypes and Immunoglobulin Heavy Gamma IGHG Genes in Berbers, Arabs and Sub-Saharan Africans from Jerba Island, Tunisia," *European Journal of Immunogenetics*, 2001, vol. 28 (5), pp. 531-538.

Luby T.M., et al., "The μ Switch Region Tandem Repeats are Important, but not Required, for Antibody Class Switch Recombination," *The Journal of Experimental Medicine*, 2001, vol. 193 (2), pp. 159-168.

Luciw P.A., et al., "Location and Function of Retroviral and SV40 Sequences that Enhance Biochemical Transformation after Microinjection of DNA," *Cell*, 1983, vol. 33 (3), pp. 705-716.

Luo G., et al., "Chromosomal Transposition of a Tc1/Mariner-like Element in Mouse Embryonic Stem Cells," *Proceedings of the National Academy of Sciences of the U.S.A.*, 1998, vol. 95 (18), pp. 10769-10773.

Lyon C., Attorney for Applicant, Third-Party Pre-Issuance Submission Under 37 CFR Sec. 1.290 in U.S. Appl. No. 14/056,700, dated Nov. 28, 2014, 6 pages.

Lyon C., Attorney for Applicant, Third-Party Pre-Issuance Submission Under 37 CFR Sec. 1.290 in U.S. Appl. No. 14/056,707, dated Nov. 28, 2014, 10 pages.

Lyon C., Attorney for Applicant, Third-Party Pre-Issuance Submission Under 37 CFR Sec. 1.290 in U.S. Appl. No. 13/846,672, dated Mar. 17, 2015, 32 pages.

Lyon C., Attorney for Applicant, Third-Party Pre-Issuance Submission Under 37 CFR Sec. 1.290 in U.S. Appl. No. 13/875,892, dated May 5, 2015, 49 pages.

Lyon C., Attorney for Applicant, Third-Party Pre-Issuance Submission Under 37 CFR Sec. 1.290 in U.S. Appl. No. 13/886,511, dated May 5, 2015, 18 pages.

Lyon C., Attorney for Applicant, Third-Party Pre-Issuance Submission Under 37 CFR Sec. 1.290 in U.S. Appl. No. 14/040,405, dated Jan. 16, 2015, 18 pages.

Lyon C., Attorney for Applicant, Third-Party Pre-Issuance Submission Under 37 CFR Sec. 1.290 in U.S. Appl. No. 14/040,427, dated Jan. 16, 2015, 20 pages.

Lyon C., Attorney for Applicant, Third-Party Pre-Issuance Submission Under 37 CFR Sec. 1.290 in U.S. Appl. No. 14/056,434, dated Dec. 15, 2014, 6 pages.

Lyon C., Attorney for Applicant, Third-Party Pre-Issuance Submission Under 37 CFR Sec. 1.290 in U.S. Appl. No. 14/080,630, dated Oct. 31, 2014, 8 pages.

Lyon C., Attorney for Applicant, Third-Party Pre-Issuance Submission Under 37 CFR Sec. 1.290 in U.S. Appl. No. 14/137,902, dated Nov. 13, 2014, 9 pages.

Lyon C., Attorney for Applicant, Third-Party Pre-Issuance Submission Under 37 CFR Sec. 1.290 in U.S. Appl. No. 14/220,080, dated Jul. 28, 2015, 28 pages.

Lyon C., Attorney for Applicant, Third-Party Pre-Issuance Submission Under 37 CFR Sec. 1.290 in U.S. Appl. No. 14/220,095, dated Aug. 4, 2015, 19 pages.

Lyon C., Attorney for Applicant, Third-Party Pre-Issuance Submission Under 37 CFR Sec. 1.290 in U.S. Appl. No. 14/220,099, dated Apr. 29, 2015, 43 pages.

Lyon C., Attorney for Applicant, Third-Party Pre-Issuance Submission Under 37 CFR Sec. 1.290 in U.S. Appl. No. 14/226,706, dated Jul. 28, 2015, 53 pages.

Lyon C., Attorney for Applicant, Third-Party Pre-Issuance Submission Under 37 CFR Sec. 1.290 in U.S. Appl. No. 14/263,158, dated Apr. 29, 2015, 16 pages.

Lyon C., Attorney for Applicant, Third-Party Pre-Issuance Submission Under 37 CFR Sec. 1.290 in U.S. Appl. No. 14/263,176, dated Apr. 29, 2015, 16 pages.

Lyon C., Attorney for Applicant, Third-Party Pre-Issuance Submission Under 37 CFR Sec. 1.290 in U.S. Appl. No. 14/497,054, dated Oct. 21, 2015, 81 pages.

Lyon C., Attorney for Applicant, Third-Party Pre-Issuance Submission Under 37 CFR Sec. 1.290 in U.S. Appl. No. 14/498,685, dated Sep. 18, 2015, 37 pages.

Lyon C., Attorney for Applicant, Third-Party Pre-Issuance Submission Under 37 CFR Sec. 1.290 in U.S. Appl. No. 14/516,461, dated Aug. 4, 2015, 27 pages.

Lyon C., Attorney for Applicant, Third-Party Pre-Issuance Submission Under 37 CFR Sec. 1.290 in U.S. Appl. No. 14/543,359, dated Nov. 13, 2015, 36 pages.

Lyon C., Attorney for Applicant, Third-Party Pre-Issuance Submission Under 37 CFR Sec. 1.290 in U.S. Appl. No. 14/226,698, dated Jun. 3, 2015, 53 pages.

Ma B., et al., "Human Antibody Expression in Transgenic Rats: Comparison of Chimeric IgH Loci with Human $V_H$, D and $J_H$ but Bearing Different Rat C-Gene Regions," *Journal of Immunological Methods*, 2013, vols. 400-401, pp. 78-86.

MacDonald L., Curriculum Vitae of Lynn E. MacDonald, Ph.D., 3 pages.

MacDonald L., Declaration of Lynn E. MacDonald with Exhibits, dated Feb. 3, 2015, relating to International Application No. PCT/US02/04500 (Published as WO02/066630 A1), 13 pages.

Macdonald L., Declaration of Lynne E. Macdonald, dated Jun. 29, 2016, 4 pages.

MacDonald L., et al., Expanded Poster: "Velocigene® Technology Extended to Humanization of Several Megabases of Complex Gene Loci," Sep. 2006, 6 pages.

MacDonald L., et al., Poster (Exhibit IJR-47): "Velocigene® Technology Extended to Humanization of Several Megabases of Complex Gene Loci," and evidence of unavailability, Sep. 2006, 42 pages.

MacDonald L., et al., "Velocigene® Technology Extended to Humanization of Several Megabases of Complex Gene Loci," (Abstract-21) 1st International MUGEN Conference on Animal Models for Human Immunological Disease, Athens Greece, Sep. 10-13, 2006, 1 page.

MacDonald L.E., et al., "Precise and in Situ Genetic Humanization of 6 Mb of Mouse Immunoglobulin Genes," *Proceedings of the National Academy of Sciences of the U.S.A.*, 2014, vol. 111 (14), pp. 5147-5152.

Mack M., et al., "A Small Bispecific Antibody Construct Expressed as a Functional Single-Chain Molecule with High Tumor Cell Cytotoxicity," *Proceedings of the National Academy of Sciences of the U.S.A.*, 1995, vol. 92 (15), pp. 7021-7025.

Magadán S., et al., "Production of Antigen-Specific Human Monoclonal Antibodies: Comparison of Mice Carrying IgH/κ or IgH/κ/λ transloci," *Biotechniques*, 2002, vol. 33 (3), pp. 680, 682, 684 passim.

Maitta R.W., et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," *Infection and Immunity*, 2004, vol. 72 (1), pp. 196-208.

Makris J.C., et al., "Mutational Analysis of Insertion Sequence 50 (IS50) and Transposon 5 (Tn5) Ends," *Proceedings of the National Academy of Sciences of the U.S.A.*, 1988, vol. 85 (7), pp. 2224-2228.

Mallender W.D., et al., "Construction, Expression, and Activity of a Bivalent Bispecific Single-Chain Antibody," *The Journal of Biological Chemistry*, 1994, vol. 269 (1), pp. 199-206.

Manis J.P., et al., "Mechanism and Control of Class-Switch Recombination," *Trends in Immunology*, 2002, vol. 23 (1), pp. 31-39.

Marcello M.R., et al., "Lack of Tyrosylprotein Sulfotransferase-2 Activity Results in Altered Sperm-Egg Interactions and Loss of ADAM3 and ADAM6 in Epididymal Sperm," *The Journal of Biological Chemistry*, 2011, vol. 286 (15), pp. 13060-13070.

Marchalonis J.J., et al., "Emergence of the immunoglobulin family: conservation in protein sequence and plasticity in gene organization," *Glycobiology*, vol. 6, 1996, pp. 657-663.

Mårtensson I.L., et al., "Role of the Surrogate Light Chain and the Pre-B-Cell Receptor in Mouse B-Cell Development," *Immunology*, 2000, vol. 101 (4), pp. 435-441.

(56) References Cited

OTHER PUBLICATIONS

Martinez C., et al., "The Mouse (*Mus musculus*) Immunoglobulin Kappa Variable (IGKV) Genes and Joining (IGKJ) Segments," *Experimental and Clinical Immunogenetics*, Jul. 1998, vol. 15, pp. 184-193.
Martínez P., et al., "Antibody Synthesis in Vitro," Encyclopedia of Life Sciences, 2005, pp. 1-8.
Martinez-Jean C., et al., "Nomenclature and Overview of the Mouse (*Mus musculus* and *Mus* sp.) Immunoglobulin Kappa (IGK) Genes," *Experimental and Clinical Immunogenetics*, 2001, vol. 18 (4), pp. 255-279.
Matthews V.B., et al., "A Locus Affecting Immunoglobulin Isotype Selection (Igis1) Maps to the MHC Region in C57BL, BALB/c and NOD Mice," *Immunology and Cell Biology*, 2001, vol. 79 (6), pp. 576-582.
Mattila P.S., et al., "Extensive Allelic Sequence Variation in the J Region of the Human Immunoglobulin Heavy Chain Gene Locus," *European Journal of Immunology*, 1995, vol. 25 (9), pp. 2578-2582.
Maul R.W., et al., "AID and Somatic Hypermutation," *Advances in Immunology*, Chapter 6, 2010, vol. 105, pp. 159-191.
McCreath K.J., et al., "Production of Gene-Targeted Sheep by Nuclear Transfer from Cultured Somatic Cells," *Nature*, 2000, vol. 405 (6790), pp. 1066-1069.
McMurry M.T., et al., "Enhancer Control of Local Accessibility to V(D)J Recombinase," *Molecular and Cellular Biology*, Aug. 1997, vol. 17 (8), pp. 4553-4561.
Mejía J.E., et al., "The Assembly of Large BACs by in Vivo Recombination," *Genomics*, 2000, vol. 70 (2), pp. 165-170.
Mendez M.J., et al., "Functional Transplant of Megabase Human Immunoglobulin Loci Recapitulates Human Antibody Response in Mice," *Nature Genetics*, Feb. 1997, vol. 15 (2), pp. 146-156.
Mester G., European Patent Attorney, Grund Intellectual Property Group, Third-Party Observations according to Article 115 EPC regarding 12778780.2, dated Sep. 30, 2016, 5 pages.
MGI, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml].
Mills F., et al., "Enhancer Complexes Located Downstream of Both Human Immunoglobulin Cα Genes," *The Journal of Experimental Medicine*, Sep. 1997, vol. 186 (6), pp. 845-858.
Milner E.C., et al., "Polymorphism and Utilization of Human $V_H$ Genes," *Annals of the New York Academy of Sciences*, 1995, vol. 764, pp. 50-61.
Minaee S., et al., "Mapping and Functional Analysis of Regulatory Sequences in the Mouse λ5-VpreB1 Domain," *Molecular Immunology*, 2005, vol. 42 (11), pp. 1283-1292.
Mir K.U., "Sequencing Genomes: From Individuals to Populations," *Briefings in Functional Genomics & Proteomics*, 2009, vol. 8 (5), pp. 367-378.
Müller U., "Ten Years of Gene Targeting: Targeted Mouse Mutants, from Vector Design to Phenotype Analysis," *Mechanisms of Development*, 1999, vol. 82 (1-2), pp. 3-21.
Moffatt S., et al., "PEGylated J591 mAb loaded in PLGA-PEG-PLGA tri-block copolymer for targeted delivery: In vitro evaluation in human prostate cancer cells," *International Journal of Pharmaceutics*, 2006, vol. 317, pp. 10-13.
Monaco A.P., et al., "YACs, BACs, PACs and MACs: Artificial Chromosomes as Research Tools," *Trends in Biotechnology*, Jul. 1994, vol. 12 (7), pp. 280-286.
Moran N., et al., "Mouse Platforms Jostle for Slice of Humanized Antibody Market," *Nature Biotechnology*, Apr. 2013, vol. 31 (4), pp. 267-268.
Moreau P., et al., "The SV40 72 Base Repair Repeat has a Striking Effect on Gene Expression Both in SV40 and Other Chimeric Recombinants," *Nucleic Acids Research*, 1981, vol. 9 (22), pp. 6047-6068.
Moreno R.D., et al., "The Emerging Role of Matrix Metalloproteases of the ADAM Family in Male Germ Cell Apoptosis," *Spermatogenesis*, 2011, vol. 1 (3), pp. 195-208.
Mortuza F.Y., et al., "Immunoglobulin Heavy-Chain Gene Rearrangement in Adult Acute Lymphoblastic Leukemia Reveals Preferential Usage of $J_H$-Proximal Variable Gene Segments," *Blood*, 2001, vol. 97 (9), pp. 2716-2726.
Mullins L.J., et al., "Transgenesis in the Rat and Larger Mammals," Perspective Series: Molecular Medicine in Genetically Engineered Animals, *Journal of Clinical Investigation*, Apr. 1996, vol. 97 (7), pp. 1557-1560.
Muñoz M., et al., "Constraints to Progress in Embryonic Stem Cells from Domestic Species," *Stem Cell Review and Reports*, 2009, vol. 5, pp. 6-9.
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., dated Oct. 6, 2014, 62 pages.
Murphy A., "VelocImmune: Immunoglobulin Variable Region Humanized Mice," *Recombinant Antibodies for Immunotherapy*, 1st Edition, Chapter 8, 2009, pp. 100-108.
Murphy A.J., et al., "Mice with megabase humanization of their Immunoglobulin Genes Generate Antibodies as Efficiently as Normal Mice," *Proceedings of the National Academy of Sciences of the U.S.A.*, 2014, vol. 111 (14), pp. 5153-5158.
Murphy D., "BAC-based Modifications of the Mouse Genome: The Big and the Backward," The Advanced Course: Genetic Manipulation of ES Cells, dated Nov. 3, 2009, VP Target Discovery, Regeneron Pharmaceuticals, 58 pages.
Murphy K., et al., The Generation of Lymphocyte Antigen Receptors, excerpt from *Janeway's Immunobiology*, Seventh edition, Chapter 4, 2008, p. 158.
Muyrers J.P.P., et al., "Rapid Modification of Bacterial Artificial Chromosomes by ET-Recombination," *Nucleic Acids Research*, 1999, vol. 27 (6), pp. 1555-1557.
Nadel B., et al., "Sequence of the Spacer in the Recombination Signal Sequence Affects V(D)J Rearrangement Frequency and Correlates with Nonrandom Vκ Usage in Vivo," *The Journal of Experimental Medicine*, 1998, vol. 187 (9), pp. 1495-1503.
Nagle M., "Regeneron Helps Make Sanofi Velocimmune to its 'Weak' Pipeline," 2007, 2 pages.
Nandi A.K., et al., "Regulated Expression of Genes Inserted at the Human Chromosomal β-globin Locus by Homologous Recombination," *Proceedings of the National Academy of Sciences of the U.S.A.*, 1988, vol. 85 (11), pp. 3845-3849.
Narayanan K., et al., "Bacterial Artificial Chromosome Mutagenesis Using Recombineering, Article ID: 971296," Journal of Biomedicine and Biotechnology, 2010, vol. 2011, Article ID No. 971296, 10 pages.
Narayanan K., et al., "Efficient and Precise Engineering of a 200 kb β-Globin Human/Bacterial Artificial Chromosome in *E. coli* DH10B using an Inducible Homologous Recombination System," *Gene Therapy*, 1999, vol. 6 (3), pp. 442-447.
Nelson A.L., et al., "Development Trends for Human Monoclonal Antibody Therapeutics," *Nature Reviews Drug Discovery*, 2010, vol. 9 (10), pp. 767-774.
Neuberger M.S., et al., "Isotype Exclusion and Transgene Down-Regulation in Immunoglobulin-λ Transgenic Mice," *Nature*, Mar. 1989, vol. 338 (6213), pp. 350-352.
Neuberger M.S., et al., "Somatic Hypermutation," *Current Opinion in Immunology*, 1995, vol. 7 (2), pp. 248-254.
Neuberger M.S., "Expression and regulation of immunoglobulin heavy chain gene transfected into lymphoid cells," *The EMBO Journal*, 1983, vol. 2 (8), pp. 1373-1378.
New Zealand Patent Office, Simon Maguire, Authorized Officer, Further Examination Report for Patent No. 623756, dated Sep. 9, 2015, 3 pages.
Nicholson I.C., et al., "Antibody Repertoires of Four- and Five-Feature Translocus Mice Carrying Human Immunoglobulin Heavy Chain and κ and λ Light Chain Yeast Artificial Chromosomes," *Journal of Immunology*, 1999, vol. 163 (12), pp. 6898-6906.

(56) References Cited

OTHER PUBLICATIONS

Niemann H., et al., "Transgenic Farm Animals: Present and Future," *Revue scientifique et technique (International Office of Epizootics)*, 2005, vol. 24 (1), pp. 285-298.
Nucleotide Sequence RID Y55HBK1W114, accessed Aug. 6, 2014, 2 pages.
Oancea A.E., et al., "Expression of the (recombinant) Endogenous Immunoglobulin Heavy-Chain Locus Requires the Intronic Matrix Attachment Regions," *Molecular and Cellular Biology*, 1997, vol. 17 (5), pp. 2658-2668.
Oberdoerffer P., et al., "Unidirectional Cre-Mediated Genetic Inversion in Mice using the Mutant loxP Pair lox66/lox71," *Nucleic Acids Research*, 2003, vol. 31 (22), pp. e140-1-e140-7.
Ohlin M., et al., "The Human Antibody Repertoire to Infectious Agents: Implications for Disease Pathogenesis," Molecular Immunology, 2003, vol. 40 (1), pp. 1-11.
Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," *Immunogenetics*, 2005, vol. 57 (9), pp. 621-627.
Osborn M.J., et al., "High-Affinity IgG Antibodies Develop Naturally in Ig-Knockout Rats Carrying Germline Human IgH/Igκ/Igλ Loci Bearing the Rat $C_H$ Region," *Journal of Immunology*, 2013, vol. 190 (4), pp. 1481-1490.
Osoegawa K., et al., "Bacterial Artificial Chromosome Libraries for Mouse Sequencing and Functional Analysis," *Genome Research*, 2000, vol. 10 (1), pp. 116-128.
Oumard A. et al., "Recommended method for chromosome exploitation: RMCE-based cassette-exchange systems in animal cell biotechnology," *Cytotechnology*, 2006, vol. 50, pp. 93-108.
Parng C.L., et al., "Gene Conversion Contributes to Ig Light Chain Diversity in Cattle," *Journal of Immunology*, 1996, vol. 157 (12), pp. 5478-5486.
Pavlicek A., et al., "Ancient Transposable Elements, Processed Pseudogenes, and Endogenous Retroviruses," *Genomic Disorders*, Chapter 4, 2006, pp. 57-72.
Pear W.S., et al., "Localization of the Rat Immunoglobulin Heavy Chain Locus to Chromosome 6," *Immunogenetics*, 1986, vol. 23 (6), pp. 393-395.
Pelham H., et al., "Expression of a *Drosophila* Heat Shock Protein in Mammalian Cells: Transient Association with Nucleoli After Heat Shock," *Philosophical Transactions of the Royal Society B: Biological Sciences*, 1984, vol. 307 (1132), pp. 301-307.
Pera, M.F., et al., "Human embryonic stem cells," *Journal of Cell Science*, 2000, vol. 113, pp. 5-10.
Pérez-Luz S. et al., "Factor VIII mRNA expression from a BAC carrying the intact locus made by homologous recombination," *Genomics*, 2007, vol. 90, pp. 610-619.
Perlot T., et al., "Antisense Transcripts from Immunoglobulin Heavy-Chain Locus V(D)J and Switch Regions," *Proceedings of the National Academy of Sciences of the U.S.A.*, 2008, vol. 105 (10), pp. 3843-3848.
Perlot T., et al., "Cis-Regulatory Elements and Epigenetic Changes control genomic rearrangements of the IgH locus," *Advances in Immunology*, Chapter 1, 2008, vol. 99, pp. 1-32.
Pettersson S., et al., "A second B cell-specific enhancer 3' of the immunoglobulin heavy-chain locus," *Nature*, Mar. 1990, vol. 344, pp. 165-168.
Pettitt S.J., et al., "Agouti C57BL/6N Embryonic Stem Cells for Mmouse Genetic Resources," *Nature Methods*, 2009, vol. 6 (7), pp. 493-495.
Plasterk R.H., et al., "Resident Aliens: the Tc1/Mariner Superfamily of Transposable Elements," *Trends Genetics*, 1999, vol. 15(8), pp. 326-332.
Pobursky K., Third-Party Pre-Issuance Submission Under 37 CFR 1.290 in U.S. Appl. No. 13/843,528, dated Mar. 18, 2014, 14 pages.
Pobursky K., Third-Party Pre-Issuance Submission Under 37 CFR 1.290 in U.S. Appl. No. 13/433,084, dated Apr. 1, 2014, 15 pages.
Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 CFR 1.290 in U.S. Appl. No. 13/740,727, dated May 27, 2014, 25 pages.
Ponsel D., et al., "High Affinity, Developability and Functional Size: the Holy Grail of Combinatorial Antibody by Library Generation," *Molecules*, 2011, vol. 16 (5), pp. 3675-3700.
Popov A.V., et al., "A Human Immunoglobulin λ Locus is Similarly Well Expressed in Mice and Humans," *The Journal of Experimental Medicine*, 1999, vol. 189 (10), pp. 1611-1620.
Pramanik S., et al., "Segmental Duplication as One of the Driving Forces Underlying the Diversity of the Human Immunoglobulin Heavy Chain Variable Gene Region," *BMC Genomics*, Jan. 2011, vol. 12 (1), p. 78.
Presta L., "Molecular engineering and design of therapeutic antibodies," *Current Opinion in Immunology*, 2008, vol. 20, pp. 460-470.
Primakoff P., et al., "Penetration, Adhesion, and Fusion in Mammalian Sperm-Egg Interaction," *Science*, 2002, vol. 296 (5576), pp. 2183-2185.
Primakoff P., et al., "The ADAM Gene Family: Surface Proteins with Adhesion and Protease Activity," *Trends Genetics*, 2000, vol. 16 (2), pp. 83-87.
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Prosser H.M., et al., "A Resource of Vectors and ES Cells for Targeted Deletion of MicroRNAs in Mice," *Nature Biotechnology*, 2011, vol. 29 (9), pp. 840-845.
Prosser H.M., et al., "Mosaic Complementation Demonstrates a Regulatory Role for Myosin VIIa in Actin Dynamics of Stereocilia," *Molecular and Cellular Biology*, 2008, vol. 28 (5), pp. 1702-1712.
Pruzina S., et al., "Human Monoclonal Antibodies to HIV-1 gp140 from Mice Bearing YAC-Based Human Immunoglobulin Transloci," *Protein Engineering, Design & Selection*, 2011, vol. 24 (10), pp. 791-799.
Puente X.S., et al., "Comparative Genomic Analysis of Human and Chimpanzee Proteases," *Genomics*, 2005, vol. 86 (6), pp. 638-647.
Qi N.R., et al., "A New Transgenic Rat Model of Hepatic Steatosis and the Metabolic Syndrome," *Hypertension*, 2005, vol. 45 (5), pp. 1004-1011.
Qu S., et al., "Gene Targeting of ErbB3 Using a Cre-Mediated Unidirectional DNA Inversion Strategy," *Genesis*, 2006, vol. 44 (10), pp. 477-486.
Ramírez-Solis R., et al., "Chromosome Engineering in Mice," *Nature*, 1995, vol. 378 (6558), pp. 720-724.
Ramsden D.A., et al., "Conservation of Sequence in Recombination Signal Sequence Spacers," *Nucleic Acids Research*, 1994, vol. 22 (10), pp. 1785-1796.
Ray P., et al., "Ectopic Expression of a c-kit$^{VT42}$ Minigene in Transgenic Mice: Recapitulation of W Phenotypes and Evidence for c-kit Function in Melanoblast Progenitors," *Genes & Development*, 1991, vol. 5 (12A), pp. 2265-2273.
Raynard S.J., et al., "Cis-Acting Regulatory Sequences Promote High-Frequency Gene Conversion between Repeated Sequences in Mammalian Ccells," *Nucleic Acids Research*, 2004, vol. 32 (19), pp. 5916-5927.
Reddy S.T., et al., "Monoclonal Antibiotics Isolated without Screening by Analysing the Variable-Gene Repertoire of Plasma Cells," *Nature Biotechnology*, 2010, vol. 28 (9), pp. 965-971.
Regeneron. Pharmaceuticals, Inc., et al., "Big Pharma Vies for Mice," *Nature Biotechnology*, 2007, vol. 25 (6), pp. 613.
Regeneron Pharmaceuticals, Inc., Press Release—"Astellas Licenses Regeneron's VelocImmune® Technology for Discovering Human Monoclonal Antibodies," dated Mar. 30, 2007, 2 pages.
Regeneron Pharmaceuticals, Inc., Press Release—"AstraZeneca Licenses Regeneron's VelocImmune® Technology for Discovering Human Monoclonal Antibodies—AstraZeneca Is First Licensee of Novel VelocImmune Technology License Fees Total up to $120 Million Over Six Years," dated Feb. 5, 2007, 2 pages.

(56) References Cited

OTHER PUBLICATIONS

Regeneron Pharmaceuticals, Inc., Press Release—"Regeneron Initiates Major Global Collaboration with Sanofi-aventis of Develop and Commercialize Fully-Human Therapeutic Antibodies," dated Nov. 29, 2007, 2 pages.

Ren S.Y., et al., "Targeted Insertion Results in a Rhombomere 2-Specific Hoxa2 Knockdown and Ectopic Activation of Hoxa1 Expression," *Developmental Dynamics*, 2002, vol. 225 (3), pp. 305-315.

Renaut L., et al., "Affinity Maturation of Antibodies: Optimized Methods to Generate High-Quality ScFv Libraries and Isolate IgG Candidates by High-Throughput Screening," *Antibody Engineering: Methods and Protocols*, Second Edition, Chapter 26, 2012, vol. 907, pp. 451-461.

Retter I., et al., "Sequence and Characterization of the Ig Heavy Chain Constant and Partial Variable Region of the Mouse Strain 129S1," *The Journal of Immunology*, 2007, vol. 179 (4), pp. 2419-2427.

Ricker M., European Patent Attorney, Opposition against EP2421357B1 in the name of Kymab Limited Statement of Facts and Arguments pertaining to Application No. 10734546.4, dated Oct. 23, 2013, 29 pages.

Ristevski S., "Making Better Transgenic Models: Conditional, Temporal, and Spatial Approaches," *Molecular Biotechnology*, 2005, vol. 29 (2), pp. 153-163.

Rivera J., et al., "Genetic Background and the Dilemma of Translating Mouse Studies to Humans," *Immunity*, 2008, vol. 28 (1), pp. 1-4.

Rock E.P., et al., "CDR3 Lenth in Antigen-specific Immune Receptors", Jan. 1994, vol. 179, pp. 323-328.

Rodríguez C.I., et al., "High-Efficiency Deleter Mice Show that FLPe is an Alternative to Cre-loxP," *Nature Genetics*, 2000, vol. 25 (2), pp. 139-140.

Rogozin I.B., et al., "Cutting edge: DGYW/WRCH is a Better Predictor of Mmutability at G:C bases in Lg Hypermutation than the Widely Accepted RGYW/WRCY Motif and Probably Reflects a Two-Step Activation-Induced Cytidine Deaminase-Triggered Process," *The Journal of Immunology*, 2004, vol. 172 (6), pp. 3382-3384.

Rosner K., et al., "Third Complementarity-Determining Region of Mutated $V_H$ Immunoglobulin Genes Contains Shorter V, D, J, P, and N Components than Non-Mutated Genes," *Immunology*, 2001, vol. 103 (2), pp. 179-187.

Rourke J., Declaration of Jeffrey Rourke, Registered Patent Attorney for Regeneron Pharmaceuticals, Inc.—In the matter of Patent Acceptance 2011266843 in the Name of Kymab Limited and in the Matter of Opposition thereto by Regeneron Pharmaceuticals, Inc., dated Jan. 29, 2016, 5 pages.

Rusk N., "Making Mice at High Speed," *Nature Methods*, Mar. 2007, vol. 4 (3), pp. 196-197.

Sabbattini P., et al., "Analysis of Mice with Single and Multiple Copies of Transgenes Reveals a Novel Arrangement for the $\lambda 5\text{-}V_{preB1}$ Locus Control Region," *Molecular and Cellular Biology*, Jan. 1999, vol. 19 (1), pp. 671-679.

Sakai E., et al., "Recombination and Transcription of the Endogenous Ig Heavy Chain Locus is Effected by the Ig Heavy Chain Intronic Enhancer Core Region in the Absence of the Matrix Attachment Regions," *Proceedings of the National Academy of Sciences of the U.S.A.*, 1999, vol. 96 (4), pp. 1526-1531.

Sarkar A., et al., "Molecular Evolutionary Analysis of the Widespread PiggyBac Transposon Family and Related "Domesticated" Sequences," *Molecular Genetics & Genomics*, 2003, vol. 270 (2), pp. 173-180.

Sasso E.H., et al., "Ethnic Differences of Polymorphism of an Immunoglobulin $V_H3$ Gene," *Journal of Clinical Investigation*, 1995, vol. 96 (3), pp. 1591-1600.

Sasso E.H., et al., "Expression of the Immunoglobulin $V_H$ Gene 51p1 is Proportional to its Germline Gene Copy Number," *Journal of Clinical Investigation*, 1996, vol. 97 (9), pp. 2074-2080.

Sauer B., et al., "Cre-Stimulated Recombination at loxP-Containing DNA Sequences Placed into the Mammalian Genome," *Nucleic Acids Research*, 1989, vol. 17 (1), pp. 147-161.

Sauer B., et al., "Site-Specific DNA Recombination in Mammalian Cells by the Cre Recombinase of Bacteriophage P1," *Proceedings of the National Academy of Sciences of the U.S.A.*, 1988, vol. 85 (14), pp. 5166-5170.

Sauer B., "Functional Expression of the cre-lox Site-Specific Recombination System in the Yeast *Saccharomyces cerevisiae*," *Molecular and Cellular Biology*, 1987, vol. 7 (6), pp. 2087-2096.

Scapini P., et al., "Myeloid Cells, BAFF, and IFN-γ Establish an Inflammatory Loop that Exacerbates Autoimmunity in Lyn-Deficient Mice," *The Journal of Experimental Medicine*, Jul. 2010, vol. 207 (8), pp. 1757-1773.

Schlake T., et al., "Use of Mutated FLP Recognition Target (FRT) Sites for the Exchange of Expression Cassettes at Defined Chromosomal Loci," *Biochemistry*, 1994, vol. 33 (43), pp. 12746-12751.

Schnütgen F., et al., "A Directional Strategy for Monitoring Cre-Mediated Recombination at the Cellular Level in the Mouse," *Nature Biotechnology*, 2003, vol. 21 (5), pp. 562-565.

Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.

Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.

Schonewald, S.L., Attorney for Applicant, Third-Party Pre-Issuance Submission Under 37 CFR Sec. 1.290 in U.S. Appl. No. 14/818,162, dated May 24, 2016, 47 pages.

Schonewald, S.L., Attorney for Applicant, Third-Party Pre-Issuance Submission Under 37 CFR Sec. 1.290 in U.S. Appl. No. 14/935,010, dated Aug. 19, 2016, 27 pages.

Schroeder Jr. H.W., et al., "Preferential Utilization of Conserved Immunoglobulin Heavy Chain Variable Gene Segments During Human Fetal Life," *Proceedings of the National Academy of Sciences of the U.S.A.*, 1990, vol. 87 (16), pp. 6146-6150.

Schroeder, Jr. H.W., "Similarity and divergence in the development and expression of the mouse and human antibody repertoires," *Developmental and Comparative Immunology*, vol. 30, 2006, pp. 119-135.

Schröck E., et al., "Comparative Genomic Hybridization (CGH)—Detection of Unbalanced Genetic Aberrations Using Conventional and Micro-Array Techniques," *Current Protocols in Cytometry*, Chapter 8, 2001, Unit 8.12.1, Supplement 18, 30 pages.

Schweinfest C.W., et al., "A Heat-Shock-Inducible Eukaryotic Expression Vector," *Gene*, 1988, vol. 71 (1), pp. 207-210.

Scott C.T., "Mice with a Human Touch," *Nature Biotechnology*, 2007, vol. 25 (10), pp. 1075-1077.

Seals D.F., et al., "The ADAMs Family of Metalloproteases: Multidomain Proteins with Multiple Functions," *Genes & Development*, 2003, vol. 17 (1), pp. 7-30.

Seed B., "Purification of Genomic Sequences from Bacteriophage Libraries by Recombination and Selection in Vivo," *Nucleic Acids Research*, 1983, vol. 11 (8), pp. 2427-2445.

Seidl K.J., et al., "An Expressed $neo^r$ Cassette Provides Required Functions of the $1_\gamma 2b$ Exon for Class Switching," *International Immunology*, 1998, vol. 10 (11), pp. 1683-1692.

Seidl K.J., et al., "Position-Dependent Inhibition of Class-Switch Recombination by PGK-$neo^r$ Cassettes Inserted into the Immunoglobulin Heavy Chain Constant Region Locus," *Proceedings of the National Academy of Sciences of the U.S.A.*, Mar. 1999, vol. 96 (6), pp. 3000-3005.

Sekiguchi J., et al., "The Mechanism of V(D)J Recombination," *Molecular Biology of B Cells*, Chapter 5, 2004, pp. 61-82.

Sen R., et al., "Multiple Nuclear Factors Interact with the Immunoglobulin Enhancer Sequences," *Cell*, 1986, vol. 46 (5), pp. 705-716.

Seong E., et al., "To Knockout in 129 or in C57BL/6: That is the Question," *Trends in Genetics*, 2004, vol. 20 (2), pp. 59-62.

Sequence Listing to WO2008054606A2, 163 pages.

(56) References Cited

OTHER PUBLICATIONS

Serwe M., et al., "V(D)J Recombination in B Cells is Impaired but not Blocked by Targeted Deletion of the Immunoglobulin Heavy Chain Intron Enhancer," *The EMBO Journal*, 1993, vol. 12 (6), pp. 2321-2327.
Sharon J., et al., "Expression of a VHC Kappa Chimaeric Protein in Mouse Myeloma Cells," *Nature*, 1984, vol. 309 (5966), pp. 364-367.
Shaul Y., et al., "Homologous Recombination Between a Defective Virus and a Chromosomal Sequence in Mammalian Cells," *Proceedings of the National Academy of Sciences of the U.S.A.*, 1985, vol. 82 (11), pp. 3781-3784.
Shi B., et al., "Comparative Analysis of Human and Mouse Immunoglobulin Variable Heavy Regions from IMGT/LIGM-DB with IMGT/HighV-QUEST," *Theoretical Biology and Medical Modelling*, 2014, vol. 11, pp. 1-11.
Shi Y.P., et al., "The Mapping of Transgenes by Fluorescence in Situ Hybridization on G-Banded Mouse Chromosomes," *Mammalian Genome*, 1994, vol. 5 (6), pp. 337-341.
Shih H.H., "Discovery Process for Antibody-Based Therapeutics," *Development of Antibody-Based Therapeutics*, Chapter 2, 2012, pp. 9-32.
Shimizu A., et al., "Immunoglobulin Double-Isotype Expression by Trans-mRNA in a Human Immunoglobulin Transgenic Mouse," *Proceedings of the National Academy of Sciences of the U.S.A.*, 1989, vol. 86 (20), pp. 8020-8023.
Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Shultz L.D., et al., "Humanized Mice in Translational Biomedical Research," *Nature Reviews / Immunology*, 2007, vol. 7 (2), pp. 118-130.
Sigmund C.D., "Viewpoint: Are Studies in Genetically Altered Mice Out of Control?," *Arteriosclerosis, Thrombosis, and Vascular Biology*, Jun. 2000, vol. 20 (6), pp. 1425-1429.
Simpson E.M., et al., "Genetic Variation Among 129 Substrains and its Importance for Targeted Mutagenesis in Mice," *Nature Genetics*, 1997, vol. 16 (1), pp. 19-27.
Sirac C., et al., "Role of the Monoclonal κ Chain V Domain and Reversibility of Renal Damage in a Transgenic Model of Acquired Fanconi Syndrome," *Blood*, 2006, vol. 108 (2), pp. 536-543.
Skarnes W.C., et al., "A Conditional Knockout Resource for the Genome-Wide Study of Mouse Gene Function," *Nature*, 2011, vol. 474 (7351), pp. 337-342.
Skoultchi A.I., et al., "Expression of Genes Inserted at the Human β-Globin Locus by Homologous Recombination," *Progress in Clinical and Biological Research*, 1987, vol. 251, pp. 581-594.
Smith K.R., "Gene Transfer in Higher Animals: Theoretical Considerations and Key Concepts," *Journal of Biotechnology*, 2002, vol. 99 (1), pp. 1-22.
Smithies O., "Direct Alteration of a Gene in the Human Genome," *Journal of Inherited Metabolic Disease*, 1986, vol. 9 (Suppl. 1), pp. 92-97.
Smithies O., et al., "Insertion of DNA Sequences into the Human Chromosomal β-Globin Locus by Homologous Recombination," *Nature*, 1985, vol. 317 (6034), pp. 230-234.
Sohn J., et al., "Somatic Hypermutation of an Immunoglobulin μ Heavy Chain Transgene," *The Journal of Experimental Medicine*, 1993, vol. 177 (2), pp. 493-504.
Song K., et al., "Accurate Modification of a Chromosomal Plasmid by Homologous Recombination in Human Cells," *Proceedings of the National Academy of Sciences of the U.S.A.*, 1987, vol. 84 (19), pp. 6820-6824.
Sonoda E., et al., "B Cell Development Under the Condition of Allelic Inclusion," *Immunity*, 1997, vol. 6 (3), pp. 225-233.
Sopher B., et al., "Efficient recombination-based methods for bacterial artificial chromosome fusion and mutagenesis," *Gene*, 2006, vol. 371, pp. 136-143.
Sorrell D.A., et al., "Targeted modification of mammalian genomes," *Biotechnology Advances*, vol. 23, 2005, pp. 431-469.
Soukharev S., et al., "Segmental Genomic Replacement in Embryonic Stem Cells by Double Lox Targeting," *Nucleic Acids Research*, 1999, vol. 27 (18), pp. e21.
Spanopoulou E., et al., "Functional Immunoglobulin Transgenes Guide Ordered B-Cell Differentiation in Rag-1-Deficient Mice," *Genes & Development*, 1994, vol. 8 (9), pp. 1030-1042.
Stavnezer J., et al., "Mechanism and Regulation of Class Switch Recombination," *Annual Review of Immunology*, 2008, vol. 26, pp. 261-292.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Stephen R., Kymab Limited Statement of Facts and Evidence in opposition to EP2550363, Olswang LLP, dated Sep. 10, 2015, 22 pages.
Stephen R., Olswang, Response to Examination Report dated Jun. 6, 2016 for Application No. 14176740.0, as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.
Stevens S., et al., Expanded Poster: "VelocImmune$^{TM}$: Humanization of immunoglobulin loci using VelociGene® technology," Sep. 2006, 6 pages.
Stevens S., et al., Poster (Exhibit IJR-46): "VelocImmune$^{TM}$: Humanization of immunoglobulin loci using VelociGene® technology," and evidence of unavailability, Sep. 2006, 42 pages.
Stevens S. et al., "VelocImmune$^{TM}$: Humanization of immunoglobulin loci using VelociGene® technology," (Abstract-4) Presented at 1st International MUGEN Conference on Animal Models for Human Immunological Disease, Athens, Greece, Sep. 10-13, 2006, 1 page.
Stevens S., "Human Antibody Discovery, VelocImmune—A Novel Platform," *Pharma Focus Asia*, 2008, vol. 8, pp. 72-74.
Storb U., et al., "Physical Linkage of Mouse λ Genes by Pulsed-Field Gel Electrophoresis Suggests that the Rearrangement Process Favors Proximate Target Sequences," *Molecular and Cellular Biology*, 1989, vol. 9 (2), pp. 711-718.
Sun Y., et al., "Repertoire of Human Antibodies against the Polysaccharide Capsule of Streptococcus pneumoniae Serotype 6B," *Infection and Immunity*, Mar. 1999, vol. 67 (3), pp. 1172-1179.
Suárez E., et al., "Rearrangement of Only One Human IGHV Gene is Sufficient to Generate a Wide Repertoire of Antigen Specific Antibody Responses in Transgenic Mice," *Molecular Immunology*, 2006, vol. 43 (11), pp. 1827-1835.
Takeda S., et al., "Construction of Chimaeric Processed Immunoglobulin Genes Containing Mouse Variable and Human Constant Region Sequences," *Nature*, Apr. 1985, vol. 314 (6010), pp. 452-454.
Taki S., et al., "Targeted Insertion of a Variable Region Gene into the Immunoglobulin Heavy Chain Locus," *Science*, 1993, vol. 262 (5137), pp. 1268-1271.
Talbot P., et al., "Cell Adhesion and Fertilization: Steps in Oocyte Transport, Sperm-Zona Pellucida Interactions, and Sperm-Egg Fusion," *Biology of Reproduction*, 2003, vol. 68 (1), pp. 1-9.
Tan L.K., et al., "A Human-Mouse Chimeric Immunoglobulin Gene with a Human Variable Region is Expressed in Mouse Myeloma Cells," *Journal of Immunology*, Nov. 1985, vol. 135 (5), pp. 3564-3567.
Tanimoto Y., et al., "Embryonic Stem Cells Derived from C57BL/6J and C57BL/6N Mice," *Comparative Medicine*, Aug. 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," *International Immunology*, 1994, vol. 6 (4), pp. 579-591.
Te Riele H., et al., "Highly Efficient Gene Targeting in Embryonic Stem Cells through Homologous Recombination with Isogenic

(56) References Cited

OTHER PUBLICATIONS

DNA Constructs," *Proceedings of the National Academy of Sciences of the U.S.A.*, 1992, vol. 89 (11), pp. 5128-5132.
The Jackson Laboratory, "Breeding Strategies for Maintaining Colonies of Laboratory Mice," A *Jackson Laboratory Resource Manual*, 2007, pp. 1-29.
Thomas K.R., et al., "High Frequency Targeting of Genes to Specific Sites in the Mammalian Genome," *Cell*, 1986, vol. 44 (3), pp. 419-428.
Thomas K.R., et al., "Introduction of Homologous DNA Sequences into Mammalian Cells Induces Mutations in the Cognate Gene," *Nature*, 1986, vol. 324 (6092), pp. 34-38.
Thomas K.R., et al., "Site-Directed Mutagenesis by Gene Targeting in Mouse Embryo-Derived Stem Cells," *Cell*, 1987, vol. 51 (3), pp. 503-512.
Thykjaer T., et al., "Gene Targeting Approaches Using Positive-Negative Selection and Large Flanking Regions," *Plant Molecular Biology*, 1997, vol. 35 (4), pp. 523-530.
Tomizuka K., et al., "Double Trans-Chromosomic Mice: Maintenance of Two Individual Human Chromosome Fragments Containing Ig Heavy and κ Loci and Expression of Fully Human Antibodies," *Proceedings of the National Academy of Sciences of the U.S.A.*, Jan. 2000, vol. 97 (2), pp. 722-727.
Tonegawa S., "Somatic Generation of Antibody Diversity," *Nature*, Apr. 1983, vol. 302 (5909), pp. 575-581.
Tong C., et al., "Production of p53 gene knockout rats by homologous recombination in embryonic stem cells," *Nature*, Sep. 2010, vol. 467 (7312), pp. 211-213.
Torres R., et al., "Laboratory Protocols for Conditional Gene Targeting", *Institute for Genetics*, University of Cologne, 1997, pp. 37-40.
Tuaillon N., et al., "Human immunoglobulin heavy-chain minilocus recombination in transgenic mice: Gene-segment use in μ and γ transcripts," *Proceedings of the National Academy of Sciences of the U.S.A.*, Apr. 1993, vol. 90, pp. 3720-3724.
Tucker P.W., et al., "Mouse IgA Heavy Chain Gene Sequence: Implications for Evolution of Immunoglobulin Hinge Axons," *Proceedings of the National Academy of Sciences of the U.S.A.*, Dec. 1981, vol. 78 (12), pp. 7684-7688.
Ungrin M.D., et al., "Strict Control of Telomerase Activation Using Cre-Mediated Inversion," *BMC Biotechnology*, 2006, vol. 6, pp. 1-9, 2006.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected Search Report Under Section 17 for Application No. GB1122047.2, dated Apr. 20, 2012, 5 pages.
United Kingdom Intellectual Property Office, Search Report under Section 17 for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.
Valenzuela D.M., et al., "High-Throughput Engineering of the Mouse Genome Coupled with High-Resolution Expression Analysis," *Nature Biotechnology*, 2003, vol. 21 (6), pp. 652-659 and vol. 21 (7), p. 822.
Van Der Weyden L., et al., "Mouse Chromosome Engineering for Modeling Human Disease," *Europe PMC Funders Group*, Author Manuscript, Dec. 2008, 32 pages.
Van Dijk M., Declaration of Marcus Van Dijk with exhibits, Apr. 30, 2016, 139 pages.
Van Loo, P.F., et al., "Surrogate-Light-Chain Silencing Is Not Critical for the Limitation of Pre-B Cell Expansion but Is for the Termination of Constitutive Signaling," *Immunity*, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, Sep. 1983, vol. 26 (9), pp. 1085-1090.
Van Spriel A.B., et al., "Immunotherapeutic Perspective for Bispecific Antibodies," *Immunology Today*, 2000, vol. 21 (8), pp. 391-397.
Vasicek T.J., et al., "Structure and Expression of the Human Immunoglobulin λ Genes," *The Journal of Experimental Medicine*, 1990, vol. 172 (2), pp. 609-620.
Vassilieva S., et al., "Establishment of SSEA-1- and Oct-4-Expressing Rat Embryonic Stem-Like Cell Lines and Effects of Cytokines of the IL-6 Family on Clonal Growth," *Experimental Cell Research*, 2000, vol. 258 (2), pp. 361-373.
Venken K.J., et al., "P[acman]: a BAC Transgenic Platform for Targeted Insertion of Large DNA Fragments in *D. melanogaster*," *Science*, 2006, vol. 314 (5806), pp. 1747-1751.
Vieira P., et al., "The half-lives of serum immunoglobulins in adult mice," *European Journal of Immunology*, 1988, vol. 18, pp. 313-316.
Vollmer J., et al., "Antigen Contacts by Ni-Reactive TCR: Typical αβ Chain Cooperation Versus α Chain-Dominated Specificity," *International Immunology*, 2000, vol. 12 (12), pp. 1723-1731.
Vora K.A., et al., "Altering the Antibody Repertoire via Transgene Homologous Recombination: Evidence for Global and Clone-Autonomous Regulation of Antigen-Driven B Cell Differentiation," *The Journal of Experimental Medicine*, 1995, vol. 181 (1), pp. 271-281.
Wagner S.D., et al., "Antibodies Generated from Human Immunoglobulin Miniloci in Transgenic Mice," *Nucleic Acids Research*, 1994, vol. 22 (8), pp. 1389-1393.
Wallace H.A.C., et al., "Manipulating the Mouse Genome to Engineer Precise Functional Syntenic Replacements with Human Sequence," *Cell*, 2007, vol. 128 (1), pp. 197-209.
Wang M., et al., "AID Upmutants Isolated Using a High-Throughput Screen Highlight the Immunity/Cancer Balance Limiting DNA Deaminase Activity," *Nature Structural & Molecular Biology*, 2009, vol. 16 (7), pp. 769-776.
Wang M., et al., "Altering the Spectrum of Immunoglobulin V Gene Somatic Hypermutation by Modifying the Active Site of AID," *The Journal of Experimental Medicine*, 2010, vol. 207 (1), pp. 141-153.
Wang T.T., et al., "Catching a Moving Target," *Science*, 2011, vol. 333 (6044), pp. 834-835.
Wang W., et al., "Chromosomal Transposition of PiggyBac in Mouse Embryonic Stem Cells," *Proceedings of the National Academy of Sciences of the U.S.A.*, 2008, vol. 105 (27), pp. 9290-9295.
Wang X., et al., "Recombination, transcription, and diversity of a partially germline-joined VH in a mammal," *Immunogenetics*, 2012, vol. 64, pp. 713-717.
Wang Y., et al., "Many Human Immunoglobulin Heavy-Chain IGHV Gene Polymorphisms have been Reported in Error," *Immunology and Cell Biology*, 2008, vol. 86 (2), pp. 111-115.
Wasserman R., et al., "The Pattern of Joining ($J_H$) Gene Usage in the Human IgH Chain Is Established Predominantly at the B PreCursor Cell Stage," *The Journal of Immunology*, Jul. 1992, vol. 149 (2), pp. 511-516.
Waterhouse P., et al., "Combinatorial Infection and in Vivo Recombination: a Strategy for Making Large Phage Antibody Repertoires," *Nucleic Acids Research*, 1993, vol. 21 (9), pp. 2265-2266.
Waterston R.H., et al., "Initial Sequencing and Comparative Analysis of the Mouse Genome," *Nature*, Dec. 2002, vol. 420 (6915), pp. 520-562.
Webpage corroborating non-confidential nature of 2006 MUGEN Conference, Athens (www.mugen.noe.org), accessed Aug. 9, 2016, 4 pages.
Weichhold G.M., et al., "Megabase Inversions in the Human Genome as Physiological Events," *Nature*, Sep. 1990, vol. 347 (6288), pp. 90-92.

(56) References Cited

OTHER PUBLICATIONS

Weichhold G.M., et al., "The Human Immunoglobulin κ Locus Consists of Two Copies that are Organized in Opposite Polarity," *Genomics*, 1993, vol. 16 (2), pp. 503-511.
Weiner L.M., "Fully Human Therapeutic Monoclonal Antibodies," *Journal of Immunology*, Jan./Feb. 2006, vol. 29 (1), pp. 1-9.
White J.K., et al., "Genome-Wide Generation and Systematic Phenotyping of Knockout Mice Reveals New Roles for Many Genes," *Cell*, 2013, vol. 154 (2), pp. 452-464.
Wikipedia, "Monoclonal antibody," 2008, 8 pages.
Wikipedia, "Polyclonal antibodies," 2008, 5 pages.
Wilke K., et al., "Diagnosis of Haploidy and Triploidy Based on Measurement of Gene Copy Number By Real-Time PCR," *Human Mutation*, 2000, vol. 16 (5), pp. 431-436.
Wilkie T.M., et al., "Analysis of the Integrant in MyK-103 Transgenic Mice in which Males Fail to Transmit the Integrant," *Molecular and Cellular Biology*, 1987, vol. 7 (5), pp. 1646-1655.
Williams G.S., et al., "Unequal $V_H$ Gene Rearrangement Frequency within the Large $V_H$7183 Gene Family is not due to Recombination Signal Sequence Variation, and Mapping of the Genes Shows a Bias of Rearrangement Based on Chromosomal Location," *Journal of Immunology*, 2001, vol. 167 (1), pp. 257-263.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S-S Synapsis During Class Switch Recombination is Promoted by Distantly Located Transcriptional Elements and Activation-Induced Deaminase," *Immunity*, Nov. 2007, vol. 27 (5), pp. 711-722.
Xu L., et al., "Combinatorial Surrobody Libraries," *Proceedings of the National Academy of Sciences of the U.S.A.*, 2008, vol. 105 (31), pp. 10756-10761.
Xu Y., et al., "Deletion of the Igκ Light Chain Intronic Enhancer/Matrix Attachment Region Impairs but does not Abolish VκJκ Rearrangement," *Immunity*, Apr. 1996, vol. 4 (4), pp. 377-385.
Yamada M., et al., "Preferential Utilization of Specific Immunoglobulin Heavy Chain Diversity and Joining Segments in Adult Human Peripheral Blood B Lymphocytes," *Journal of Experimental Medicine*, Feb. 1991, vol. 173, pp. 395-407.
Yancopoulos G.D., et al., "Preferential Utilization of the Most $J_H$-Proximal $V_H$ Gene Segments in Pre-B-Cell Lines," *Nature*, 1984, vol. 311 (5988), pp. 727-733.
Yang X.W., et al., "Homologous Recombination Based Modification in *Escherichia coli* and Germline Transmission in Transgenic Mice of a Bacterial Artificial Chromosome," *Nature Biotechnology*, Sep. 1997, vol. 15 (9), pp. 859-865.
Yu C.C.K., et al., "Differential Usage of $V_H$ Gene Segments is Mediated by cis Elements," *Journal of Immunology*, 1998, vol. 161 (7), pp. 3444-3454.
Yu Y., et al., "Engineering Chromosomal Rearrangements in Mice," *Nature Reviews Genetics*, 2001, vol. 2 (10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, 2003, vol. 334 (4), pp. 733-749.
Zhang X., et al., "Combination of overlapping bacterial artificial chromosones by a two-step recombinogenic engineering method," *Nucleic Acids Research*, 2003, vol. 31 (15), pp. e81-1-e81-6.
Zhang Y., et al., "A New Logic for DNA Engineering Using Recombination in *Escherichia coli*," *Nature Genetics*, 1998, vol. 20 (2), pp. 123-128.
Zhao S., "A Comprehensive BAC Resource," *Nucleic Acids Research*, 2001, vol. 29 (1), pp. 141-143.
Zhao Y., et al., "Physical Mapping of the Bovine Immunoglobulin Heavy Chain Constant Region Gene Locus," *Journal of Biological Chemistry*, Sep. 2003, vol. 278 (37), pp. 35024-35032.
Zheng B., et al., "Engineering Mouse Chromosomes with Cre-loxP: Range, Efficiency, and Somatic Applications," *Molecular and Cellular Biology*, 2000, vol. 20 (2), pp. 648-655.
Zheng J., et al., "Immunoglobulin Gene Transcripts Have distinctive $V_HDJ_H$ Recombination Characteristics in Human Epithelial Cancer Cells", *Journal of Biological Chemistry*, Mar. 2009, vol. 284 (20), pp. 13610-13619.
Zou X., et al., "Removal of the BiP-Retention Domain in Cμ Permits Surface Deposition and Developmental Progression Without L-Chain," *Molecular Immunology*, 2008, vol. 45 (13), pp. 3573-3579.
Zou X., et al., "Subtle differences in antibody responses and hypermutation of lambda λ chains in mice with a disrupted x contant region," *European Journal of Immunology*, 1995, vol. 25, pp. 2154-2162.
Zou Y., et al., "Cre-loxP-Mediated Gene Replacement: a Mouse Strain Producing Humanized Antibodies," *Current Biology*, 1994, vol. 4 (12), pp. 1099-1103.
Shore, D.E., Attorney for Applicant, Third-Party Pre-Issuance Submission Under 37 CFR Sec. 1.290 in U.S. Appl. No. 15/199,375, filed May 31, 2017, 37 pages.
Collins A.M., et al., "The reported germline repertoire of human immunoglobulin kappa chain genes is relatively complete and accurate," *Immunogenetics*, 2008, vol. 60, pp. 669-676.
Grandea A.G., III., et al., "Human antibodies reveal a protective epitope that is highly conserved among human and nonhuman influenza A viruses," *Proceedings of the National Academy of Sciences of the U.S.A.*, Jul. 2010, vol. 107 (28), pp. 12658-12663.
Magdelaine-Beuzelin C., et al., "Structure-function relationships of the variable domains of monoclonal antibodies approved for cancer treatment," *Critical Reviews in Oncology Hematology*, 2007, vol. 64, pp. 210-225.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
U.S. Appl. No. 14/263,176, filed Apr. 28, 2014.
U.S. Appl. No. 14/497,054, filed Sep. 25, 2014.
U.S. Appl. No. 14/498,685, filed Sep. 26, 2014.
U.S. Appl. No. 14/516,461, filed Oct. 16, 2014.
U.S. Appl. No. 14/543,359, filed Nov. 17, 2014.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015, issued Nov. 29, 2016 as U.S. Pat. No. 9,504,236.
U.S. Appl. No. 15/016,211, filed Feb. 4, 2016.
U.S. Appl. No. 15/018,670, filed Feb. 8, 2016.
U.S. Appl. No. 15/095,315, filed Apr. 11, 2016.
U.S. Appl. No. 15/199,575, filed Jun. 30, 2016.
U.S. Appl. No. 15/214,963, filed Jul. 20, 2016.
U.S. Appl. No. 15/232,122, filed Aug. 9, 2016.
U.S. Appl. No. 15/251,969, filed Aug. 30, 2016.
U.S. Appl. No. 15/360,502, filed Nov. 23, 2016.
U.S. Appl. No. 15/369,595, filed Dec. 5, 2016.
U.S. Appl. No. 15/383,101, filed Dec. 19, 2016.
U.S. Appl. No. 15/383,188, filed Dec. 19, 2016.
U.S. Appl. No. 15/383,196, filed Dec. 19, 2016.
U.S. Appl. No. 15/383,202, filed Dec. 19, 2016.
U.S. Appl. No. 15/383,342, filed Dec. 19, 2016.
U.S. Appl. No. 15/383,353, filed Dec. 19, 2016.
U.S. Appl. No. 15/385,348, filed Dec. 20, 2016.
U.S. Appl. No. 15/385,372, filed Dec. 20, 2016.
U.S. Appl. No. 15/656,897, filed Jul. 21, 2017.
U.S. Appl. No. 15/690,183, filed Aug. 29, 2017.
U.S. Appl. No. 15/786,281, filed Oct. 17, 2017.
1st International MUGEN Conference on Animal Models for Human Immunological Disease, Sep. 10-13, 2006—Athens Greece (Scientific Programme & Presentations), 4 pages.
Bentham A., JA Kemp, Final Written Submissions for Application No. 12171793.8, dated May 17, 2018, 20 pages.
Brüggemann M., "The Preparation of Human Antibodies from Mice Harbouring Human Immunoglobulin Loci," *Transgenic Animals.*

(56) References Cited

OTHER PUBLICATIONS

*Generation and Use*, 1997, Chapter 58, Part IV, Section A, pp. 397-402 (including cover and copyright pages).

Calame K., et al., "Regulation of immunoglobulin gene transcription," *Immunoglobulin Genes*, 2nd edition, Chapter 18, 1995, pp. 397-422.

European Patent Office, Opposition against EP2798950 Animal Models and Therapeutic Molecules in the name of Kymab Limited pertaining to Application No. 14170196.1, dated Jan. 18, 2018, 33 pages.

European Patent Office, Examination Report for Application No. 16151215.7, dated Jan. 23, 2017, 5 pages.

European Patent Office, Extended European Search Report for Application No. 18153171.6, dated Jun. 28, 2018, 15 pages.

Evans M.J., Declaration of Martin J. Evans with appendices, dated Dec. 23, 2016, 99 pages.

Genbank, "*Homo sapiens* DNA, immunoglobulin heavy-chain variable region, complete sequence, 5 of 5," AB019441.1, dated Jun. 18, 2018, 36 pages.

Grund M., European Patent Attorney, Grund Intellectual Property Group, Third-Party Observations according to Article 115 EPC regarding 12171793.8, dated Oct. 10, 2013, 10 pages.

Grund M., European Patent Attorney, Grund Intellectual Property Group, Third-Party Observations according to Article 115 EPC regarding 12171793.8, dated Mar. 17, 2015, 4 pages.

Grund M., European Patent Attorney, Grund Intellectual Property Group, Third-Party Observations according to Article 115 EPC regarding 12171793.8, dated May 22, 2015, 5 pages.

Grund M., European Patent Attorney, Grund Intellectual Property Group, Third-Party Observations according to Article 115 EPC regarding 14781635.9, dated May 18, 2018, 4 pages.

Grund M., European Patent Attorney, Grund Intellectual Property Group, Third-Party Observations according to Article 115 EPC regarding 17174426.1, dated Jun. 27, 2018, 7 pages.

Janeway C.A. et al., "Structure of the Antibody Molecule and the Immunoglobulin Genes," excerpts from *Immunobiology: The Immune System in Health and Disease*, 4th Edition, 1999, 4 pages.

Li Z., et al., "The generation of antibody diversity through somatic hypermutation and class switch recombination," *Genes & Development*, vol. 18, pp. 1-11 (2004).

Lonberg N., et al., "Antigen-specific human antibodies from mice comprising four distinct genetic modifications," *Nature*, Apr. 1994, vol. 368, pp. 856-859.

Macdonald L., Declaration of Lynne E. Macdonald, dated May 16, 2018, including Annex 1, 10 pages.

Meier I.D., et al., "Short DNA sequences inserted for gene targeting can accidentally interfere with off-target gene expression," *The FASEB Journal*, Research Communication, Jun. 2010, vol. 24, pp. 1714-1724.

Missirlis P.I., et al., "A high-throughout screen identifying sequence and promiscuity characteristics of the loxP spacer region in Cre-mediated recombination," *BMC Genomics*, Apr. 2006, vol. 7(73), 13 pages.

Muramatsu M., et al., "Specific Expression of Activation-induced Cytidine Deaminase (AID), a Novel Member of the RNA-editing Deaminase Family in Germinal Center B Cells," 1999, *The Journal of Biological Chemistry*, vol. 274 (26), pp. 18470-18476.

Newcombe C., et al., "Antibody production: Polyclonal-derived biotherapeutics," *Journal of Chromatography B*, 2007 vol. 848, pp. 2-7.

Okada A., et al., "The variable region gene assembly mechanism," *Immunoglobulin Genes*, 2nd edition, Chapter 10, 1995, pp. 205-234.

Pinaud E., et al., "The IgH Locus 3' Regulatory Region: Pulling the Strings from Behind," *Advances in Immunology*, Chapter 2, 2011, vol. 11, pp. 27-70.

Shore D.E., Attorney for Applicant, Third-Party Pre-Issuance Submission Under 37 CFR Sec. 1.290 in U.S. Appl. No. 15/656,897, filed May 4, 2018, 55 pages.

Shore D.E., Attorney for Applicant, Third-Party Pre-Issuance Submission Under 37 CFR Sec. 1.290 in U.S. Appl. No. 15/690,183, filed Feb. 28, 2018, 60 pages.

Shore D.E., Attorney for Applicant, Third-Party Pre-Issuance Submission Under 37 CFR Sec. 1.290 in U.S. Appl. No. 15/786,281, filed Jun. 27, 2018 (First Submission), 63 pages.

Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.

Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.

Stephen R., Olswang LLP, Response to Third-Party Observations for Application No. 12171793.8, as filed with the European Patent Office on Apr. 17, 2015, 3 pages.

Stephen R., Olswang LLP, Response to Opposition (as filed by Regeneron Pharmaceuticals, Inc. on Jan. 11, 2017) for Application No. 12171793.8, as filed with the European Patent Office on Jun. 23, 2017, 8 pages.

Stephen R., Olswang LLP, Response to Summons and Preliminary Opinion pertaining to Patent No. EP2517557 for Application No. 12171793.8, as filed with the European Patent Office on May 17, 2018, 4 pages.

Stephen R., Olswang LLP, Response to Opposition in the name of Kymab Limited filed against EP2758535B1, dated Mar. 22, 2018, 26 pages.

Adekar S.P., et al., "A Natural Human IgM Antibody that Neutralizes Botulinum Neurotoxin in vivo," *Hybridoma*, 2008, vol. 27 (2), pp. 65-69.

Aizenshtein E., et al., "Immunological complex for enhancement of innate immune response in passive vaccination," *Vaccine*, Jan. 2013, vol. 31 (4), pp. 626-631 [abstract only—1 page].

Australian IP Office, Examination Report No. 1 for Standard Patent Application for Application No. 2016244295, dated Aug. 18, 2017, 4 pages.

Australian IP Office, Notification of material filed by a third-party for Application No. 2012311288 in the name of Kymab Ltd., Applicant, dated Nov. 20, 2017, 14 pages.

Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.

Bradley A., Declarations of Allan Bradley (Tanamachi/Grosveld), as submitted in U.S. Appl. No. 13/416,684, 5 pages.

Bradley A., Declaration of Allan Bradley (commercial success), with exhibits, as submitted in U.S. Appl. No. 13/416,684, dated Feb. 12, 2015, 15 pages.

Bradley A., Declaration of Allan Bradley (mouse strain), with exhibits, as submitted in U.S. Appl. No. 13/416,684, dated Feb. 12, 2015, 68 pages.

Bradshaw, et al., "*Handbook of Cell Signalling*," 2010, Chapter 5, p. 33 (excerpt).

Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.

Burton D.R., et al., "Antibody vs. HIB in a clash of evolutionary titans," *Proceedings of the National Academy of Sciences of the U.S.A*, Oct. 2005, vol. 102 (42), pp. 14943-14948.

Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].

Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.

Davis C.G., et al., "Production of Human Antibodies from Transgenic Mice," *Antibody Engineering, Methods and Protocols, Methods in Molecular Biology*, Chapter 10, 2004, pp. 191-200.

Delves P.J., et al., "Antibodies," Chapter 3, *Roitt's Essential Immunology*, Eleventh edition, 2006, pp. 37-60.

(56) References Cited

OTHER PUBLICATIONS

Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.

Dörner T., et al., "Analysis of the targeting of the hypermutational machinery and the impact of subsequent selection on the distribution of nucleotide changes in human $V_H DJ_H$ rearrangements," *Immunologic Reviews*, Apr. 1998, vol. 162 (1), pp. 161-171.

Dörner T., et al., "Somatic hypermutation of human immunoglobulin heavy chain genes: targeting of RGYW motifs on both DNA strands," *European Journal of Immunology*, 1998, vol. 28, pp. 3384-3396.

Dübel S., et al., "Therapeutic Antibodies—From Past to Future," in *Handbook of Therapeutic Antibodies—Technologies, Emerging Developments and Approved Therapeutics*, 2010, Chapter 1 (excerpt: pp. 3-5).

European Patent Office, Examination Report for Application No. 13723933.1, dated Jan. 17, 2018, 6 pages.

European Patent Office, Examination Report for Application No. 15188522.5, dated Aug. 11, 2017, 6 pages.

European Patent Office, Extended European Search Report for Application No. 17174426.1, dated Sep. 14, 2017, 10 pages.

European Patent Office, Extended European Search Report for Application No. 17196214.5, dated Jan. 2, 2018, 13 pages.

European Patent Office, Opposition against EP2604110 Animal Models and Therapeutic Molecules in the name of Kymab Limited pertaining to Application No. 12194777.0, dated Aug. 28, 2017, 73 pages.

European Patent Office, Opposition against EP2758535 Antibodies, Variable Domains and Chains Tailored for Human Use in the name of Kymab Limited pertaining to Application No. 12772122.3, dated Aug. 9, 2017, 75 pages.

Frigerio B., et al., "Antibody Engineering as Opportunity for Selection and Organization of Anti-HIV Therapeutic Agents," *The Open Autoimmunity Journal*, 2010, vol. 2, pp. 127-138.

Genbank, "*Homo sapiens* partial IGHJ6 gene for immunoglobulin heavy joining 6, exon 1, allele 4," AJ879487.1, dated Jul. 26, 2016, 1 page.

Giudicelli V., et al., "IMGT/GENE-DB: a comprehensive database for human and mouse immunoglobulin and T cell receptor genes," *Nucleic Acids Research*, 2005, vol. 33, pp. D256-D261.

He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.

HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.org/cgi-bin/genefamilies/set/349].

Hülseweh B., et al, "Human-like antibodies neutralizing Western equine encephalitis virus," *mAbs*, May/Jun. 2014, vol. 6 (3), pp. 718-727.

Imbimbo B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].

IMGT, the International ImMunoGeneTics Information system database, IMGT/GENE-DB entry for *Homo sapiens* IGHD3-9, 2007, 2 pages.

IMGT, the International ImMunoGeneTics Information system database, "Alignment of alleles: Human IGHJ6," dated Jun. 29, 2011, 1 page.

IMGT, the International ImMunoGeneTics Information system database, IMGT/GENE-DB entry for *Homo sapiens* IGHJ6, dated Jul. 26, 2017, version 3.1.17, 4 pages.

IMGT, the International ImMunoGeneTics Information system database, "IMGT/GENE-DB reference sequences," Nucleotide sequences of the four human IGHJ6 alleles, dated Jul. 26, 2017, version 3.1.17, 1 page.

IMGT, the International ImMunoGeneTics Information system database, "IMGT/GENE-DB reference sequences," Amino acid sequences of the four human IGHJ6 alleles, dated Jul. 26, 2017, version 3.1.17, 7 pages.

Jackson S.M., et al., "Human B Cell Subsets," *Advances in Immunology*, Chapter 5, 2008, vol. 98, pp. 151-224.

Kim S.J., et al., "Antibody Engineering for the Development of Therapeutic Antibodies," *Mol. Cells*, 2005, vol. 20 (1), pp. 17-29.

Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.

Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.

Lonberg N., et al., "Human Antibodies from Transgenic Mice," *Intern. Rev. Immunol.*, 1995, vol. 13, pp. 65-93.

Lonberg N., "Human Monoclonal Antibodies from Transgenic Mice," *Therapeutic Antibodies. Handbook of Experimental Pharmacology*, 2008, pp. 69-97.

Mårtensson I.L., et al., "The pre-B-cell receptor," *Current Opinion in Immunology*, 2007, vol. 19, pp. 137-142.

O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.

O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.

O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.

Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.

Prak E.T.L, et al., "B cell receptor editing in tolerance and autoimmunity," *Annals of the New York Academy of Sciences*, Jan. 2011, vol. 1217, pp. 96-121.

Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.

Ren L., et al., "Silencing of the immunoglobulin heavy chain locus by removal of all eight constant-region genes in a 200-kb region," *Genomics*, Aug. 2004, vol. 84, pp. 686-695.

Ricker M., European Patent Attorney, Opposition against EP2758535 in the name of Kymab Limited Statement of Facts and Arguments pertaining to Application No. 12772122.3, dated Aug. 9, 2017, 42 pages.

Rudolf M.P., et al., "Molecular basis for nonanaphylactogenicity of a monoclonal anti-IgE antibody," *Journal of Immunology*, Jul. 2010, vol. 165 (2), pp. 813-819.

Ruiz M., et al, "The Human Immunoglobulin Heavy Diversity (IGHD) and Joining (IGHJ) Segments," *Experimental and Clinical Immunogenetics*, 1999, vol. 16, pp. 173-184.

Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.

Siman-Tov D.D., et al., "Differentiation of a passive vaccine and the humoral immune response toward infection: Analysis of phage displayed peptides," *Vaccine*, Jan. 2006, vol. 24, pp. 607-612.

Taylor L.D., et al., "A transgenic mouse that expresses a diversity of human sequence heavy and light chain immunoglobulins," *Nucleic Acids Research*, 1992, vol. 20 (23), pp. 6287-6295.

Zwick M.B., et al., "The Long Third Complementarity-Determining Region of the Heavy Chain Is Important in the Activity of the Broadly Neutralizing Anti-Human Immunodeficiency Virus Type 1 Antibody 2F5," *Journal of Virology*, Mar. 2004, vol. 78 (6), pp. 3155-3161.

Stevens, S., et al. (Sep. 10-13, 2006). Velocimmune: Humanization of Immunoglobulin Loci Using Velocigene Technology.†

(56) References Cited

OTHER PUBLICATIONS

Macdonald, et al. (Sep. 10-13, 2006). Velocigene Technology Extended to Humanization of Several Megabases of Complex Gene Loci.†
Lefranc, Marie-Paule, and Gérard Lefranc. Immunoglobulin Facts Book. London: Academic Press, 2001. Print. (457 pp.; hereafter the Immunoglobulin Facts Book).†
U.S. Pat. No. 6,596,541 with Supporting Exhibits 1-3.†
Aguilera, et al., Characterization of immunoglobulin enhancer deletions in murine plasmacytomas. EMBO 4(13B): 3689-3693, 1985.†
Declaration of Dr. Allan Bradley, executed Feb. 12, 2015, as submitted in U.S. Appl. No. 13/416,684.†
Zemlin, et al., Expressed Murine and Human CDR-H3 Intervals of Equal Length Exhibit Distinct Repertoires that Differ in their Amino Acid Composition and Predicted Range of Structures. JMB 334:733-749, 2003.†

† cited by third party

ANIMAL MODELS AND THERAPEUTIC MOLECULES

CROSS REFERENCE

This application is a continuation of PCT/GB2014/052971, filed Oct. 1, 2014, which claims the benefit of FR1359518 filed Oct. 1, 2013 and of GB1317410.7 filed Oct. 1, 2013, the contents of each of which are incorporated by reference herein in their entirety.

BACKGROUND

The present invention relates inter alia to non-human animals and cells that are engineered to contain exogenous DNA, such as human immunoglobulin gene DNA, their use in medicine and the study of disease, methods for production of non-human animals and cells, and antibodies and antibody chains produced by such animals and derivatives thereof.

SUMMARY OF THE INVENTION

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see World Wide Web (www) genome.ucsc.edu and World Wide Web (www) genome.ucsc.edu/FAQ/FAQreleases.html) unless otherwise specified. Human nucleotides coordinates are those corresponding to GRCh37 (e.g. UCSC version hg 19, World Wide Web (www) genome.ucsc.edu/FAQ/FAQreleases.html), February 2009 ENSEMBL Release 55.37, or are those corresponding to NCBI36, Ensemble release 54 unless otherwise specified. Rat nucleotides are those corresponding to RGSC 3.4 December 2004 ENSEMBL release 55.34w, or Baylor College of Medicine HGSC v3.4 November 2004 (e.g., UCSC m4, see World Wide Web (www) genome.ucsc.edu and World Wide Web (www) genome.ucsc.edu/FAQ/FAQreleases.html) unless otherwise specified. Reference to work in mice herein is by way of example only, and reference to mice is taken to include reference to all non-human mammals unless otherwise apparent from the disclosure, with mice being preferred as the non-human mammal.

The disclosures of US2012/0204278 and PCT/GB2013/050682 are incorporated herein by reference. All definitions disclosed in US2012/0204278 and PCT/GB2013/050682 are specifically and explicitly disclosed herein.

Reference to human gene segments herein encompasses both the germline human gene segment sequence or the recombined form of the gene segment that can include one or more mutations relative to the germline human gene segment sequence, for example alleles disclosed in the IMGT database and 1000 Genomes database, as well as in WO2013041844 (such alleles and their sequences being explicitly incorporated herein by reference).

All gene segments referred to herein can be identified using standard sequence analysis by comparison to human germline gene segment sequences optionally by reference to the public sequence databases, such as the IMGT or 1000 Genomes database.

In one aspect the invention relates to a non-human vertebrate (e.g., a mouse or rat) or cell whose genome comprises human VH, D and JH gene segments upstream of a constant region at a heavy chain locus and/or human VL and JL gene segments upstream of a constant region at a light chain locus, wherein the gene segments are operably linked to the constant region thereof so that the vertebrate or cell is capable of expressing immunoglobulin heavy and/or light chains comprising human VH and VL domains respectively, wherein the heavy chain locus comprises a human 01 allele VH gene segment capable of recombining with a human D and JH gene segment to produce a VH domain, wherein the light chain locus comprises a human 01 allele VL gene segment capable of recombining with a human JL gene segment to produce a VL domain, or wherein the cell can develop into a vertebrate that expresses said heavy and/or light chains.

As explained further in the examples below, the inventors have surprisingly shown that human 01 alleles can be used to produce antigen-specific binding sites, wherein these are properly recombined in a non-human vertebrate, display junctional and somatic mutations and can be properly expressed and isolated.

In another aspect the invention relates to a non-human vertebrate or cell (eg, a mouse cell or rat cell) whose genome comprises (a) human JH2*01 and/or human JH6*01 or JH6*02 and/or JH3*02, one or more human VH gene segments and one or more human D gene segments upstream of a constant region at a heavy chain locus and/or (b) human Jκ2*01 and/or human Jκ4*01 and one or more human Vκ gene segments upstream of a constant region at a light chain locus, wherein the gene segments in each locus are operably linked to the constant region thereof so that the vertebrate or cell is capable of producing an antibody heavy chain and an antibody light chain, or where the cell can develop into a vertebrate that expresses an antibody heavy chain and an antibody light chain, wherein the heavy chain is produced by recombination of the human JH2*01 and/or JH6*01 or JH6*02 segment and/or JH3*02 with a D segment and a VH segment and the light chain is produced by recombination of the human Jκ2*01 and/or Jκ4*01 segment with a Vκ segment. In an example, the genome comprises human JH2*01. In an example, the genome comprises human JH2*01 and JH6*01. In an example, the genome comprises human JH2*01, JH6*01 and JH3*02. In an example, the genome comprises human JH6*01. In an example, the genome comprises human JH6*01 and JH3*02. In an example, the genome comprises human JH3*02. In an example, the heavy chain is produced by recombination of the human JH2*01 segment with a D segment and a VH segment. In an example, the heavy chain is produced by recombination of the human JH6*01 segment with a D segment and a VH segment. In an example, the heavy chain is produced by recombination of the human JH6*02 segment with a D segment and a VH segment. In an example, the heavy chain is produced by recombination of the human JH3*02 segment with a D segment and a VH segment.

In another aspect the invention relates to a non-human vertebrate whose genome comprises (i) human JH1*01, JH2*01, JH3*02, JH4*02, JH5*02 and/or JH6*01 or JH6*02, one or more human VH gene segments and one or more human D gene segments upstream of a constant region at a heavy chain locus and/or (ii) human Jκ1*01, Jκ2*01, Jκ3*01, Jκ4*01 and/or Jκ5*01 and one or more human Vκ gene segments upstream of a constant region at a light chain locus, wherein the gene segments in each locus are operably linked to the constant region thereof so that the vertebrate or cell is capable of producing an antibody heavy chain and an antibody light chain, or where the cell can develop into a vertebrate that expresses an antibody heavy chain and/or an antibody light chain, wherein the heavy chain is produced by recombination of the human JH1*01, JH2*01, JH3*02, JH4*02, JH5*02 and/or JH6*01 or JH6*02 segment with a D segment and a VH segment and the light chain is produced by recombination of the human Jκ1*01, Jκ2*01, Jκ3*01, Jκ4*01 and/or Jκ5*01 segment with a Vκ segment. In an example, the genome comprises human JH1*01, JH2*01, JH3*02, JH4*02, JH5*02 and JH6*01. In an example, the genome comprises human JH1*01, JH2*01, JH3*02, JH4*02, JH5*02 and JH6*02. In an example, the heavy chain is produced by recombination of the human JH2*01 segment with a D segment and a VH segment. In an example, the heavy chain is produced by recombination of the human JH6*01 segment with a D segment and a VH segment. In an example, the heavy chain is produced by recombination of the human JH6*02 segment with a D segment and a VH segment. In an example, the heavy chain is produced by recombination of the human JH3*02 segment with a D segment and a VH segment. Additionally or alternatively to these heavy chain examples, in an example the light chain is produced by recombination of the human Jκ2*01 segment with a Vκ segment.

In one embodiment, the non-human vertebrate further comprises one or more of the VH gene segments and/or one or more of the D gene segments from Table 7 and/or one or more Vκ gene segments from Table 12. In a further embodiment, the non-human vertebrate further comprises the VH gene segments and D gene segments from Table 3 and/or the Vκ gene segments from Table 10 or 11.

The segments described herein have been identified by the inventors as being widely and highly used across diverse human ethnic populations, and thus widely tolerated for antibody generation and efficacy in humans in general.

In a further embodiment, the invention relates to a non-human vertebrate or vertebrate cell (e.g. a mouse cell or rat cell) whose genome comprises one or more human VH gene segments, one or more human JH gene segments and one or more human D gene segments upstream of a constant region at a heavy chain locus and one or more human JL gene segments and one or more human VL gene segments upstream of a constant region at a light chain locus, wherein the gene segments in each locus are operably linked to the constant region thereof so that the vertebrate or cell is capable of producing an antibody heavy chain and an antibody light chain, or where the cell can develop into a vertebrate that expresses an antibody heavy chain and an antibody light chain, wherein said one or more human VH gene segments of the heavy chain locus comprise or consist of one, more or all human VH gene segments selected from the group consisting of VH3-23*04, VH7-4-1*01, VH4-4*02, VH1-3*01, VH3-13*01, VH3-7*01, VH3-20*d01 and VH3-9*01.

In a further embodiment, the invention relates to a non-human vertebrate or vertebrate cell (e.g. a mouse cell or rat cell) whose genome comprises one or more human VH gene segments, one or more human JH gene segments and one or more human D gene segments upstream of a constant region at a heavy chain locus and one or more human Jκ gene segments and one or more human Vκ gene segments upstream of a constant region at a light chain locus, wherein the gene segments in each locus are operably linked to the constant region thereof so that the veretebrate or cell is capable of producing an antibody heavy chain and an antibody light chain, or where the cell can develop into a vertebrate that expresses an antibody heavy chain and an antibody light chain, wherein said one or more human Vκ gene segments comprise or consist of one, more or all human Vκ gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1 D-16*01 and Vκ1-9*d01.

In another embodiment the invention relates to a non-human vertebrate or vertebrate cell (eg, a mouse cell or rat cell) whose genome comprises human JH2*01 and/or human JH6*02, one or more human VH gene segments and one or more human D gene segments upstream of a constant region at a heavy chain locus and/or human Jκ2*01 and/or human Jκ4*01 and one or more human Vκ gene segments upstream of a constant region at a light chain locus, wherein the gene segments in each locus are operably linked to the constant region thereof so that the cell or vertebrate is capable of producing an antibody heavy chain and an antibody light chain, or where the cell can develop into a vertebrate that expresses an antibody heavy chain and an antibody light chain, wherein the heavy chain is produced by recombination of the human JH2*01 and/or JH6*02 segment with a D segment and a VH segment and/or the light chain is produced by recombination of the human Jκ2*01 and/or Jκ4*01 segment with a Vκ segment;

wherein said one or more human VH gene segments of the heavy chain locus comprise or consist of one, more or all human VH gene segments selected from the group consisting of VH3-23*04, VH7-4-1*01, VH4-4*02, VH1-3*01, VH3-13*01, VH3-7*01 and VH3-20*d01 and/or wherein said one or more human Vκ gene segments comprise or consist of one, more or all human VH gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1D-16*01 and Vκ1-9*d01.

Optionally reference to a human gene segment herein is the recombined form of the gene segment.

As explained further in the examples below, the inventors have surprisingly shown that heavy and/or light chains produced according to the invention can be used to produce antigen-specific binding sites, wherein these are properly recombined in a non-human vertebrate, display junctional and somatic mutations and can be properly expressed and isolated.

In another aspect the invention relates to a non-human vertebrate (eg, a mouse or rat) or cell whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments are selected from one, more or all of the segments of Table 18 and have been provided by insertion into an endogenous light chain locus of the vertebrate or cell, wherein the vertebrate comprises immunoglobulin light chains comprising lambda variable regions (lambda light chains) or the cell can develop into a vertebrate that expresses said immunoglobulin light chains, wherein the lambda light chains comprise immunoglobulin light chains comprising lambda variable regions recombinants of one, more or all of the human Vλ and Jλ gene segments of Table 18.

Endogenous Light Chain Inactivation & High Expression of Human Lambda Variable Regions in Transgenic Non-Human Vertebrates & Cells As explained further in the examples below, the inventors have surprisingly observed very high expression levels of light chains comprising human lambda variable regions (at least 70 or 80% human V lambda) from transgenic light chain loci produced by targeted insertion of human lambda gene segments into endogenous non-human vertebrate light chain loci. This is possible even in the presence of endogenous non-human vertebrate V and J gene segments in the vertebrate genome. Also, the surprisingly high levels of expression are achieved when insertion of human lambda gene segments are in the endogenous kappa or lambda locus. Such high levels by targeted insertion has not hitherto been published in the art.

The inventors also surprisingly observed that endogenous kappa chain expression can be completely inactivated by targeted insertion of human lambda gene sequence into the endogenous kappa locus, as explained further in the examples.

The targeted insertion of human gene segments into endogenous Ig loci is advantageous because it enables the operable location of inserted human Ig sequences with respect to endogenous Ig constant regions and endogenous control regions, such as enhancers and other locus control regions for example. Thus, targeted insertion allows one to harness endogenous control important in one or more of Ig gene segment recombination, allelic exclusion, affinity maturation, class switching, levels of Ig expression and desirable development of the B-cell compartment. As such, targeted insertion is superior to early attempts in the art to produce transgenic Ig loci and expression, which attempts relied on the introduction into non-human vertebrate cells of vectors such as YACs bearing human Ig gene segments. YACs are randomly integrated into the vertebrate cell genome, so that it is difficult to achieve the control provided by targeted insertion and the concomitant benefits that are brought in terms of harnessing endogenous control mechanisms. In addition, random insertion often results in the inserted human Ig gene segments coming under the control of heterologous control elements and/or epigenetic chromosomal modifications such as methylation and chromatin confirmations, either of which can be detrimental to proper Ig gene segment recombination, allelic exclusion, affinity maturation, class switching, levels of Ig expression and desirable development of the B-cell compartment. Random insertion typically results in 2 or more copies of the introduced transgene which can cause chromosomal instability and therefore result in poor breeding performance of the animals in addition to detrimental effects on proper Ig gene segment recombination, allelic exclusion, affinity maturation, class switching, levels of Ig expression and desirable development of the B-cell compartment. Thus, prior art attempts using random insertion have tended to lead to poor B-cell development, relatively small B-cell compartments and inferior Ig expression and a concomitant difficulty in isolating an antibody with a desired characteristic.

The invention therefore provides the following aspects:

Expression of Human Lambda Variable Regions

Every embodiment of the invention disclosed herein can be put into practice with a specific lambda allele disclosed in Table 18, or any combination thereof. Where gene segments are referred to herein without reference to a specific allele, these can optionally be the specific alleles disclosed in any one of Tables 1 to 18.

1. A non-human vertebrate (eg, a mouse or rat) whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate, wherein the vertebrate expresses immunoglobulin light chains comprising lambda variable regions (lambda light chains), wherein the lambda light chains comprise immunoglobulin light chains comprising lambda variable regions derived from recombination of human Vλ and Jλ gene segments.

A non-human vertebrate (eg, a mouse or rat) whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate, wherein the vertebrate expresses immunoglobulin light chains comprising lambda variable regions (lambda light chains), and wherein at least 70 or 80% of the variable regions of the lambda light chains expressed by the vertebrate are derived from recombination of human Vλ and Jλ gene segments. This is demonstrated in the examples below.

For example, at least 70, 75, 80, 84, 85, 90, 95, 96, 97, 98 or 99%, or 100% of the variable regions of the lambda light chains expressed by the vertebrate are derived from recombination of human Vλ and Jλ gene segments. This is demonstrated in the examples below.

In embodiments, there is provided

A non-human vertebrate ES cell (eg, a mouse ES cell or rat ES cell) whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate cell, wherein the cell can develop into a vertebrate that expresses immunoglobulin light chains comprising lambda variable regions (lambda light chains), wherein the lambda light chains comprise immunoglobulin light chains comprising lambda variable regions derived from recombination of human Vλ and Jλ gene segments.

A non-human vertebrate ES cell (eg, a mouse ES cell or rat ES cell) whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate cell, wherein the cell can develop into a vertebrate that expresses immunoglobulin light chains comprising lambda variable regions (lambda light chains), and wherein at least 70 or 80% (for example, at least 70, 75, 80, 84, 85, 90, 95, 96, 97, 98 or 99%, or 100%) of the variable regions of the lambda light chains expressed by the vertebrate are derived from recombination of human Vλ and Jλ gene segments.

In an example, surprisingly expression of immunoglobulin light chains comprising lambda variable regions derived from recombination of human Vλ and Jλ gene segments is achieved even when the genome comprises endogenous non-human vertebrate lambda variable region gene segments (eg, endogenous Vλ and/or Jλ gene segments, optionally a complete endogenous repertoire of Vλ and Jλ gene segments). Thus, in an example, the genome comprises endogenous non-human vertebrate lambda variable region gene segments (eg, endogenous Vλ and/or Jλ gene segments, optionally a complete endogenous repertoire of Vλ and Jλ gene segments). In another example, such endogenous gene segments are absent from the genome.

2. The vertebrate or cell of aspect 1, optionally wherein the human Vλ and Jλ insertion comprises at least the functional human V and J gene segments (optionally also human Cλ) comprised by a human lambda chain Ig locus from Vλ2-18 to Cλ7. In one example, the insertion also comprises lambda inter-gene segment sequences. These are human sequences or they can be sequences of the non-human vertebrate species (eg, where the vertebrate is a mouse, sequences between corresponding mouse lambda gene segments can be used).

In one embodiment, the V and J gene segments are the alleles of Table 18. In a further embodiment, the Cλ gene segments are the alleles disclosed in Table 18.

3. The vertebrate or cell of aspect 1 or 2, optionally wherein the genome is homozygous for the human Vλ and Jλ gene segment insertion and endogenous kappa chain expression in said vertebrate is substantially or completely inactive. In one example, less than 10, 5, 4, 3, 2, 1 or 0.5% of light chains are provided by endogenous kappa chains (ie, kappa chains whose variable regions are derived from recombination of non-human vertebrate V and J gene segments).

4. The vertebrate or cell of any preceding aspect, optionally wherein the endogenous locus is an endogenous kappa locus.

5. The vertebrate or cell of any preceding aspect, optionally wherein the endogenous locus is an endogenous lambda locus.

≥60% of all light chains have human lambda V regions

6. A non-human vertebrate (eg, a mouse or rat) whose genome comprises an Ig gene segment repertoire produced by targeted insertion of human Ig gene segments into one or more endogenous Ig loci, the genome comprising (i) human Vλ and Jλ gene segments upstream of a constant region, wherein the human Vλ and Jλ gene segments have been provided by insertion into an endogenous light chain locus of the vertebrate and (ii) kappa V gene segments upstream of a constant region, wherein the vertebrate expresses immunoglobulin light chains comprising human lambda variable regions (human lambda light chains), and wherein at least 60% of the light chains expressed by the vertebrate are provided by said human lambda light chains. This is demonstrated in the examples below.

For example, at least 65, 70, 80, 84, 85, 90, 95, 96, 97, 98 or 99%, or 100% of the light chains expressed by the vertebrate are provided by said human lambda light chains. For example, at least 84% of the light chains expressed by the vertebrate are provided by said human lambda light chains. For example, at least 95% of the light chains expressed by the vertebrate are provided by said human lambda light chains. This is demonstrated in the examples below.

In one embodiment, there is provided a non-human vertebrate ES cell (eg, a mouse ES cell or rat ES cell) whose genome comprises an Ig gene segment repertoire produced by targeted insertion of human Ig gene segments into one or more endogenous Ig loci, the genome comprising (i) human Vλ and Jλ gene segments upstream of a constant region, wherein the human Vλ and Jλ gene segments have been provided by insertion into an endogenous light chain locus of the vertebrate and (ii) kappa V gene segments upstream of a constant region, wherein the cell can develop into a vertebrate that expresses immunoglobulin light chains comprising human lambda variable regions (human lambda light chains), and wherein at least 60% of the light chains expressed by the vertebrate are provided by said human lambda light chains.

7. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising a targeted insertion of human immunoglobulin Vλ and Jλ gene segments into an endogenous non-human vertebrate light kappa or lambda chain locus downstream of endogenous VL and JL gene segments for expression of light chains comprising human lambda variable regions; wherein the human Vλ and Jλ insertion comprises at least the functional human V and J (and optionally also functional human Cλ) gene segments comprised by a human lambda chain Ig locus from Vλ2-18 to Cλ7

As demonstrated in the examples, endogenous light chain expression from said locus is inactivated and also human lambda variable region expression dominates over endogenous lambda variable region expression.

By "downstream" is meant 3' of the gene segments on the same chromosome. In one example, the endogenous V and J gene segments are inverted with respect to the human gene segments and optionally moved out of the endogenous light chain locus. In one example, the human gene segments are downstream of all of the endogenous V and J segments of said kappa or lambda locus. The possibility of retaining the endogenous V-J sequences and intergenic sequences is advantageous since embedded control regions and/or genes are retained that may be desirable in the vertebrate.

Optionally the insertion also comprises lambda inter-gene segment sequences. These are human sequences or they can be sequences of the non-human vertebrate species (eg, where the vertebrate is a mouse, sequences between corresponding mouse lambda gene segments can be used).

Expression of VJCλ Lambda Chains

8. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising a targeted insertion of human immunoglobulin Vλ, Jλ and Cλ genes into an endogenous non-human vertebrate kappa or lambda light chain locus upstream of an endogenous non-human vertebrate kappa or lambda constant region for expression of a human VJC light chain; optionally wherein the human VJC insertion comprises at least the functional human V, J and C gene segments comprised by a human lambda chain Ig locus from Vλ3-1 to Cλ7 (eg, comprised by a human lambda chain Ig locus from 2-18 to Cλ7).

In one embodiment, the V and J gene segments are the alleles of Table 18. In a further embodiment, the Cλ gene segments are the alleles disclosed in Table 18, As demonstrated in the examples, human lambda variable region expression dominates over endogenous kappa variable region expression. Endogenous kappa chain expression from the endogenous locus can be inactivated.

Optionally the insertion also comprises lambda inter-gene segment sequences. These are human sequences or they can be sequences of the non-human vertebrate species (eg, where the vertebrate is a mouse, sequences between corresponding mouse lambda gene segments can be used);

9. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising a targeted insertion of at least the functional human Vλ and Jλ (and optionally human functional Cλ) gene segments comprised by a human lambda chain Ig locus from Vλ3-1 to Cλ7 (optionally from Vλ2-18 to Cλ7, further optionally the specific alleles of Table 18) into an endogenous non-human vertebrate kappa light chain locus downstream of the mouse Vκ and Jκ gene segments for expression of a light chain comprising a human lambda variable region, whereby in the presence of said insertion expression of endogenous kappa light chains derived from said mouse Vκ and Jκ gene segments is substantially or completely inactivated.

In one example, less than 10, 5, 4, 3, 2, 1 or 0.5% of light chains are provided by endogenous kappa chains (ie, kappa chains whose variable regions are derived from recombination of non-human vertebrate Vκ and Jκ gene segments).

Optionally the insertion also comprises lambda inter-gene segment sequences. These are human sequences or they can be sequences of the non-human vertebrate species (eg, where the vertebrate is a mouse, sequences between corresponding mouse lambda gene segments can be used).

10. A non-human vertebrate or a non-human vertebrate cell (eg, a mouse, rat, mouse cell or a rat cell), wherein in the genome of which the mouse IgK-VJ has been moved away from the mouse Eκ enhancer, thereby inactivating endogenous IgK-VJ regions. This is demonstrated in the examples.

11. The vertebrate of cell of aspect 10, optionally wherein the IgK-VJ has been moved away from the mouse Eκ enhancer by insertion of human VL and JL gene segments between the mouse IgK-VJ and the Eκ enhancer; optionally wherein the insertion is an insertion as recited in any preceding aspect 1-9 or an insertion of human Vκ and Jκ gene segments.

12. The vertebrate or cell of any preceding aspect, optionally wherein the human Vλ and Jλ gene segments have been inserted within 100, 75, 50, 40, 30, 20, 15, 10 or 5 kb of an endogenous non-human vertebrate light chain enhancer. In one example, the enhancer is a lambda enhancer (eg, mouse Eλ2-4, Eλ4-10 or Eλ3-1) when the insertion is into an endogenous lambda locus. In one example, the enhancer is a kappa enhancer (eg, iEκ or 3'Eκ) when the insertion is into an endogenous kappa locus.

13. The vertebrate or cell of any preceding aspect, optionally wherein the human Vλ and Jλ gene segments are provided in the genome by the targeted insertion of at least 10 human Vλ gene segments with human Jλ gene segments upstream of an endogenous non-human vertebrate light chain constant region of said light chain locus. For example, the human gene segments are provided by insertion of at least a portion of a human Ig lambda chain locus from Vλ2-18 to Vλ3-1; or at least a portion of a human Ig lambda chain locus from Vλ2-18 to Vλ3-1 inserted with Jλ1, Jλ2, Jλ3, Jλ6 and Jλ7; or at least a portion of a human Ig lambda chain locus from Vλ2-18 to Cλ7 (optionally excluding Jλ4Cλ4 and/or Jλ5Cλ5).

Optionally at least 2, 3, 4 or 5 human Jλ are inserted. In one embodiment, the inserted Jλs are different from each other. For example, human Jλ1, Jλ2, Jλ3, Jλ6 and Jλ7 are inserted, optionally as part of respective human JλCλ clusters.

Optionally a human light chain enhancer, eg Eλ, is inserted. For example, insertion of human Eλ between the human Jλ segments and the endogenous constant region; or between human Cλ gene segments (when these are inserted) and the endogenous constant region.

14. The vertebrate or cell of any preceding aspect, optionally wherein the lambda light chains provide a repertoire of human lambda variable regions derived from human Vλ gene segments Vλ3-1 and optionally one or more of Vλ2-18, Vλ3-16, V2-14, Vλ3-12, Vλ2-11, Vλ3-10, Vλ3-9, Vλ2-8 and Vλ4-3 that have been provided in the genome by targeted insertion into said light chain locus.

This is useful because Vλ3-1 is a highly-used lambda gene segment in humans (FIG. 59; Ignatovich et al 1997) and thus it is desirable that cells and vertebrates of the invention provide for the inclusion of lambda variable regions based on this gene segment for selection against antigen, particularly for the development of antibody therapeutics for human use.

15. The vertebrate or cell of any preceding aspect, optionally wherein the lambda light chains provide a repertoire of human lambda variable regions derived from human Vλ gene segments Vλ2-14 and one or more of Vλ2-18, Vλ3-16, Vλ3-12, Vλ2-11, Vλ3-10, Vλ3-9, Vλ2-8, Vλ4-3 and Vλ3-1 that have been provided in the genome by targeted insertion into said light chain locus.

This is useful because Vλ2-14 is a highly-used lambda gene segment in humans and thus it is desirable that cells and vertebrates of the invention provide for the inclusion of lambda variable regions based on this gene segment for selection against antigen, particularly for the development of antibody therapeutics for human use.

The vertebrate or cell of any preceding aspect, optionally wherein the lambda light chains provide a repertoire of human lambda variable regions derived from human Vλ gene segments Vλ2-8 and one or more of Vλ2-18, Vλ3-16, V2-14, Vλ3-12, Vλ2-11, Vλ3-10, Vλ3-9, Vλ2-8, Vλ4-3 and Vλ3-1 that have been provided in the genome by targeted insertion into said light chain locus.

This is useful because Vλ2-8 is a highly-used lambda gene segment in humans and thus it is desirable that cells and vertebrates of the invention provide for the inclusion of lambda variable regions based on this gene segment for selection against antigen, particularly for the development of antibody therapeutics for human use.

The vertebrate or cell of any preceding aspect, optionally wherein the lambda light chains provide a repertoire of human lambda variable regions derived from human Vλ gene segments Vλ3-10 and one or more of Vλ2-18, Vλ3-16, V2-14, Vλ3-12, Vλ2-11, Vλ2-14, Vλ3-9, Vλ2-8, Vλ4-3 and Vλ3-1 that have been provided in the genome by targeted insertion into said light chain locus.

This is useful because Vλ3-10 is a highly-used lambda gene segment in humans and thus it is desirable that cells and vertebrates of the invention provide for the inclusion of lambda variable regions based on this gene segment for selection against antigen, particularly for the development of antibody therapeutics for human use.

16. The vertebrate or cell of any preceding aspect, optionally wherein the human Vλ gene segments comprise the functional Vλ comprised by a human lambda chain Ig locus from Vλ2-18 to Vλ3-1.

For example, the human Vλ gene segments comprise at least human V gene segment Vλ3-1 or at least segments Vλ2-18, Vλ3-16, V2-14, Vλ3-12, Vλ2-11, Vλ3-10, Vλ3-9, Vλ2-8, Vλ4-3 and Vλ3-1.

17. The vertebrate of any preceding aspect, optionally wherein the vertebrate expresses more lambda chains than kappa chains. Lambda chains comprise variable regions derived from recombination of Vλ and Jλ gene segments—for example, expressed with a lambda constant region. Kappa chains comprise variable regions derived from recombination of Vκ and Jκ gene segments—for example, expressed with a kappa constant region.

18. The vertebrate of any preceding aspect, optionally wherein the vertebrate expresses no endogenous kappa chains. For example, endogenous kappa chain expression can be inactivated by any of the means described herein, such as by inversion of all or part of the endogenous kappa VJ region or by insertion of a marker (eg, neo) or other interfering sequence in an endogenous kappa locus (a locus not comprising human lambda gene segments according to the invention).

19. The vertebrate of any preceding aspect, optionally wherein kappa chain expression is substantially or completely inactive in said vertebrate. In one example, less than 10, 5, 4, 3, 2, 1 or 0.5% of light chains are provided by kappa chains.

20. The vertebrate or cell of any preceding aspect, optionally wherein a human Eλ enhancer is inserted in said endogenous non-human vertebrate locus. For example, there is inserted a human 5' MAR and human Eλ (and optionally the human 3' MAR) in germline configuration. For example, there is inserted a sequence corresponding to the human lambda intronic region immediately 3' of human Jλ7-Cλ7 to, and including, at least the human Eλ (and optionally also the human 3' MAR)—optionally including at least 30 kb of intronic region 3' of the human Eλ.

21. The vertebrate or cell of any preceding aspect, wherein optionally at least human JC gene segments Jλ1-Cλ1, Jλ2-Cλ2, Jλ3-Cλ3, Jλ6-Cλ6 and Jλ7-Cλ7 are inserted in addition to the other human gene segments.

22. The vertebrate or cell of any preceding aspect, wherein optionally the inserted human gene segments are in germline configuration; optionally with the human inter-gene segment sequences or the corresponding endogenous non-human vertebrate inter-gene segment sequences.

23. The vertebrate or cell of any preceding aspect, wherein optionally an endogenous non-human vertebrate light chain enhancer is maintained in the endogenous locus; optionally in germline configuration. For example, when the endogenous locus is a kappa locus, an endogenous kappa enhancer is maintained. This can be the iEk and/or the 3'Ek, optionally in germline configuration with respect to an endogenous light chain constant region. This may be useful to help control of light chain expression in the non-human vertebrate or cell.

24. The vertebrate or cell of any preceding aspect, optionally wherein the genome is heterozygous for the human lambda insertion at the endogenous locus. For example, heterozygous for the human VJ or VJC insertion at an endogenous kappa (eg, mouse or rat kappa) locus. This aids and simplifies breeding of the vertebrates since the other endogenous locus (eg, the other kappa locus) can be used to provide a different transgenic Ig locus, such as a transgenic kappa locus comprising human kappa V and J gene segments either upstream of the endogenous mouse kappa constant region or upstream of a human kappa constant region. In this case, the kappa enhancers (iEk and/or the 3'Ek) can be maintained in that kappa locus to aid expression in the vertebrate by using endogenous control mechanisms.

In another embodiment, there is provided a non-human vertebrate or cell according to any preceding aspect, wherein (a) the endogenous locus is an endogenous lambda locus (eg, in a mouse), the genome being heterozygous for the insertion at the lambda locus, thus one allele of the lambda locus comprising the human Vλ and Jλ gene segment insertion (optionally with the human Cλ gene segment insertion; optionally with the human Eλ insertion) as described above;

(b) the other endogenous lambda allele comprises a plurality of human Vκ gene segments and one or more human Jκ gene segments upstream of a constant region (eg, a kappa constant region of said non-human vertebrate species; a human kappa constant region; the endogenous lambda constant region; or a human lambda constant region); optionally with one or more kappa enhancers (eg, iEk and/or the 3'Ek, eg, of said non-human vertebrate species); and (c) endogenous lambda and kappa chain expression has been inactivated.

Thus, there is no expression of light chains comprising variable regions derived from recombination of endogenous V and J regions, but there is expression of human lambda and human kappa light chains from the alleles at the endogenous lambda locus. This is beneficial, since the design greatly aids construction and breeding of vertebrates by avoiding need to provide transgenic loci at both the endogenous lambda and kappa loci. The endogenous kappa locus (and thus endogenous kappa chain expression) can be inactivated by inversion, deletion of kappa gene segments (eg, endogenous V and/or and/or C kappa) and/or by insertion of an interrupting sequence such as a marker (eg, neo) into the endogenous kappa locus.

The human kappa segment insertion into the endogenous lambda can be carried out, for example, by inserting a sequence corresponding to a portion of a human kappa locus comprising in germline configuration all functional human Vκ and Jκ (ie, optionally excluding pseudogenes and ORFs; see the IMGT database); and optionally also a human iEκ.

25. The vertebrate or cell of aspect 24, optionally wherein the genome comprises said human lambda gene segment insertion at one endogenous non-human vertebrate kappa locus allele, and wherein the other endogenous kappa locus allele comprises an insertion of human kappa immunoglobulin V and J genes upstream of an endogenous non-human vertebrate kappa constant region; optionally wherein an endogenous kappa light chain enhancer is maintained in one or both kappa locus; optionally in germline configuration.

The vertebrate or cell of aspect 24, optionally wherein the genome comprises said human lambda gene segment insertion at one endogenous non-human vertebrate lambda locus allele, and wherein the other endogenous lambda locus allele comprises an insertion of human kappa immunoglobulin V and J genes upstream of an endogenous non-human vertebrate kappa constant region; optionally wherein an endogenous lambda light chain enhancer is maintained in one or both lambda locus; optionally in germline configuration.

26. The vertebrate or cell of claim 24, optionally wherein the genome comprises said human lambda gene segment insertion at one endogenous non-human vertebrate lambda locus allele, and wherein the other endogenous lambda locus allele comprises an insertion of human kappa immunoglobulin V and J genes upstream of an endogenous non-human vertebrate kappa constant region; optionally wherein an endogenous lambda light chain enhancer is maintained in one or both kappa locus; optionally in germline configuration.

27. The vertebrate or cell of any one of aspects 1 to 23, optionally wherein the genome is homozygous for the human lambda insertion at the endogenous non-human vertebrate locus.

28. The vertebrate or cell of any one of aspects 1 to 23, optionally wherein the genome is homozygous for a human lambda gene segment insertion at the endogenous non-human vertebrate kappa and lambda loci.

29. The vertebrate or cell of any one of aspects 1 to 23 and 28, optionally wherein the genome is homozygous for a human lambda gene segment insertion at the endogenous non-human vertebrate lambda loci, one endogenous kappa locus allele comprising a human lambda gene segment insertion and the other endogenous kappa locus allele comprising an insertion of a plurality of human Vκ and Jκ gene segments upstream of a Cκ region for the expression of kappa light chains comprising human kappa variable regions. Human kappa variable regions are those derived from the recombination of human Vκ and Jκ.

30. The vertebrate or cell of aspect 27 or 28, optionally wherein the human lambda gene segment insertions at the kappa and lambda loci are insertions of the same repertoire of human lambda gene segments.

31. The vertebrate or cell of aspect 27 or 28, optionally wherein the human lambda gene segment insertions at the kappa loci are different from the human lambda gene segment insertions at the lambda loci. This is useful for expanding the potential repertoire of variable regions for subsequent selection against antigen.

32. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising the following light chain loci arrangement
  (a) L at one endogenous kappa chain allele and K at the other endogenous kappa chain allele; or
  (b) L at one endogenous lambda chain allele and K at the other endogenous lambda chain allele; or
  (c) L at both endogenous kappa chain alleles;
  (d) L at both endogenous lambda chain alleles;
  (e) L at one endogenous kappa chain allele and the other endogenous kappa chain allele has been inactivated; or
  (f) L at one endogenous lambda chain allele and the other endogenous lambda chain allele has been inactivated;
  Wherein
  L represents a human lambda gene segment insertion of at least the functional human Vλ and Jλ (optionally also Cλ gene segments) comprised by a human lambda chain Ig locus from Vλ3-1 to Cλ7 (eg, comprised by a human lambda chain Ig locus from 2-18 to Cλ7); and
  K represents a human Vκ and Jκ insertion;
  Wherein in the genome the human gene segments are inserted upstream of a constant region for expression of light chains comprising variable regions derived from the recombination of human V and J gene segments.

33. The vertebrate or cell according to aspect 32, optionally wherein the genome comprises arrangement
  (a) and L at one or both endogenous lambda chain alleles; or
  (a) and K at one or both endogenous lambda chain alleles; or
  (a) and L at one endogenous lambda chain allele and K at the other endogenous lambda chain allele; or
  (b) and L at one or both endogenous kappa chain alleles; or
  (b) and K at one or both endogenous kappa chain alleles; or
  (b) and L at one endogenous kappa chain allele and K at the other endogenous kappa chain allele; or
  (c) and K at one or both endogenous lambda chain alleles; or
  (c) and L at one or both endogenous lambda chain alleles; or
  (c) and L at one endogenous lambda chain allele and K at the other endogenous lambda chain allele; or
  (c) and both endogenous lambda chain alleles have been inactivated; or
  (d) and L at one or both endogenous kappa chain alleles; or
  (d) and K at one or both endogenous kappa chain alleles; or
  (d) and L at one endogenous kappa chain allele and K at the other endogenous kappa chain allele; or
  (d) and both endogenous kappa chain alleles have been inactivated.

34. The vertebrate or cell of aspect 32 or 33, optionally wherein endogenous kappa chain expression is substantially or completely inactivated. Endogenous kappa chains are kappa light chains comprising variable regions derived from the recombination of endogenous (non-human vertebrate) Vκ and Jκ gene segments.

35. The vertebrate or cell of aspect 32, 33 or 34, optionally wherein endogenous lambda chain expression is substantially or completely inactive. Endogenous lambda chains are lambda light chains comprising variable regions derived from the recombination of endogenous (non-human vertebrate) Vλ and Jλ gene segments.

36. The vertebrate or cell of any one of aspects 32 to 35, optionally wherein each L insertion is upstream of an endogenous lambda or kappa constant region.

37. The vertebrate or cell of any one of aspects 32 to 36, optionally wherein each L insertion into a lambda locus is upstream of an endogenous lambda constant region.

38. The vertebrate or cell of any one of aspects 32 to 36, optionally wherein each L insertion into a kappa locus is upstream of an endogenous kappa constant region.

39. The vertebrate or cell of any one of aspects 32 to 35, optionally wherein each L insertion into a lambda locus is upstream of a human lambda constant region.

40. The vertebrate or cell of any one of aspects 32 to 35, optionally wherein each L insertion into a kappa locus is upstream of a human kappa constant region.

41. The vertebrate or cell of any one of aspects 32 to 40, optionally wherein each K insertion is upstream of an endogenous lambda or kappa constant region.

42. The vertebrate or cell of any one of aspects 32 to 41, optionally wherein each K insertion into a lambda locus is upstream of an endogenous lambda constant region.

43. The vertebrate or cell of any one of aspects 32 to 42, optionally wherein each K insertion into a kappa locus is upstream of an endogenous kappa constant region.

44. The vertebrate or cell of any one of aspects 32 to 40, optionally wherein each K insertion into a lambda locus is upstream of a human lambda constant region.

45. The vertebrate or cell of any one of aspects 32 to 40 and 44, optionally wherein each K insertion into a kappa locus is upstream of a human kappa constant region.

46. The vertebrate or cell of any one of aspects 32 to 45, optionally wherein the insertions are according to any one of aspects 1 to 9, 11 to 16 and 20 to 31.

47. The vertebrate or cell of any one of aspects 32 to 46, optionally wherein each human lambda insertion is according to any one of aspects 1 to 9, 11 to 16 and 20 to 31.

48. The vertebrate or cell of any one of aspects 32 to 47, optionally wherein each human kappa insertion is according to any one of aspects 1 to 9, 11 to 16 and 20 to 31.

49. The vertebrate or cell of any one of aspects 32 to 48, optionally wherein each human lambda insertion comprises the repertoire of human Vλ and Jλ (and optionally Cλ) gene segments.

50. The vertebrate or cell of any one of aspects 32 to 48, optionally wherein first and second (and optionally third) human lambda insertions are made and the insertions comprise different repertoires of human Vλ and Jλ (and optionally Cλ) gene segments.

51. The vertebrate or cell of any one of aspects 32 to 50, optionally wherein each human kappa insertion comprises the repertoire of human Vκ and Jκ (and optionally Cκ) gene segments.

52. The vertebrate or cell of any one of aspects 32 to 50, optionally wherein first and second (and optionally third) human kappa insertions are made and the insertions comprise different repertoires of human Vκ and Jκ (and optionally Cκ) gene segments.

53. The vertebrate or cell of any preceding aspect, optionally wherein the genome comprises an immunoglobulin heavy chain locus comprising human VH gene segments, eg, a heavy chain locus as herein described which comprises human V, D and J gene segments.

54. A method for producing an antibody or light chain comprising a lambda variable region specific to a desired antigen, the method comprising immunizing a vertebrate according to any preceding aspect with the desired antigen and recovering the antibody or light chain or recovering a cell producing the antibody or light chain.

55. A method for producing a fully humanised antibody or antibody light chain comprising carrying out the method of aspect 54 to obtain an antibody or light chain comprising a lambda chain non-human vertebrate constant region, and replacing the non-human vertebrate constant region with a human constant region, optionally by engineering of the nucleic acid encoding the antibody or light chain.

56. A humanised antibody or antibody light chain produced according to aspect 54 or a derivative thereof; optionally for use in medicine.

57. Use of a humanised antibody or chain produced according to aspect 54 or a derivative thereof in medicine.

58. A method of inactivating endogenous Ig-VJ regions in the genome of a non-human vertebrate or a non-human vertebrate cell (eg, a mouse, rat, mouse cell or a rat cell), wherein the method comprises inserting human immunoglobulin gene segments (eg, V and J gene segments) in the genome between the endogenous Ig-VJ and an endogenous enhancer or endogenous constant region to move the endogenous Ig-VJ away from the enhancer or constant region, thereby inactivating endogenous Ig-VJ regions.

In one embodiment, the endogenous Ig-VJ are heavy chain gene segments, the enhancer is an endogenous heavy chain enhancer, the constant region is an endogenous heavy chain constant region and the human Ig gene segments comprise human VH, DH and JH gene segments.

In one embodiment, the endogenous Ig-VJ are lambda light chain gene segments, the enhancer is an endogenous lambda chain enhancer, the constant region is an endogenous lambda chain constant region and the human Ig gene segments comprise human Vλ and Jλ gene segments.

In one embodiment, the endogenous Ig-VJ are kappa light chain gene segments, the enhancer is an endogenous kappa chain enhancer, the constant region is an endogenous kappa chain constant region and the human Ig gene segments comprise human Vκ and Jκ gene segments.

A method of inactivating endogenous IgK-VJ regions in the genome of a non-human vertebrate or a non-human vertebrate cell (eg, a mouse, rat, mouse cell or a rat cell), wherein the method comprises inserting human immunoglobulin gene segments in the genome between the endogenous IgK-VJ and Eκ enhancer to move the IgK-VJ away from the Eκ enhancer, thereby inactivating endogenous IgK-VJ regions.

59. The method of aspect 58, wherein optionally the human gene segments comprise human VL and JL gene segments; optionally wherein the insertion is an insertion as recited in any one of aspects 1 to 9, 11 to 16 and 20 to 31 or an insertion of human Vκ and Jκ gene segments.

60. A method of expressing immunoglobulin light chains in a non-human vertebrate (eg, a mouse or rat), the light chains comprising lambda variable regions (lambda light chains), wherein at least 70 or 80% (for example, at least 70, 75, 80, 84, 85, 90, 95, 96, 97, 98 or 99%) of the variable regions of the lambda light chains expressed by the vertebrate are derived from recombination of human Vλ and Jλ gene segments, the method comprising providing in the genome of the vertebrate an Ig gene segment repertoire produced by targeted insertion of human Ig gene segments into one or more endogenous Ig loci, the genome comprising human Vλ and Jλ gene segments upstream of a constant region, wherein the method comprises inserting at least the functional human Vλ and Jλ (optionally also human Cλ) gene segments (and optionally inter-gene segment sequences) comprised by a human lambda chain Ig locus from Vλ2-18 to Cλ7 into an endogenous light chain locus of the vertebrate, wherein at least 70 or 80% (for example, at least 70, 75, 80, 84, 85, 90, 95, 96, 97, 98 or 99%) of the variable regions of the lambda light chains expressed by the vertebrate are derived from recombination of human Vλ and Jλ gene segments; the method comprising expressing said light chains in the vertebrate and optionally isolating one or more of said light chains (eg, as part of a 4-chain antibody).

In one embodiment, the method further comprises isolating from the vertebrate a lambda light chain comprising a variable region derived from recombination of human Vλ and Jλ gene segments. In an example, the method comprises immunising the mouse with an antigen (eg, a human antigen) prior to isolating the lambda light chain. In an example, the light chain is part of an antibody, eg, an antibody that specifically binds the antigen.

In one embodiment, the use further comprises isolating splenic tissue (eg, the spleen) from the mouse; optionally followed by isolating at least one antigen-specific B-cell from the tissue, wherein the B-cell(s) expresses said lambda light chain. For example, said lambda light chain is provided by an antibody that specifically binds a predetermined antigen (eg, a human antigen). In one example, the use comprises immunising the mouse with the antigen (eg, a human antigen) prior to isolating the splenic tissue or lambda light chain. In an example, the use comprises isolating the lambda light chain produced by the B-cell (or by a hybridoma produced by fusion of the B-cell with a myeloma cell). In an example, the use comprises making a hybridoma from a B-cell isolated from the splenic tissue, wherein the hybridoma expresses said lambda light chain or a derivative thereof. Optionally, the use comprises making a derivative of the isolated antibody or lambda light chain. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen. Mutation or adaptation to produce a derivative includes, eg, mutation to produce Fc enhancement or inactivation. A derivative can be an antibody following conjugation to a toxic payload or reporter or label or other active moiety. In another example, a chimaeric antibody chain or antibody isolated from a cell of vertebrate of the invention is modified by replacing one or all human constant regions thereof by a corresponding human constant region. For example, all constant regions of an antibody isolated from such a cell or vertebrate are replaced with human constant regions to produce a fully human antibody (ie, comprising human variable and constant regions). Such an antibody is useful for administration to human patients to reduce anti-antibody reaction by the patient.

61. A method of expressing immunoglobulin light chains in a non-human vertebrate (eg, a mouse or rat), wherein at least 60% (for example, at least 65, 70, 80, 84, 85, 90, 95, 96, 97, 98 or 99%) of the light chains expressed by the vertebrate are provided by human lambda light chains, the method comprising providing in the genome of the vertebrate an Ig gene segment repertoire produced by targeted insertion of human Ig gene segments into one or more endogenous Ig loci, the genome comprising (i) human Vλ and Jλ gene segments upstream of a constant region, wherein the human Vλ and Jλ gene segments are provided by inserting at least the functional human Vλ and Jλ (optionally also human Cλ) gene segments (and optionally inter-gene segment sequences) comprised by a human lambda chain Ig locus from Vλ2-18 to Cλ7 into an endogenous light chain locus of the vertebrate and (ii) kappa V gene segments upstream of a constant region, wherein the vertebrate expresses immunoglobulin light chains comprising human lambda variable regions (human lambda light chains) and at least 60% (for example, greater than 65, 70, 80, 84, 85, 90, 95, 96, 97, 98 or 99%) of the light chains expressed by the vertebrate are provided by said human lambda light chains; the method comprising expressing said light chains in the vertebrate and optionally isolating one or more of said light chains (eg, as part of a 4-chain antibody).

In one embodiment, the method further comprises isolating from the vertebrate a lambda light chain comprising a variable region derived from recombination of human Vλ and Jλ gene segments. In an example, the method comprises immunising the mouse with an antigen (eg, a human antigen) prior to isolating the lambda light chain. In an example, the light chain is part of an antibody, eg, an antibody that specifically binds the antigen.

In one embodiment, the use further comprises isolating splenic tissue (eg, the spleen) from the mouse; optionally followed by isolating at least one antigen-specific B-cell from the tissue, wherein the B-cell(s) expresses said lambda light chain. For example, said lambda light chain is provided by an antibody that specifically binds a predetermined antigen (eg, a human antigen). In one example, the use comprises immunising the mouse with the antigen (eg, a human antigen) prior to isolating the splenic tissue or lambda light chain. In an example, the use comprises isolating the lambda light chain produced by the B-cell (or by a hybridoma produced by fusion of the B-cell with a myeloma cell). In an example, the use comprises making a hybridoma from a B-cell isolated from the splenic tissue, wherein the hybridoma expresses said lambda light chain or a derivative thereof. Optionally, the use comprises making a derivative of the isolated antibody or lambda light chain. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

62. A method of expressing human immunoglobulin VJC light chains in a non-human vertebrate (eg, a mouse or rat), the method comprising providing in the genome of the vertebrate an Ig gene segment repertoire produced by targeted insertion of human Ig gene segments into one or more endogenous Ig loci, wherein the method comprises inserting at least the functional human Vλ, Jλ and Cλ gene segments (and optionally inter-gene segment sequences) comprised by a human lambda chain Ig locus from Vλ3-1 to Cλ7 (eg, comprised by a human lambda chain Ig locus from 2-18 to Cλ7) into an endogenous non-human vertebrate kappa light chain locus upstream of an endogenous non-human vertebrate kappa constant region for expression of a human VJC light chain; the method comprising expressing said light chains in the vertebrate and optionally isolating one or more of said light chains (eg, as part of a 4-chain antibody).

In one embodiment, the method further comprises isolating from the vertebrate a lambda light chain comprising a variable region derived from recombination of human Vλ and Jλ gene segments. In an example, the method comprises immunising the mouse with an antigen (eg, a human antigen) prior to isolating the lambda light chain. In an example, the light chain is part of an antibody, eg, an antibody that specifically binds the antigen.

In one embodiment, the use further comprises isolating splenic tissue (eg, the spleen) from the mouse; optionally followed by isolating at least one antigen-specific B-cell from the tissue, wherein the B-cell(s) expresses said lambda light chain. For example, said lambda light chain is provided by an antibody that specifically binds a predetermined antigen (eg, a human antigen). In one example, the use comprises immunising the mouse with the antigen (eg, a human antigen) prior to isolating the splenic tissue or lambda light chain. In an example, the use comprises isolating the lambda light chain produced by the B-cell (or by a hybridoma produced by fusion of the B-cell with a myeloma cell). In an example, the use comprises making a hybridoma from a B-cell isolated from the splenic tissue, wherein the hybridoma expresses said lambda light chain or a derivative thereof. Optionally, the use comprises making a derivative of the isolated antibody or lambda light chain. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

63. The method of any one of aspects 38 to 40, optionally wherein the vertebrate is according to any one of the other aspects.

64. An antibody light chain isolated according to the method of any one of aspects 58 to 63 or a derivative thereof, or an antibody comprising such a light chain or derivative; optionally for use in medicine.

65. Use of an antibody light chain isolated according to the method of any one of aspects 58 to 63 or a derivative thereof (or an antibody comprising such a light chain or derivative) in medicine.

66. A non-human vertebrate (eg, a mouse or rat) according to any one of aspects 1 to 53 for expressing light chains comprising lambda variable regions (lambda light chains), wherein at least 70 or 80% (for example, at least 70, 75, 80, 84, 85, 90, 95, 96, 97, 98 or 99% or 100%) of the variable regions of the lambda light chains expressed by the vertebrate are derived from recombination of human Vλ and Jλ gene segments.

A non-human vertebrate (eg, a mouse or rat) according to any one of aspects 1 to 53 expressing light chains comprising lambda variable regions (lambda light chains), wherein at least 70 or 80% (for example, at least 70, 75, 80, 84, 85, 90, 95, 96, 97, 98 or 99% or 100%) of the variable regions of the lambda light chains expressed by the vertebrate are derived from recombination of human Vλ and Jλ gene segments.

67. A non-human vertebrate (eg, a mouse or rat) according to any one of aspects 1 to 53 for expressing light chains, wherein at least 60% (for example, greater than 65, 70, 80, 84, 85, 90, 95, 96, 97, 98 or 99% or 100%) of the light chains expressed by the vertebrate are provided by human lambda light chains.

A non-human vertebrate (eg, a mouse or rat) according to any one of aspects 1 to 53 expressing light chains, wherein at least 60% (for example, greater than 65, 70, 80, 84, 85, 90, 95, 96, 97, 98 or 99% or 100%) of the light chains expressed by the vertebrate are provided by human lambda light chains.

68. A non-human vertebrate (eg, a mouse or rat) according to aspect 7 for expressing light chains comprising lambda variable regions (lambda light chains), wherein expression of lambda light chains comprising human lambda variable regions dominates over expression of lambda light chains comprising endogenous non-human vertebrate lambda variable regions: and optionally for inactivating expression of endogenous non-human vertebrate lambda variable regions from the endogenous light chain locus.

A non-human vertebrate (eg, a mouse or rat) according to aspect 7 expressing light chains comprising lambda variable regions (lambda light chains), wherein expression of lambda light chains comprising human lambda variable regions dominates over expression of lambda light chains comprising endogenous non-human vertebrate lambda variable regions: and optionally for inactivating expression of endogenous non-human vertebrate lambda variable regions from the endogenous light chain locus.

69. A non-human vertebrate (eg, a mouse or rat) according to aspect 7, 8, 9 or 10 for inactivating expression of endogenous non-human vertebrate lambda variable regions from the endogenous light chain locus.

The percentage expression or level of expression of antibody chains can be determined at the level of light chain mRNA transcripts in B-cells (eg, peripheral blood lymphocytes). Alternatively or additionally, the percentage expression is determined at the level of antibody light chains in serum or blood of the vertebrates. Additionally or alternatively, the expression can be determined by FACS (fluorescence activated cell sorting) analysis of B cells. For example, by assessing mouse C kappa or human C lambda expression on cell surface when the human lambda variable regions are expressed with mouse C kappa or human C lambda regions respectively.

The term a "lambda light chain" in these aspects refers to a light chain comprising a variable region sequence (at RNA or amino acid level) derived from the recombination of Vλ and Jλ gene segments. Thus a "human lambda variable region", for example, is a variable region derived from the recombination of human Vλ and Jλ gene segments. The constant region can be a kappa or lambda constant region, eg, a human or mouse constant region.

The vertebrate in these aspects is, for example naïve (ie, not immunised with a predetermined antigen, as the term is understood in the art; for example, such a vertebrate that has been kept in a relatively sterile environment as provided by an animal house used for R&D). In another example, the vertebrate has been immunised with a predetermined antigen, eg, an antigen bearing a human epitope.

Reference to "functional" human gene segments acknowledges that in a human Ig lambda locus some V gene segments are non-functional pseudogenes (eg. Vλ3-17, Vλ3-15, Vλ3-13, Vλ3-7, Vλ3-6, Vλ2-5, Vλ3-4, Vλ3-2; see the IMGT database; at World Wide Web (www) imgt.org/IMGTrepertoire/index.php?section=LocusGenes&repertoire=locus&species=human&group=IGL. Also, Jλ4-Cλ4 and Jλ5-Cλ5 are not functional in humans. The term "functional" when referring to gene segments excludes pseudogenes. An example of functional human Vλ gene segments is the group Vλ2-18, Vλ3-16, V2-14, Vλ3-12, Vλ2-11, Vλ3-10, Vλ3-9, Vλ2-8, Vλ4-3 and Vλ3-1. An example of functional human Jλ gene segments is the group Jλ1, Jλ2 and Jλ3; or Jλ1, Jλ2 and Jλ7; or Jλ2, Jλ3 and Jλ7; or Jλ1, Jλ2, Jλ3 and Jλ7. An example of functional human Cλ gene segments is the group Cλ1, Cλ2 and Cλ3; or Cλ1, Cλ2 and Cλ7; or Cλ2, Cλ3 and Cλ7; or Cλ1, Cλ2, Cλ3 and Cλ7.

In one embodiment, the lambda light chains, together with heavy chains expressed in the cells or vertebrates of the invention, form antibodies. The heavy chains can be expressed from a transgenic heavy chain locus as herein described. For example the genome of the cell or vertebrate comprises a heavy chain locus in which is a chimaeric immunoglobulin heavy chain locus comprising one or more human V gene segments, one or more human D gene segments and one or more human J gene segments upstream of a mu constant region of said non-human species; endogenous heavy chain expression has been substantially inactivated; and the heavy chain locus comprises an Eμ enhancer of said non-human vertebrate species.

In one embodiment of the vertebrate or cell, all endogenous enhancers are deleted from the endogenous locus in which the human gene segments are inserted. Thus, when a human enhancer (eg, Eλ) is inserted, this controls the transgenic locus in the absence of the effect of other, endogenous, enhancers (for example, kappa enhancers if the locus is an endogenous kappa enhancer). This may be useful to avoid non-human vertebrate-like kappa:lambda expression ratios (eg, to steer expression to a higher ratio of lambda:kappa in mice).

When endogenous light chain (eg, kappa or lambda) expression is substantially inactive or inactivated as described herein, less than 10, 5, 4, 3, 2, 1 or 0.5% of such endogenous light chains are expressed or expressible. In one example, there is complete inactivation so no such light chains are expressed or expressible.

Optionally the vertebrate of the invention is naïve. Thus, the vertebrate has not been immunised with a predetermined antigen.

Where, for example, a cell of the invention is an ES cell or other IPS stem cell or other pluripotent stem cell, the cell can develop into a vertebrate of the invention. For example, the cell can be implanted into a blastocyst from a foster mother and developed into an embryo and animal according to standard techniques.

In one embodiment, where human kappa gene segments are inserted, each insertion comprises human kappa gene segments (i) Vκ1-5, Vκ1-6, Vκ1-8 and Vκ1-9 (and optionally Vκ5-2 and Vκ4-1); or (ii) Vκ1-5, Vκ1-6, Vκ1-8, Vκ1-9, Vκ3-11, Vκ1-12, Vκ3-15, Vκ1-16, Vκ1-17, Vκ3-20 (and optionally Vκ 2-24 and/or Vκ1-13); or (iii) Vκ1-5, Vκ1-6, Vκ1-8, Vκ1-9, Vκ3-11, Vκ1-12, Vκ3-15, Vκ1-16, Vκ1-17, Vκ3-20, Vκ 2-24, Vκ1-27, Vκ2-28, Vκ2-30 and Vκ1-33 (and optionally Vκ 2-29 and/or Vκ2-40 and/or Vκ1-39);

and optionally (iv) Jκ1, Jκ2, Jκ3, Jκ4 and Jκ5.

In one embodiment, the human kappa insertion also comprises a human iEκ and/or human 3'Eκ downstream of the human J gene segments in the locus.

Transgenic Mice of the Invention Expressing Essentially Exclusively Human Heavy Chain Variable Regions Develop Normal Splenic and BM Compartments & Normal Ig Expression in which the Ig Comprise Human Heavy Chain Variable Regions The present inventors surprisingly observed normal Ig subtype expression & B-cell development in transgenic mice of the invention expressing antibodies with human heavy chain variable regions substantially in the absence of endogenous heavy and kappa chain expression. See Example 16 below.

The inventors observed that surprisingly the inactivation of endogenous heavy chain variable region expression in the presence of human variable region expression does not change the ratio of B-cells in the splenic compartment (FIG. 66) or bone marrow B progenitor compartment (FIG. 67) and the immunoglobulin levels in serum are normal and the correct Ig subtypes are expressed (FIG. 68). These data demonstrate that inserted human heavy chain gene segments according to the invention (eg, an insertion of at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6, optionally the alleles of Table 7) are fully functional for VDJ gene segment rearrangement from the transgenic heavy chain locus, B-cell receptor (BCR) signalling and proper B-cell maturation The invention therefore provides the following aspects (numbering starting at aspect 70):

70. A mouse that expresses or for expressing immunoglobulin heavy chains comprising human variable regions, wherein the heavy chains expressed by the mouse are essentially exclusively said heavy chains comprising human variable regions; and said heavy chains comprising human variable regions are expressed as part of serum IgG1,IgG2b and IgM (and optionally IgG2a) antibodies in the mouse;

the mouse comprising an immunoglobulin heavy chain locus comprising human VH, DH and JH gene segments upstream of a mouse constant region (eg, C-mu and/or C-delta and/or C-gamma; such as (in a 5' to 3' orientation) mouse C-mu and mouse C-delta and mouse C-gamma), wherein (a) the mouse is capable of expressing immunoglobulin heavy chains comprising human variable regions and the heavy chains expressed by the mouse are essentially exclusively said heavy chains comprising human variable regions; and (b) the mouse expresses serum IgG1,IgG2b and IgM (and optionally IgG2a) antibodies comprising said heavy chains.

Ig isotypes can be determined, for example, using isotype-matched tool antibodies as will be readily familiar to the skilled person (and as illustrated in Example 16).

In an embodiment, the mouse is naïve.

71. The mouse of aspect 70 for expressing a normal relative proportion of serum IgG1, IgG2a, IgG2b and IgM antibodies.

By "normal" is meant comparable to expression in a mouse (eg, a naïve mouse) expressing only mouse antibody chains, eg, a mouse whose genome comprises only wild-type functional Ig heavy and light chain loci, eg, a wild-type mouse.

72. The mouse of aspect 70 or 71, wherein the mouse expresses a normal relative proportion of serum IgG1, IgG2a, IgG2b and IgM antibodies.

By "normal" is meant comparable to expression in a mouse (eg, a naïve mouse) expressing only mouse antibody chains, eg, a mouse whose genome comprises only wild-type functional Ig heavy and light chain loci, eg, a wild-type mouse.

73. The mouse of any one of aspects 70 to 72, for expressing in the mouse
(i) serum IgG1 at a concentration of about 25-350 µg/ml;
(ii) serum IgG2a at a concentration of about 0-200 µg/ml;
(iii) serum IgG2b at a concentration of about 30-800 µg/ml; and
(iv) serum IgM at a concentration of about 50-300 µg/ml;
or
(i) serum IgG1 at a concentration of about 10-600 µg/ml;
(ii) serum IgG2a at a concentration of about 0-500 µg/ml;
(iii) serum IgG2b at a concentration of about 20-700 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, for expressing in the mouse
(i) serum IgG1 at a concentration of about 25-150 µg/ml;
(ii) serum IgG2a at a concentration of about 0-200 µg/ml;
(iii) serum IgG2b at a concentration of about 30-300 µg/ml; and
(iv) serum IgM at a concentration of about 50-200 µg/ml;
or
(i) serum IgG1 at a concentration of about 10-200 µg/ml;
(ii) serum IgG2a at a concentration of about 0-500 µg/ml;
(iii) serum IgG2b at a concentration of about 20-400 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

The mouse of any one of aspects 70 to 72, for expressing in the mouse Ig in the relative proportions of
(i) serum IgG1 at a concentration of about 25-350 µg/ml;
(ii) serum IgG2a at a concentration of about 0-200 µg/ml;
(iii) serum IgG2b at a concentration of about 30-800 µg/ml; and
(iv) serum IgM at a concentration of about 50-300 µg/ml;
or
(i) serum IgG1 at a concentration of about 10-600 µg/ml;
(ii) serum IgG2a at a concentration of about 0-500 µg/ml;
(iii) serum IgG2b at a concentration of about 20-700 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, for expressing in the mouse Ig in the relative proportions of
(i) serum IgG1 at a concentration of about 25-150 µg/ml;
(ii) serum IgG2a at a concentration of about 0-200 µg/ml;
(iii) serum IgG2b at a concentration of about 30-300 µg/ml; and
(iv) serum IgM at a concentration of about 50-200 µg/ml;
or
(i) serum IgG1 at a concentration of about 10-200 µg/ml;
(ii) serum IgG2a at a concentration of about 0-500 µg/ml;
(iii) serum IgG2b at a concentration of about 20-400 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

74. The mouse of any one of aspects 70 to 73, wherein the mouse expresses
(i) serum IgG1 at a concentration of about 25-350 µg/ml;
(ii) serum IgG2a at a concentration of about 0-200 µg/ml;
(iii) serum IgG2b at a concentration of about 30-800 µg/ml; and
(iv) serum IgM at a concentration of about 50-300 µg/ml;
or
(i) serum IgG1 at a concentration of about 10-600 µg/ml;
(ii) serum IgG2a at a concentration of about 0-500 µg/ml;
(iii) serum IgG2b at a concentration of about 20-700 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, the mouse expresses
(i) serum IgG1 at a concentration of about 25-150 µg/ml;
(ii) serum IgG2a at a concentration of about 0-200 µg/ml;
(iii) serum IgG2b at a concentration of about 30-300 µg/ml; and
(iv) serum IgM at a concentration of about 50-200 µg/ml;
or
(i) serum IgG1 at a concentration of about 10-200 µg/ml;
(ii) serum IgG2a at a concentration of about 0-500 µg/ml;
(iii) serum IgG2b at a concentration of about 20-400 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

The mouse of any one of aspects 70 to 73, wherein the mouse expresses Ig in the relative proportions of
(i) serum IgG1 at a concentration of about 25-350 µg/ml;
(ii) serum IgG2a at a concentration of about 0-200 µg/ml;
(iii) serum IgG2b at a concentration of about 30-800 µg/ml; and
(iv) serum IgM at a concentration of about 50-300 µg/ml;
or
(i) serum IgG1 at a concentration of about 10-600 µg/ml;
(ii) serum IgG2a at a concentration of about 0-500 µg/ml;
(iii) serum IgG2b at a concentration of about 20-700 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, the mouse expresses Ig in the relative proportions of
(i) serum IgG1 at a concentration of about 25-150 µg/ml;
(ii) serum IgG2a at a concentration of about 0-200 µg/ml;
(iii) serum IgG2b at a concentration of about 30-300 µg/ml; and
(iv) serum IgM at a concentration of about 50-200 µg/ml;
or
(i) serum IgG1 at a concentration of about 10-200 µg/ml;
(ii) serum IgG2a at a concentration of about 0-500 µg/ml;
(iii) serum IgG2b at a concentration of about 20-400 µg/ml; and
(iv) serum IgM at a concentration of about 50-700 µg/ml;
as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

75. The mouse of any one of aspects 70 to 74 for expressing said heavy chains from splenic B-cells in a mouse that produces a normal proportion or percentage of mature splenic B-cells, eg as determined by FACS.

By "normal" is meant comparable to mature splenic B-cell production in a mouse (eg, a naïve mouse) expressing only mouse antibody chains, eg, a mouse whose genome comprises only wild-type functional Ig heavy and light chain loci, eg, a wild-type mouse.

For example, at least 40, 50, 60 or 70% of total splenic B-cells produced by the mouse of the invention are mature B-cells. Splenic B-cells are B220$^+$ and express B220 at relatively high levels as the skilled person will know. Mature splenic B-cells express B220 and IgD, both at relatively high levels as will be known by the skilled person. IgM expression is relatively low in mature splenic B-cells, again as is known in the art. For example, see J Exp Med. 1999 Jul. 5; 190(1):75-89; "B cell development in the spleen takes place in discrete steps and is determined by the quality of B cell receptor-derived signals"; Loder F et al.

Optionally the mouse produces a normal ratio of T1, T2 and mature splenic B-cells, eg, as determined by FACS. For example, the mouse of the invention produces about 40-70% mature splenic B-cells. 15-35% splenic T1 cells; and 5-10% splenic T2 cells (percentage with reference to the total splenic B220-positive (high) population). For example, about 40-60% mature splenic B-cells, 15-30% splenic T1 cells; and 5-10% splenic T2 cells. By "normal" is meant comparable to a T1/T2/mature splenic B-cell proportion in a mouse (eg, a naïve mouse) expressing only mouse antibody chains, eg, a mouse whose genome comprises only wild-type functional Ig heavy and light chain loci, eg, a wild-type mouse.

76. The mouse of any one of aspects 70 to 75, wherein the mouse produces a normal proportion or percentage of mature splenic B-cells, eg as determined by FACS.

77. A mouse that expresses or for expressing immunoglobulin heavy chains comprising human variable regions, wherein the heavy chains expressed by the mouse are essentially exclusively said heavy chains comprising human variable regions and are expressed in a mouse that produces a normal proportion or percentage of mature splenic B-cells (eg, as determined by FACS); the mouse comprising an immunoglobulin heavy chain locus comprising human VH, DH and JH gene segments upstream of a mouse constant region (eg, C-mu and/or C-delta and/or C-gamma; such as (in a 5' to 3' orientation) and wherein the mouse produces a normal proportion or percentage of mature splenic B-cells.

By "normal" is meant comparable to mature splenic B-cell production in a mouse (eg, a naïve mouse) expressing only mouse antibody chains, eg, a mouse whose genome comprises only wild-type functional Ig heavy and light chain loci, eg, a wild-type mouse.

For example, at least 40, 50, 60 or 70% of total splenic B-cells produced by the mouse of the invention are mature B-cells. Splenic B-cells are B220$^+$ and express B220 at relatively high levels as the skilled person will know. Mature splenic B-cells express B220 and IgD, both at relatively high levels as will be known by the skilled person. IgM expression is relatively low in mature splenic B-cells, again as is known in the art. For example, see J Exp Med. 1999 Jul. 5; 190(1):75-89; "B cell development in the spleen takes place in discrete steps and is determined by the quality of B cell receptor-derived signals"; Loder F et al.

Optionally the mouse produces a normal ratio of T1, T2 and mature splenic B-cells, eg, as determined by FACS. For example, the mouse of the invention produces about 40-70% mature splenic B-cells, 15-35% splenic T1 cells; and 5-10% splenic T2 cells (percentage with reference to the total splenic B220-positive (high) population). For example, about 40-60% mature splenic B-cells, 15-30% splenic T1 cells; and 5-10% splenic T2 cells. By "normal" is meant comparable to a T1/T2/mature splenic B-cell proportion in a mouse (eg, a naïve mouse) expressing only mouse antibody chains, eg, a mouse whose genome comprises only wild-type functional Ig heavy and light chain loci, eg, a wild-type mouse.

78. The mouse of any one of aspects 70 to 77 for expressing said heavy chains in a mouse that produces a normal proportion or percentage of bone marrow B-cell progenitor cells (eg as determined by FACS).

In one embodiment, the mouse is for expressing said heavy chains in a mouse that produces a normal proportion or percentage of bone marrow pre-, pro and prepro-B-cells (eg as determined by FACS). See J Exp Med. 1991 May 1; 173(5):1213-25; "Resolution and characterization of pro-B and pre-pro-B cell stages in normal mouse bone marrow"; Hardy R R et al for more discussion on progenitor cells.

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

79. The mouse of any one of aspects 70 to 78, wherein the mouse produces a normal proportion or percentage of bone marrow B-cell progenitor cells (eg, as determined by FACS).

In one embodiment, the mouse produces a normal proportion or percentage of bone marrow pre-, pro and prepro-B-cells (eg as determined by FACS).

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

80. A mouse that expresses or for expressing immunoglobulin heavy chains comprising human variable regions, wherein the heavy chains expressed by the mouse are essentially exclusively said heavy chains comprising human variable regions and are expressed in a mouse that produces a normal proportion or percentage of bone marrow B-cell progenitor cells (eg, as determined by FACS), the mouse comprising an immunoglobulin heavy chain locus comprising human VH, DH and JH gene segments upstream of a mouse constant region (eg, C-mu and/or C-delta and/or C-gamma; such as (in a 5' to 3' orientation) and wherein the mouse produces a normal proportion or percentage of bone marrow B-cell progenitor cells.

In one embodiment, the mouse is for expressing said heavy chains in a mouse that produces a normal proportion or percentage of bone marrow pre-, pro and prepro-B-cells (eg as determined by FACS).

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

81. The mouse of any one of aspects 70 to 80, wherein at least 90% of the heavy chains are heavy chains comprising human variable regions.

For example, at least 90, 95, 96, 97, 98, 99 or 99.5% or 100% of the heavy chains comprise human variable regions, ie, variable regions derived from the recombination of human VH with human D and JH gene segments.

82. The mouse of any one of aspects 70 to 81, wherein the mouse constant region comprises a mouse C-mu region, a C-delta region and a C-gamma region.

In one embodiment, each of the C regions is an endogenous, mouse C-region. In one embodiment at least the C-mu and the C-delta regions are mouse C regions. This is useful for harnessing the endogenous control mechanisms involved in the development of the various B-cell types and progenitors in the spleen and bone marrow.

In one embodiment, the C-gamma region is a human C-gamma region. This is beneficial for producing class-switched gamma-type heavy chains in the mouse in which essentially all of the expressed heavy chains have human variable regions and human constant regions.

83. The mouse of any one of aspects 70 to 82, wherein there is a mouse heavy chain enhancer between the human gene segments and the mouse constant region. This is useful for harnessing the endogenous mouse antibody- and B-cell development control mechanisms.

84. The mouse of any one of aspects 70 to 83, wherein there is a mouse S-mu switch between the human gene segments and the mouse constant region.

85. The mouse of any one of aspects 70 to 84, wherein the genome of the mouse comprises endogenous mouse heavy chain locus V, D and J gene segments upstream of the human gene segments.

86. The mouse of aspect 85, wherein the mouse V, D and J gene segments are present together with the endogenous inter-gene segment sequences.

87. The mouse of aspect 85 or 86, wherein the mouse gene segments are in inverted orientation. Thus, they are inverted with respect to the wild-type orientation in a mouse genome. They are thus inverted relative to the orientation of the mouse constant region.

88. The mouse of any one of aspects 70 to 87, wherein the mouse expresses light chains comprising human variable regions (eg, kappa light chains comprising human kappa variable regions). Thus, the human variable regions are derived from the recombination of human VL and JL gene segments, eg, human Vκ and human Jκ.

89. The mouse of aspect 88, comprising human Vκ and Jκ gene segments upstream of a mouse CL (eg, endogenous Cκ); optionally wherein the human Vκ and Jκ gene segments comprise Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5. Optionally wherein the gene segments are the alleles of Table 12.

90. The mouse of any one of aspects 70 to 89, wherein the human VH, DH and JH gene segments comprise human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6. For example, the human VH, DH and JH gene segments comprise human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 3-10, 4-11, 5-12, 6-13, 1-14, 2-15, 3-16, 4-17, 5-18, 6-19, 1-20, 2-21, 3-22, 4-23, 5-24, 6-25, 1-26 and 7-27; and J1, J2, J3, J4, J5 and J6. Optionally wherein the gene segments are the alleles of Table 7.

91. Use of the mouse of any one of aspects 70 to 90 for expressing immunoglobulin heavy chains comprising human variable regions, wherein the heavy chains expressed by the mouse are essentially exclusively said heavy chains comprising human variable regions; and said heavy chains comprising human variable regions are expressed as part of serum IgG1,IgG2b and IgM (and optionally IgG2a) antibodies in the mouse. The use is non-therapeutic, non-diagnostic and non-surgical use.

In one embodiment, the use comprises immunising the mouse with an antigen (eg, a human antigen) and isolating an IgG1 antibody that specifically binds the antigen.

In one embodiment, the use comprises immunising the mouse with an antigen (eg, a human antigen) and isolating an IgG2a antibody that specifically binds the antigen.

In one embodiment, the use comprises immunising the mouse with an antigen (eg, a human antigen) and isolating an IgG2b antibody that specifically binds the antigen. Optionally, the use comprises making a derivative of the isolated antibody. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

92. Use of the mouse of any one of aspects 70 to 90 for expressing immunoglobulin heavy chains comprising human variable regions, wherein the heavy chains expressed by the mouse are essentially exclusively said heavy chains comprising human variable regions and are expressed in a mouse that produces a normal proportion or percentage of mature splenic B-cells. The use is non-therapeutic, non-diagnostic and non-surgical use.

In one embodiment, the use further comprises isolating splenic tissue (eg, the spleen) from the mouse; optionally followed by isolating at least one antigen-specific B-cell from the tissue, wherein the B-cell(s) expresses an antibody that specifically binds a predetermined antigen. In one example, the use comprises immunising the mouse with the antigen prior to isolating the splenic tissue. In an example, the use comprises isolating an antibody produced by the B-cell (or by a hybridoma produced by fusion of the B-cell with a myeloma cell). Optionally, the use comprises making a derivative of the isolated antibody. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

93. Use of the mouse of any one of aspects 70 to 90 for expressing immunoglobulin heavy chains comprising human variable regions, wherein the heavy chains expressed by the mouse are essentially exclusively said heavy chains comprising human variable regions and are expressed in a mouse that produces a normal proportion or percentage of bone marrow B-cell progenitor cells. The use is non-therapeutic, non-diagnostic and non-surgical use.

94. Use of the mouse of any one of aspects 70 to 90 for the purpose stated in one or more of aspects 70, 71, 73, 75 and 78.

The expression (eg, percentage expression or expression proportion or level) of Ig can be determined at the level of antibody chain mRNA transcripts in B-cells (eg, peripheral blood lymphocytes). Alternatively or additionally, the percentage expression is determined at the level of antibody in serum or blood of the vertebrates. Additionally or alternatively, the expression can be determined by FACS analysis of B cells.

In these aspects, "heavy chains comprising human variable regions" means variable regions derived from the recombination of human VH, D and JH gene segments.

"Essentially exclusively" the expressed heavy chains comprise human variable regions, ie, there is only a relatively very low or even no endogenous mouse heavy chain variable region expression. For example, at least 90, 95, 96, 97, 98, 99 or 99.5% or 100% of the heavy chains are heavy chains comprising human variable regions. In one embodiment, at least 90% of the heavy chains are heavy chains comprising human variable regions. The percentage expression can be determined at the level of heavy chain mRNA transcripts in B-cells (eg, peripheral blood lymphocytes). Alternatively or additionally, the percentage expression is determined at the level of heavy chains or antibodies in serum or blood of the mice. Additionally or alternatively, the expression can be determined by FACS analysis of B-cells.

The mouse can comprise any endogenous heavy chain locus in which human V, D and J gene segments are present, as described herein. In one example, the mouse genome comprises a mouse heavy chain locus in which at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6 are upstream of the mouse constant region.

The vertebrate in these aspects is, for example naïve (ie, not immunised with a predetermined antigen, as the term is understood in the art; for example, such a vertebrate that has been kept in a relatively sterile environment as provided by an animal house used for R&D). In another example, the vertebrate has been immunised with a predetermined antigen, eg, an antigen bearing a human epitope.

In one embodiment, the heavy chains, together with light chains expressed in the mice of the invention, form antibodies (Ig). The light chains can be expressed from any transgenic light chain locus as herein described. For example the genome of the mouse comprises a heavy chain locus in which is a chimaeric immunoglobulin heavy chain locus comprising one or more human V gene segments, one or more human D gene segments and one or more human J gene segments upstream of a mu constant region of said non-human species; endogenous heavy chain expression has been substantially inactivated; and the heavy chain locus comprises an Eμ enhancer of said non-human vertebrate species.

In one embodiment of any aspect, endogenous light chain (eg, kappa and/or lambda) expression is substantially inactive or inactivated, for example using method as described herein. In this case, less than 10, 5, 4, 3, 2, 1 or 0.5% of such endogenous lambda light chains are expressed or expressible. Additionally or alternatively, less than 10, 5, 4, 3, 2, 1 or 0.5% of such endogenous kappa light chains are expressed or expressible. In one example, there is complete inactivation of endogenous kappa and/or lambda expression so no such light chains are expressed or expressible.

In one embodiment, the genome of the mouse comprises human kappa gene segments (optionally the alleles of Table 12)
  (i) Vκ1-5, Vκ1-6. Vκ1-8 and Vκ1-9 (and optionally Vκ5-2 and Vκ4-1); or
  (ii) Vκ1-5, Vκ1-6, Vκ1-8, Vκ1-9, Vκ3-11, Vκ1-12, Vκ3-15, Vκ1-16, Vκ1-17, Vκ3-20 (and optionally Vκ 2-24 and/or Vκ1-13); or
  (iii) Vκ1-5, Vκ1-6, Vκ1-8, Vκ1-9, Vκ3-11, Vκ1-12, Vκ3-15, Vκ1-16, Vκ1-17, Vκ3-20, Vκ 2-24, Vκ1-27, Vκ2-28, Vκ2-30 and Vκ1-33 (and optionally Vκ 2-29 and/or Vκ2-40 and/or Vκ1-39);
  and optionally
  (iv) Jκ1, Jκ2, Jκ3, Jκ4 and Jκ5.

In one embodiment, the genome also comprises (i) at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6 (optionally the alleles of Table 7) and (ii) at least human gene segments Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5 (optionally the alleles of Table 12). As demonstrated in Example 16, such mice are fully functional in the aspect of rearrangement, BCR signalling and B cell maturation. Greater than 90% of the antibodies expressed by the mice comprised human heavy chain variable regions and human kappa light chain variable regions. These mice are, therefore, very useful for the selection of antibodies having human variable regions that specifically bind human antigen following immunisation of the mice with such antigen. Following isolation of such an antibody, the skilled person can replace the mouse constant regions with human constant regions using conventional techniques to arrive at totally human antibodies which are useful as drug candidates for administration to humans (optionally following mutation or adaptation to produce a further derivative, eg, with Fc enhancement or inactivation or following conjugation to a toxic payload or reporter or label or other active moiety).

In one embodiment, the genome also comprises a human iEκ and/or human 3'Eκ downstream of the human J gene segments in the locus.

The invention also includes the following clauses:

Clause 1. A mouse that expresses immunoglobulin heavy chains containing human variable regions,
  wherein the mouse comprises a genome that includes an immunoglobulin heavy chain locus comprising human VH, DH, and JH gene segments positioned upstream to a mouse constant region;
  wherein the mouse expresses immunoglobulin heavy chains, characterized in that at least 90% of the immunoglobulin heavy chains expressed by the mouse comprise a human variable region; and
  wherein the mouse expresses serum IgG1, IgG2b, and IgM antibodies comprising said heavy chains containing a human variable region.

Clause 2. A mouse that expresses immunoglobulin heavy chains containing human variable regions,
  wherein the mouse comprises a genome that includes an immunoglobulin heavy chain locus comprising human VH, DH, and JH gene segments which are positioned upstream to a mouse constant region;
  wherein the mouse expresses immunoglobulin heavy chains, characterized in that at least 90% of the immunoglobulin heavy chains expressed by the mouse comprise a human variable region; and
  wherein the mouse produces a normal proportion of mature splenic B-cells;
  wherein said normal proportion is a proportion of mature splenic B-cells produced by a mouse that expresses immunoglobulin heavy chains containing mouse variable regions and does not express immunoglobulin heavy chains containing human variable regions.

Clause 3. A mouse that expresses immunoglobulin heavy chains containing human variable regions,
  wherein the mouse comprises a genome that includes an immunoglobulin heavy chain locus comprising human VH, DH, and JH gene segments which are positioned upstream to a mouse constant region;
  wherein the mouse expresses immunoglobulin heavy chains, characterized in that it at least 90% of the immunoglobulin heavy chains expressed by the mouse comprise a human variable region; and
  wherein the mouse produces a normal proportion of bone marrow B-cell progenitor cells;
  wherein the normal proportion is a proportion of bone marrow B-cell progenitor cells produced by a mouse that expresses immunoglobulin heavy chains containing mouse variable regions and does not expresses immunoglobulin heavy chains containing human variable regions.

Clause 4. The mouse of any of the preceding clauses, wherein the mouse expresses a normal proportion of IgG1, IgG2b, and IgM in a sample of serum obtained from the mouse;

wherein the normal proportion is as produced by a mouse that expresses immunoglobulin heavy chains containing mouse variable regions and does not expresses immunoglobulin heavy chains containing human variable regions.

Clause 5. The mouse of any of the preceding clauses, wherein the mouse constant region is C-mu, C-delta, and/or C-gamma.

Clause 6. The mouse of clause 5, wherein the mouse constant region is at least C-mu, C-delta and C-gamma.

Clause 7. The mouse of any of the preceding clauses, wherein the mouse constant region is an endogenous mouse C-region.

Clause 8. The mouse of any of the preceding clauses, wherein the mouse expresses a human C-gamma region.

Clause 9. The mouse of any of the preceding clauses, wherein the mouse is a naïve mouse.

Clause 10. The mouse of clause 1, wherein the mouse expresses serum IgG2a comprising said heavy chains containing a human variable region.

Clause 11. The mouse of any of the preceding clauses, wherein the mouse expresses Ig subtypes in a relative proportion of
  (i) serum IgG1 at a concentration of about 25-350 µg/ml;
  (ii) serum IgG2a at a concentration of about 0-200 µg/ml;
  (iii) serum IgG2b at a concentration of about 30-800 µg/ml; and
  (iv) serum IgM at a concentration of about 50-300 µg/ml;
  Or
  (i) serum IgG1 at a concentration of about 10-600 µg/ml;
  (ii) serum IgG2a at a concentration of about 0-500 µg/ml;
  (iii) serum IgG2b at a concentration of about 20-700 µg/ml; and
  (iv) serum IgM at a concentration of about 50-700 µg/ml;
  as determined by immunoglobulin capture on a plate followed by incubation with an anti-mouse isotype-specific antibodies each comprising a label and quantification of each immunoglobulin based on the level of each label.

Clause 12. The mouse of any of the preceding clauses, wherein the mouse expresses Ig subtypes in a relative proportion of
  (i) total serum IgG and IgM at a concentration of about 200-2500 µg/ml; and
  (ii) serum IgM at a concentration of about 100-800 µg/ml;
  as determined by immunoglobulin capture on a plate followed by incubation with an anti-mouse isotype-specific antibodies each comprising a label and quantification of each immunoglobulin based on the level of each label.

Clause 13. The mouse of any of the preceding clauses, wherein the mouse expresses said immunoglobulin heavy chains from splenic B-cells and wherein the mouse produces a normal proportion of mature splenic B-cells in total spleen cells comprising mature B-cells, and splenic T1 and T2 cells.

Clause 14. The mouse of any one of clauses 1-3, wherein, at least 95, 96, 97, 98, 99, or 99.5% of the immunoglobulin heavy chains expressed by the mouse are immunoglobulin heavy chains comprising human variable regions.

Clause 15. The mouse of any of the preceding clauses, wherein a mouse immunoglobulin heavy chain enhancer is positioned in said mouse heavy chain immunoglobulin locus between the human VH, DH, and JH gene segments and the mouse constant region.

Clause 16. The mouse of any of the preceding clauses, wherein a mouse S-mu switch is positioned in said mouse heavy chain immunoglobulin locus between the human VH, DH, and JH gene segments and the mouse constant region.

Clause 17. The mouse of any of the preceding clauses, wherein endogenous mouse immunoglobulin heavy chain V, D and J gene segments are positioned in said mouse heavy chain immunoglobulin locus upstream to the human VH, DH, and JH gene segments.

Clause 18. The mouse of clause 17, wherein the mouse immunoglobulin heavy chain V, D and J gene segments are present in said mouse heavy chain immunoglobulin locus with endogenous inter-gene segment sequences.

Clause 19. The mouse of clause 17 or 18, wherein the mouse immunoglobulin heavy chain V, D and J gene segments are positioned in said mouse heavy chain immunoglobulin locus in an orientation that is inverted relative to its natural endogenous orientation.

Clause 20. The mouse of any of the preceding clauses, wherein the mouse expresses light chains containing human kappa variable regions.

Clause 21. The mouse of clause 20, wherein the mouse expresses immunoglobulin light chains derived from recombination of Vκ with human Jκ.

Clause 22. The mouse of any of the preceding clauses, wherein the mouse expresses light chains containing human lambda variable regions.

Clause 23. The mouse of clause 22, wherein the mouse expresses immunoglobulin light chains derived from recombination of Vλ with human Jλ.

Clause 24. The mouse of clause 21, comprising a genome that includes human Vκ and Jκ gene segments positioned in said mouse heavy chain immunoglobulin locus upstream to a mouse CL.

Clause 25. The mouse of clause 24, wherein the mouse CL is an endogenous Cκ.

Clause 26. The mouse of clauses 24 or 25, wherein the human Vκ and Jκ gene segments comprise Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5.

Clause 27. The mouse of any the preceding clauses, wherein the human VH, DH and JH gene segments contain
  human VH gene segments: VH2-5, 7-4-1, 4-4, 1-3, 1-2, 6-1;
  human DH gene segments: D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and
  human JH gene segments: J1, J2, J3, J4, J5 and J6.

Clause 28. A method for obtaining one or more immunoglobulin heavy chains containing human variable regions, comprising providing the mouse of any of the preceding clauses and
  isolating one or more immunoglobulin heavy chains.

Clause 29. The method of clause 28, wherein each immunoglobulin heavy chain is included in an antibody.

Clause 30. The method of clause 29, wherein said heavy chain and/or said antibody containing said heavy chain is modified after said isolating.

Clause 31. The method of clause 28, wherein a step of immunizing the mouse with an antigen is performed before the step of isolating the immunoglobulin heavy chains.

Clause 31a. The method of clause 30, wherein the antigen is a human antigen.

Clause 32. The method of clause 30, 31, or 31a, wherein the immunoglobulin heavy chains are included in an IgG1 antibody, antibody fragment, or antibody derivative that specifically binds the antigen.

Clause 33. The method of clause 30, 31, or 31a, wherein the immunoglobulin heavy chains are included in an IgG2a antibody, antibody fragment, or antibody derivative that specifically binds the antigen.

Clause 34. The method of clause 30, 31, or 31a, wherein the immunoglobulin heavy chains are included in an IgG2b antibody, antibody fragment, or antibody derivative that specifically binds the antigen.

Clause 35. The method of clause 30, 31, or 31a, wherein the immunoglobulin heavy chains are included in an IgM antibody, antibody fragment, or antibody derivative that specifically binds the antigen.

Clause 36. An antibody or immunoglobulin heavy chain isolated in the method of any one of clauses 28 to 35, or a antigen-binding fragment or derivative of the antibody or heavy chain.

Clause 37. A pharmaceutical composition comprising the antibody, antibody fragment, or antibody derivative of clause 36 and a pharmaceutically acceptable carrier, excipient, or diluent.

Clause 38. A method for isolating splenic tissue comprising providing the mouse of 1 to 27,
    collecting a spleen or portion thereof from the mouse, and
    obtaining tissue from the spleen or portion.

Clause 39. The method of clause 38, further comprising isolating at least one antigen-specific B-cell from the splenic tissue, wherein the B-cell expresses a heavy chain containing a human variable region.

Clause 40. The method of clause 38 or 39, wherein a step of immunizing the mouse with an antigen is performed before the step of collecting a spleen from the mouse.

Clause 41. The method of clause 40, wherein the antigen is a human antigen.

Clause 42. The method of clause 40 or 41 wherein the at least one antigen-specific B-cell produces an IgG1, IgG2a, IgG2b or IgM antibody comprising said heavy chain, wherein the antibody specifically binds the antigen.

Clause 43. The method of clauses 38 to 42, wherein the at least one antigen-specific B-cell that produces said heavy chain is fused with an immortal myeloma cell to produce a hybridoma cell.

Clause 44. The method of clauses 38 to 43, further comprising a step of isolating an immunoglobulin heavy chain from the B-cell or the hybridoma cell.

Clause 45. An antibody or immunoglobulin heavy chain isolated in the method of clause 44, or a antigen-binding fragment or derivative of the antibody or heavy chain.

Clause 46. A pharmaceutical composition comprising the antibody, antibody fragment, or antibody derivative of clause 45 and a pharmaceutically acceptable carrier, excipient, or diluent.

Clause 47. A method for obtaining a humanised antibody, comprising
    selecting a mouse that expresses immunoglobulin heavy chains containing human variable regions,
    wherein the mouse comprises a genome that includes an immunoglobulin heavy chain locus comprising human VH, DH, and JH gene segments positioned upstream to a mouse constant region,
    wherein the mouse expresses immunoglobulin heavy chains, characterised in that at least 90% of the immunoglobulin heavy chains expressed by the mouse are immunoglobulin heavy chains containing a human variable region,
    wherein the mouse expresses serum IgG1, IgG2b, and IgM antibodies comprising said heavy chains containing a human variable region,
    wherein the mouse produces a normal proportion of mature splenic B-cells,
    wherein the mouse produces a normal proportion of bone marrow B-cell progenitor cells, and
    wherein the mouse expresses a normal proportion of IgG1, IgG2a, IgG2b, and IgM in a sample of serum obtained from the mouse, and
    wherein each said normal proportion is a proportion produced by a mouse that expresses immunoglobulin heavy chains containing mouse variable regions and does not expresses immunoglobulin heavy chains containing human variable regions;
    collecting serum from said mouse; and
    obtaining a pool of humanised antibodies comprising IgG1, IgG2b, and IgM antibodies from the serum.

Clause 48. The method of clause 47, comprising a step of immunizing the mouse with an antigen before the step of collecting serum from said mouse.

Clause 49. The method of clause 48, further comprising steps of
    contacting said pool of humanised antibodies with said antigen;
    binding said antigen with a humanised antibody in said pool of humanised antibodies; and
    isolating the humanised antibody that binds to said antigen.

Clause 50. The method of clause 49, further comprising steps of
    contacting the humanised antibody that binds to said antigen with an isotype-specific antibody, wherein the isotype-specific antibody recognizes IgG1 IgG2a, IgG2b, or IgM; and
    isolating the humanised antibody that binds to said isotype-specific antibody.

Clause 51. The method of clause 48, further comprising the steps of
    collecting the spleen or tissue thereof from said mouse,
    isolating B-cells from splenic tissue,
    fusing said B-cells with immortal myeloma cells to produce hybridoma cells expressing a pool of humanised antibodies comprising IgG antibodies from the serum, wherein the pool of antibodies is used in the method of clause 48.

Clause 52. The method of any of clauses 47-51, wherein said selected mouse comprises mouse immunoglobulin heavy chain V, D and J gene segments which are positioned in said mouse heavy chain immunoglobulin locus in an orientation that is inverted relative to its natural endogenous orientation.

Clause 53. The method of any of clauses 47-52 wherein the mouse expresses Ig subtypes in a relative proportion of
    (i) serum IgG1 at a concentration of about 25-350 µg/ml;
    (ii) serum IgG2a at a concentration of about 0-200 µg/ml;
    (iii) serum IgG2b at a concentration of about 30-800 µg/ml; and
    (iv) serum IgM at a concentration of about 50-300 µg/ml;
    Or
    (i) serum IgG1 at a concentration of about 10-600 µg/ml;
    (ii) serum IgG2a at a concentration of about 0-500 µg/ml;

(iii) serum IgG2b at a concentration of about 20-700 µg/ml; and
(iv) serum IgM at a concentration of about 50-700 µg/ml;
as determined by immunoglobulin capture on a plate followed by incubation with an anti-mouse isotype-specific antibodies each comprising a label and quantification of each immunoglobulin based on the level of each label.

Clause 54. The method of any one of clauses 47 to 53, wherein, at least 95, 96, 97, 98, 99, or 99.5% of the immunoglobulin heavy chains expressed by the mouse are immunoglobulin heavy chains comprising human variable regions.

Clause 55. The method of any clauses 47-54, wherein a mouse immunoglobulin heavy chain enhancer is positioned in said mouse heavy chain immunoglobulin locus between the human VH. DH, and JH gene segments and the mouse constant region.

Clause 56. The method of any of clauses 47-55, wherein a mouse S-mu switch is positioned in said mouse heavy chain immunoglobulin locus between the human VH, DH, and JH gene segments and the mouse constant region.

Clause 57. The method of any of clauses 47-56, wherein endogenous mouse immunoglobulin heavy chain V, D and J gene segments are positioned in said mouse heavy chain immunoglobulin locus upstream to the human VH, DH, and JH gene segments.

Clause 58. The method of clause 57, wherein the mouse immunoglobulin heavy chain V, D and J gene segments are present in said mouse heavy chain immunoglobulin locus with endogenous inter-gene segment sequences.

Clause 59. The method of clause 57 or 58, wherein the mouse immunoglobulin heavy chain V, D and J gene segments are positioned in said mouse heavy chain immunoglobulin locus in an orientation that is inverted relative to its natural endogenous orientation.

Clause 60. The method of any of clauses 47-59, wherein the mouse expresses light chains containing human kappa variable regions.

Clause 61. The method of clause 60, wherein the mouse expresses immunoglobulin light chains containing human Jκ.

Clause 62. The method of any of clauses 47-51, wherein the mouse expresses light chains containing human lambda variable regions.

Clause 63. The method of clause 62, wherein the mouse expresses immunoglobulin light chains containing human Jλ.

Clause 64. The method of clause 61, comprising a genome that includes human Vκ and Jκ gene segments positioned in said mouse heavy chain immunoglobulin locus upstream to a mouse CL.

Clause 65. The mouse of clause 64, wherein the mouse CL is an endogenous Cκ.

Clause 66. The mouse of clauses 64 or 65, wherein the human Vκ and Jκ gene segments comprise Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5.

Clause 67. The method of any of clauses 47-51, wherein the human VH, DH and JH gene segments contain
human VH gene segments: VH2-5, 7-4-1, 4-4, 1-3, 1-2, 6-1;
human DH gene segments: D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and
human JH gene segments: J1, J2, J3, J4, J5 and J6.

Non-Human Vertebrates Expressing Kappa & Lambda Variable Regions
(i) K and L Chains Produced in Human-Like Ratios This aspect of the invention is useful for producing light chains that are not skewed to non-human-like ratios. For example, in mice kappa-type light chains predominate by far over lambda-type light chains (typically of the order of 95% kappa light chains:5% lambda light chains in a wild-type mouse). Humans, on the other hand, typically display around 60% kappa:around 40% lambda. Thus, lambda expression is much higher than found in a mouse. It would be desirable to provide a non-human vertebrate, such as a mouse or a rat, in which a higher proportion of lambda-type light chains can be expressed. This is useful when the vertebrate expresses light chains bearing human lambda variable regions and other light chains bearing human kappa variable regions. To this end, the inventors have demonstrated for the first time such a vertebrate that expresses elevated lambda light chains, and thus the invention provides:

A non-human vertebrate (eg, a mouse or rat) whose genome comprises an Ig gene segment repertoire produced by targeted insertion of human Ig gene segments into one or more endogenous Ig loci, the genome comprising human Vλ and Jλ gene segments provided by insertion into an endogenous light chain locus of the vertebrate upstream of a constant region, the genome comprising human Vκ and Jκ gene segments provided by insertion into an endogenous light chain locus of the vertebrate upstream of a constant region, wherein the vertebrate expresses immunoglobulin light chains comprising kappa light chain variable regions and immunoglobulin light chains comprising lambda light chain variable regions, wherein more than 20% of the light chains expressed by the vertebrate comprise lambda variable regions (eg, as determined by FACS of splenic B The remaining light chains express kappa variable regions.

WO03047336 teaches the desirability of producing human-like kappa:lambda ratios, but this does not provide an enabled or plausible disclosure of how to achieve this.
(ii) K and L Chains Produced with Normal B-Cell Compartments The inventors have successfully generated non-human vertebrates containing targeted insertion of human V and J lambda gene segments to enable expression of light chains comprising human lambda variable regions by normal (ie, comparable to wild-type vertebrate) B-cell compartments. Thus, the inventors have provided such vertebrates that can usefully produce such light chains with good repertoires and more reliably than prior art transgenic non-human vertebrates that display comprised B-cell compartments of reduced size and maturity, and indeed which may not even produce light chains having human lambda variable regions. Thus, the invention provides:

A non-human vertebrate (eg, a mouse or rat) whose genome comprises an Ig gene segment repertoire produced by targeted insertion of human Ig gene segments into one or more endogenous Ig loci, the genome comprising human Vλ and Jλ gene segments provided by insertion into an endogenous light chain locus of the vertebrate upstream of a constant region, the genome comprising human Vκ and Jκ gene segments provided by insertion into an endogenous light chain locus of the vertebrate upstream of a constant region, wherein the vertebrate expresses immunoglobulin light chains comprising kappa light chain variable regions and immunoglobulin light chains comprising lambda light chain variable regions, and wherein the vertebrate produces a normal proportion or percentage of mature splenic B-cells (eg, as determined by FACS of splenic B cells).

With regard to non-human vertebrates (i) and (ii), the following embodiments are contemplated (unless specified, each embodiment applies to (i) or (ii)):

In an embodiment, the human Vλ and Jλ insertion comprises at least the functional human V and J gene segments comprised by a human lambda chain Ig locus from Vλ3-27 to Cλ7.

In an embodiment, the human Vλ and Jλ insertion comprises at least human V gene segments Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 and Vλ3-1, optionally the alleles of Table 18.

In an embodiment, the human Vλ and Jλ insertion comprises one, more or all of human J gene segments Jλ1, Jλ2, Jλ3, Jλ6 and Jλ7.

In an embodiment, the human Vλ and Jλ insertion comprises an insertion of a human Jλ-Cλ cluster, wherein the cluster comprises the J and C gene segments from Jλ1 to Cλ7.

In an embodiment, the human Vλ and Jλ insertion comprises an insertion of a human Eλ enhancer. For example, the Eλ enhancer is provided in germline configuration with respect to a human Jλ7 that is also comprised by the insertion. For example, the Eλ enhancer is provided in germline configuration with respect to a human Jλ-Cλ cluster that is also comprised by the insertion, wherein the cluster comprises Jλ1 to Cλ7 in human germline configuration. In a human germline configuration the Eλ enhancer is 3' of the Jλ-Cλ cluster.

In an embodiment or vertebrate (i) or (ii), the human Vλ and Jλ insertion is provided by an insertion of a sequence corresponding to coordinates 22886217 to 23327884 of human chromosome 22.

In an embodiment or vertebrate (ii), the human Vλ and Jλ insertion is provided by an insertion of a sequence corresponding to coordinates 23064876 to 23327884 of human chromosome 22.

In an embodiment, the human Vκ and Jκ insertion comprises at least the functional human V and J gene segments comprised by a human kappa chain Ig locus from Vκ1-33 to Jκ5.

In an embodiment, the human Vκ and Jκ insertion comprises at least human V gene segments Vκ1-33, Vκ2-30, Vκ2-29, Vκ2-28, Vκ1-27, Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2 and Vκ4-1, optionally the alleles of Table 12.

In an embodiment, the human Vκ and Jκ insertion comprises one, more or all of human J gene segments Jκ1, Jκ2, Jκ3, Jκ4 and Jκ5, optionally the alleles of Table 12.

In an embodiment, more than 30, 35, 40, 45 or 50% of the light chains expressed by the vertebrate comprise lambda variable regions.

In an embodiment, from 20 to 40, 45 or 50% of the light chains expressed by the vertebrate comprise lambda variable regions. In an embodiment, from 30 to 40, 45 or 50% of the light chains expressed by the vertebrate comprise lambda variable regions.

In an embodiment, said kappa light chain variable regions are human kappa light chain variable regions.

In an embodiment, the human Vκ and Jκ gene segments are in an endogenous kappa light chain locus of the vertebrate upstream of a kappa constant region.

In an embodiment, the human Vλ and Jλ gene segments are in an endogenous kappa light chain locus of the vertebrate.

In an embodiment, the human Vλ and Jλ gene segments are in an endogenous lambda light chain locus of the vertebrate.

In an embodiment, the vertebrate expresses light chains comprising human kappa variable regions and expresses light chains comprising human lambda variable regions. In an example, endogenous (non-human vertebrate) kappa chain expression is substantially inactive or is inactive and/or endogenous (non-human vertebrate) lambda chain expression is substantially inactive or is inactive. Where the vertebrate is a mouse, mouse lambda chain expression is typically very low (around 5% or less) and in this case it may not be necessary to engineer the mouse genome to further inactivate endogenous lambda chain expression. Thus, where the vertebrate is s mouse, endogenous kappa chain expression is substantially inactive or is inactive and mouse lambda chain expression is 5% or less of all light chain expression.

In an embodiment, the vertebrate produces a normal proportion or percentage of mature splenic B-cells. For example, this can be determined by FACS of splenic B cells isolated from the vertebrate.

In an embodiment, the vertebrate produces a normal ratio of T1, T2 and mature splenic B-cells. For example, this can be determined by FACS of splenic B cells isolated from the vertebrate.

In an embodiment, at least 40, 50, 60 or 70% of total splenic B-cells produced by the vertebrate are mature B-cells. For example, this can be determined by FACS of splenic B cells isolated from the vertebrate.

Further Statements of Invention

In one embodiment the invention relates to the following:

A non-human vertebrate (eg, a mouse or rat) or vertebrate cell whose genome comprises human VH, D and JH gene segments upstream of a constant region at a heavy chain locus and/or human VL and JL gene segments upstream of a constant region at a light chain locus, wherein the gene segments are operably linked to the constant region thereof so that the vertebrate or cell is capable of expressing immunoglobulin heavy and/or light chains comprising human VH and VL domains respectively, wherein the heavy chain locus comprises a human VH gene segment capable of recombining with a human D and JH gene segment to produce a VH domain, wherein the light chain locus comprises a human VL gene segment capable of recombining with a human JL gene segment to produce a VL domain, or wherein the cell can develop into a vertebrate that expresses said heavy and light chain variable domains.

A non-human vertebrate (eg, a mouse or rat) or vertebrate cell whose genome comprises human VH, D and JH gene segments upstream of a constant region at a heavy chain locus, wherein the gene segments are operably linked to the constant region thereof so that the vertebrate or cell is capable of expressing immunoglobulin heavy chains comprising human VH domains, wherein the heavy chain locus comprises a human 01 allele VH gene segment capable of recombining with a human D and JH gene segment to produce a VH domain, or wherein the cell can develop into a vertebrate that expresses said heavy chain variable domain.

A non-human vertebrate (eg, a mouse or rat) or vertebrate cell whose genome comprises VL and JL gene segments upstream of a constant region at a light chain locus, wherein the gene segments are operably linked to the constant region thereof so that the vertebrate or cell is capable of expressing immunoglobulin light chains comprising human VL domains, wherein the light chain locus comprises a human 01 allele VL gene segment capable of recombining with a human JL gene segment to produce a VL domain, or wherein the cell can develop into a vertebrate that expresses said light chain variable domain.

Optionally the vertebrate or cell has a genome comprising the heavy chain locus and the light chain locus defined above and therefore comprises a heavy chain locus comprising a human 01 allele VH gene segment capable of recombining with a human D and JH gene segment to produce a VH domain and a light chain locus comprising a human 01 allele VL gene segment capable of recombining with a human JL gene segment to produce a VL domain.

In an alternative embodiment, the invention relates to a non-human vertebrate or vertebrate cell (e.g. a mouse cell or rat cell) whose genome comprises one or more human VH gene segments, one or more human JH gene segments and one or more human D gene segments upstream of a constant region at a heavy chain, wherein the gene segments are operably linked to the constant region thereof so that the cell or vertebrate is capable of producing an antibody heavy chain, or where the cell can develop into a vertebrate that expresses an antibody heavy chain, wherein said one or more human VH gene segments of the heavy chain locus comprise or consist of one, more or all human VH gene segments selected from the group consisting of VH3-23*04, VH7-4-1*01, VH4-4*02, VH1-3*01, VH3-13*01, VH3-7*01, VH3-20*d01 and VH3-9*01.

In an embodiment of the invention, the VH gene segments are selected from the group consisting of VH3-23*04, VH7-4-1*01, VH4-4*02, VH1-3*01, VH3-13*01, VH3-7*01 and VH3-20*d01.

For embodiments of the invention, which, for example, define human heavy chain gene segments only, the light chain locus can comprise rearranged or unrearranged VL and JL gene segments, e.g. a single rearranged VJ (such as a single rearranged Vk1-39/J). Additionally or alternatively the light chain locus can be randomly integrated. In another embodiment the VL and JL segments are upstream of an endogenous constant light gene segment.

In a further alternative embodiment, the invention relates to a non-human vertebrate or vertebrate cell (e.g. a mouse cell or rat cell) whose genome comprises one or more human Jκ gene segments and one or more human Vκ gene segments upstream of a constant region at a light chain locus, wherein the gene segments are operably linked to the constant region thereof so that the cell or vertebrate is capable of producing an antibody light chain, or where the cell can develop into a vertebrate that expresses an antibody light chain, wherein said one or more human Vκ gene segments comprise or consist of one, more or all human Vκ gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1D-16*01 and Vκ1-9*d01.

In an alternative embodiment, the invention relates to a non-human vertebrate (eg, a mouse or rat) or vertebrate cell whose genome comprises human VH, D and JH gene segments upstream of a constant region at a heavy chain locus, wherein the JH gene segments comprise JH1*01, JH2*01, JH3*02, JH4*02, JH5*02 and/or JH6*01 or JH6*02 and the gene segments are operably linked to the constant region thereof so that the vertebrate or cell is capable of expressing immunoglobulin heavy chains comprising human VH domains, wherein the heavy chain locus comprises a human VH gene segment capable of recombining with a human D and one of said JH gene segments to produce a VH domain, or wherein the cell can develop into a vertebrate that expresses said heavy chain variable domain.

In a preferred embodiment, the JH gene segments are JH1*01, JH2*01, JH3*02, JH4*02, JH5*02 and JH6*02. In another embodiment, the JH gene segments are JH1*01, JH2*01. JH3*02, JH4*02, JH5*02 and JH6*01.

In one embodiment, the non-human vertebrate further comprises one or more of the VH gene segments and/or one or more of the D gene segments from Table 7. In a further embodiment, the non-human vertebrate further comprises the VH gene segments and D gene segments from Table 3.

A non-human vertebrate (eg, a mouse or rat) or vertebrate cell whose genome comprises VL and JL gene segments upstream of a constant region at a light chain locus, wherein the JL gene segments comprise Jκ1*01, Jκ2*01, Jκ3*01, Jκ4*01 and/or Jκ5*01 and the gene segments are operably linked to the constant region thereof so that the vertebrate or cell is capable of expressing immunoglobulin light chains comprising human VL domains, wherein the light chain locus comprises a human VL gene segment capable of recombining with one of said human JL gene segments to produce a VL domain, or wherein the cell can develop into a vertebrate that expresses said light chain variable domain.

In one embodiment, the non-human vertebrate further comprises one or more or all Vκ gene segments from Table 12. In a further embodiment, the non-human vertebrate further comprises the Vκ gene segments from Table 10 or 11.

Optionally the vertebrate or cell has a genome comprising the heavy chain locus and the light chain locus defined above and therefore comprises a heavy chain locus comprising a human VH gene segment capable of recombining with a human D and one of said JH gene segments to produce a VH domain and a light chain locus comprising a human VL gene segment capable of recombining with one of said human JL gene segments to produce a VL domain.

It is envisaged that in all embodiments of the invention, the genome of the cell or vertebrate in accordance with the invention may not comprise a second human allele of one, more or all of the human gene segment(s).

In all embodiments of the invention, the human JH gene segments, D gene segments and VH gene segments can be upstream of a constant region at an endogenous heavy chain locus and/or the human Jκ gene segments and Vκ gene segments can be upstream of a constant region at an endogenous light chain locus.

In one embodiment, the endogenous light chain locus is the endogenous kappa locus, and in another embodiment it is the endogenous lambda locus.

Allele Combinations

In one embodiment, the allele of the gene segment is a d01 allele, optionally a d01 allele disclosed in Table 7, Table 12 or Table 18.

In one embodiment, vertebrate or cell has a genome further comprising a 02, 03, 04, 05, 10, 12, 18 or d03 allele disclosed in Table 7, Table 12 or Table 18.

The preferred alleles of the invention are set out in Tables 1 to 18 as follows:

TABLE 1

| IgH Alleles #1 - S1 alleles | |
|---|---|
| | Allele |
| $J_H6$ | 02 |
| $J_H5$ | 02 |

TABLE 1-continued

IgH Alleles #1 - S1 alleles

| | Allele |
|---|---|
| $J_H4$ | 02 |
| $J_H3$ | 02 |
| $J_H2$ | 01 |
| $J_H1$ | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-2 | 02 |
| D1-1 | 01 |
| $V_H6-1$ | 01 |
| $V_H1-2$ | 02 or 04 |
| $V_H1-3$ | 01 |
| $V_H4-4$ | 02 |
| $V_H7-4$ | 01 |
| $V_H2-5$ | 01 or 10 |

In an alternative Table 1, the JH6 allele can be JH6*01.

TABLE 2

IgH Alleles #2 - S2 alleles

| | ID |
|---|---|
| $J_H6$ | 02 |
| $J_H5$ | 02 |
| $J_H4$ | 02 |
| $J_H3$ | 02 |
| $J_H2$ | 01 |
| $J_H1$ | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-2 | 02 |
| D1-1 | 01 |
| $V_H6-1$ | 01 |
| $V_H1-2$ | 02 or 04 |
| $V_H1-3$ | 01 |
| $V_H4-4$ | 02 |
| $V_H7-4$ | 01 |
| $V_H2-5$ | 01 or 10 |
| $V_H3-7$ | 01 |

TABLE 2-continued

IgH Alleles #2 - S2 alleles

| | ID |
|---|---|
| $V_H1-8$ | 01 |
| $V_H3-9$ | 01 |
| $V_H3-11$ | 01 |
| $V_H3-13$ | 01 |

In an alternative Table 2, the JH6 allele can be JH6*01.

TABLE 3

IgH Alleles #3 - S3 alleles

| ID | Allele |
|---|---|
| $J_H6$ | 02 |
| $J_H5$ | 02 |
| $J_H4$ | 02 |
| $J_H3$ | 02 |
| $J_H2$ | 01 |
| $J_H1$ | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-2 | 02 |
| D1-1 | 01 |
| $V_H6-1$ | 01 |
| $V_H1-2$ | 02 or 04 |
| $V_H1-3$ | 01 |
| $V_H4-4$ | 02 |
| $V_H7-4$ | 01 |
| $V_H2-5$ | 01 or 10 |
| $V_H3-7$ | 01 |
| $V_H1-8$ | 01 |
| $V_H3-9$ | 01 |
| $V_H3-11$ | 01 |
| $V_H3-13$ | 01 |
| $V_H3-15$ | 01 |
| $V_H1-18$ | 01 |
| $V_H3-20$ | 01 or d01 |
| $V_H3-21$ | 01 or 03 |
| $V_H3-23$ | 04 |
| $V_H1-24$ | 01 or d01 |
| $V_H2-26$ | 01 or d01 |

In an alternative Table 3, the JH6 allele can be JH6*01.

In an alternative Table 4, the JH6 allele can be JH6*01.

TABLE 4

| IgH Alleles #4 - S4 alleles | |
|---|---|
| ID | Allele |
| $J_H6$ | 02 |
| $J_H5$ | 02 |
| $J_H4$ | 02 |
| $J_H3$ | 02 |
| $J_H2$ | 01 |
| $J_H1$ | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-2 | 02 |
| D1-1 | 01 |
| $V_H6$-1 | 01 |
| $V_H1$-2 | 02 or 04 |
| $V_H1$-3 | 01 |
| $V_H4$-4 | 02 |
| $V_H7$-4 | 01 |
| $V_H2$-5 | 01 or 10 |
| $V_H3$-7 | 01 |
| $V_H1$-8 | 01 |
| $V_H3$-9 | 01 |
| $V_H3$-11 | 01 |
| $V_H3$-13 | 01 |
| $V_H3$-15 | 01 |
| $V_H1$-18 | 01 |
| $V_H3$-20 | 01 or d01 |
| $V_H3$-21 | 01 or 03 |
| $V_H3$-23 | 04 |
| $V_H1$-24 | 01 or d01 |
| $V_H2$-26 | 01 or d01 |
| $V_H4$-28 | 05 |
| $V_H3$-30 | 18 |
| $V_H4$-31 | 03 |
| $V_H3$-33 | 01 |
| $V_H4$-34 | 01 |
| $V_H4$-39 | 01 |

TABLE 5

| IgH Alleles #5 - S5 alleles | |
|---|---|
| ID | Allele |
| $J_H6$ | 02 |
| $J_H5$ | 02 |
| $J_H4$ | 02 |
| $J_H3$ | 02 |
| $J_H2$ | 01 |
| $J_H1$ | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-2 | 02 |
| D1-1 | 01 |
| $V_H6$-1 | 01 |
| $V_H1$-2 | 02 or 04 |
| $V_H1$-3 | 01 |
| $V_H4$-4 | 02 |
| $V_H7$-4 | 01 |
| $V_H2$-5 | 01 or 10 |
| $V_H3$-7 | 01 |
| $V_H1$-8 | 01 |
| $V_H3$-9 | 01 |
| $V_H3$-11 | 01 |
| $V_H3$-13 | 01 |
| $V_H3$-15 | 01 |
| $V_H1$-18 | 01 |
| $V_H3$-20 | 01 or d01 |
| $V_H3$-21 | 01 or 03 |
| $V_H3$-23 | 04 |
| $V_H1$-24 | 01 or d01 |
| $V_H2$-26 | 01 or d01 |
| $V_H4$-28 | 05 |
| $V_H3$-30 | 18 |
| $V_H4$-31 | 03 |
| $V_H3$-33 | 01 |
| $V_H4$-34 | 01 |
| $V_H4$-39 | 01 |
| $V_H3$-43 | 01 |
| $V_H1$-45 | 02 |

TABLE 5-continued

| IgH Alleles #5 - S5 alleles | |
|---|---|
| ID | Allele |
| $V_H$1-46 | 01 |
| $V_H$3-48 | 01 |

In an alternative Table 5, the JH6 allele can be JH6*01,

TABLE 6

| IgH Alleles #6 - S6 alleles | |
|---|---|
| ID | Allele |
| $J_H$6 | 02 |
| $J_H$5 | 02 |
| $J_H$4 | 02 |
| $J_H$3 | 02 |
| $J_H$2 | 01 |
| $J_H$1 | 01 |
| D7-27 | 02 |
| D1-26 | 01 |
| D6-25 | 01 |
| D5-24 | 01 |
| D4-23 | 01 |
| D3-22 | 01 |
| D2-21 | 02 |
| D1-20 | 01 |
| D6-19 | 01 |
| D5-18 | 01 |
| D4-17 | 01 |
| D3-16 | 02 |
| D2-15 | 01 |
| D1-14 | 01 |
| D6-13 | 01 |
| D5-12 | 01 |
| D4-11 | 01 |
| D3-10 | 01 |
| D3-9 | 01 |
| D2-2 | 02 |
| D1-1 | 01 |
| $V_H$6-1 | 01 |
| $V_H$1-2 | 02 or 04 |
| $V_H$1-3 | 01 |
| $V_H$4-4 | 02 |
| $V_H$7-4 | 01 |
| $V_H$2-5 | 01 or 10 |
| $V_H$3-7 | 01 |
| $V_H$1-8 | 01 |
| $V_H$3-9 | 01 |
| $V_H$3-11 | 01 |
| $V_H$3-13 | 01 |
| $V_H$3-15 | 01 |
| $V_H$1-18 | 01 |
| $V_H$3-20 | 01 or d01 |
| $V_H$3-21 | 01 or 03 |
| $V_H$3-23 | 04 |
| $V_H$1-24 | 01 or d01 |
| $V_H$2-26 | 01 or d01 |
| $V_H$4-28 | 05 |
| $V_H$3-30 | 18 |
| $V_H$4-31 | 03 |

TABLE 6-continued

| IgH Alleles #6 - S6 alleles | |
|---|---|
| ID | Allele |
| $V_H$3-33 | 01 |
| $V_H$4-34 | 01 |
| $V_H$4-39 | 01 |
| $V_H$3-43 | 01 |
| $V_H$1-45 | 02 |
| $V_H$1-46 | 01 |
| $V_H$3-48 | 01 |
| $V_H$3-49 | 05 |
| $V_H$5-51 | 01 |
| $V_H$3-53 | 01 |
| $V_H$1-58 | 01 |
| $V_H$4-59 | 01 or 05 |
| $V_H$4-61 | 01 |
| $V_H$3-64 | 02 |
| $V_H$3-66 | 03 |
| $V_H$1-69 | 12 |

In an alternative Table 6, the JH6 allele can be JH6*01.

TABLE 7

| IgH Alleles #7 - S7 alleles (a complete repertoire of fundional IgH gene segments) | | |
|---|---|---|
| | ID | Allele |
| 1 | $J_H$6 | 02 |
| 2 | $J_H$5 | 02 |
| 3 | $J_H$4 | 02 |
| 4 | $J_H$3 | 02 |
| 5 | $J_H$2 | 01 |
| 6 | $J_H$1 | 01 |
| 7 | D7-27 | 02 |
| 8 | D1-26 | 01 |
| 9 | D6-25 | 01 |
| 10 | D5-24 | 01 |
| 11 | D4-23 | 01 |
| 12 | D3-22 | 01 |
| 13 | D2-21 | 02 |
| 14 | D1-20 | 01 |
| 15 | D6-19 | 01 |
| 16 | D5-18 | 01 |
| 17 | D4-17 | 01 |
| 18 | D3-16 | 02 |
| 19 | D2-15 | 01 |
| 20 | D1-14 | 01 |
| 21 | D6-13 | 01 |
| 22 | D5-12 | 01 |
| 23 | D4-11 | 01 |
| 24 | D3-10 | 01 |
| 25 | D3-9 | 01 |
| 26 | D2-2 | 02 |
| 27 | D1-1 | 01 |
| 28 | $V_H$6-1 | 01 |
| 29 | $V_H$1-2 | 02 or 04 |
| 30 | $V_H$1-3 | 01 |
| 31 | $V_H$4-4 | 02 |
| 32 | $V_H$7-4 | 01 |

TABLE 7-continued

IgH Alleles #7 - S7 alleles (a complete repertoire of fundional IgH gene segments)

| ID | Allele | |
|---|---|---|
| 33 | $V_H2-5$ | 01 or 10 |
| 34 | $V_H3-7$ | 01 |
| 35 | $V_H1-8$ | 01 |
| 36 | $V_H3-9$ | 01 |
| 37 | $V_H3-11$ | 01 |
| 38 | $V_H3-13$ | 01 |
| 39 | $V_H3-15$ | 1.1 01 |
| 40 | $V_H1-18$ | 01 |
| 41 | $V_H3-20$ | 01 or d01 |
| 42 | $V_H3-21$ | 01 or 03 |
| 43 | $V_H3-23$ | 04 |
| 44 | $V_H1-24$ | 01 or d01 |
| 45 | $V_H2-26$ | 01 or d01 |
| 46 | $V_H4-28$ | 05 |
| 47 | $V_H3-30$ | 18 |
| 48 | $V_H4-31$ | 03 |
| 49 | $V_H3-33$ | 01 |
| 50 | $V_H4-34$ | 01 |
| 51 | $V_H4-39$ | 01 |
| 52 | $V_H3-43$ | 01 |
| 53 | $V_H1-45$ | 02 |
| 54 | $V_H1-46$ | 01 |
| 55 | $V_H3-48$ | 01 |
| 56 | $V_H3-49$ | 05 |
| 57 | $V_H5-51$ | 01 |
| 58 | $V_H3-53$ | 01 |
| 59 | $V_H1-58$ | 01 |
| 60 | $V_H4-59$ | 01 or 05 |
| 61 | $V_H4-61$ | 01 |
| 62 | $V_H3-64$ | 02 |
| 63 | $V_H3-66$ | 03 |
| 64 | $V_H1-69$ | 12 |
| 65 | $V_H2-70$ | 04 |
| 66 | $V_H3-72$ | 01 |
| 67 | $V_H3-73$ | 02 |
| 68 | $V_H3-74$ | 01 |

In an alternative Table 7, the JH6 allele can be JH6*01.

TABLE 8

IgK Alleles #1 - K1 alleles

| ID | Allele |
|---|---|
| JK5 | 01 |
| JK4 | 01 |
| JK3 | 01 |
| JK2 | 01 or 04 |
| JK1 | 01 |
| VK4-1 | 01 |
| VK5-2 | 01 or d01 |
| VK1-5 | 03 |
| VK1-6 | 01 |
| VK1-8 | 01 |
| VK1-9 | 01 or d01 |

TABLE 9

IgK Alleles #2 - K2 alleles

| 1.2 ID | Allele |
|---|---|
| JK5 | 01 |
| JK4 | 01 |
| JK3 | 01 |
| JK2 | 01 or 04 |
| JK1 | 01 |
| VK4-1 | 01 |
| VK5-2 | 01 or d01 |
| VK1-5 | 03 |
| VK1-6 | 01 |
| VK1-8 | 01 |
| VK1-9 | 01 or d01 |
| VK3-11 | 01 |
| VK1-12 | 01 |
| VK1-13 | 01 |
| VK3-15 | 01 |
| VK1-16 | 02 |
| VK1-17 | 01 |
| VK3-20 | 01 |
| VK6-21 | 01 |
| VK2-24 | 01 |

TABLE 10

IgK Alleles #3 - K3 alleles

| 1.3 ID | Allele |
|---|---|
| JK5 | 01 |
| JK4 | 01 |
| JK3 | 01 |
| JK2 | 01 or 04 |
| JK1 | 01 |
| VK4-1 | 01 |
| VK5-2 | 01 or d01 |
| VK1-5 | 03 |
| VK1-6 | 01 |
| VK1-8 | 01 |
| VK1-9 | 01 or d01 |
| VK3-11 | 01 |
| VK1-12 | 01 |
| VK1-13 | 01 |
| VK3-15 | 01 |
| VK1-16 | 02 |
| VK1-17 | 01 |
| VK3-20 | 01 |
| VK6-21 | 01 |
| VK2-24 | 01 |
| VK1-27 | 01 |
| VK2-28 | 01 |
| VK2-29 | 01 |
| VK2-30 | 01 |

TABLE 10-continued

IgK Alleles #3 - K3 alleles

| 1.3 ID | Allele |
|---|---|
| VK1-33 | 01 |
| VK1D-39 | 01 |
| VK2D-40 | 01 |

TABLE 11

IgK Alleles #4 - K4 alleles

| 1.4 ID | Allele |
|---|---|
| JK5 | 01 |
| JK4 | 01 |
| JK3 | 01 |
| JK2 | 01 or 04 |
| JK1 | 01 |
| VK4-1 | 01 |
| VK5-2 | 01 or d01 |
| VK1-5 | 03 |
| VK1-6 | 01 |
| VK1-8 | 01 |
| VK1-9 | 01 or d01 |
| VK3-11 | 01 |
| VK1-12 | 01 |
| VK1-13 | 01 |
| VK3-15 | 01 |
| VK1-16 | 02 |
| VK1-17 | 01 |
| VK3-20 | 01 |
| VK6-21 | 01 |
| VK2-24 | 01 |
| VK1-27 | 01 |
| VK2-28 | 01 |
| VK2-29 | 01 |
| VK2-30 | 01 |
| VK1-33 | 01 |
| VK1D-39 | 01 |
| VK2D-40 | 01 |
| VK3D-7 | 01 |
| VK1D-8 | 01 or d01 |
| VK1D-43 | 01 |
| VK3D-11 | 01 or d01 |
| VK1D-12 | 02 |
| VK1D-13 | d01 |
| VK3D-15 | d01 |
| VK1D-16 | 01 |
| VK1D-17 | 01 |
| VK3D-20 | 01 |

TABLE 12

IgK Alleles #5 - K5 alleles (a complete repertoire of functional human kappa gene segments)

| 1.5 ID | Allele |
|---|---|
| JK5 | 01 |
| JK4 | 01 |
| JK3 | 01 |
| JK2 | 01 or 04 |
| JK1 | 01 |
| VK4-1 | 01 |
| VK5-2 | 01 or d01 |
| VK1-5 | 03 |
| VK1-6 | 01 |
| VK1-8 | 01 |
| VK1-9 | 01 or d01 |
| VK3-11 | 01 |
| VK1-12 | 01 |
| VK1-13 | 01 |
| VK3-15 | 01 |
| VK1-16 | 02 |
| VK1-17 | 01 |
| VK3-20 | 01 |
| VK6-21 | 01 |
| VK2-24 | 01 |
| VK1-27 | 01 |
| VK2-28 | 01 |
| VK2-29 | 01 |
| VK2-30 | 01 |
| VK1-33 | 01 |
| VK1D-39 | 01 |
| VK2D-40 | 01 |
| VK3D-7 | 01 |
| VK1D-8 | 01 or d01 |
| VK1D-43 | 01 |
| VK3D-11 | 01 or d01 |
| VK1D-12 | 02 |
| VK1D-13 | d01 |
| VK3D-15 | d01 |
| VK1D-16 | 01 |
| VK1D-17 | 01 |
| VK3D-20 | 01 |
| VK2D-26 | 01 or d01 |
| VK2D-28 | 01 or d01 |
| VK2D-29 | 01 |
| VK2D-30 | 01 |
| VK1D-33 | 01 |
| VK1D-39 | 01 |

In one aspect of Table 12 there no VκID-39 gene segment present in the genome.

For the avoidance of doubt, any reference to Table 12 herein, including in the claims, can be read with or without the limitation that in one aspect of Table 12, there no Vκ1D-39 gene segment present in the genome.

In an alternative Table 12, the Vκ2D-26 allele is Vκ2D-26*d02.

TABLE 13

Igλ Alleles #1 - L1 or P1 Alleles

| ID | Allele |
|---|---|
| Cλ7 | 01 |
| Jλ7 | 01 |
| Cλ6 | 04 |
| Jλ6 | 01 |
| Cλ3 | 03 |
| Jλ3 | 02 |
| Cλ2 | 02 |
| Jλ2 | 01 |
| Cλ1 | 02 |
| Jλ1 | 01 |
| Vλ3-1 | 01 |

TABLE 14

Igλ Alleles #2 - L2 or P2 Alleles

| ID | Allele |
|---|---|
| Cλ7 | 01 |
| Jλ7 | 01 |
| Cλ6 | 04 |
| Jλ6 | 01 |
| Cλ3 | 03 |
| Jλ3 | 02 |
| Cλ2 | 02 |
| Jλ2 | 01 |
| Cλ1 | 02 |

TABLE 14-continued

Igλ Alleles #2 - L2 or P2 Alleles

| ID | Allele |
|---|---|
| Jλ1 | 01 |
| Vλ3-1 | 01 |
| Vλ4-3 | 01 |
| Vλ2-8 | 01 |
| Vλ3-9 | 01 |
| Vλ3-10 | 01 |
| Vλ2-11 | 01 |
| Vλ3-12 | 02 |
| Vλ2-14 | 01 |
| Vλ3-16 | 01 |
| Vλ2-18 | 01 |

TABLE 15

Igλ Alleles #3 - L3 or P3 Alleles

| ID | Allele |
|---|---|
| Cλ7 | 01 |
| Jλ7 | 01 |
| Cλ6 | 04 |
| Jλ6 | 01 |
| Cλ3 | 03 |
| Jλ3 | 02 |
| Cλ2 | 02 |
| Jλ2 | 01 |
| Cλ1 | 02 |
| Jλ1 | 01 |
| Vλ3-1 | 01 |
| Vλ4-3 | 01 |
| Vλ2-8 | 01 |
| Vλ3-9 | 01 |
| Vλ3-10 | 01 |
| Vλ2-11 | 01 |
| Vλ3-12 | 02 |
| Vλ2-14 | 01 |
| Vλ3-16 | 01 |
| Vλ2-18 | 01 |
| Vλ3-19 | 01 |
| Vλ3-21 | 01 or d01 |
| Vλ3-22 | 01 |
| Vλ2-23 | 02 or d02 |
| Vλ3-25 | 01 or d03 |
| Vλ3-27 | 01 |

TABLE 16

Igλ Alleles #4 - L4 or P4 Alleles

| ID | Allele |
|---|---|
| Cλ7 | 01 |
| Jλ7 | 01 |
| Cλ6 | 04 |
| Jλ6 | 01 |
| Cλ3 | 03 |
| Jλ3 | 02 |
| Cλ2 | 02 |
| Jλ2 | 01 |
| Cλ1 | 02 |
| Jλ1 | 01 |
| Vλ3-1 | 01 |
| Vλ4-3 | 01 |
| Vλ2-8 | 01 |
| Vλ3-9 | 01 |
| Vλ3-10 | 01 |
| Vλ2-11 | 01 |
| Vλ3-12 | 02 |
| Vλ2-14 | 01 |
| Vλ3-16 | 01 |
| Vλ2-18 | 01 |

TABLE 16-continued

Igλ Alleles #4 - L4 or P4 Alleles

| ID | Allele |
|---|---|
| Vλ3-19 | 01 |
| Vλ3-21 | 01 or d01 |
| Vλ3-22 | 01 |
| Vλ2-23 | 02 or d02 |
| Vλ3-25 | 01 or d03 |
| Vλ3-27 | 01 |
| Vλ1-36 | 01 |
| Vλ5-37 | 01 |
| Vλ5-39 | 01 |
| Vλ1-40 | 01 |
| Vλ7-43 | 01 |
| Vλ1-44 | 01 |
| Vλ5-45 | 03 |
| Vλ7-46 | 01 |

TABLE 17

Igλ Alleles #5 - L5 or P5 Alleles

| ID | Allele |
|---|---|
| Cλ7 | 01 |
| Jλ7 | 01 |
| Cλ6 | 04 |
| Jλ6 | 01 |
| Cλ3 | 03 |
| Jλ3 | 02 |
| Cλ2 | 02 |
| Jλ2 | 01 |
| Cλ1 | 02 |
| Jλ1 | 01 |
| Vλ3-1 | 01 |
| Vλ4-3 | 01 |
| Vλ2-8 | 01 |
| Vλ3-9 | 01 |
| Vλ3-10 | 01 |
| Vλ2-11 | 01 |
| Vλ3-12 | 02 |
| Vλ2-14 | 01 |
| Vλ3-16 | 01 |
| Vλ2-18 | 01 |
| Vλ3-19 | 01 |
| Vλ3-21 | 01 or d01 |
| Vλ3-22 | 01 |
| Vλ2-23 | 02 or d02 |
| Vλ3-25 | 01 or d03 |
| Vλ3-27 | 01 |
| Vλ1-36 | 01 |
| Vλ5-37 | 01 |
| Vλ5-39 | 01 |
| Vλ1-40 | 01 |
| Vλ7-43 | 01 |
| Vλ1-44 | 01 |
| Vλ5-45 | 03 |
| Vλ7-46 | 01 |
| Vλ1-47 | 01 |
| Vλ9-49 | 01 |
| Vλ1-51 | 01 |
| Vλ5-52 | 01 |
| Vλ10-54 | 02 |

TABLE 18

Igλ Alleles #6 - L6 or P6 Alleles (a complete repertoire of functional human lambda alleles)

| 1.6 ID | Allele |
|---|---|
| Cλ7 | 01 |
| Jλ7 | 01 |
| Cλ6 | 04 |

TABLE 18-continued

Igλ Alleles #6 - L6 or P6 Alleles (a complete repertoire of functional human lambda alleles)

| L6 ID | Allele |
|---|---|
| Jλ6 | 01 |
| Cλ3 | 03 |
| Jλ3 | 02 |
| Cλ2 | 02 |
| Jλ2 | 01 |
| Cλ1 | 02 |
| Jλ1 | 01 |
| Vλ3-1 | 01 |
| Vλ4-3 | 01 |
| Vλ2-8 | 01 |
| Vλ3-9 | 01 |
| Vλ3-10 | 01 |
| Vλ2-11 | 01 |
| Vλ3-12 | 02 |
| Vλ2-14 | 01 |
| Vλ3-16 | 01 |
| Vλ2-18 | 01 |
| Vλ3-19 | 01 |
| Vλ3-21 | d01 |
| Vλ3-22 | 01 |
| Vλ2-23 | 02 or d02 |
| Vλ3-25 | 01 or d03 |
| Vλ3-27 | 01 |
| Vλ1-36 | 01 |
| Vλ5-37 | 01 |
| Vλ5-39 | 01 |
| Vλ1-40 | 01 |
| Vλ7-43 | 01 |
| Vλ1-44 | 01 |
| Vλ5-45 | 03 |
| Vλ7-46 | 01 |
| Vλ1-47 | 01 |
| Vλ9-49 | 01 |
| Vλ1-51 | 01 |
| Vλ5-52 | 01 |
| Vλ10-54 | 02 |
| Vλ6-57 | 01 |
| Vλ4-60 | 03 or d03 |
| Vλ8-61 | 01 |
| Vλ4-69 | 01 |

With respect to Table 18, in one aspect there is no Cλ6 or Jλ6 gene segment present in the genome. In another aspect, additionally or alternatively, there is no Vλ3-22 and/or Vλ5-39 and/or Vλ10-54 gene segment.

For the avoidance of doubt, any reference to Table 18 herein, including in the claims, can be read with or without the limitation that, in one aspect of Table 18, there no Cλ6 or Jλ6 present, and without or without the limitation that there is no Vλ3-22 and/or Vλ5-39 and/or Vλ10-54 gene segment.

The disclosure of WO2013/041844 is incorporated herein by reference. The examples of gene segments in WO2013/041844 are specifically incorporated herein as though specifically and explicitly disclosed herein as possible gene segments with respect to the present invention and for possible inclusion in one or more claims herein.

Each aspect, embodiment, clause or provision described herein can be combined in a non-human vertebrate capable of expressing one or more human gene segments disclosed in WO2013/041844 and/or described herein or a binding site or antibody that is a product of recombination of one or more human gene segments disclosed in WO2013/041844 and/or described herein, as appropriate, The gene segments disclosed in Tables 1-7 of WO2013/041844 are specifically and explicitly disclosed herein as possible gene segment sequences with respect to the present invention and for possible inclusion in one or more claims herein. The sequences are set out in the sequence listing filed with that application.

Further examples of sequences of gene segments for use in the context of the invention are set out in the sequences included at the end of the description.

In a preferred embodiment, the genome of the vertebrate or cell of the invention comprises one or more gene segments from any one of Tables 1 to 18. In a further preferred embodiment, the genome of the vertebrate or cell of the invention comprises a combination of any two gene segments from any one of Tables 1 to 18. In a yet further preferred embodiment, the genome of the vertebrate or cell of the invention comprises a combination of any three gene segments from any one of Tables 1 to 18.

In the most preferred embodiment, the genome of the vertebrate or cell of the invention comprises a combination of any four gene segments from any one of Tables 1 to 18. Preferably a VH and a JH heavy chain segment is selected from Table 7 and a VL and a JL light chain segment is selected from Table 12 or Table 18. Optionally a D heavy chain segment is selected from Table 7.

The invention further relates to a non-human vertebrate (eg, a mouse or rat) or cell whose genome comprises human VL and JL gene segments upstream of a constant region at an endogenous light chain locus, wherein the vertebrate or cell expresses immunoglobulin light chains comprising human variable regions, or where the cell can develop into a vertebrate that expresses said light chains, wherein said immunoglobulin light chains comprise light chains comprising human variable regions derived from recombination of (i) human Vκ and Jκ gene segments selected from the group consisting of Vκ and Jκ gene segments of any one of Tables 8 to 12 or (ii) human Vλ and Jλ gene segments selected from the group consisting of Vλ and Jλ gene segments of any one of Tables 12 to 18.

In one embodiment the vertebrate or cell of the invention expresses light chains comprising human lambda variable regions and wherein at least 60%, 70%, 80%, 85%, 90% or 95% of the variable regions of such light chains are derived from recombination of human Vλ and Jλ gene segments.

Optionally the light chains are expressed as IgG antibodies, for example IgG1 or IgG2b, optionally IgG2a.

The constant region can be a kappa or lambda constant region; optionally human, mouse or rat constant region. Said endogenous light chain locus can be a kappa or lambda locus: optionally wherein the genome comprises at least the V and J gene segments of Table 8 at an endogenous light chain locus, for example the kappa locus and/or at least the V and J gene segments of Table 13 at an endogenous light chain locus, for example the lambda or kappa locus.

Said light chains can comprise immunoglobulin light chains comprising human variable regions that derived from recombination of (ii), each such variable region being expressed with a constant region encoded by a Cλ gene segment selected from the group consisting of the Cλ gene segments of Table 18.

In this embodiment of the invention, the vertebrate or cell can express light chains comprising human lambda variable regions and at least 60%, 70% or 80% of the variable regions of such light chains can be derived from recombination of human Vλ and Jλ gene segments, for example the V and J segments listed in Table 18. A invention also relates to a non-human vertebrate (eg, a mouse or rat) or cell whose genome comprises human VH, D and JH gene segments upstream of a constant region at an endogenous heavy chain locus, wherein the vertebrate or cell expresses immunoglobulin heavy chains comprising human variable regions or the cell can develop into a vertebrate that expresses said heavy chains, or where the cell can express immunoglobulin heavy chains comprising human variable regions, wherein said immunoglobulin heavy chains comprise heavy chains comprising human variable regions derived from recombination of (iii) human VH, D and JH gene segments selected from the group consisting of VH, D and JH gene segments of Table 7.

In one embodiment said light chains are co-expressed with said heavy chains to form antibodies, eg, IgG antibodies.

A non-human vertebrate (eg, a mouse or rat) or cell whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate or cell, wherein the vertebrate comprises immunoglobulin light chains comprising lambda variable regions (lambda light chains) or the cell can develop into a vertebrate that expresses said immunoglobulin light chains, wherein the lambda light chains comprise immunoglobulin light chains comprising lambda variable regions derived from recombination of human Vλ and Jλ gene segments; wherein at least 60%, 70%, 80% or 90% of the variable regions of the lambda light chains expressed by the vertebrate are derived from recombination of human Vλ and Jλ gene segments; optionally wherein the vertebrate or cell any vertebrate or cell disclosed herein.

A variable domain or region derived from, or produced as a result of, recombination of human gene segments is also referred to herein as a recombinant of said gene segments.

The gene segments in the heavy and/or light locus are operably linked to the constant region, so that the vertebrate is capable of producing an antibody heavy or light chain produced by recombination of the gene segments.

In one embodiment the cell or non-human vertebrate has a genome comprising the kappa segments of table 8, or table 9 or table 10, table 11 or table 12, or any combination thereof.

In one embodiment the cell or non-human vertebrate has a genome comprising the lambda segments of table 13 or table 14 or table 15 or table 16 or table 17 or table 18, or any combination thereof.

In one embodiment the cell or non-human vertebrate has a genome comprising the heavy chain segments of table 1 or table 2 or table 3 or table 4 or table 5 or table 6 or table 7 or any combination thereof.

In one embodiment the cell or non-human vertebrate of the invention can express light chains comprising human variable regions derived from recombination (i.e. recombinants) of (i) human Vκ and Jκ gene segments selected from the group consisting of Vκ and Jκ gene segments of Table 8, or table 9, or table 10, or table 11 or table 12, or any combination thereof In one embodiment the cell or non-human vertebrate of the invention can express light chains comprising human variable regions derived from recombination (i.e. recombinants) of (ii) human Vλ and Jλ gene segments selected from the group consisting of Vλ and Jλ gene segments of Table 13 or table 14 or table 15 or table 16 or table 17 or table 18, or any combination thereof.

In one embodiment the cell or vertebrate of the invention can express heavy chains comprising human variable regions derived from recombination (i.e. recombinants) of human VH, D and JH gene segments selected from the group consisting of VH, D and JH gene segments of table 1 or table 2, or table 3, or table 4 or table 5 or table 6 or table 7, or any combination thereof.

The invention further includes the following provisions

Provision 1—The vertebrate or cell of the invention has a genome comprising one or more alleles selected from alleles numbered 1 to 68 in Table 7.

Provision 2—The vertebrate or cell according to provision 1 comprising allele number 1 from Table 1 and one or more alleles selected from alleles numbered 2 to 68 of Table 7.

Provision 3—The vertebrate or cell according to any preceding provision comprising allele number 2 from Table 7 and one or more alleles selected from alleles numbered 3 to 68 of Table 7.

Provision 4—The vertebrate or cell according to any preceding provision comprising allele number 3 from Table 7 and one or more alleles selected from alleles numbered 4 to 68 of Table 7.

Provision 5—The vertebrate or cell according to any preceding provision comprising allele number 4 from Table 7 and one or more alleles selected from alleles numbered 5 to 68 of Table 7.

Provision 6—The vertebrate or cell according to any preceding provision comprising allele number 5 from Table 7 and one or more alleles selected from alleles numbered 6 to 68 of Table 7.

Provision 7—The vertebrate or cell according to any preceding provision comprising allele number 6 from Table 7 and one or more alleles selected from alleles numbered 7 to 68 of Table 7.

Provision 8—The vertebrate or cell according to any preceding provision comprising allele number 7 from Table 7 and one or more alleles selected from alleles numbered 8 to 68 of Table 7.

Provision 9—The vertebrate or cell according to any preceding provision comprising allele number 8 from Table 7 and one or more alleles selected from alleles numbered 9 to 68 of Table 7.

Provision 10—The vertebrate or cell according to any preceding provision comprising allele number 9 from Table 7 and one or more alleles selected from alleles numbered 10 to 68 of Table 7.

Provision 11—The vertebrate or cell according to any preceding provision comprising allele number 10 from Table 7 and one or more alleles selected from alleles numbered 11 to 68 of Table 7.

Provision 12—The vertebrate or cell according to any preceding provision comprising allele number 11 from Table 7 and one or more alleles selected from alleles numbered 12 to 68 of Table 7.

Provision 13—The vertebrate or cell according to any preceding provision comprising allele number 12 from Table 7 and one or more alleles selected from alleles numbered 13 to 68 of Table 7.

Provision 14—The vertebrate or cell according to any preceding provision comprising allele number 13 from Table 7 and one or more alleles selected from alleles numbered 14 to 68 of Table 7.

Provision 15—The vertebrate or cell according to any preceding provision comprising allele number 14 from Table 7 and one or more alleles selected from alleles numbered 15 to 68 of Table 7.

Provision 16—The vertebrate or cell according to any preceding provision comprising allele number 15 from Table 7 and one or more alleles selected from alleles numbered 16 to 68 of Table 7.

Provision 17—The vertebrate or cell according to any preceding provision comprising allele number 16 from Table 7 and one or more alleles selected from alleles numbered 17 to 68 of Table 7.

Provision 18—The vertebrate or cell according to any preceding provision comprising allele number 17 from Table 7 and one or more alleles selected from alleles numbered 18 to 68 of Table 7.

Provision 19—The vertebrate or cell according to any preceding provision comprising allele number 18 from Table 7 and one or more alleles selected from alleles numbered 19 to 68 of Table 7.

Provision 20—The vertebrate or cell according to any preceding provision comprising allele number 19 from Table 7 and one or more alleles selected from alleles numbered 20 to 68 of Table 7.

Provision 21—The vertebrate or cell according to any preceding provision comprising allele number 20 from Table 7 and one or more alleles selected from alleles numbered 21 to 68 of Table 7.

Provision 22—The vertebrate or cell according to any preceding provision comprising allele number 21 from Table 7 and one or more alleles selected from alleles numbered 22 to 68 of Table 7.

Provision 23—The vertebrate or cell according to any preceding provision comprising allele number 22 from Table 7 and one or more alleles selected from alleles numbered 23 to 68 of Table 7.

Provision 24—The vertebrate or cell according to any preceding provision comprising 4allele number 23 from Table 7 and one or more alleles selected from alleles numbered 24 to 68 of Table 7.

Provision 25—The vertebrate or cell according to any preceding provision comprising allele number 24 from Table 7 and one or more alleles selected from alleles numbered 25 to 68 of Table 7.

Provision 26—The vertebrate or cell according to any preceding provision comprising allele number 25 from Table 7 and one or more alleles selected from alleles numbered 26 to 68 of Table 7.

Provision 27 The vertebrate or cell according to any preceding provision comprising allele number 26 from Table 7 and one or more alleles selected from alleles numbered 27 to 68 of Table 7.

Provision 28—The vertebrate or cell according to any preceding provision comprising allele number 27 from Table 7 and one or more alleles selected from alleles numbered 28 to 68 of Table 7.

Provision 29—The vertebrate or cell according to any preceding provision comprising allele number 28 from Table 7 and one or more alleles selected from alleles numbered 29 to 68 of Table 7.

Provision 30—The vertebrate or cell according to any preceding provision comprising allele number 29 from Table 7 and one or more alleles selected from alleles numbered 30 to 68 of Table 7.

Provision 31—The vertebrate or cell according to any preceding provision comprising allele number 30 from Table 7 and one or more alleles selected from alleles numbered 31 to 68 of Table 7.

Provision 32—The vertebrate or cell according to any preceding provision comprising allele number 31 from Table 7 and one or more alleles selected from alleles numbered 32 to 68 of Table 7.

Provision 33—The vertebrate or cell according to any preceding provision comprising allele number 32 from Table 7 and one or more alleles selected from alleles numbered 33 to 68 of Table 7.

Provision 34—The vertebrate or cell according to any preceding provision comprising allele number 33 from Table 7 and one or more alleles selected from alleles numbered 34 to 68 of Table 7.

Provision 35—The vertebrate or cell according to any preceding provision comprising allele number 34 from Table 7 and one or more alleles selected from alleles numbered 35 to 68 of Table 7.

Provision 36—The vertebrate or cell according to any preceding provision comprising allele number 35 from Table 7 and one or more alleles selected from alleles numbered 36 to 68 of Table 7.

Provision 37—The vertebrate or cell according to any preceding provision comprising allele number 36 from Table 7 and one or more alleles selected from alleles numbered 37 to 68 of Table 7.

Provision 38—The vertebrate or cell according to any preceding provision comprising allele number 37 from Table 7 and one or more alleles selected from alleles numbered 38 to 68 of Table 7.

Provision 39—The vertebrate or cell according to any preceding provision comprising allele number 38 from Table 7 and one or more alleles selected from alleles numbered 39 to 68 of Table 7.

Provision 40—The vertebrate or cell according to any preceding provision comprising allele number 39 from Table 7 and one or more alleles selected from alleles numbered 40 to 68 of Table 7.

Provision 41—The vertebrate or cell according to any preceding provision comprising allele number 40 from Table 7 and one or more alleles selected from alleles numbered 41 to 68 of Table 7.

Provision 42—The vertebrate or cell according to any preceding provision comprising allele number 41 from Table 7 and one or more alleles selected from alleles numbered 42 to 68 of Table 7.

Provision 43—The vertebrate or cell according to any preceding provision comprising allele number 42 from Table 7 and one or more alleles selected from alleles numbered 43 to 68 of Table 7.

Provision 44—The vertebrate or cell according to any preceding provision comprising allele number 43 from Table 7 and one or more alleles selected from alleles numbered 44 to 68 of Table 7.

Provision 45—The vertebrate or cell according to any preceding provision comprising allele number 44 from Table 7 and one or more alleles selected from alleles numbered 45 to 68 of Table 7.

Provision 46—The vertebrate or cell according to any preceding provision comprising allele number 45 from Table 7 and one or more alleles selected from alleles numbered 46 to 68 of Table 7.

Provision 47—The vertebrate or cell according to any preceding provision comprising allele number 46 from Table 7 and one or more alleles selected from alleles numbered 47 to 68 of Table 7.

Provision 48—The vertebrate or cell according to any preceding provision comprising allele number 47 from Table 7 and one or more alleles selected from alleles numbered 48 to 68 of Table 7.

Provision 49—The vertebrate or cell according to any preceding provision comprising allele number 48 from Table 7 and one or more alleles selected from alleles numbered 49 to 68 of Table 7.

Provision 50—The vertebrate or cell according to any preceding provision comprising allele number 49 from Table 7 and one or more alleles selected from alleles numbered 50 to 68 of Table 7.

Provision 51—The vertebrate or cell according to any preceding provision comprising allele number 50 from Table 7 and one or more alleles selected from alleles numbered 51 to 68 of Table 7.

Provision 52—The vertebrate or cell according to any preceding provision comprising allele number 51 from Table 7 and one or more alleles selected from alleles numbered 52 to 68 of Table 7.

Provision 53—The vertebrate or cell according to any preceding provision comprising allele number 52 from Table 7 and one or more alleles selected from alleles numbered 53 to 68 of Table 7.

Provision 54—The vertebrate or cell according to any preceding provision comprising allele number 53 from Table 7 and one or more alleles selected from alleles numbered 54 to 68 of Table 7.

Provision 55—The vertebrate or cell according to any preceding provision comprising allele number 54 from Table 7 and one or more alleles selected from alleles numbered 55 to 68 of Table 7.

Provision 56—The vertebrate or cell according to any preceding provision comprising allele number 56 from Table 7 and one or more alleles selected from alleles numbered 57 to 68 of Table 7.

Provision 57—The vertebrate or cell according to any preceding provision comprising allele number 57 from Table 7 and one or more alleles selected from alleles numbered 58 to 68 of Table 7.

Provision 58—The vertebrate or cell according to any preceding provision comprising allele number 58 from Table 7 and one or more alleles selected from alleles numbered 59 to 68 of Table 7.

Provision 59 The vertebrate or cell according to any preceding provision comprising allele number 59 from Table 7 and one or more alleles selected from alleles numbered 60 to 68 of Table 7.

Provision 60—The vertebrate or cell according to any preceding provision comprising allele number 60 from Table 7 and one or more alleles selected from alleles numbered 61 to 68 of Table 7.

Provision 61—The vertebrate or cell according to any preceding provision comprising allele number 61 from Table 7 and one or more alleles selected from alleles numbered 62 to 68 of Table 7.

Provision 62—The vertebrate or cell according to any preceding provision comprising allele number 62 from Table 7 and one or more alleles selected from alleles numbered 63 to 68 of Table 7.

Provision 63—The vertebrate or cell according to any preceding provision comprising allele number 63 from Table 7 and one or more alleles selected from alleles numbered 64 to 68 of Table 7.

Provision 64—The vertebrate or cell according to any preceding provision comprising allele number 64 from Table 7 and one or more alleles selected from alleles numbered 65 to 68 of Table 7.

Provision 65—The vertebrate or cell according to any preceding provision comprising allele number 65 from Table 7 and one or more alleles selected from alleles numbered 66 to 68 of Table 7.

Provision 66—The vertebrate or cell according to any preceding provision comprising allele number 66 from Table 7 and one or more alleles selected from alleles numbered 67 or 68 of Table 7.

Provision 67—The vertebrate or cell according to any preceding provision comprising allele number 67 from Table 7 and allele number 68 from Table 7.

In an example, the vertebrate or cell according to any preceding provision comprises one or more or all JH alleles from Table 7, eg, JH2*02 and/or at least JH6*02 (which is useful for producing long HCDR3 V domains for human therapeutic use as shown in the examples).

Thus, each allele combined with any other allele in Table 7 is explicitly disclosed herein. The same structure of combinations is disclosed in relation to the alleles of Table 12 and Table 18. Therefore, each allele in Table 7 combined with any other allele in Table 12 or Table 18 is disclosed, and each allele in Table 12 is disclosed in combination with every other allele in Table 12, and each allele in Table 18 is disclosed in combination with every other allele in Table 18.

In an example, the vertebrate or cell according to any preceding provision comprises one or more or all Jκ alleles from Table 12, eg, at least Jκ2*01 and/or Jκ4*01 (which is useful for producing Vκ domains for human therapeutic use as shown in the examples).

In one embodiment, the cell or vertebrate of the invention has a genome comprising the gene segments VH3-23*04, JH2*01, VK4-1*01 and/or JK2*01.

In a further embodiment, the cell or vertebrate of the invention has a genome comprising the gene segments VH3-7*01, JH6*02, VK2-28*01 and/or JK4*01.

In a further embodiment, the cell or vertebrate of the invention has a genome comprising the gene segments VH7-4-1*01, JH6*02, VK2-28*01 and/or JK4*01. Optionally the genome further comprises D3-16*02.

In a further embodiment, the cell or vertebrate of the invention has a genome comprising the gene segments VH4-4-1*02, JH6*02, VK1D-13*01 and/or JK4*01. Optionally the genome further comprises D3-10*01.

In a further embodiment, the cell or vertebrate of the invention has a genome comprising the gene segments VH1-3*01, JH6*02, VK1-12*01 and/or JK4*01. Optionally the genome further comprises D3-10*01.

In a further embodiment, the cell or vertebrate of the invention has a genome comprising the gene segments VH3-13*01, JH6*02, VK1D-12*02 and/or JK4*01. Optionally the genome further comprises D3-9*01.

In a further embodiment, the cell or vertebrate of the invention has a genome comprising the gene segments VH4-4*02, JH6*02, VK1D-13*01 and/or JK4*01. Optionally the genome further comprises D3-10*01.

In a further embodiment, the cell or vertebrate of the invention has a genome comprising the gene segments VH3-13*01, JH6*02, VK3-20*01 and/or JK4*01. Optionally the genome further comprises D3-10*01.

In a further embodiment, the cell or vertebrate of the invention has a genome comprising the gene segments VH3-23*04, JH6*02, VK1-17*01 and/or JK4*01. Optionally the genome further comprises D3-22*01.

In a further embodiment, the cell or vertebrate of the invention has a genome comprising the gene segments VH3-7*01, JH6*02, VK1D-39*01 and/or JK4*01. Optionally the genome further comprises D3-9*01.

In a further embodiment, the cell or vertebrate of the invention has a genome comprising the gene segments VH3-13*01, JH6*02, VK1D-39*01 and/or JK4*01. Optionally the genome further comprises D3-10*01.

In a further embodiment, the cell or vertebrate of the invention has a genome comprising the gene segments VH3-13*01, JH6*02, VK3-11*01 and/or JK4*01. Optionally the genome further comprises D3-10*01.

In a further embodiment, the cell or vertebrate of the invention has a genome comprising the gene segments VH4-4*02, JH6*02, VK1D-16*01 and/or JK4*01. Optionally the genome further comprises D3-9*01.

In a further embodiment, the cell or vertebrate of the invention has a genome comprising the gene segments VH3-20*d01, JH6*02, VK1-9*d01 and/or JK4*01. Optionally the genome further comprises D3-10*01.

In a further embodiment, the cell or vertebrate of the invention has a genome comprising the human gene segment VH3-23*04. Additionally or alternatively, heavy chain variable domains of the antibody of the invention are encoded by (i) human VH3-23*04, D and JH segments.

In a further embodiment, the cell or vertebrate of the invention has a genome comprising the human gene segment VH3-9*01. Additionally or alternatively, heavy chain variable domains of the antibody of the invention are encoded by (i) human VH3-9*01, D and JH segments.

In a further embodiment, the cell or vertebrate of the invention has a genome comprising the human gene segment Vκ1-12*02 or Vκ1D-12*02. Additionally or alternatively, light chain variable domains of the antibody of the invention are encoded by (i) human Vκ1-12*02 or Vκ1D-12*02 and Jκ segments.

In a further embodiment, the cell or vertebrate of the invention has a genome comprising the human gene segment Vκ2-28*01. Additionally or alternatively, light chain variable domains of the antibody of the invention are encoded by (i) human Vκ2-28*01 and Jκ segments.

In a further embodiment, the cell or vertebrate of the invention has a genome comprising the human gene segment Vκ4-1*01. Additionally or alternatively, light chain variable domains of the antibody of the invention are encoded by (i) human Vκ4-1*01 and Jκ segments. In a further embodiment, the cell or vertebrate of the invention has a genome comprising the combination of gene segments described above with JH6*01 in place of JH6*02.

In all embodiments described herein, the heavy chain V and J region can optionally be recombined with each other and with a D region defined herein to form a heavy chain variable domain. In addition, the light chain V and J regions can optionally be recombined to form a light chain variable domain.

The invention extends to an antibody or antigen binding fragment comprising human variable domains produced or derived from recombination of any of the above combinations of gene segments.

Antibodies or fragments according to the invention are shown in the examples to be useful for producing productive gene segment recombination in vivo, which display junctional mutation and somatic mutation, and produce domains that can specifically bind antigen with good binding kinetics.

The invention includes antibodies or antigen binding fragments thereof that are obtained or obtainable by recombination, in vivo in a mouse, mammal or vertebrate of the invention following immunisation, of one or more D gene segments, one or more VH gene segments and one or more of the human JH gene segments $J_H2^*01$ and $J_H6^*02$.

In one embodiment, the cell or vertebrate of the invention can express heavy chains comprising human variable regions derived from recombination of one or more D gene segments, one or more JH gene segments and one or more of the following VH gene segments $V_H3$-20*d01, $V_H1$-24*d01 and $V_H2$-26*d01.

Therefore, the invention includes antibodies or antigen binding fragments thereof that are obtained or obtainable by recombination, in vivo in a mouse, mammal or vertebrate of the invention following immunisation, of one or more D gene segments, one or more JH gene segments and one or more of the human VH gene segments $V_H3$-20*d01, $V_H1$-24*d01 and $V_H2$-26*d01.

In a further embodiment, the cell or vertebrate of the invention can additionally or alternatively express light chains comprising human variable regions derived from recombination of one or more Jκ gene segments and one or more of the human Vκ gene segments Vκ5-2*d01, Vκ1-9*d01, Vκ1D-8*d01, Vκ3D-11*d01, Vκ1D-13*d01, Vκ3D-15*d01, Vκ2D-26*d01 and Vκ2D-28*d01 or recombination of one or more Jλ gene segments and one or more of the human Vλ gene segments Vλ2-22*d01, Vλ2-23*d02, Vλ3-25*d03 and Vλ4-60*d03.

Therefore, the invention includes antibodies or antigen binding fragments thereof that are obtained or obtainable by recombination, in vivo in a mouse, mammal or vertebrate of the invention following immunisation, of one or more Jκ gene segments and one or more of the human Vκ gene segments Vκ5-2*d01, Vκ1-9*d01, Vκ1D-8*d01, Vκ3D-11*d01, Vκ2D-26*d01 and Vκ2D-28*d01 or of one or more Jλ gene segments and one or more of the human Vλ gene segments Vλ2-22*d01, Vλ2-23*d02, Vλ3-25*d03 and Vλ4-60*d03.

In all aspects of the invention, the cell can be a hybridoma cell, a B cell, optionally an immortalised B cell, or an embryonic stem cell.

In one embodiment the vertebrate or cell comprises a constant region that is a kappa or lambda constant region; optionally a mouse or rat constant region. In one embodiment the constant region may be a human constant region.

In one embodiment the vertebrate or cell disclosed herein comprises an endogenous light chain locus which is a kappa or lambda locus; optionally wherein the genome comprises at least the V and J gene segments of Table 8, 9 or 10 at an endogenous light chain locus, eg the kappa locus and/or at least the V and J gene segments of Table 13 or 14 at an endogenous light chain locus, eg either the lambda or kappa locus.

In one embodiment the vertebrate or cell disclosed herein comprises comprise immunoglobulin light chains comprising human variable regions that are derived from recombination of human Vλ and Jλ gene segments selected from the group consisting of Vλ and Jλ gene segments of Table 18, each such variable region being expressed with a constant region encoded by a Cλ gene segment selected from the group consisting of the Cλ gene segments of Table 18.

In one embodiment the light chains comprise human variable regions derived from recombination of human Vλ and Jλ gene segments selected from the group consisting of Vλ and Jλ gene segments of Table 18.

In all embodiments of the invention, the VH and VL domains can optionally form an antigen binding site.

The cell of any aspect of the invention can be a hybridoma cell or a B cell, optionally an immortalised B cell. The cell can also be an ES cell. The ES cell can be part of a population of at least 90, 150 or more than 200 cells. In an example, the population of cells is contained on one or more multi-well plates (eg, 96-well plates) and may, for example, be a sorted population where single cells are comprised by different, respective wells of a plate. The vertebrate of any aspect can be comprised within a container comprising filtered air, optionally comprising an air filter.

In an embodiment, the container inner environment is sterile, eg, as possible using a standard animal container, eg, a Techniplast™ mouse loft (http://www.tecniplast.it/us/product/mouse-loft.html). In an example, the container has a plastic body, eg, a translucent or transparent body.

The container comprising the vertebrates may have a volume of no more than four, 3, 2 or 1 meters$^3$. The container can comprise a plurality of vertebrates, eg, a male and a female (eg, a fertile pair).

In one embodiment the vertebrates of the invention are at least 3.5 weeks old, eg 4 weeks, 5 weeks, 6 weeks, 7 weeks old.

The use of the gene segments as claimed, specifically as indicated in tables 1-18, provides for the advantages seen in the Examples.

The invention further relates to a method of producing an antibody or an antigen binding fragment thereof, the method comprising immunising a vertebrate of the invention with an antigen and recovering the antibody or fragment or recovering a cell producing the antibody or fragment; optionally modifying the isolated antibody or fragment so that it comprises human constant regions.

The invention also includes a method of producing an antibody or an antigen binding fragment thereof, the method comprising isolating an antibody or antigen binding fragment thereof from a cell of the invention; and optionally modifying the isolated antibody or fragment so that it comprises human constant regions.

Recombinant DNA technology can be used to produce a modified nucleotide sequence encoding the modified antibody or fragment.

The method may comprise (a) isolating from the vertebrate a B-cell encoding an antibody that binds the antigen, (b) identifying or copying a nucleotide sequence of the B-cell that encodes a VH domain of the antibody and/or identifying or copying nucleotide sequence of the B-cell that encodes a VL domain of the antibody; and (c) using the sequence(s) to produce an isolated antibody comprising the VH and/or VL domain; optionally wherein the isolated antibody comprises human constant regions.

The invention includes a method for producing a fully humanised antibody comprising immunizing a vertebrate as disclosed herein and then replacing the non-human vertebrate constant region of an antibody specifically reactive with the antigen with a human constant region, suitably by engineering of the nucleic acid encoding the antibody.

The invention also relates to a humanised antibody produced according to any methods disclosed herein and use of a humanised antibody so produced in medicine. In a further embodiment, the invention includes isolating an IgG1, IgG2b and/or IgM antibody that specifically binds the target antigen.

An isolated antibody of the invention may be produced by expression from a host cell selected from a CHO, HEK293, Cos or yeast (eg, *Picchia*) cell. In a preferred embodiment, the antibody is an antibody produced by expression from a CHO cell.

In a further embodiment the isolated antibody or fragment may be formulated with a diluent, carrier, excipient or a drug to produce a pharmaceutical composition for human medical use. Optionally the formulated antibody may be packaged in a sterile container, for example, a vial, tube, IV bag or syringe, further optionally producing a kit comprising combining the package with a label or instructions indicating use of the antibody composition for human medical use; optionally wherein the label or instructions comprises a medicament batch number and/or a marketing authorisation number, further optionally an EMA or FDA marketing authorisation number. In an example, the isolated antibody (eg, produced by a CHO cell) (i) is formulated with a diluent, carrier, excipient or a drug to produce a pharmaceutical composition for human medical use, (ii) the formulated antibody is packaged in a sterile container combined with a label or instructions indicating use of the antibody composition for human medical use; wherein the label or instructions comprises a medicament batch number and/or a marketing authorisation number (eg, an EMA or FDA marketing authorisation number). In an embodiment of such an example, the antibody specifically binds human PCSK9 and the use is for treating or preventing hyperlipidaemia or for reducing cholesterol in a human. In an embodiment of such an example, the antibody specifically binds human IL6Ra and the use is for treating or preventing an inflammatory condition or rheumatoid arthritis in a human. In an embodiment of such an example, the antibody specifically binds human IL4Ra and the use is for treating or preventing an atopic disease, atopic dermatitis or asthma in a human.

The invention relates to the antibody or fragment produced by the method of the invention for human medical use and to use of the isolated antibody or fragment produced by the method of the invention in the manufacture of a medicament for human medical use.

The medicament may be a composition or kit disclosed herein.

The invention includes antibodies and antigen binding fragments thereof comprising human variable domains produced by or derived from recombination of any combination of gene segments disclosed herein, optionally wherein the antibody and fragments are obtained or obtainable by recombination, in vivo in a mouse, mammal or other vertebrate of the invention following immunisation.

In one embodiment the immunoglobulin heavy chains expressed by the cell or vertebrate are essentially exclusively said heavy chains comprising human variable regions; and said heavy chains comprising human variable regions are expressed as part of serum IgG antibodies, optionally IgG1, IgG2a or IgG2b, or IgM antibodies.

In one embodiment, the cell or vertebrate of the invention expresses an IgG antibody, optionally a IgG1, IgG2a or IgG2b antibody, or a IgM antibody comprising heavy chains as defined herein, wherein the antibody specifically binds a target antigen.

The invention further relates to:

The antibody, optionally, produced by a method of the invention comprising (a) a human heavy chain variable domain derived from recombination of human VH, D and JH gene segments selected from the group consisting of VH, D and JH gene segments of any one of Tables 1-7; and (b) a human light chain variable domain derived from recombination of human V and J gene segments both selected from the V and J gene segments of any one of Tables 8-18.

An isolated antibody or antigen binding fragment thereof, optionally obtained or obtainable by the method of the invention, wherein a variable region of the antibody or fragment comprises one or more mouse or rat activation-induced deaminase (AID) pattern somatic mutations and/or mouse or rat terminal deoxynucleotidyl transferase (TdT) pattern junctional mutations.

The variable heavy or light domain or region in accordance with invention can comprises up to 10, including 1, 2, 3, 4, 5, 6, 7, 8, or 9 junctional mutations.

In a further embodiment, the variable heavy or light domain or region in accordance with invention can additionally or alternatively comprise up to 9, including 1, 2, 3, 4, 5, 6, 7, 8, or 8, including 1, 2, 3, 4, 5, 6 or 7, somatic mutations.

In a further embodiment, the invention includes an isolated antibody or antigen binding fragment thereof, optionally obtained or obtainable by the method of the invention, that binds a gamma receptor, and further optionally a human constant light chain. In one embodiment, the Fc comprises human gamma constant domains, e.g. human IgG1 IgG2, IgG3 or IgG4 constant domains.

An isolated antibody or antigen binding fragment thereof, optionally obtained or obtainable by the method of the invention, wherein the antibody comprises CHO, HEK293, Cos or yeast (eg, *Picchia*) cell glycosylation.

An antibody or fragment of the invention can specifically bind a human enzyme.

An antibody or fragment of the invention can specifically bind the human targets: proprotein convertase PC9, proprotein convertase subtilisin kexin-9 (PCSK9), CD126, IL-4, IL-4 receptor, IL-6, IL-6 receptor, IL-13, IL-18 receptor, Erbb3, cell ASIC1, ANG2, GDF-8, angiopoietin ligand-2, delta-like protein ligand 4, immunoglobulin G1, PDGF ligand, PDGF receptor or NGF receptor, toxin A or toxin B of *Clostridium difficile*, relaxin, CD48, Cd20, glucagon receptor, protease activated receptor 2, TNF-Like ligand 1A (TL1A), angiopoietin related-2 (AR-2), angiopoietin-like protein 4, RANKL, angiopoietin-like protein 3 (ANGPTL3), delta-like ligand 4 (DLL4), big endothelin-1 (ET-1), activin A, receptor tyrosine kinases, for example human AR-1 and tyrosine kinase with Ig and EGF homology domains (TIE) or TIE-2 receptor. In an example, the target is PCSK9. In an example, the target is IL-6 receptor (eg, IL6Ra). In an example, the target is IL-4 receptor (eg, IL4Ra).

Preferred aspects of the invention include:

The use of the antibody or fragment thereof in the manufacture of a medicament for use to attenuate or inhibit an IL-4Ra-mediated disease or disorder in a human. IL-4Ra-mediated or related disorders which are treated by the ligand, antibody or fragment of the invention include, for example, arthritis (including septic arthritis), herpetiformis, chronic idiopathic urticaria, scleroderma, hypertrophic scarring, Whipple's Disease, benign prostate hyperplasia, lung disorders, such as mild, moderate or severe asthma, inflammatory disorders such as inflammatory bowel disease, allergic reactions, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis.

Further IL-4Ra-mediated or related disorders which are treated by the ligand, antibody or fragment of the invention include, for example, asthma, COPD (eg, chronic bronchitis, small airway disease or emphysema), inflammatory bowel disease, a fibrotic condition (eg, systemic sclerosis, pulmonary fibrosis, parasite-induced liver fibrosis, or cystic fibrosis), allergy (for example atopic dermatitis, dust mite allergy, pet allergy or food allergy), transplantation therapy to prevent transplant rejection, suppression of a delayed-type hypersensitivity or a contact hypersensitivity reaction, as an adjuvant to allergy immunotherapy or as a vaccine adjuvant.

Further encompassed by the invention is the use of the antibody or fragment thereof in the manufacture of a medicament for prevention or treatment of a IL-4Ra-mediated or related disorder, wherein said disease or condition is an inflammatory disease or condition; an atopic disease or condition; a respiratory disease or condition; a disease or condition associated with elevated IgE; or a disease or condition associated with elevated IL-4 and/or IL-13 activity.

Further encompassed by the invention is the use of the antibody or fragment thereof in the manufacture of a medicament for prevention or treatment of a IL-4Ra-mediated or related disease or condition, wherein said disease or condition is selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.

Further encompassed by the invention is an anti-IL-4Ra antibody or fragment thereof, as disclosed herein, for prevention or treatment of any disease or disorder disclosed herein.

Further encompassed by the invention is the use of an anti-IL-4Ra antibody or fragment thereof, in a method of medical treatment of a disease or disorder disclosed herein.

Further encompassed by the invention is the use of the ligand, antibody or fragment of the invention in the manufacture of a medicament for use to attenuate or inhibit a PCSK9-mediated disease or disorder in a human. Non-limiting examples of such diseases or conditions can include, for example, a lipid disorder, hyperlipoproteinemia, hyperlipidemia; dyslipidemia; hypercholesterolemia, a heart attack, a stroke, coronary heart disease, atherosclerosis, peripheral vascular disease, claudication, type II diabetes, high blood pressure, and a cardiovascular disease or condition.

Further encompassed by the invention is an anti-PCSK9 antibody or fragment thereof, as disclosed herein, for prevention or treatment of any disease or disorder disclosed herein.

Further encompassed by the invention is the use of an anti-PSCK9 antibody or fragment thereof, in a method of medical treatment of a disease or disorder disclosed herein.

Further encompassed by the invention is the use of the ligand, antibody or fragment of the invention in the manufacture of a medicament for use to attenuate or inhibit an IL-6Ra-mediated disease or disorder in a human.

Said IL-6Ra-mediated disease or condition can be an inflammatory disease or condition. Said IL-6Ra-mediated disease or condition can be selected from the group consisting of an inflammatory bowel disease (IBD), Crohn's disease, rheumatoid arthritis, psoriasis, bronchiolitis, gingivitis, transplant rejection, allogenic transplant rejection, graft-versus-host disease (GvHD), asthma, adult respiratory distress syndrome (ARDS), septic shock, ulcerative colitis, Sjogren's syndrome, airway inflammation, Castleman's disease, periodontitis, atopic dermatitis, systemic lupus erythematosus and coronary heart disease.

Further encompassed by the invention is an anti-IL-6Ra antibody or fragment thereof, as disclosed herein, for prevention or treatment of any disease or disorder disclosed herein.

Further encompassed by the invention is the use of an anti-IL-6Ra antibody or fragment thereof, in a method of medical treatment of a disease or disorder disclosed herein.

In a further embodiment, the invention relates to the following aspects:

1. A non-human vertebrate or vertebrate cell (eg, a mouse or rat) whose genome comprises human JH2*01 and/or human JH6*02, one or more human VH gene segments and one or more human D gene segments upstream of a constant region at an endogenous heavy chain locus and/or human Jκ2*01 and/or human Jκ4*01 and one or more human Vκ gene segments upstream of a constant region at an endogenous light chain locus, wherein the gene segments in each locus are operably linked to the constant region thereof so that the cell or vertebrate is capable of producing an antibody heavy chain and an antibody light chain, or where the cell can develop into a vertebrate that expresses an antibody heavy chain and an antibody light chain, wherein the heavy chain is produced by recombination of the human JH2*01 and/or JH6*02 segment with a D segment and a VH segment and/or the antibody light chain is produced by recombination of the human Jκ2*01 and/or Jκ4*01 segment with a Vκ segment wherein said one or more human VH gene segments of the heavy chain locus comprise or consist of one, more or all human VH gene segments selected from the group consisting of VH3-23*04, VH7-4-1*01, VH4-4*02, VH1-3*01, VH3-13*01, VH3-7*01 and VH3-20*d01 or wherein said one or more human Vκ gene segments comprise or consist of one, more or all human VH gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1D-16*01 and Vκ1-9*d01.

Optionally the human gene segment is the recombined form of the gene segment that includes one or more mutations relative to the germline human gene segment sequence 2. The cell or vertebrate of aspect 1 wherein the genome comprises human JH2*01 and/or human JH6*02, one or more human VH gene segments and one or more human D gene segments upstream of a constant region at an endogenous heavy chain locus and or human Jκ2*01 and/or human Jκ4*01 and one or more human Vκ gene segments upstream of a constant region at an endogenous light chain locus.

3. The cell or vertebrate of aspect 2 wherein said one or more human VH gene segments of the heavy chain locus comprise or consist of one, more or all human VH gene segments selected from the group consisting of VH3-23*04, VH7-4-1*01, VH4-4*02, VH1-3*01, VH3-13*01, VH3-7*01 and VH3-20*d01 and wherein said one or more human Vκ gene segments comprise or consist of one, more or all human VH gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1D-16*01 and Vκ1-9*d01.

4 The cell or vertebrate of aspect 1-3 wherein the genome comprises VH3-23*04, optionally wherein the heavy chain is produced by recombination of a human JH segment with a D segment and said VH segment.

5 The cell or vertebrate of aspect 1-4 wherein the genome comprises Vκ4-1*01, optionally wherein the heavy chain is produced by recombination of a human JH segment with a D segment and said VH segment 6 The cell or vertebrate of aspect 1-5 wherein the genome comprises Vκ2-28*01, optionally wherein the heavy chain is produced by recombination of a human JH segment with a D segment and said VH segment 7 The cell or vertebrate of aspect 1-6 wherein the genome comprises Vκ1-12*01, optionally wherein the heavy chain is produced by recombination of a human JH segment with a D segment and said VH segment 8 The cell or vertebrate of aspect 1-7 wherein the genome comprises JH2*01 and Jκ2*01.

9 The cell or vertebrate of aspect 1-8 wherein the genome comprises JH6*02 and Jκ4*01.

10 The cell or vertebrate of aspect 1-9 wherein said heavy chain locus comprises VH3-23*04 recombined with JH2*01; or VH3-7*01 recombined with JH6*02.

11 The cell or vertebrate of aspect 1-10 wherein said light chain locus comprises Vκ4-1*01 recombined with Jκ2*01; or Vκ2-28*01 recombined with Jκ4*01.

12 The cell or vertebrate of any preceding aspect, wherein the genome comprises VH3-23*04, JH2*01 (optionally recombined with the VH3-23*04), Vκ4-1*01 and Jκ2*01(optionally recombined with the Vκ4-1*01).

13 The cell or vertebrate of any preceding aspect, wherein the genome comprises VH3-7*01, JH6*02 (optionally recombined with the VH3-7*01), Vκ2-28*01 and Jκ4*01 (optionally recombined with the Vκ2-28*01).

14 The cell or vertebrate of any preceding aspect, the heavy chain locus further comprising one or more additional heavy chain gene segments from Table 7.

15 The cell or vertebrate of any preceding aspect, the heavy chain locus comprising all of the gene segments of Table 1, all of the gene segments of Table 2, all of the gene segments of Table 3, all of the gene segments of Table 4, all of the gene segments of Table 5, all of the gene segments of Table 6 or all of the gene segments of Table 7.

16 The cell or vertebrate of any preceding aspect, the light chain locus further comprising one or more additional light chain segments from Table 12.

17 The cell or vertebrate of any preceding aspect, the light chain locus comprising all of the gene segments of Table 8, all of the gene segments of Table 9, all of the gene segments of Table 10, all of the gene segments of Table 11 or all of the gene segments of Table 12.

18 The cell or vertebrate of any preceding aspect, wherein the cell is a hybridoma or a B-cell (eg, an immortalised B cell).

19 The vertebrate or cell of any preceding aspect, wherein the immunoglobulin heavy chains expressed by the mouse are essentially exclusively said heavy chains comprising human variable regions; and said heavy chains comprising human variable regions are expressed as part of serum IgG1, IgG2b and IgM (and optionally IgG2a) antibodies.

20 A method of producing an antibody or an antigen binding fragment thereof, the method comprising immunising a vertebrate of aspects 1 to 19 with an antigen and recovering the antibody or fragment or recovering a cell producing the antibody or fragment; optionally modifying the produced antibody or fragment so that it comprises human constant regions,
wherein the variable domains of said antibody are encoded by
human gene segments JH2*01 or JH6*02 and one or more human VH gene segments and one or more human D gene segments;
wherein the human VH gene segment is selected from the group consisting of VH3-23*04, VH7-4-1*01, VH4-4*02, VH1-3*01, VH3-13*01, VH3-7*01 and VH3-20*d01.
and
(b) human gene segments Jκ2*01 or Jκ4*01 and one or more human Vκ gene segments,
wherein the human Vk gene segment is selected from the group consisting of Vκ4-1*01, Vκ2-28*01, Vκ1D-13*d01, Vκ1-12*01, Vκ1D-12*02, Vκ3-20*01, Vκ1-17*01. Vκ1D-39*01, Vκ3-11*01, Vκ1D-16*01 and Vκ1-9*d01.

21 A method according to aspect 20 wherein the antigen is a multi-subunit human protein, a bacterial cytotoxin or a protein expressed as a transmembrane protein on human cells.

22 A method of producing an antibody or an antigen binding fragment thereof, the method comprising isolating an antibody or antigen binding fragment thereof from a cell according to any one of aspects 1 to 20; and optionally modifying the isolated antibody or fragment so that it comprises human constant regions.

23 The method of aspect 20, further comprising
(a) isolating from the vertebrate a B-cell encoding an antibody that binds the antigen,
(b) identifying or copying a nucleotide sequence of the B-cell that encodes a VH domain of the antibody and/or identifying or copying nucleotide sequence of the B-cell that encodes a VL domain of the antibody; and
(c) using the sequence(s) to produce an isolated antibody or fragment comprising the VH and/or VL domain; optionally wherein the isolated antibody or fragment comprises human constant regions.

24 The method of any one of aspects 20-23, wherein the antibody or fragment is produced by expression from a host cell selected from a CHO, HEK293, Cos or yeast (eg, *Picchia*) cell.

25 The method of aspect 24, wherein the antibody or fragment is produced by expression from a CHO cell.

26 The method of any one of aspects 20-25, further comprising formulating the antibody or fragment with a diluent, carrier, excipient or a drug to produce a pharmaceutical composition for human medical use, optionally further comprising packaging the composition in a sterile container, for example, a vial, tube, IV bag or syringe, further optionally producing a kit comprising combining the package with a label or instructions indicating use of the antibody composition for human medical use; optionally wherein the label or instructions comprises a medicament batch number and/or a marketing authorisation number, further optionally an EMA or FDA marketing authorisation number.

27 The method of any one of aspects 20-26, wherein the vertebrate is according to any one of aspects 1 to 19 and the antibody or fragment produced by the method comprises
(a) a human heavy chain variable domain is a recombinant of human JH2*01 or human JH6*02, one or more human VH gene segments and one or more human D gene segments; and
(b) a human light chain variable domain is a recombinant of human JK2*01 or human JK4*01 and one or more human Vκ gene segments.

28 The method of aspect 27, wherein the antibody or fragment produced by the method comprises a human heavy chain variable domain recombinant of VH3-23*04 and JH2*01 and a human light chain variable domain recombinant of Vκ4-1*01 and Jκ2*01.

29 The method of aspect 27, wherein the antibody or fragment produced by the method comprises a human heavy chain variable domain recombinant of VH3-7*01 and JH6*02 and a human light chain variable domain recombinant of Vκ2-28*01 and Jκ4*01.

30 An isolated antibody or fragment or kit produced by the method of any one of aspects 20-29

31 An isolated antibody or antigen binding fragment thereof or kit produced by the method of aspects 20-29 wherein the antibody is humanised.

32 A composition comprising an antibody or fragment or kit produced by the method of aspects 20-29 wherein the antibody or fragment is the only therapeutic agent.

33 A composition comprising an antibody or fragment or kit produced by the method of aspects 20-29 further comprising an additional therapeutic agent, for example, an anti-hypercholesterolemia drug.

34 An isolated antibody or fragment or kit produced by the method of any one of aspects 20-29 for human medical use.

35 Use of the isolated antibody or fragment produced by the method of any one of aspects 20-29 in the manufacture of a medicament for human medical use.

36 The use of aspect 35, wherein the medicament is comprised by a composition or kit as recited in aspect 26.

37 An isolated antibody or fragment or kit according to aspect 30-34, or use according to aspect 35-36, which can specifically bind a human target selected from: proprotein convertase PC9, proprotein convertase subtilisin kexin-9 (PCSK9), CD126, IL-4, IL-4 receptor, IL-6, IL-6 receptor, IL-13, IL-18 receptor, Erbb3, cell ASIC1, ANG2, GDF-8, angiopoietin ligand-2, delta-like protein ligand 4, immunoglobulin G1, PDGF ligand, PDGF receptor or NGF receptor, toxin A or toxin B of *Clostridium difficile*, relaxin, CD48, Cd20, glucagon receptor, protease activated receptor 2, TNF-Like ligand 1A (TL1A), angiopoietin related-2 (AR-2), angiopoietin-like protein 4, RANKL, angiopoietin-like protein 3 (ANGPTL3), delta-like ligand 4 (DLL4), big endothelin-1 (ET-1), activin A, receptor tyrosine kinases, for example human AR-1 and tyrosine kinase with Ig and EGF homology domains (TIE) and TIE-2 receptor.

38 An isolated antibody or fragment or kit according to aspect 30-34, or use according to aspect 35-36, for use in treatment of a human in need thereof, wherein the treatment comprises delivery of an effective amount of an antibody or fragment which specifically binds to a virus or an antigen selected from a human cytokine, growth factor, hormone, enzyme and a serum protein.

39 A host cell, for example a CHO, HEK293, Cos or yeast (eg, *Picchia*) cell, expressing an antibody or fragment produced by the method of any one of aspects 20-29.

In the aspects described above, JH6*02 can be replaced with JH6*01.

In a further aspect, the invention includes the following clauses:

Clauses

1. A non-human vertebrate cell (eg, a mouse cell or rat cell) whose genome comprises human JH2*01 and/or human JH6*02, one or more human VH gene segments and one or more human D gene segments upstream of a constant region at an endogenous heavy chain locus and human Jκ2*01 and/or human Jκ4*01 and one or more human Vκ gene segments upstream of a constant region at an endogenous light chain locus, wherein the gene segments in each locus are operably linked to the constant region thereof so that the cell is capable of producing an antibody heavy chain and an antibody light chain, or where the cell can develop into a vertebrate that expresses an antibody heavy chain and an antibody light chain, wherein the heavy chain is produced by recombination of the human JH2*01 and/or JH6*02 segment with a D segment and a VH segment and the light chain is produced by recombination of the human Jκ2*01 and/or Jκ4*01 segment with a Vκ segment.

2. A non-human vertebrate (eg, a mouse or rat) whose genome comprises human JH2*01 and/or human JH6*02, one or more human VH gene segments and one or more human D gene segments upstream of a constant region at an endogenous heavy chain locus and human Jκ2*01 and/or human Jκ4*01 and one or more human Vκ gene segments upstream of a constant region at an endogenous light chain locus, wherein the gene segments in each locus are operably linked to the constant region thereof so that the vertebrate is capable of producing an antibody heavy chain and an antibody light chain, wherein the heavy chain is produced by recombination of the human JH2*01 and/or JH6*02 segment with a D segment and a VH segment and the antibody light chain is produced by recombination of the human Jκ2*01 and/or Jκ4*01 segment with a Vκ segment.

3. The cell of clause 1 or vertebrate of clause 2, wherein the genome comprises JH2*01 and Jκ2*01.

4. The cell of clause 1 or 3 or the vertebrate of clause 2 or 3, wherein the genome comprises JH6*02 and Jκ4*01.

5. The cell or vertebrate of any preceding clause, wherein said one or more human VH gene segments of the heavy chain locus comprise or consist of one, more or all human VH gene segments selected from the group consisting of VH3-23*04, VH7-4-1*01, VH4-4*02, VH1-3*01, VH3-13*01, VH3-7*01 and VH3-20*d01.

6. The cell or vertebrate of clause 5, wherein said heavy chain locus comprises VH3-23*04 recombined with JH2*01; or VH3-7*01 recombined with JH6*02.

7. The cell or vertebrate of any preceding clause, wherein said one or more human Vκ gene segments comprise or consist of one, more or all human VH gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1D-16*01 and Vκ1-9*d01.

8. The cell or vertebrate of clause 5, wherein said light chain locus comprises Vκ4-1*01 recombined with Jκ2*01; or Vκ2-28*01 recombined with Jκ4*01.

9. The cell or vertebrate of any preceding clause, wherein the genome comprises VH3-23*04, JH2*01 (optionally recombined with the VH3-23*04), Vκ4-1*01 and Jκ2*01(optionally recombined with the Vκ4-1*01).

10. The cell or vertebrate of any preceding clause, wherein the genome comprises VH3-7*01, JH6*02 (optionally recombined with the VH3-7*01), Vκ2-28*01 and Jκ4*01 (optionally recombined with the Vκ2-28*01).

11. The cell or vertebrate of any preceding clause, the heavy chain locus further comprising one or more additional heavy chain gene segments from Table 7.

12. The cell or vertebrate of any preceding clause, the heavy chain locus comprising all of the gene segments of Table 1, all of the gene segments of Table 2, all of the gene segments of Table 3, all of the gene segments of Table 4, all of the gene segments of Table 5, all of the gene segments of Table 6 or all of the gene segments of Table 7.

13. The cell or vertebrate of any preceding clause, the light chain locus further comprising one or more additional light chain segments from Table 12.

14. The cell or vertebrate of any preceding clause, the light chain locus comprising all of the gene segments of Table 8, all of the gene segments of Table 9, all of the gene segments of Table 10, all of the gene segments of Table 11 or all of the gene segments of Table 12.

15. The cell or vertebrate of any preceding clause, wherein the cell is a hybridoma or a B-cell (eg, an immortalised B cell).

16. The vertebrate or cell of any preceding clause, wherein the immunoglobulin heavy chains expressed by the mouse are essentially exclusively said heavy chains comprising human variable regions; and said heavy chains comprising human variable regions are expressed as part of serum IgG1, IgG2b and IgM (and optionally IgG2a) antibodies.

17. A method of producing an antibody or an antigen binding fragment thereof, the method comprising immunising a vertebrate of clauses 2 to 16 with an antigen and recovering the antibody or fragment or recovering a cell producing the antibody or fragment; optionally modifying the produced antibody or fragment so that it comprises human constant regions.

18. A method of producing an antibody or an antigen binding fragment thereof, the method comprising isolating an antibody or antigen binding fragment thereof from a cell according to any one of clauses 1 and 3 to 16; and optionally modifying the isolated antibody or fragment so that it comprises human constant regions.

19. The method of clause 17 or clause 18, further comprising
(a) isolating from the vertebrate a B-cell encoding an antibody that binds the antigen,
(b) identifying or copying a nucleotide sequence of the B-cell that encodes a VH domain of the antibody and/or identifying or copying nucleotide sequence of the B-cell that encodes a VL domain of the antibody; and
(c) using the sequence(s) to produce an isolated antibody or fragment comprising the VH and/or VL domain; optionally wherein the isolated antibody or fragment comprises human constant regions.
20. The method of any one of clauses 17-19, wherein the antibody or fragment is produced by expression from a host cell selected from a CHO, HEK293, Cos or yeast (eg, *Picchia*) cell.
21. The method of any one of clauses 17-20, further comprising formulating the antibody or fragment with a diluent, carrier, excipient or a drug to produce a pharmaceutical composition for human medical use, optionally further comprising packaging the composition in a sterile container, for example, a vial, tube, IV bag or syringe, further optionally producing a kit comprising combining the package with a label or instructions indicating use of the antibody composition for human medical use; optionally wherein the label or instructions comprises a medicament batch number and/or a marketing authorisation number, further optionally an EMA or FDA marketing authorisation number.
22. The method of any one of clauses 17-21, wherein the vertebrate is according to any one of clauses 2 to 16 and the antibody or fragment produced by the method comprises
   (a) a human heavy chain variable domain is a recombinant of human JH2*01 or human JH6*02, one or more human VH gene segments and one or more human D gene segments; and
   (b) a human light chain variable domain is a recombinant of human JK2*01 or human JK4*01 and one or more human Vκ gene segments.
23. The method of clause 22, wherein the antibody or fragment produced by the method comprises a human heavy chain variable domain recombinant of VH3-23*04 and JH2*01 and a human light chain variable domain recombinant of Vκ4-1*01 and Jκ2*01.
24. The method of clause 22, wherein the antibody or fragment produced by the method comprises a human heavy chain variable domain recombinant of VH3-701 and JH6*02 and a human light chain variable domain recombinant of Vκ2-28*01 and Jκ4*01.
25. An isolated antibody or antigen binding fragment thereof obtained or obtainable by the method of any one of clauses 17-24, wherein a heavy and/or light chain variable domain of the antibody or fragment comprises one or more mouse or rat activation-induced deaminase (AID) pattern somatic mutations and/or mouse or rat terminal deoxynucleotidyl transferase (TdT) pattern junctional mutations.
26. An isolated antibody or antigen binding fragment thereof obtained or obtainable by the method of any one of clauses 17-24, or an antibody according to clause 25 comprising a human heavy chain Fc fragment, optionally that binds a gamma receptor, and further optionally a human constant light chain.
27. An isolated antibody or antigen binding fragment thereof obtained or obtainable by the method of any one of clauses 17-24, or an antibody according to clause 25 or clause 26 comprising an antigen binding site capable of specifically binding to a virus or an antigen selected from a human cytokine, growth factor, hormone, enzyme and a serum protein.
28. An isolated antibody or antigen binding fragment thereof obtained or obtainable by the method of any one of clauses 17-24, or an antibody according to any one of clauses 25-27, wherein said antibody or fragment is glycosylated, optionally comprising CHO, HEK293, Cos or yeast (eg, *Picchia*) cell glycosylation.
29. An isolated antibody or antigen binding fragment thereof, wherein the variable domains of said antibody are encoded by
   (a) human gene segments JH2*01 or JH6*02 and one or more human VH gene segments and one or more human D gene segments; and
   (b) human gene segments Jκ2*01 or Jκ4*01 and one or more human Vκ gene segments.
30. The antibody of clause 29, wherein the variable domains are encoded by the human gene segments (i) JH2*01 and VH3-23*04 for the VH domain and (ii) Vκ4-1*01 and Jκ2*01 for the VL domain.
31. The antibody of clause 29, wherein the variable domains are encoded by the human gene segments (i) JH6*02 and VH3-7*01 for the VH domain and (ii) Vκ2-28*01 and Jκ4*01 for the VL domain.
32. An isolated antibody or antigen binding fragment thereof of any one of clauses 25-31, wherein the antibody is humanised.
33. A composition comprising an antibody or fragment of any one of clauses 25-32, wherein the antibody or fragment is the only therapeutic agent.
34. A composition comprising an antibody or fragment of any one of clauses 25-32, further comprising an additional therapeutic agent, for example, an anti-hypercholesterolemia drug.
35. The isolated antibody or fragment produced by the method of any one of clauses 17-24 or the isolated antibody or fragment of any one of clauses 25 to 34 for human medical use.
36. Use of the isolated antibody or fragment produced by the method of any one of clauses 17-24 or the isolated antibody or fragment of any one of clauses 25-34 in the manufacture of a medicament for human medical use.
37. The use of clause 36, wherein the medicament is comprised by a composition or kit as recited in clause 21.
38. A method of medical treatment comprising delivery an effective amount of isolated antibody or fragment thereof according to clauses 25-34 to a human in need thereof.
39. A host cell, for example a CHO, HEK293, Cos or yeast (eg, *Picchia*) cell, expressing an antibody or fragment as defined in any one of clauses 25-34.

In the clauses described above, JH6*02 can be replaced with JH6*01.

In a further aspect, the invention includes the following provisions:
1. A non-human vertebrate (eg, a mouse or rat) cell whose genome comprises human VH, D and JH gene segments upstream of a constant region at an endogenous heavy chain locus and human VL and JL gene segments upstream of a constant region at an endogenous light chain locus, wherein the gene segments are operably linked to the constant region thereof so that the cell is capable of expressing immunoglobulin heavy and light chains comprising human VH and VL domains respectively, wherein the heavy chain locus comprises a human 01 allele VH gene segment capable of recombining with a human D and JH gene segment to produce a VH domain, wherein the light chain locus comprises a human 01 allele VL gene segment capable of recombining with a human JL gene segment to produce a VL domain, or wherein the cell can develop into a vertebrate that expresses said VH and VL domains.

2. A non-human vertebrate (eg, a mouse or rat) whose genome comprises human VH, D and JH gene segments upstream of a constant region at an endogenous heavy chain locus and human VL and JL gene segments upstream of a constant region at an endogenous light chain locus, wherein the gene segments are operably linked to the constant region thereof so that the vertebrate is capable of expressing immunoglobulin heavy and light chains comprising human VH and VL domains respectively, wherein the heavy chain locus comprises a human 01 allele VH gene segment capable of recombining with a human D and JH gene segment to produce a VH domain and wherein the light chain locus comprises a human 01 allele VL gene segment capable of recombining with a human JL gene segment to produce a VL domain.

3. The cell of provision 1 or vertebrate of provision 2, wherein one or both 01 alleles is a d01 allele.

4. The cell or vertebrate of any preceding provision, wherein the VH and VL domains form an antigen binding site.

5. The cell or vertebrate of any preceding provision, wherein the heavy chain locus comprises no second human allele of said VH gene segment.

6. The cell or vertebrate of any preceding provision, wherein the light chain locus comprises no second human allele of said VL gene segment.

7. The cell or vertebrate of any preceding provision, wherein the heavy chain locus comprises a human 01 allele D gene segment capable of recombining with a human JH gene segment and said human VH segment to produce said VH domain; optionally wherein the heavy chain locus comprises no second human allele of said D gene segment.

8. The cell or vertebrate of any preceding provision, wherein the heavy chain locus comprises a human 02 allele JH gene segment (eg, JH6*02) capable of recombining with a human D gene segment and said human VH segment to produce said VH domain; optionally wherein the heavy chain locus comprises no second human allele of said JH gene segment.

9. The cell or vertebrate of any preceding provision, wherein the light chain locus comprises a human 01 allele JL gene segment capable of recombining said human VL segment to produce said VL domain; optionally wherein the light chain locus comprises no second human allele of said JL gene segment.

10. The cell or vertebrate of any preceding provision, wherein the genome comprises VH3-23*04, JH2*01 (optionally recombined with the VH3-23*04), Vκ4-1*01 and Jκ2*01(optionally recombined with the Vκ4-1*01).

11. The cell or vertebrate of any preceding provision, wherein the genome comprises VH3-7*01, JH6*02 (optionally recombined with the VH3-7*01), Vκ2-28*01 and Jκ4*01 (optionally recombined with the Vκ2-28*01).

12. The cell or vertebrate of any preceding provision, wherein said light chain locus comprises or consists of one, more or all human VL gene segments selected from the group consisting of Vκ4-1*01, Vκ2-28*01, Vκ1D-13*d01, Vκ1-12*01, Vκ1D-12*02, Vκ3-20*01, Vκ1-17*01, Vκ1D-39*01, Vκ3-11*01, Vκ1D-16*01 and Vκ1-9*d01.

13. The cell or vertebrate of any one of provisions 1 to 9, wherein said light chain locus comprises or consists of one, more or all human VL gene segments selected from the group consisting of Jκ4*01 and Jκ2*01.

14. The cell or vertebrate of any preceding provision, wherein said heavy chain locus comprises or consists of one, more or all human VH gene segments selected from the group consisting of VH3-23*04, VH7-4-1*01, VH4-4*02, VH1-3*01, VH3-13*01, VH3-7*01 and VH3-20*d01.

15. The cell or vertebrate of any one of provisions 1 to 9 or 14, wherein the light chain locus comprises Jλ2*01.

16. The cell or vertebrate of any one of provisions 1 to 6, wherein said VH domain is a recombinant of human VH, D and JH segments, wherein the VH is selected from the group consisting of one, more or all 01 allele gene VH segments of Table 7 and/or the VL domain is a recombinant of (i) human Vκ and Jκ gene segments, wherein the Vκ is selected from the group consisting of one, more or all 01 allele Vκ gene segments of Table 12 or (ii) human Vλ and Jλ gene segments, the Vλ being selected from the group consisting of one, more or all 01 allele Vλ gene segments of Table 18; optionally wherein the VH and/or VL domains are expressed as IgG antibodies.

17. The cell or vertebrate of any one of provisions 1 to 6 and 16, wherein said VH domain is a recombinant of the human VH, D and JH segments of Table 1, Table 2, Table 3, Table 4, Table 5, Table 6 or Table 7 and/or the VL domain is a recombinant of (i) the human Vκ and Jκ gene segments of Table 8, Table 9, Table 10, Table 11 or Table 12; or (ii) the human Vλ and Jλ gene segments of Table 13, Table 14, Table 15. Table 16. Table 17 or Table 18.

18. The vertebrate of any one of provisions 2 to 17, wherein (a) the heavy chain locus comprises the human VH, D and JH segments of a Table selected from Table 1, Table 2, Table 3, Table 4, Table 5, Table 6 and Table 7 and/or (b) the light chain locus comprises (i) the human Vκ and Jκ gene segments of a Table selected from Table 8, Table 9, Table 10, Table 11 and Table 12; or (ii) the human Vλ and Jλ gene segments of a Table selected from Table 13, Table 14, Table 15, Table 16, Table 17 and Table 18; and wherein the vertebrate expresses one or a plurality of VH domains each being a recombinant of human VH, D and JH segments from a selected Table of (a) and/or expresses one or a plurality of VL domains each being a recombinant of human VL and JL segments from a selected Table of (b); optionally wherein such VH domains and VL domains form antigen binding sites.

19. A non-human vertebrate (eg, a mouse or rat) whose genome comprises human VH, D and JH gene segments upstream of a constant region at an endogenous heavy chain locus and human VL and JL gene segments upstream of a constant region at an endogenous light chain locus, wherein the gene segments are operably linked to the constant region thereof so that the vertebrate is capable of expressing immunoglobulin heavy and light chains comprising human VH and VL domains respectively, wherein (a) the heavy chain locus comprises the human VH, D and JH segments of a Table selected from Table 1, Table 2, Table 3, Table 4, Table 5, Table 6 and Table 7 and/or (b) the light chain locus comprises (i) the human Vκ and Jκ gene segments of a Table selected from Table 8, Table 9, Table 10, Table 11 and Table 12; or (ii) the human Vλ and Jλ gene segments of a Table selected from Table 13, Table 14, Table 15, Table 16, Table 17 and Table 18; and wherein the vertebrate expresses one or a plurality of VH domains each being a recombinant of human VH, D and JH segments from a selected Table of (a) and/or expresses one or a plurality of VL domains each being a recombinant of human VL and JL segments from a selected Table of (b); optionally wherein such VH domains and VL domains form antigen binding sites.
20. The cell of any preceding provision, wherein said cell is an ES cell, a hybridoma cell or an immortalised B cell.
21. The vertebrate of any preceding provision, wherein said vertebrate is comprised within a container having an air filter.
22. A population of at least 90 cells, wherein said cells are according to any one of provisions 1 to 17, 19 or 20.
23. The cell, vertebrate or population of any preceding provision, wherein said light chain locus constant region is a kappa or lambda constant region; optionally a mouse or rat constant region.
24. The cell, vertebrate or population of any preceding provision, wherein the heavy chain locus is a mouse or rat constant region (eg, comprising a gamma constant gene segment).
25. The cell, vertebrate or population of any preceding provision, wherein said endogenous light chain locus is a kappa or lambda locus; optionally wherein the genome comprises at least the V and J gene segments of Table 8 at an endogenous light chain locus and/or at least the V and J gene segments of Table 13 at an endogenous light chain locus.
26. The cell, vertebrate or population of any one of provisions 1 to 9 or 14 to 23, wherein said light chains comprise immunoglobulin light chains comprising human variable regions that derived from recombination of human Vλ and Jλ gene segments selected from the group consisting of Vλ and Jλ gene segments of Table 18, optionally each such variable region being expressed with a constant region encoded by a Cλ gene segment selected from the group consisting of the Cλ gene segments of Table 18.
27. The cell, vertebrate or population of any preceding provision, wherein the vertebrate is a mouse C57Bl/6J, 129S5 or 129Sv strain or a cross between C57Bl/6J and a 129S5 or 129Sv strain.
28. The cell, vertebrate or population of any preceding provision, wherein the immunoglobulin heavy chains expressed by the cell or vertebrate are essentially exclusively said heavy chains comprising human variable regions; and said heavy chains comprising human variable regions are expressed as part of serum IgG1, IgG2b and IgM (and optionally IgG2a) antibodies.
29. The cell, vertebrate or population of any preceding provision, wherein the vertebrate expresses light chains comprising human lambda variable regions and at least 60%, 70% or 80% of the variable regions of such light chains are derived from recombination of human Vλ and Jλ gene segments.
30. A non-human vertebrate (eg, a mouse or rat) or cell whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate or cell, wherein the vertebrate comprises immunoglobulin light chains comprising lambda variable regions (lambda light chains) or the cell can develop into a vertebrate that expresses said immunoglobulin light chains, wherein the lambda light chains comprise immunoglobulin light chains comprising lambda variable regions derived from recombination of human Vλ and Jλ gene segments; wherein at least 80% of the variable regions of the lambda light chains expressed by the vertebrate are human Vλ and Jλ gene segment recombinants; wherein the vertebrate or cell is according to any one of provisions 1 to 9 or 14 to 29.
31. A non-human vertebrate (eg, a mouse or rat) or cell whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments are selected from one, more or all of the segments of Table 18 and have been provided by insertion into an endogenous light chain locus of the vertebrate or cell, wherein the vertebrate comprises immunoglobulin light chains comprising lambda variable regions (lambda light chains) or the cell can develop into a vertebrate that expresses said immunoglobulin light chains, wherein the lambda light chains comprise immunoglobulin light chains comprising lambda variable region recombinants of one or a plurality of human Vλ and Jλ gene segment pairs, wherein each gene segment is selected from the human Vλ and Jλ gene segments of Table 18.
32. A method of producing an antibody or an antigen binding fragment thereof, the method comprising immunising a vertebrate of any one of provisions 2 to 19, 21 or 23 to 31 with an antigen and recovering the antibody or fragment or recovering a cell producing the antibody or fragment; optionally modifying the produced antibody or fragment so that it comprises human constant regions.
33. A method of producing an antibody or an antigen binding fragment thereof, the method comprising isolating an antibody or antigen binding fragment thereof from a cell according to any one of provisions 1, 3 to 17, 19 and 23 to 31; and optionally modifying the isolated antibody or fragment so that it comprises human constant regions.
34. The method of provision 33, further comprising
   (a) isolating from the vertebrate a B-cell encoding an antibody that binds the antigen,
   (b) identifying or copying a nucleotide sequence of the B-cell that encodes a VH domain of the antibody and/or identifying or copying nucleotide sequence of the B-cell that encodes a VL domain of the antibody; and
   (c) using the sequence(s) to produce an isolated antibody or fragment comprising the VH and/or VL domain; optionally wherein the isolated antibody or fragment comprises human constant regions.
35. The method of any one of provisions 32 to 34, wherein the antibody or fragment is produced by expression from a host cell selected from a CHO, HEK293, Cos or yeast (eg, *Picchia*) cell.
36. The method of provision any one of provisions 32 to 35, further comprising formulating the antibody or fragment with a diluent, carrier, excipient or a drug to produce a pharmaceutical composition for human medical use, optionally further comprising packaging the composition in a sterile container, for example, a vial, tube, IV bag or syringe, further optionally producing a kit comprising combining the package with a label or instructions indicating use of the antibody composition for human medical use; optionally wherein the label or instructions comprises a medicament batch number and/or a marketing authorisation number, further optionally an EMA or FDA marketing authorisation number.
37. The method of any one of provisions 32 to 35, wherein the vertebrate is according to any preceding provision and the antibody or fragment produced by the method comprises
   (a) a human heavy chain variable domain recombinant of human VH, D and JH gene segments selected from the group consisting of VH, D and JH gene segments of Table 7; and
   (b) a human light chain variable domain recombinant of human V and J gene segments selected from the V and J gene segments of Table 12 or selected from the V and J gene segments of Table 18.
38. An isolated antibody or antigen binding fragment thereof obtained or obtainable by the method of any one of provisions 32 to 35, wherein a heavy and/or light chain variable domain of the antibody or fragment comprises one or more mouse or rat activation-induced deaminase (AID) pattern somatic mutations and/or mouse or rat terminal deoxynucleotidyl transferase (TdT) pattern junctional mutations.
39. An isolated antibody or antigen binding fragment thereof obtained or obtainable by the method of provision 32 to 35, or an antibody according to provision 38 comprising a human heavy chain Fc fragment, optionally that binds a gamma receptor, and further optionally a human constant light chain.
40. An isolated antibody or antigen binding fragment thereof obtained or obtainable by the method of any one of provisions 32 to 35, or an antibody according to provision 38 or provision 39 comprising an antigen binding site capable of specifically binding to a virus or an antigen selected from a human cytokine, growth factor, hormone, enzyme and a serum protein.
41. An isolated antibody or antigen binding fragment thereof obtained or obtainable by the method of any one of provisions 32 to 35, or an antibody according to any one of provisions 38 to 40, wherein said antibody or fragment is glycosylated, optionally comprising CHO, HEK293, Cos or yeast (eg, *Picchia*) cell glycosylation.
42. An isolated antibody or antigen binding fragment thereof, wherein the variable domains of said antibody are encoded by (i) human VH, D and JH segments selected from the group consisting of any gene segment of Table 7 and/or (i) human Vκ and Jκ gene segments selected from the group consisting of any Vκ and Jκ gene segments of Table 12 or (ii) human Vλ and Jλ gene segments selected from the group consisting of any Vλ and Jλ gene segments of Table 18.
43. An isolated antibody or antigen binding fragment thereof of any one of provisions 38 to 42, wherein the antibody or fragment specifically binds to a virus or an antigen selected from a human cytokine, growth factor, hormone, enzyme and a serum protein.
44. An isolated antibody or antigen binding fragment thereof of any one of provisions 38 to 43, wherein the antibody is humanised.
45. A composition comprising an antibody or fragment of any one of provisions 38 to 44, wherein the antibody or fragment is the only therapeutic agent.
46. A composition comprising an antibody or fragment of any one of provisions 38 to 44, further comprising an additional therapeutic agent, for example, an anti-rheumatic drug, such as a disease modifying anti-rheumatic drug, or an anti-cancer drug or an anti-hypercholesterolaemia drug.
47. The isolated antibody or fragment produced by the method of any one of provisions 32 to 35 or the isolated antibody or fragment of any one of provisions 38 to 46 for human medical use.
48. Use of the isolated antibody or fragment produced by the method of any one of provisions 32 to 35 or the isolated antibody or fragment of provision 38 to 46 in the manufacture of a medicament for human medical use.
49. The use of provision 48, wherein the medicament is comprised by a composition or kit as recited in provision 36.
50. A method of medical treatment comprising delivery an effective amount of isolated antibody or fragment thereof according to provisions 38 to 46 to a human in need thereof.
51. A host cell, for example a CHO, HEK293, Cos or yeast (eg, *Picchia*) cell, expressing an antibody or fragment as defined in any one of provisions 38 to 43.

In the provisions described above, JH6*02 can be replaced with JH*01.

The following definitions apply to any configuration, aspect, clause, provision, example or embodiment of the invention.

"Derived from" is used in the ordinary sense of the term. Exemplary synonyms include "produced as", "resulting from", "received from", "obtained from", "a product of", "consequence of", and "modified from" For example, a human variable region of a heavy chain can be derived from recombination of human VH, D and JH gene segments and this reflects the in vivo recombination of these gene segments in, for example, a transgenic heavy chain locus according to the invention with any accompanying mutation (eg, junctional mutation).

Samples from which B-cells can be obtained include but are not limited to blood, serum, spleen, splenic tissue, bone marrow, lymph, lymph node, thymus, and appendix. Antibodies and immunoglobulin chains can be obtained from each of the previous-mentioned samples and also from the following non-limiting list of B-cells, ascites fluid, hybridomas, and cell cultures.

"Plurality" is used in the ordinary sense of the term and means "at least one" or "more than one".

The term "germline configuration" refers to a germline genomic configuration. For example, human immunoglobulin gene segments of a transgenic immunoglobulin locus are in a germline configuration when the relative order of the gene segments is the same as the order of corresponding gene segments in a human germline genome. For example, when the transgenic locus is a heavy chain locus of the invention comprising hypothetical human immunoglobulin gene segments A, B and C, these would be provided in this order (5' to 3' in the locus) when the corresponding gene segments of a human germline genome comprises the arrangement 5'-A-B-C-3'. In an example, when elements of a human immunoglobulin locus (eg, gene segments, enhancers or other regulatory elements) are provided in a transgenic immunoglobulin locus according to the invention, the human Ig locus elements are in germline configuration when when the relative order of the gene segments is the same as the order of corresponding gene segments in a human germline genome and human sequences between the elements are included, these corresponding to such sequences between corresponding elements in the human germline genome. Thus, in a hypothetical example the transgenic locus comprises human elements in the arrangement 5'-A-S1-B-S2-C-S3-3', wherein A, B and C are human immunoglobulin gene segments and S1-83 are human inter-gene segment sequences, wherein the corresponding arrangement 5'-A-S1-B-S2-C-S3-3' is present in a human germline genome. For example, this can be achieved by providing in a transgenic immunoglobulin locus of the invention a DNA insert corresponding to the DNA sequence from A to C in a human germline genome (or the insert comprising the DNA sequence from A to C). The arrangements in human germline genomes and immunoglobulin loci are known in the art (eg, see the IMGT at the World Wide Web (see above), Kabat and other antibody resources referenced herein).

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., dAb, Fab, F(ab')2, and Fv). The term "antibody" also includes H2 antibodies that comprise a dimer of a heavy chain (5'-VH-(optional Hinge)-CH2-CH3-3') and are devoid of a light chain (akin to naturally-occurring H2 antibodies; see, eg, Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). Thus, in an embodiment of the present invention, RNA produced from the transgenic heavy chain locus encodes for heavy chains that re devoid of a CH1 gene segment and comprise no functional antibody light chain. In an example, RNA produced from the transgenic heavy chain locus encodes for VH single variable domains (dAbs; domain antibodies). These can optionally comprise a constant region.

The term "immunoglobulin" (Ig) is used interchangeably with "antibody" herein.

An "isolated" antibody is one that has been identified, separated and/or recovered from a component of its production environment (e.g., naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

An "antibody fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

An antibody that "specifically binds to" or is "specific for" a particular polypeptide, antigen, or epitope is one that binds to that particular polypeptide, antigen, or epitope without substantially binding to other polypeptides, antigens or epitopes. For example, binding to the antigen or epitope is specific when the antibody binds with a $K_D$ of 100 μM or less, 10 μM or less, 1 μM or less, 100 nM or less, eg, 10 nM or less, 1 nM or less; 500 pM or less, 100 pM or less, or 10 pM or less. The binding affinity ($K_D$) can be determined using standard procedures as will be known by the skilled person, eg, binding in ELISA and/or affinity determination using surface plasmon resonance (eg, Biacore™ or KinExA™ solution phase affinity measurement which can detect down to fM affinities (Sapidyne Instruments, Idaho)).

"Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to a carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

S1F/HA, +/KA=(i) S1F—first endogenous heavy chain allele has one human heavy chain locus DNA insertion, endogenous mouse VDJ region has been inactivated by inversion and movement upstream on the chromosome; (ii) HA—second endogenous heavy chain allele has been inactivated (by insertion of an endogenous interrupting sequence); (iii) +—first endogenous kappa allele is a wild-type kappa allele; and (iv) KA—the second endogenous kappa allele has been inactivated (by insertion of an endogenous interrupting sequence). This arrangement encodes exclusively for heavy chains from the first endogenous heavy chain allele.

Figure 11A:
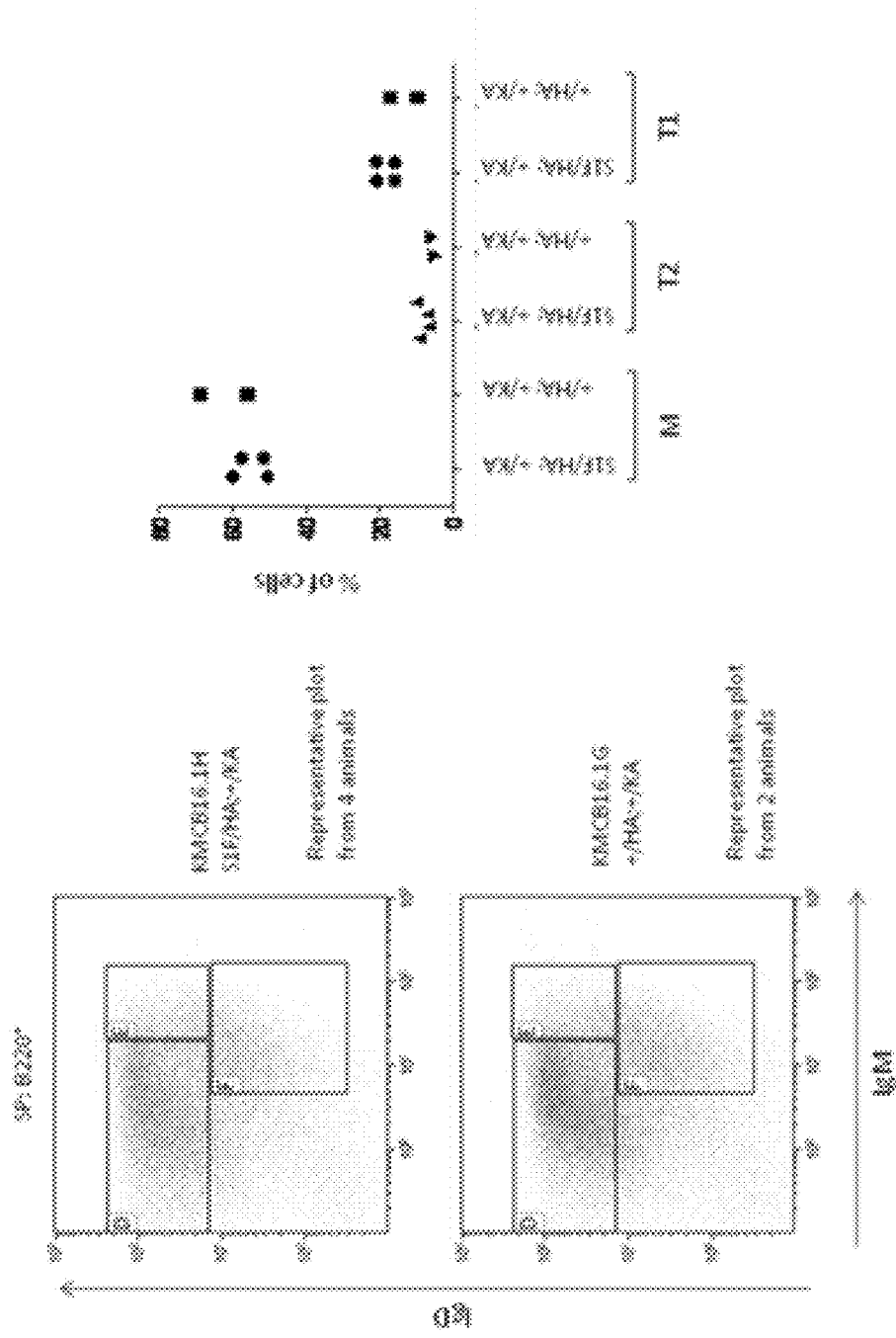
FIG. 11A: Splenic B-Cell Compartment Analysis. This figure shows the results of FACS analysis on splenic B-cells from transgenic S1F/HA, KA/+ mice of the invention expressing heavy chain variable regions which are all human (where endogenous heavy chain expression has been inactivated by inversion), compared with splenic B-cells from mice expressing only mouse antibodies. The results show that the splenic B-cell compartments in the mice of the invention are normal (ie, equivalent to the compartments of mice expressing only mouse antibody chains).
Figure 11B:
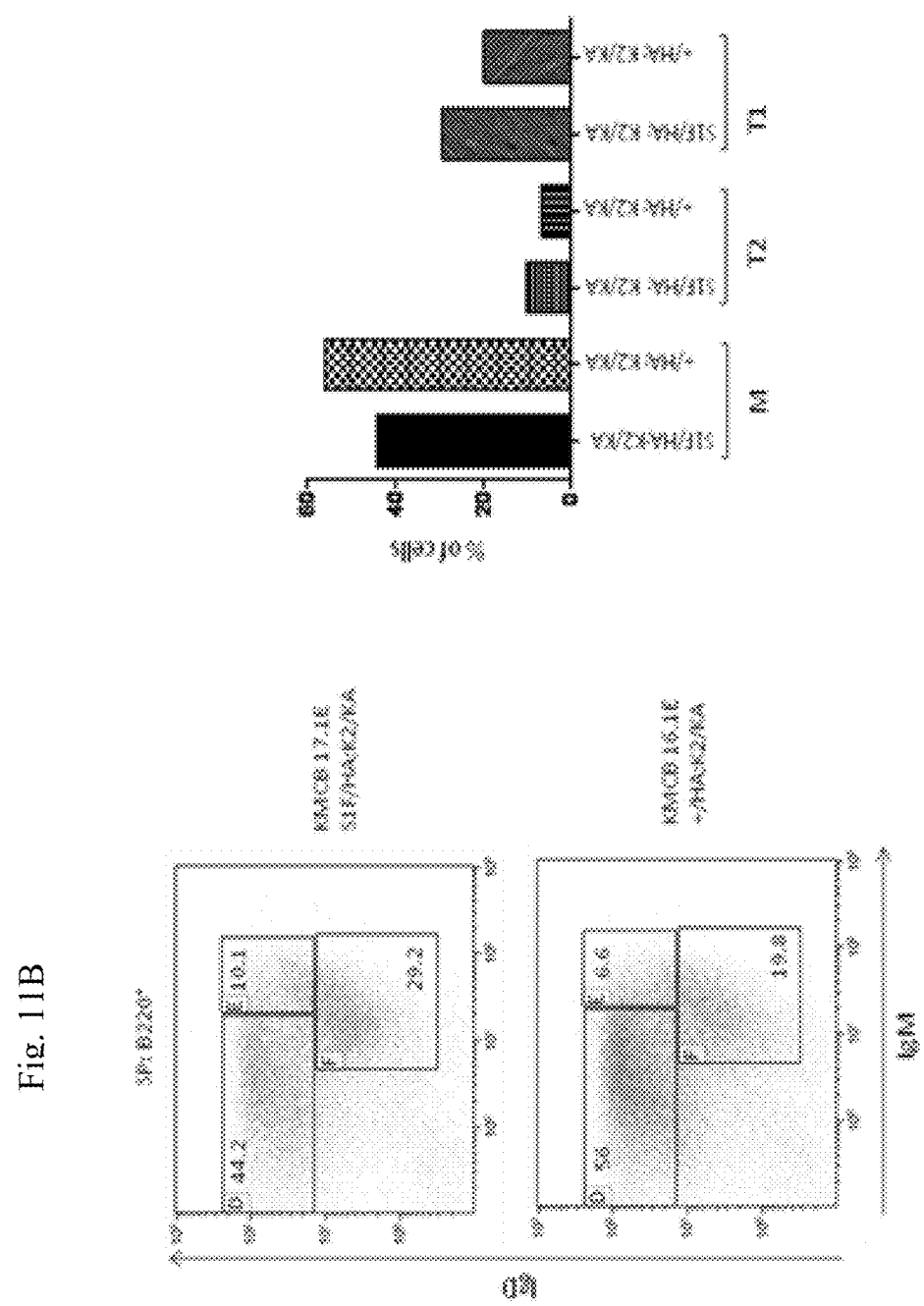

FIG. 11B: Splenic B-Cell Compartment Analysis. This figure shows the results of FACS analysis on splenic B-cells from transgenic S1F/HA, K2/KA mice of the invention expressing heavy chain variable regions which are all human (where endogenous heavy chain expression has been inactivated by inversion) and human kappa chain variable regions, compared with splenic B-cells from +/HA, K2/KA mice. The results show that the splenic B-cell compartments in the mice of the invention are normal.

S1F/HA, K2/KA=(i) K2—the first endogenous kappa allele has two kappa chain locus DNA insertions between the most 3' endogenous Jκ and the mouse Cκ, providing an insertion of 14 human Vκ and Jκ1-Jκ5; and (ii) KA—the second endogenous kappa allele has been inactivated (by insertion of an endogenous interrupting sequence). This arrangement encodes exclusively for heavy chains comprising human variable regions and substantially kappa light chains from the first endogenous kappa allele.

+/HA, K2/KA this arrangement encodes for mouse heavy chains and human kappa chains.

Figure 12A:
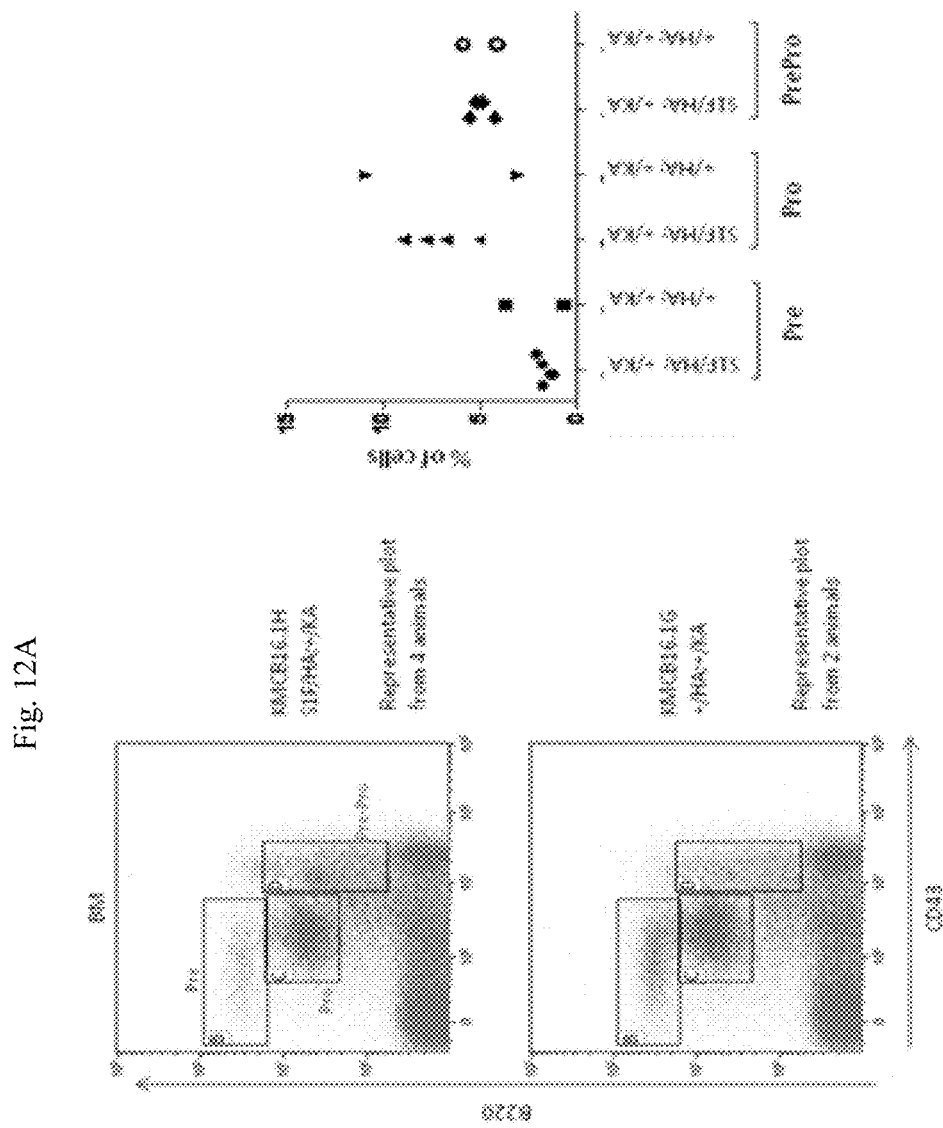

FIG. 12A: Bone marrow B progenitor compartment analysis. This figure shows the results of FACS analysis on bone marrow (BM) B-cells from transgenic S1F/HA, KA/+ mice of the invention expressing heavy chain variable regions which are all human (where endogenous heavy chain expression has been inactivated by inversion), compared with BM B-cells from mice expressing only mouse antibodies. The results show that the BM B-cell compartments in the mice of the invention are normal (ie, equivalent to the compartments of mice expressing only mouse antibody chains).

Figure 12B:
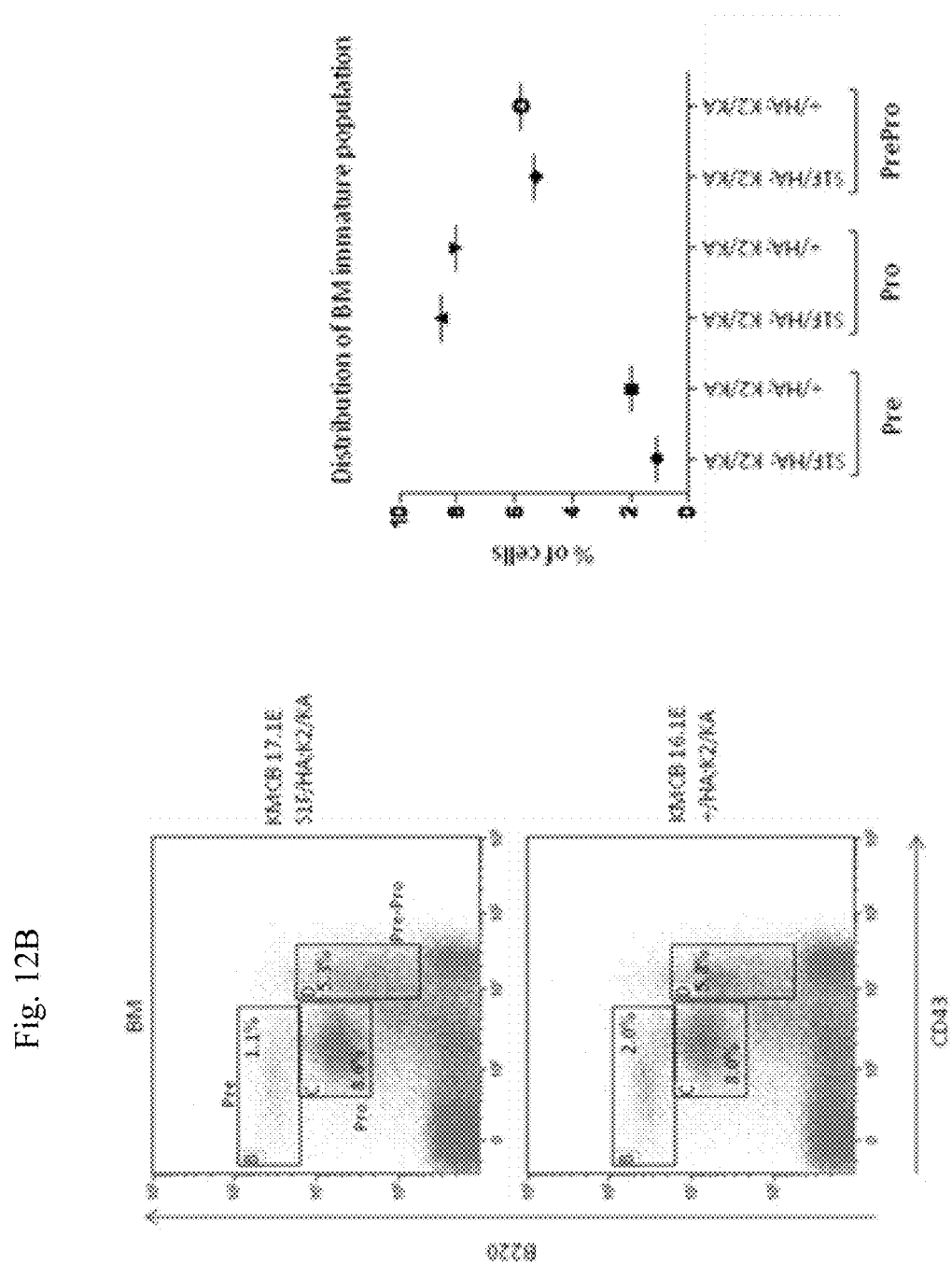

FIG. 12B: Bone marrow B progenitor compartment analysis. This figure shows the results of FACS analysis on bone marrow (BM) B-cells from transgenic S1F/HA, K2/KA mice of the invention expressing heavy chain variable regions which are all human (where endogenous heavy chain expression has been inactivated by inversion) and human kappa chain variable regions, compared with BM B-cells from +/HA, K2/KA mice. The results show that the BM B-cell compartments in the mice of the invention are normal.

Figure 13:
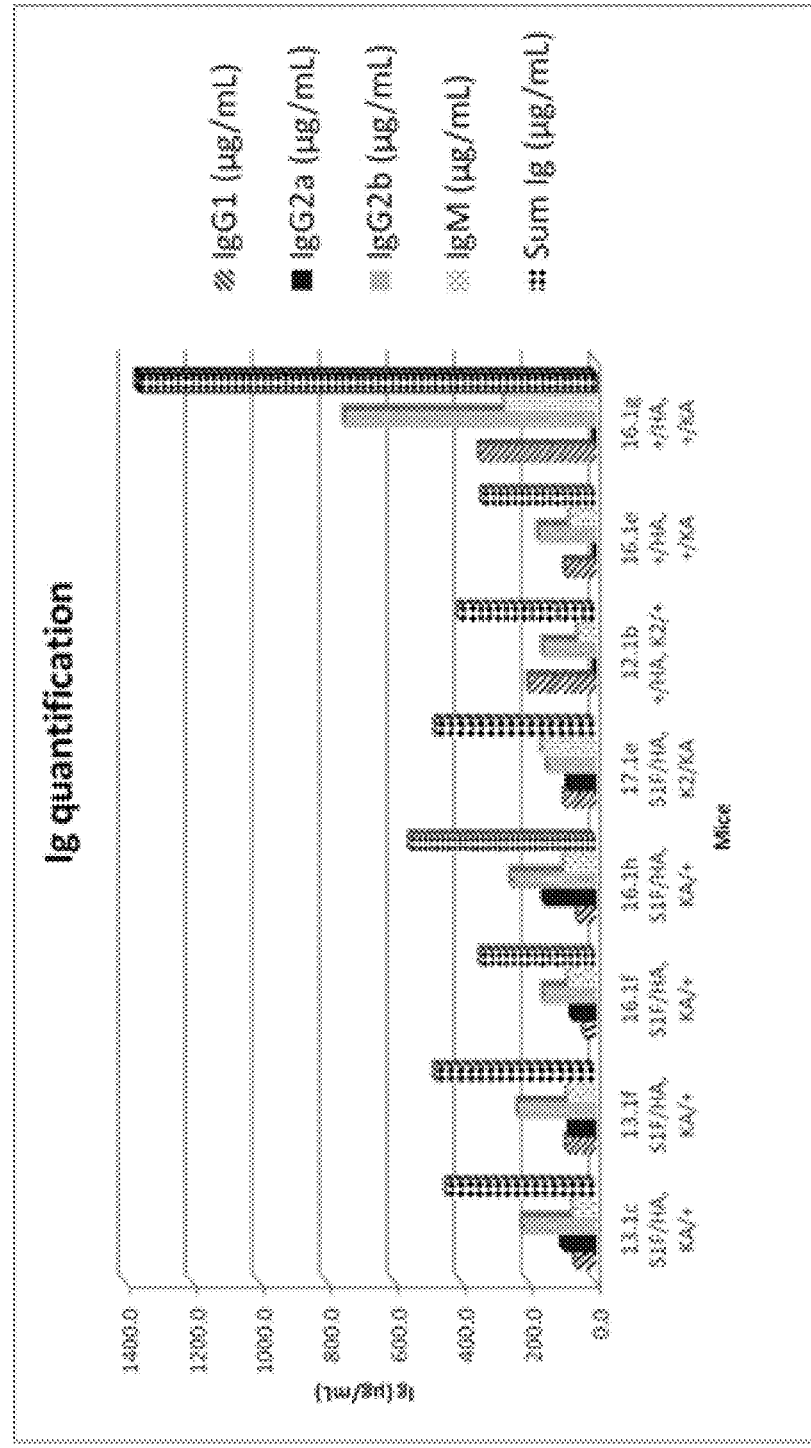

FIG. 13: shows Ig quantification for subtype and total Ig in various mice: S1F/HA, KA/+=(i) S1F—first endogenous heavy chain allele has one human heavy chain locus DNA insertion, endogenous mouse VDJ region has been inactivated by inversion and movement upstream on the chromosome; (ii) HA—second endogenous heavy chain allele has been inactivated (by insertion of an endogenous interrupting sequence); (iii) KA—the first endogenous kappa allele has been inactivated (by insertion of an endogenous interrupting sequence); and (iv) +—second endogenous kappa allele is a wild-type kappa allele. This arrangement encodes exclusively for heavy chains from the first endogenous heavy chain allele, S1F/HA, K2/KA=(i) K2—the first endogenous kappa allele has two kappa chain locus DNA insertions between the most 3' endogenous Jκ and the mouse Cκ, providing an insertion of 14 human Vκ and Jκ1-Jκ5; and (ii) KA—the second endogenous kappa allele has been inactivated (by insertion of an endogenous interrupting sequence). This arrangement encodes exclusively for heavy chains comprising human variable regions and substantially kappa light chains from the first endogenous kappa allele.

+/HA, K2/+—this arrangement encodes for mouse heavy chains and both mouse and human kappa chains.

+/HA, +/KA—this arrangement encodes for mouse heavy and kappa chains.

In this figure, "Sum Ig" is the sum of IgG and IgM isotypes.

Figure 14:
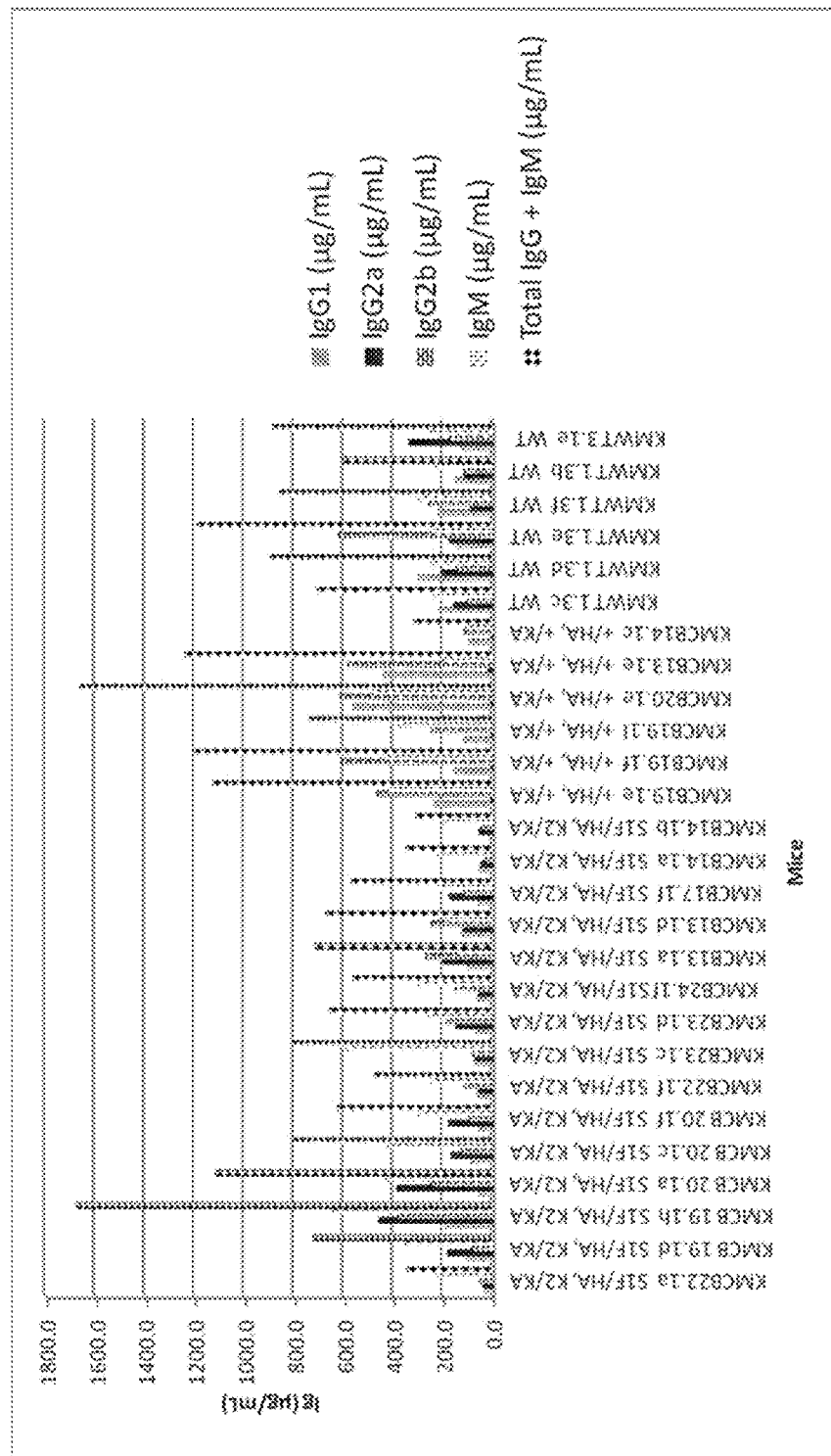

FIG. 14: shows Ig quantification for subtype and total Ig in various mice:

S1F/HA, K2/KA (n=15) and 12 mice expressing only mouse antibody chains (+/HA, +/KA (n=6) and wild-type mice (WT; n=6)).

DETAILED DESCRIPTION OF THE INVENTION

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As a source of antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII
tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest,* 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uklabs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource.com). This site describes itself as the "complete guide to antibody research and suppliers." Links to amino acid sequencing tools, nucleotide antibody sequencing tools, and hybridoma/cell-culture databases are provided.

Humanization bY Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, *Methods in Molecular Biology*™, Human Press. Also at World Wide Web (www) blogsua.com/pdf/antibody-engineering-methods-and-protocolsantibody-engineering-methods-and-protocols.pdf Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The following examples are put forth so as to provide those of ordinary skill in the art with a complete disclosure and description of how to make and use the invention, and are not intended to limit the scope of what the inventors regard as their invention.

EXAMPLES

Example 1

Figure 1:
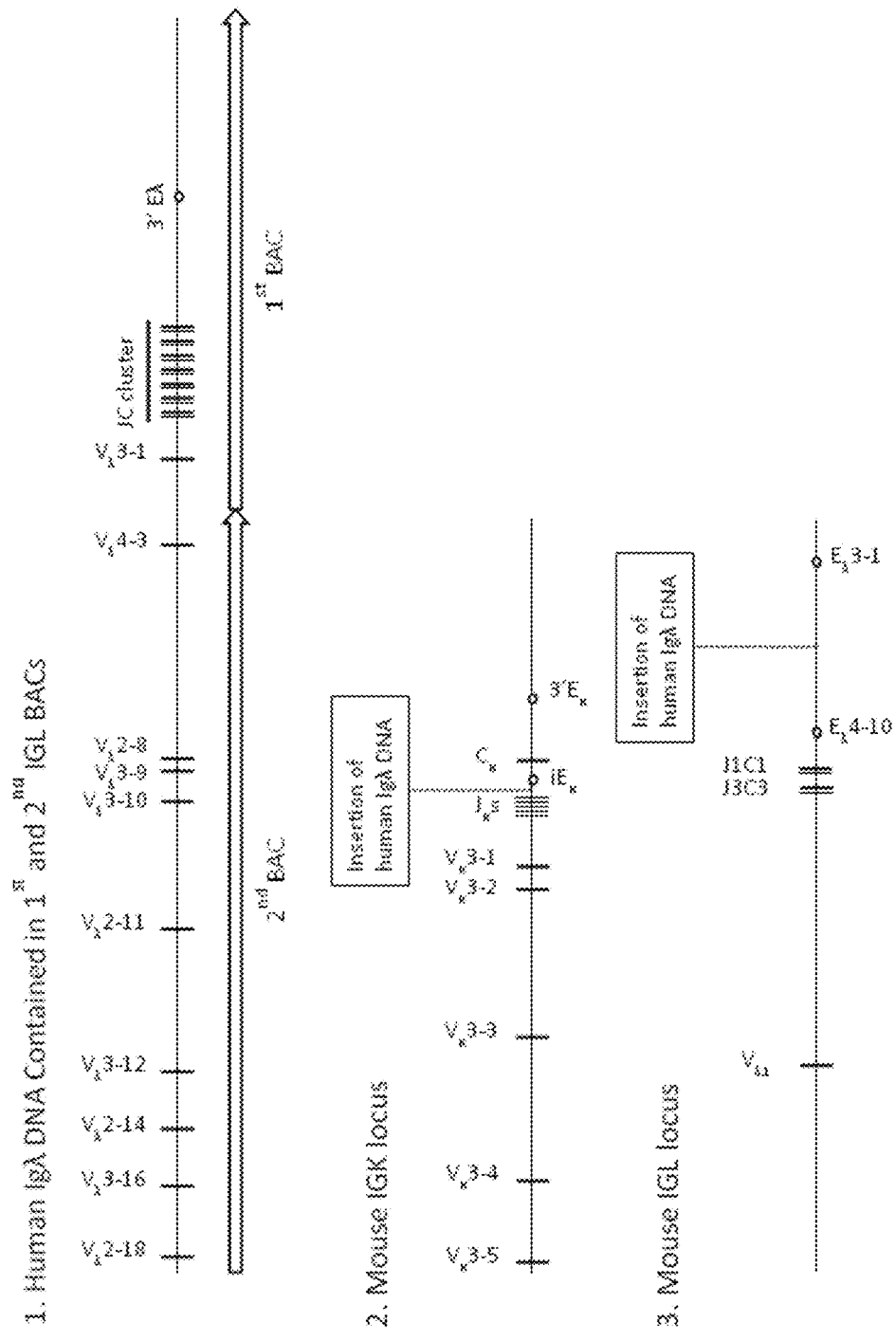
FIG. 1, part 1 illustrates the first and second BACs used for insertion into mouse endogenous light chain loci. The human DNA in each BAC is shown. Part 2 of FIG. 1 shows the insertion point of human lambda Ig locus DNA into the mouse endogenous kappa chain locus. Part 3 of FIG. 1 shows the insertion point of human lambda Ig locus DNA into the mouse endogenous lambda chain locus.

High Human Lambda Variable Region Expression in Transgenic Mice Comprising Human Lambda Gene Segments Inserted into Endogenous Kappa Locus Insertion of human lambda gene segments from a $1^{st}$ IGL BAC to the IGK locus of mouse AB2.1 ES cells (Baylor College of Medicine) was performed to create a chimaeric light chain allele denoted the P1 allele (FIG. 1). The inserted human sequence corresponds to the sequence of human chromosome 22 from position 23217291 to position 23327884 and comprises functional lambda gene segments Vλ3-1, Jλ1-Cλ1, Jλ2-Cλ2, Jλ3-Cλ3, Jλ6-Cλ6 and Jλ7-Cλ7 (the alleles of Table 13). The insertion was made between positions 70674755 and 706747756 on mouse chromosome 6, which is upstream of the mouse Cκ region and 3'Eκ (ie, within 100 kb of the endogenous light chain enhancer) as shown in FIG. 1. The mouse Vκ and Jκ gene segments were retained in the chimaeric locus, immediately upstream of the inserted human lambda DNA. The mouse lambda loci were left intact. Mice homozygous for the chimaeric P1 locus were generated from the ES cells using standard procedures.

A second type of mice were produced (P2 mice) in which more human functional Vλ gene segments were inserted upstream (5') of human Vλ3-1 by the sequential insertion of the BAC1 human DNA and then BAC2 DNA to create the P2 allele (the alleles of table 14). The inserted human sequence from BAC2 corresponds to the sequence of human chromosome 22 from position 23064876 to position 23217287 and comprises functional lambda gene segments Vλ2-18, Vλ3-16, V2-14, Vλ3-12, Vλ2-11, Vλ3-10, Vλ3-9, Vλ2-8 and Vλ4-3. Mice homozygous for the chimaeric P2 locus were generated from the ES cells using standard procedures.

FACS analysis of splenic B cells from the P1 and P2 homozygotes was performed to assess lambda versus kappa expression and human lambda versus mouse lambda expression in the transgenic mice.

Standard 5'-RACE was carried out to analyse RNA transcripts from the light chain loci in P2 homozygotes.

Light Chain Expression & FACS Analysis

To obtain a single cell suspension from spleen, the spleen was gently passage through a 30 μm cell strainer. Single cells were resuspended in Phosphate-Buffered Saline (PBS) supplemented with 3% heat inactivated foetal calf serum (FCS).

The following antibodies were used for staining:

Rat anti-mouse lambda (mCλ) phycoerythrin (PE) antibody (Southern Biotech), rat anti-mouse kappa (mCκ) (BD Pharmingen, clone 187.1) fluorescein isothiocyanate (FITC), anti-human lambda (hCλ) (eBioscience, clone 1-155-2) phycoerythrin (PE), anti-B220/CD45R (eBioscience, clone RA3-6B2) allophycocyanin (APC). NB: light chains bearing human Cλ was expected to have variable regions derived from the rearrangement of inserted human Vλ and human Jλ. Light chains bearing mouse Cλ was expected to have variable regions derived from the rearrangement of mouse Vλ and Jλ from the endogenous lambda loci.

$5 \times 10^6$ cells were added to individual tubes, spun down to remove excess of fluid, and resuspended in fresh 100 μl of PBS+3% FCS. To each individual tube the following antibodies were added:

For staining of mλ versus mκ 1 μl of each antibody was added in addition to 1 μl of B220/CD45R antibody. For detection of B cells expressing human lambda light chain, the mλ antibody was substituted with hλ antibody. Cells were incubated in the dark at 6° C. for 15 minutes followed by several washes with fresh PBS+3% FCS to remove unbound antibody. Cells were analysed using fluorescence-activated cell sorting (FACS) analyser from Miltenyi Biotech.

Alive spleenocytes were gated using side scatter (SSC) and forward scatter (FSC). Within the SSC and FSC gated population, a subpopulation of B220/CD45R (mouse B-cells) was detected using the APC fluorochrome. Single positive B220/CD45R population was further subdivided into a cell bearing either mλ or hλ PE fluorochrome in conjunction with mκ FITC fluorochrome. The percentage of each population was calculated using a gating system.

Figure 2:
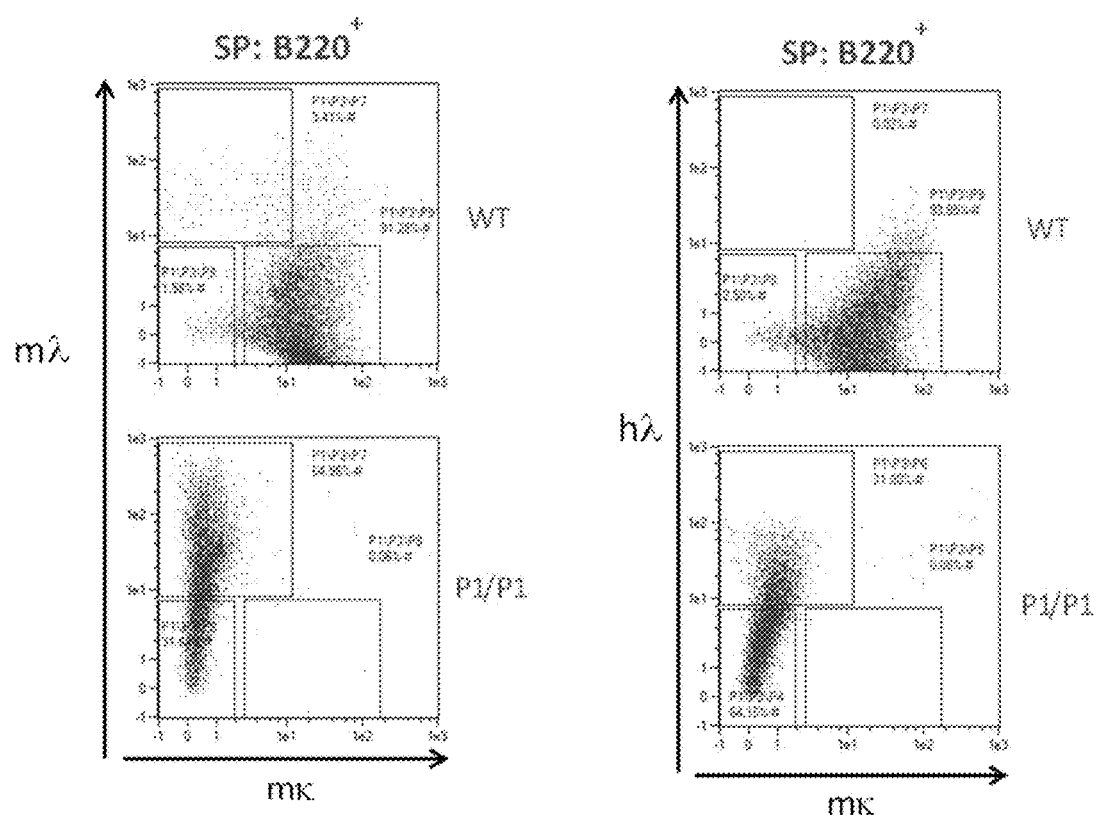
FIG. 2 shows the results of FACS analysis to determine mouse and human Cλ expression (and thus correspondingly mouse and human variable region expression) in B220+ splenic B cells from P1 homozygous mice (P1/P1) compared to wild-type mice (WT).

Surprisingly, FACS analysis of splenic B cells from the P1 homozygotes showed no detectable mouse Cκ expression (FIG. 2), indicating that insertion of the human lambda locus DNA from BAC1 interrupts expression of the endogenous IGK chain.

The strong expression of endogenous Cλ and weak expression of human Cλ in the splenic B cells grouped by FACS analysis (mouse Cλ:human Cλ=65:32) in these mice suggest that inserted human IGL sequence, although interrupts the IGK activity, cannot totally compete with the endogenous IGL genes.

Figure 3A:
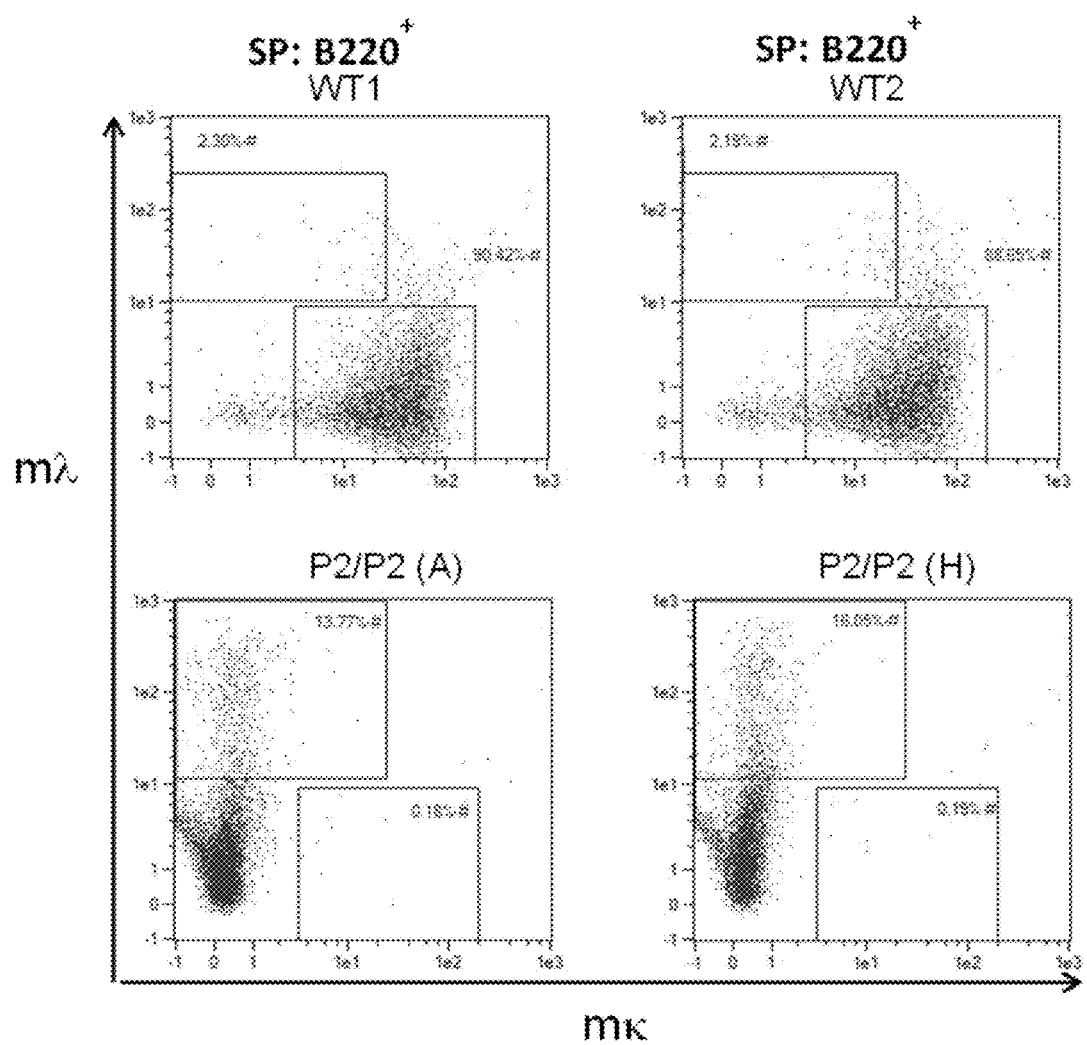
FIG. 3A shows the results of FACS analysis to determine mouse Cκ and Cλ expression in B220+ splenic B cells from P2 homozygous mice (P2/P2) compared to wild-type mice (WT). No detectable mouse Cκ expression was seen.
Figure 3B:
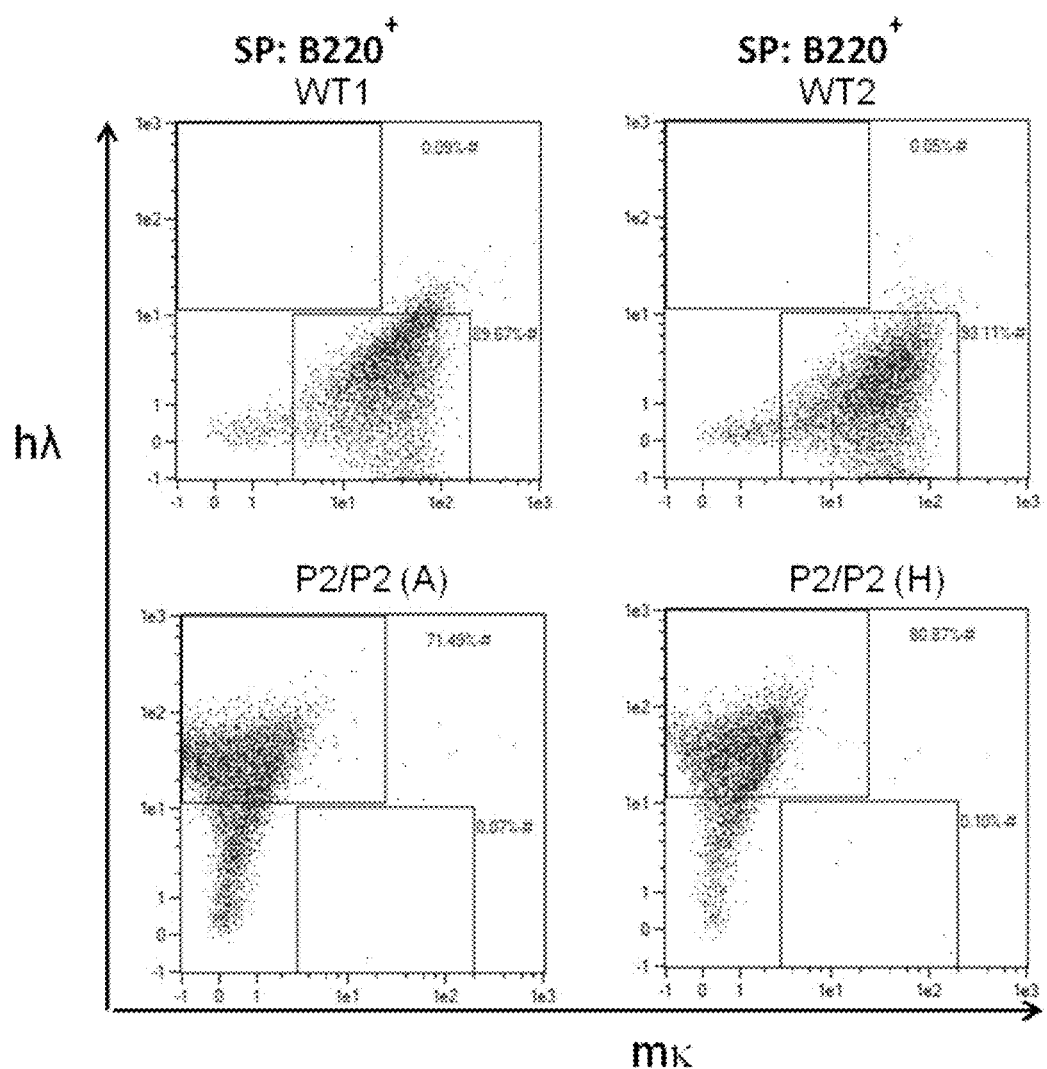
FIG. 3B shows the results of FACS analysis to determine human Cλ expression (and thus correspondingly human variable region expression) in B220+ splenic B cells from P2 homozygous mice (P2/P2) compared to wild-type mice (WT).

The FACS analysis again surprisingly showed no detectable mouse Cκ expression in the P2 homozygotes (FIGS. 3A & B). However, the human Cλ greatly predominates in expressed B cells grouped as mouse or human Cλ following FACS analysis (mouse Cλ:human Cλ=15:80 corresponding to a ratio of 15 mouse lambda variable regions: 80 human lambda variable regions, ie, 84% human lambda variable regions with reference to the grouped B-cells—which corresponds to 80% of total B-cells) from the P2 homozygotes. While not wishing to be bound by any theory, we suggest that the inserted human lambda locus sequence from the $2^{nd}$ BAC provides some advantages to compete with endogenous lambda gene segment rearrangement or expression.

Figure 4:
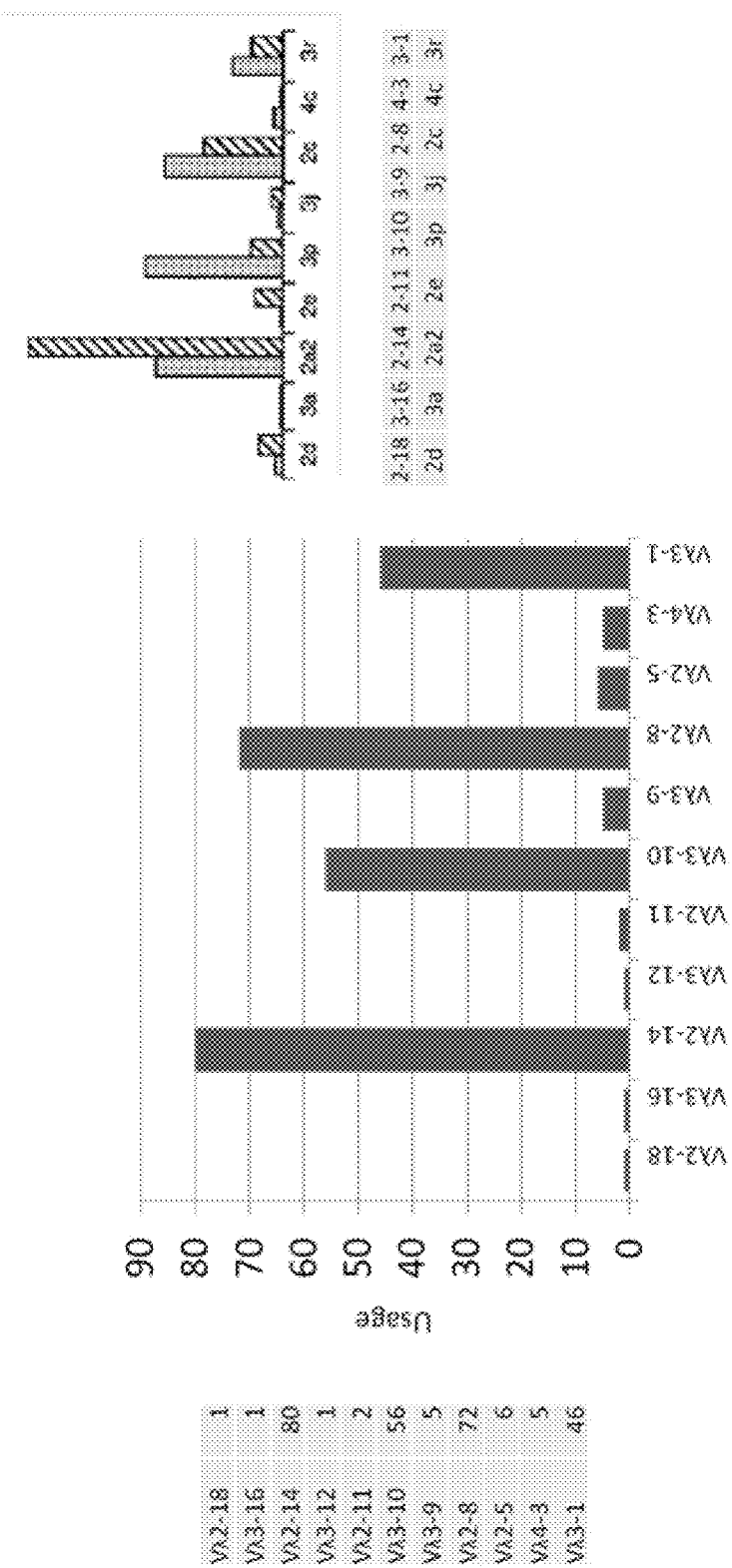
FIG. 4 shows human Vλ usage in P2 homozygous mice (P2/P2) and typical Vλ usage in humans (inset).
Figure 5:
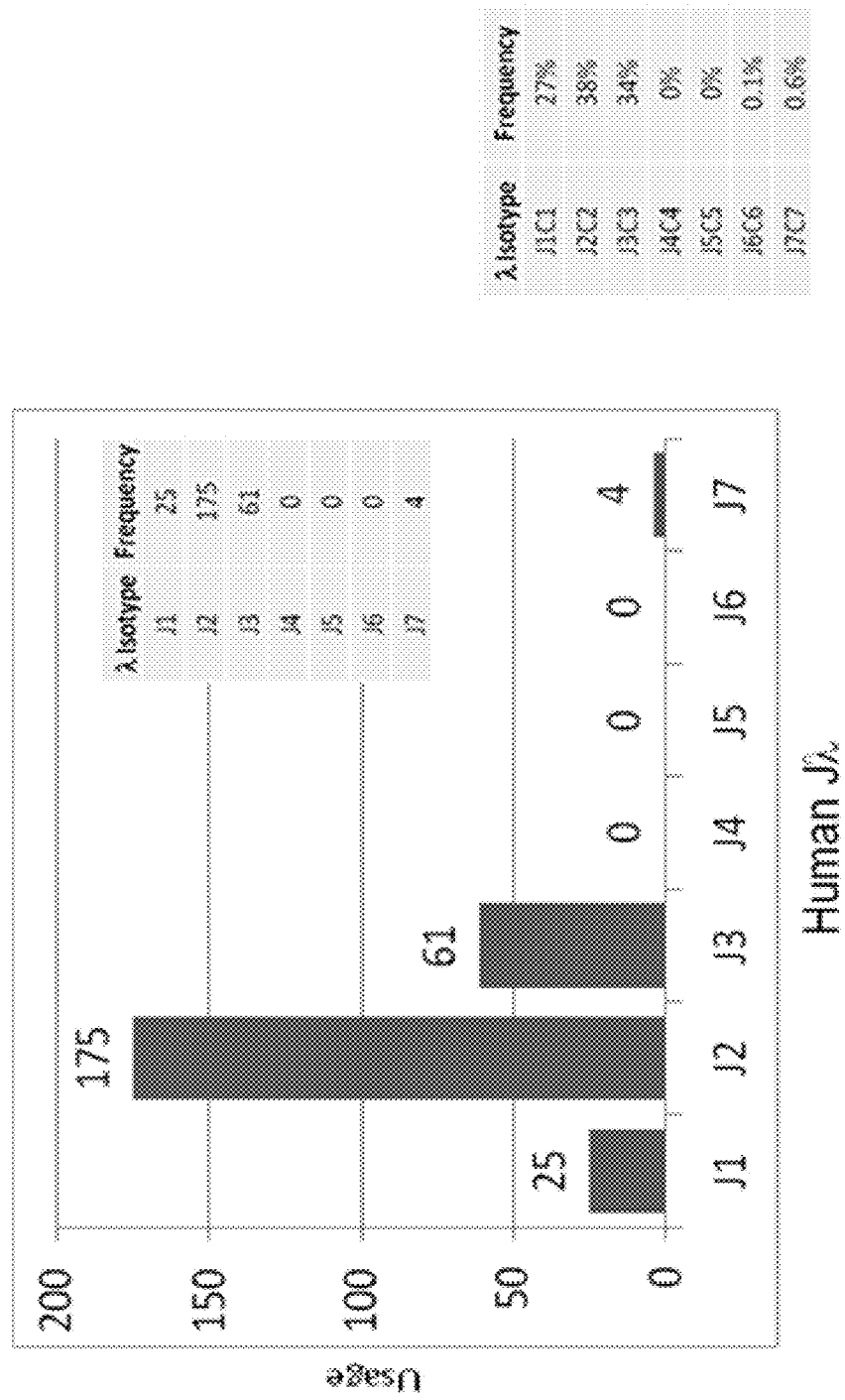
FIG. 5 shows human Jλ usage in P2 homozygous mice (P2/P2) and typical Jλ usage in humans (inset).
Figure 6:
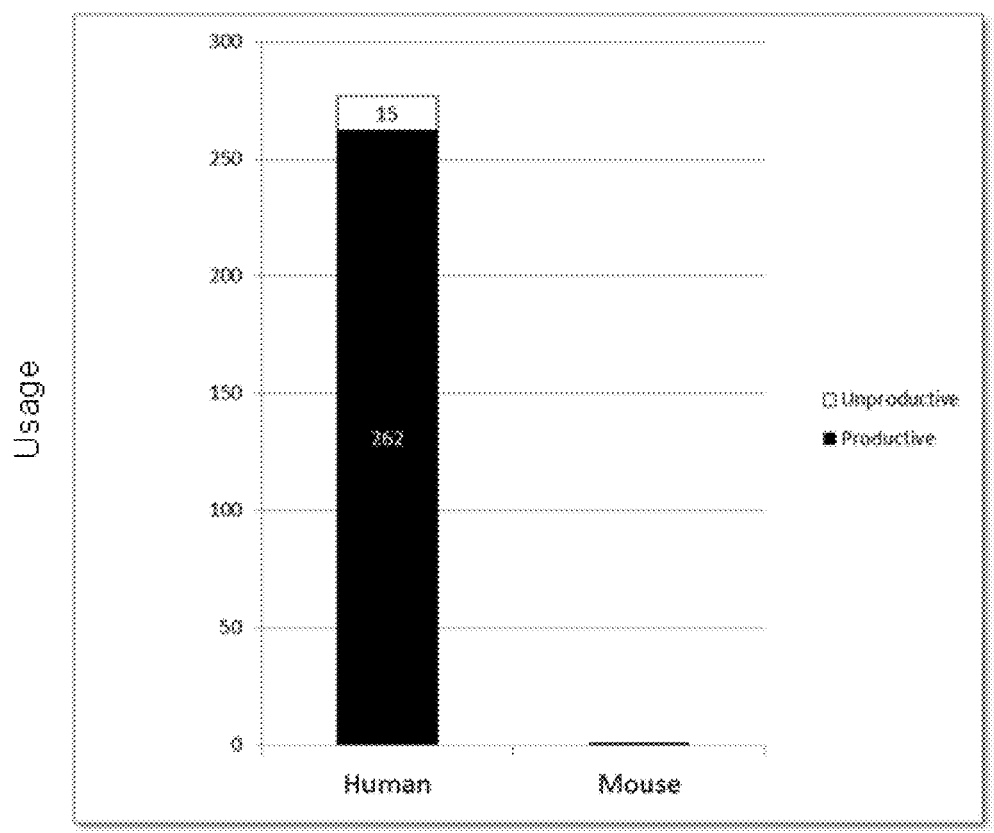
FIG. 6 shows Vλ usage is very high in P2 homozygous mice (P2/P2).
Figure 7:
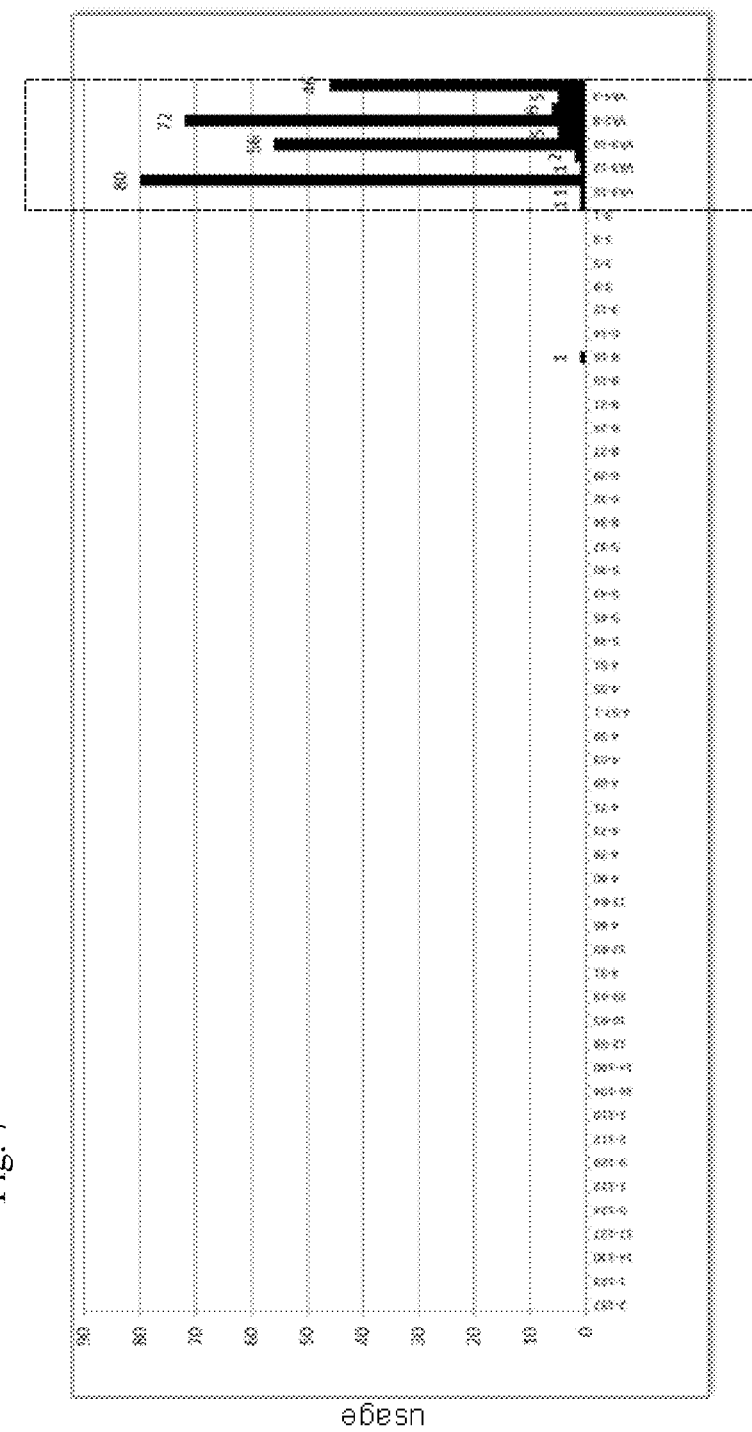
FIG. 7 shows the distribution of mouse Vκ and human Vλ gene segment usage from the chimaeric kappa locus in P2 homozygous mice (P2/P2).
Figure 8:
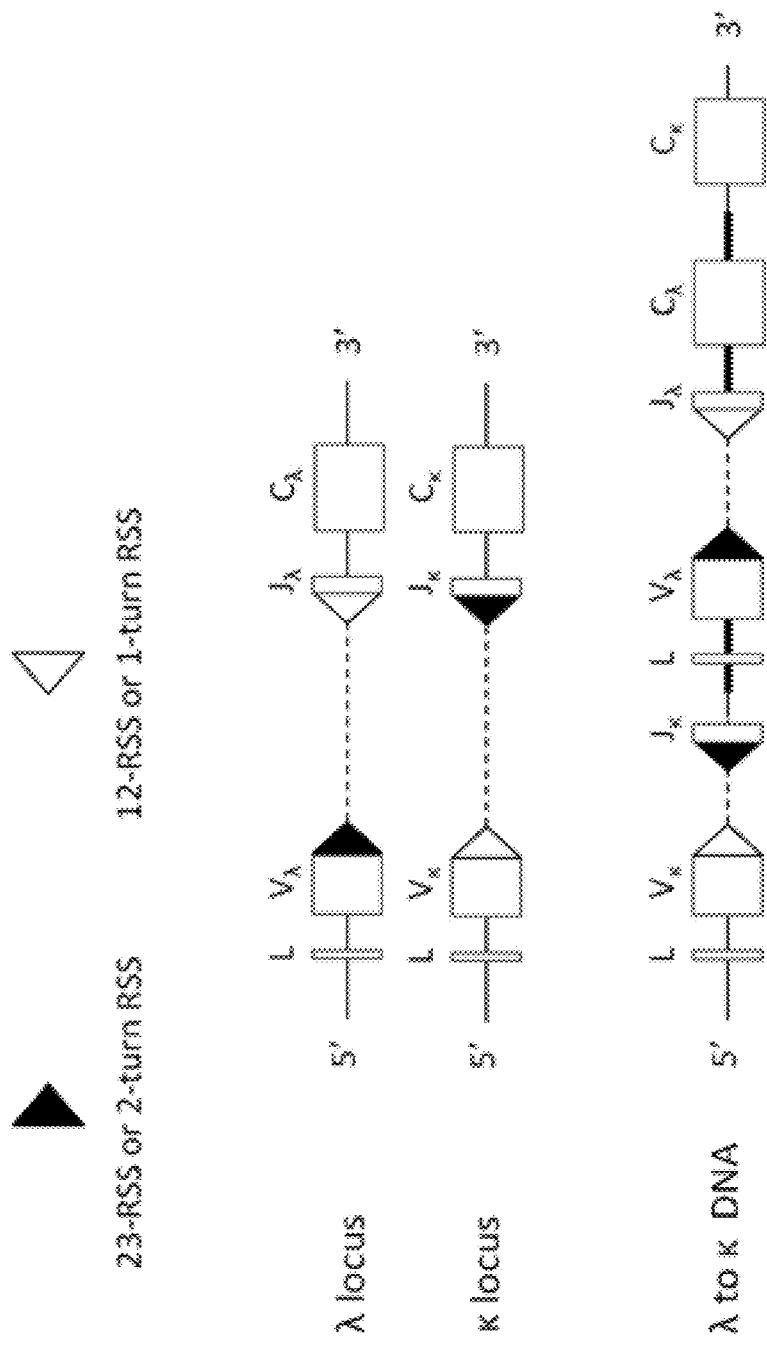
FIG. 8 illustrates RSS arrangement in the lambda and kappa loci.

We analysed human Vλ and Jλ usage in the P2 homozygotes. See FIG. 4 which shows the human Vλ usage in P2 homozygotes. The observed usage was similar to that seen in humans (as per J Mol Biol. 1997 Apr. 25; 268(1):69-77; "The creation of diversity in the human immunoglobulin V(lambda) repertoire"; Ignatovich O et al). Further, the human Jλ usage was similar to that seen in humans (FIG. 5). The Vλ versus Vκ usage analysis of human Cλ transcripts by sequencing of non-bias 5'-RACE (rapid amplification of cDNA ends) PCR clones showed that among 278 clone sequences, only one used Vκ for rearrangement to Jλ (human Jλ), and all others (277 clones) used human Vλ (FIGS. 6 & 7; Vλ2-5 was detected at the RNA transcript level, but this is a pseudogene which is usually not picked up by usage a the protein level). While not wishing to be bound by any theory, we suggest that the retained mouse Vκ gene segments essentially cannot efficiently rearrange with the inserted human Jλ gene segments because they have the same type of RSSs (recombination signal sequences; see explanation below) and are incompatible for rearrangement (FIG. 8). This result also indicates that the inactivation of the endogenous IGK activity and predominate expression of the inserted human lambda sequence can be achieved without further modification of the IGK locus, for example, deletion or inversion of endogenous kappa loci gene segments is not necessary, which greatly simplifies the generation of useful transgenic mice expressing light chains bearing human lambda variable regions (ie, variable regions produced by recombination of human Vλ and Jλ gene segments).

The arrangement of recombination signal sequences (RSSs) that mediate V(D)J recombination in vivo is discussed, eg, in Cell. 2002 April; 109 Suppl:S45-55; "The mechanism and regulation of chromosomal V(D)J recombination"; Bassing C H, Swat W, Alt F W (the disclosure of which is incorporated herein by reference). Two types of RSS element have been identified: a one-turn RSS (12-RSS) and a two-turn RSS (23-RSS). In natural VJ recombination in the lambda light chain locus, recombination is effected between a two-turn RSS that lies 3' of a V lambda and a one-turn RSS that lies 5' of a J lambda, the RSSs being in opposite orientation. In natural VJ recombination in the kappa light chain locus, recombination if effected between a one-turn RSS that lies 3' of a V kappa and a two-turn RSS that lies 5' of a J kappa, the RSSs being in opposite orientation. Thus, generally a two-turn RSS is compatible with a one-turn RSS in the opposite orientation.

Thus, the inventors have demonstrated how to (i) inactivate endogenous kappa chain expression by insertion of human lambda gene segments into the kappa locus; and (ii) how to achieve very high human lambda variable region expression (thus providing useful light chain repertoires for selection against target antigen)—even in the presence of endogenous lambda and kappa V gene segments. Thus, the inventors have shown how to significantly remove (lambda) or totally remove (kappa) V gene segment competition and thus endogenous light chain expression by the insertion of at least the functional human lambda gene segments comprised by BACs 1 and 2. In this example a very high level of human lambda variable region expression was surprisingly achieved (84% of total lambda chains and total light chains as explained above).

Example 2

High Human Lambda Variable Region Expression in Transgenic Mice Comprising Human Lambda Gene Segments Inserted into Endogenous Lambda Locus Insertion of human lambda gene segments from the 1$^{st}$ and 2$^{nd}$ IGL BACs to the lambda locus of mouse AB2.1 ES cells (Baylor College of Medicine) was performed to create a lambda light chain allele denoted the L2 allele (FIG. 1). The inserted human sequence corresponds to the sequence of human chromosome 22 from position 23064876 to position 23327884 and comprises functional lambda gene segments Vλ2-18, Vλ3-16, V2-14, Vλ3-12, Vλ2-11, Vλ3-10, Vλ3-9, Vλ2-8, Vλ4-3, Vλ3-1, Jλ1-Cλ1, Jλ2-Cλ2, Jλ3-Cλ3, Jλ6-Cλ6 and Jλ7-Cλ7. The insertion was made between positions 19047551 and 19047556 on mouse chromosome 16, which is upstream of the mouse Cλ region and between Eλ4-10 and Eλ3-1 (ie, within 100 kb of the endogenous light chain enhancers) as shown in FIG. 1. The mouse Vλ and Jλ gene segments were retained in the locus, immediately upstream of the inserted human lambda DNA. The mouse kappa loci were inactivated to prevent kappa chain expression. Mice homozygous for the L2 locus were generated from the ES cells using standard procedures.

Using a similar method to that of Example 1, FACS analysis of splenic B cells from the L2 homozygotes was performed to assess lambda versus kappa expression and human lambda versus mouse lambda expression in the transgenic mice.

Light Chain Expression & FACS Analysis

Figure 9A:
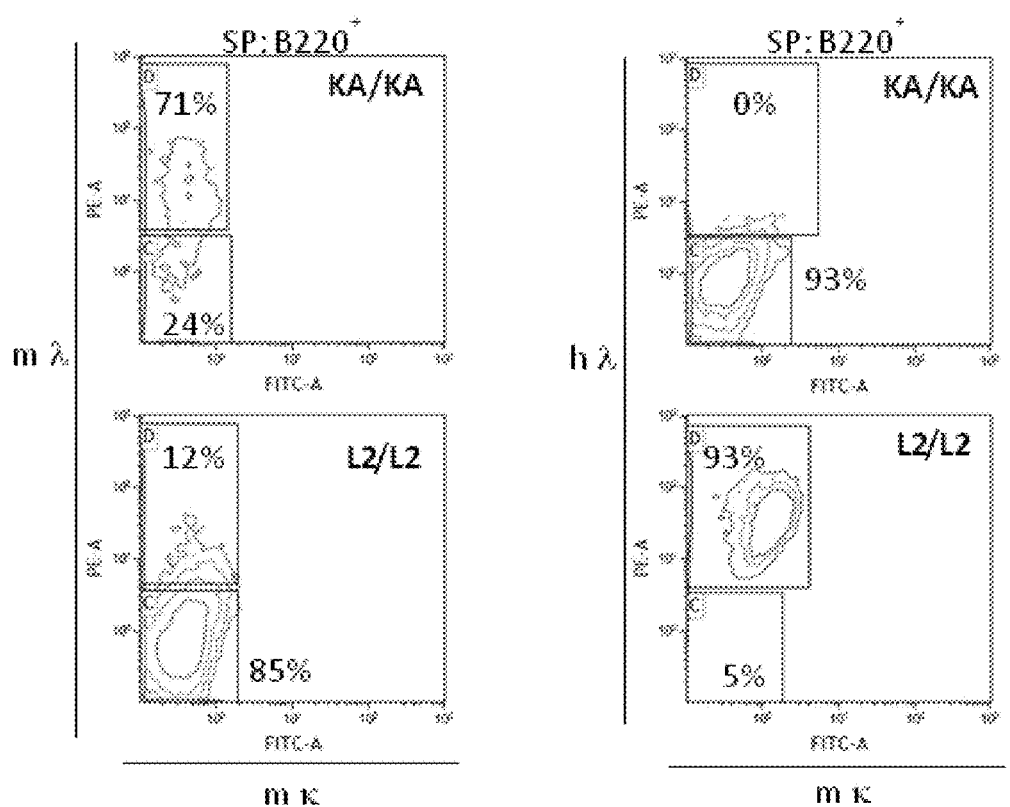
FIG. 9A shows the results of FACS analysis to determine mouse and human Cλ expression (and thus correspondingly mouse and human variable region expression) in B220+ splenic B cells from L2 homozygous mice in which endogenous kappa chain expression has been inactivated (L2/2; KA/KA) compared to mice having no human lambda DNA inserted and in which endogenous kappa chain expression has been inactivated (KA/KA). Very high human Vλ usage was seen in the L2/L2; KA/KA) mice, almost to the exclusion of mouse Vλ use.

The FACS analysis of splenic B-cells in L2 homozygotes under the IGK knockout background (in which Vκ and Jκ gene segments have been retained) surprisingly showed that expression of human Cλ greatly predominates in B-cells grouped as mouse or human Cλ following FACS analysis (mouse Cλ:human Cλ=5:93 corresponding to a ratio of 5 mouse lambda variable regions:93 human lambda variable regions, ie, 95% human lambda variable regions with reference to the grouped B-cells—which corresponds to 93% of total B-cells) (FIG. 9A), demonstrating that inserted human IGλ gene segments within the endogenous IGλ locus can outcompete the endogenous IGλ gene segment rearrangement or expression.

Thus, the inventors have demonstrated how to achieve very high human lambda variable region expression (thus providing useful light chain repertoires for selection against target antigen)—even in the presence of endogenous lambda and kappa V gene segments. Thus, the inventors have shown how to significantly remove endogenous lambda V gene segment competition and thus endogenous lambda light chain expression by the insertion of at least the functional human lambda gene segments comprised by BACs 1 and 2. In this example a very high level of human lambda variable region expression was surprisingly achieved (95% of total lambda chains and total light chains as explained above).

These data indicate that mice carrying either P (Example 1) or L (Example 2) alleles produced by targeted insertion of the functional gene segments provided by BAC1 and BAC2 can function in rearrangement and expression in mature B cells. These two types of alleles are very useful for providing transgenic mice that produce human Ig lambda chains for therapeutic antibody discovery and as research tools.

Figure 10:
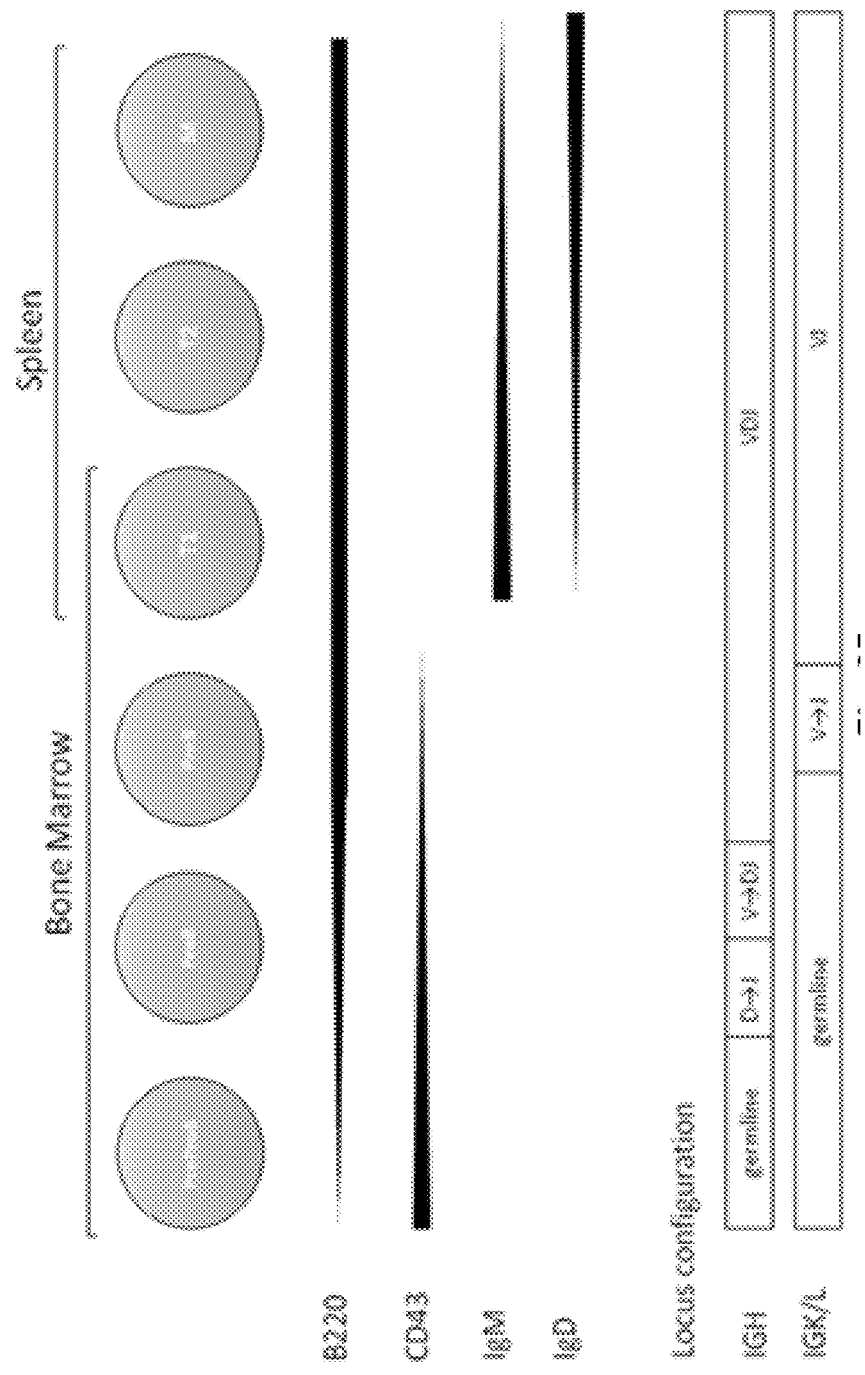
FIG. 10: B-cell development and markers in the bone marrow and splenic compartments.

Transgenic Mice of the Invention Expressing Human Lambda Variable Regions Develop Normal Splenic Compartments In spleen, B cells are characterized as immature (T1 and T2) and mature (M) based on the levels of cell surface markers, IgM and IgD. T1 cells have high IgM and low IgD. T2 cells have medium levels of both them. M cells have low IgM but high IgD (FIG. 10). See also J Exp Med. 1999 Jul. 5; 190(1):75-89; "B cell development in the spleen takes place in discrete steps and is determined by the quality of B cell receptor-derived signals"; Loder F et al.

Figure 9B:
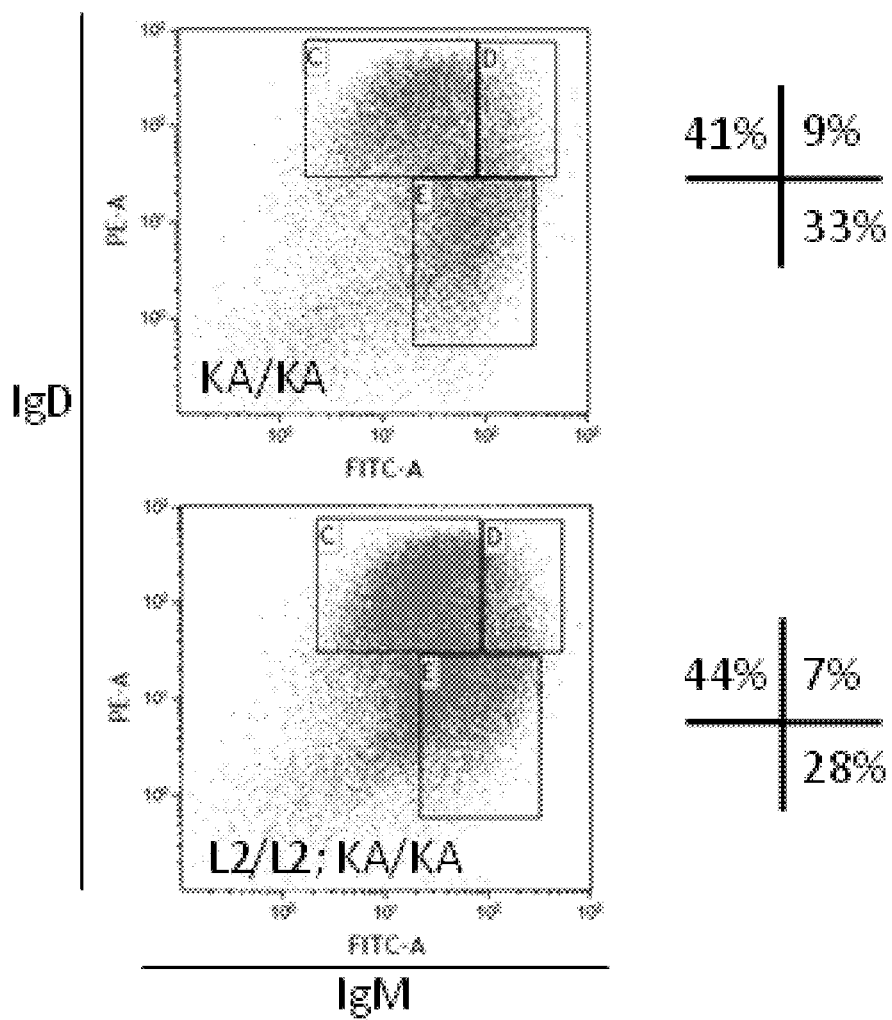
FIG. 9B: Splenic B-Cell Compartment Analysis. This figure shows the results of FACS analysis on splenic B-cells from transgenic L2/L2; KA/KA mice (L2 homozygotes; homozygous for human lambda gene segment insertion into endogenous lambda loci; endogenous kappa chain expression having been inactivated) compared with splenic B-cells from mice expressing only mouse antibodies (KA/KA mice). The results show that the splenic B-cell compartments in the mice of the invention are normal (ie, equivalent to the compartments of mice expressing only mouse antibody chains).

Using methods similar to those described in Example 3 below, splenic B-cells from the animals were scored for IgD and IgM expression using FACS. We compared control mice KA/KA (in which endogenous kappa chain expression has been inactivated, but not endogenous lambda chain expression) with L2/L2;KA/KA mice (L2 homozyotes). The L2 homozygotes surprisingly showed comparable splenic B-cell compartments to the control mice (FIG. 9B).

Example 3

Assessment of B-Cell and Ig Development in Transgenic Mice of the Invention

We observed normal Ig subtype expression & B-cell development in transgenic mice of the invention expressing antibodies with human heavy chain variable regions substantially in the absence of endogenous heavy and kappa chain expression.

Using ES cells and the RMCE genomic manipulation methods described above, mice were constructed with combinations of the following Ig locus alleles:

S1F/HA, +/KA=(I) S1F—first endogenous heavy chain allele has one human heavy chain locus DNA insertion, endogenous mouse VDJ region has been inactivated by inversion and movement upstream on the chromosome (see the description above, where this allele is referred to as $S1^{inv1}$); (ii) HA—second endogenous heavy chain allele has been inactivated (by insertion of an endogenous interrupting sequence); (iii) +—first endogenous kappa allele is a wild-type kappa allele and (iv) KA—the second endogenous kappa allele has been inactivated (by insertion of an endogenous interrupting sequence). This arrangement encodes exclusively for heavy chains from the first endogenous heavy chain allele.

S1F/HA, K2/KA=(i) K2—the first endogenous kappa allele has two kappa chain locus DNA insertions between the most 3' endogenous Jκ and the mouse Cκ, providing an insertion of 14 human Vκ and Jκ1-Jκ5; and (ii) KA—the second endogenous kappa allele has been inactivated (by insertion of an endogenous interrupting sequence). This arrangement encodes exclusively for heavy chains comprising human variable regions and substantially kappa light chains from the first endogenous kappa allele.

+/HA, K2/KA—this arrangement encodes for mouse heavy chains and human kappa chains.

+/HA, +/KA—this arrangement encodes for mouse heavy and kappa chains—the mice only produce mouse heavy and light chains.

In bone marrow, B progenitor populations are characterized based their surface markers, B220 and CD43. PreProB cells carry germline IGH and IGK/L configuration and have low B220 and high CD43 on their cell surface. ProB cells start to initiate VDJ recombination in the IGH locus and carry medium levels of both B220 and CD43. PreB cells carry rearranged IGH VDJ locus and start to initiate light chain VJ rearrangement, and have high B220 but low CD43. In spleen, B cells are characterized as immature (T1 and T2) and mature (M) based on the levels of cell surface markers, IgM and IgD. T1 cells have high IgM and low IgD. T2 cells have medium levels of both them. M cells have low IgM but high IgD (FIG. 10). See also J Exp Med. 1991 May 1; 173(5):1213-25; "Resolution and characterization of pro-B and pre-pro-B cell stages in normal mouse bone marrow"; Hardy R R et al and J Exp Med. 1999 Jul. 5; 190(1):75-89; "B cell development in the spleen takes place in discrete steps and is determined by the quality of B cell receptor-derived signals"; Loder F et al.

Transgenic Mice of the Invention Develop Normal Splenic and BM Compartments (a) Analysis of the Splenic Compartment For each mouse, to obtain a single cell suspension from spleen, the spleen was gently passaged through a 30 μm cell strainer. Single cells were resuspended in Phosphate-Buffered Saline (PBS) supplemented with 3% heat inactivated foetal calf serum (FCS). $5 \times 10^6$ cells were added to individual tubes, spun down to remove excess of fluid and resuspended in fresh 100 μl of PBS+3% FCS. To each individual tube the following antibodies were added: anti-B220/CD45R (eBioscience, clone RA3-6B2) allophycocyanin (APC), antibody against IgD receptor conjugated with phycoerythrin (PE) (eBioscience, clone 11-26) and antibody against IgM receptor conjugated with fluorescein isothiocyanate (FITC) (eBioscience, clone 11/41).

For staining of IgM vs IgD, $5 \times 10^6$ cells were used for each staining. To each vial containing splenocytes a cocktail of antibodies was added consisting of: anti-IgD (PE), anti-IgM (FITC) and anti-B220/CD45R (APC). Cells were incubated at 6° C. for 15 minutes, washed to remove excess unbound antibodies and analysed using a fluorescence-activated cell sorting (FACS) analyser from Miltenyl Biotech. B-cells were gated as $B220^{HIGH}$ $IgM^{HIGH}$ $IgD^{LOW}$ (ie, $B220^+$ $IgM^+$ $IgD^-$) for T1 population, $B220^{HIGH}$ $IgM^{HIGH}$ $IgD^{HIGH}$ ($B220^+$ $IgM^+$ $IgD^+$) for T2 population and $B220^{HIGH}$ $IgM^{LOW}$ $IgD^{HIGH}$ ($B220^+$ $IgM^-$ $IgD^+$) for M population. Percentage of cells was calculated using gating system. We used gates to identify and define subsets of cell populations on plots with logarithmic scale. Before gates are applied a single stain antibody for each fluorochrome is used to discriminate between a positive (high intensity fluorochrome) and negative (no detectable intensity fluorchrome) population. Gates are applied based on fluorochrome intensities in the same manner to all samples. The single stains were:

IgD-PE
IgM-FITC
B220-APC

Alive spleenocytes were gated using side scatter (SSC) and forward scatter (FSC), Within the SSC and FSC gated population, a subpopulation of B220/CD45R positive cells (mouse B-cells) was detected using the APC fluorochrome. The single positive B220/CD45R population was further subdivided into a cell bearing either IgM fluorescein isothiocyanate (FITC) or IgD fluorochrome in conjunction with mκ FITC fluorochrome. The percentage of each population was calculated using gating system. The splenic B-Cell compartments in the mice of the invention are normal (ie, equivalent to the compartments of mice expressing only mouse antibody chains).

(b) Bone Marrow B Progenitor Analysis

To obtain a single cell suspension from bone marrow for each mouse, the femur and tibia were flushed with Phosphate-Buffered Saline (PBS) supplemented with 3% heat inactivated foetal calf serum (FCS). Cells were further passage through a 30 μm cell strainer to remove bone pieces or cell clumps. Cells were resuspended in cold PBS supplemented with 3% serum. $2 \times 10^6$ cells were added to individual tubes, spun down to remove excess of buffer, and resuspended in fresh 100 μl of PBS+3% FCS. To each individual tube the following antibodies were added: anti-Leukosialin (CD43) fluorescein isothiocyanate (FITC) (eBioscience, clone eBioR2/60) and anti-B220/CD45R (eBioscience, clone RA3-6B2) allophycocyanin (APC). Cells were incubated in the dark at 6° C. for 15 minutes followed by several washes with fresh PBS-1-3% FCS to remove unbound antibody. Cells were analysed using a fluorescence-activated cell sorting (FACS) analyser from Miltenyi Biotech. Alive bone marrow cells were gated using side scatter (SSC) and forward scatter (FSC). We used gates to identify and define subsets of cell populations on plots with logarithmic scale.

Before gates are applied a single stain antibody for each fluorochrome is used to discriminate between a positive (high intensity fluorochrome) and negative (no detectable intensity fluorochrome) population. Gates are applied based on fluorochrome intensities in the same manner to all samples. The single stains were:
  B220-APC
  CD43-FITC Within the alive population a double population of B220/CD45R and CD43 positive cells was identified as a pre-B, pro-B and pre-pro B cells. The splenic B-Cell compartments in the mice of the invention are normal (ie, equivalent to the compartments of mice expressing only mouse antibody chains).

Transgenic Mice of the Invention Develop Normal Ig Expression

Quantification of Serum IgM and IgG 96-well NUNC plates were coated initially with a capture antibody (goat anti-mouse Fab antibody at 1 μg/ml) overnight at 4° C.). The IgG plates used anti-Fab, (M4155 Sigma) and the IgM plates used anti-Fab (OBT1527 AbD Serotec). Following three washes with phosphate buffer saline (PBS) containing 0.1% v/v Tween20, plates were blocked with 200 μl of PBS containing 1% w/v bovine serum albumin (BSA) for 1 hour at room temperature (RT). The plates were washed three times as above and then 50 μl of standards (control mouse isotype antibodies, IgG1 (M9269 Sigma), IgG2a (M9144 Sigma), IgG2b (M8894 sigma), IgM (M3795 Sigma) or serum samples diluted in PBS with 0.1% BSA were added to each well, and incubated for 1 hour at RT. After washing three times as above 100 μl of detection antibody (goat anti-mouse isotype specific antibody-horseradish peroxidase conjugated, 1/10000 in PBS with 0.1% Tween) (anti-mouse IgG1 (STAR132P AbD Serotec), anti-mouse IgG2a (STAR133P AdD Serotec), anti-mouse IgG2b (STAR134P AbD Serotec) and anti-mouse IgM (ab97230 Abcam) were added into each well and incubated for 1 hour at RT. The plates were washed three times as above and developed using tetramethylbenzidine substrate (TMB, Sigma) for 4-5 minutes in the dark at RT. Development was stopped by adding 50 μl/well of 1 M sulfuric acid. The plates were read with a Biotek Synergy HT plate reader at 450 nm.

Conclusion:

Inversion of endogenous $V_H$-D-$J_H$ following the human IGH BAC insertion results in inactivation of rearrangement of endogenous $V_H$ to inserted human D-$J_H$. The inventors observed, however, that surprisingly the inactivation of endogenous heavy chain expression does not change the ratio of B-cells in the splenic compartment (FIG. 11) or bone marrow B progenitor compartment (FIG. 12) and the immunoglobulin levels in serum are normal and the correct Ig subtypes are expressed (FIG. 13). This was shown in mice expressing human heavy chain variable regions with mouse light chains (FIGS. 11A and 12A) as well as in mice expressing both human heavy chain variable regions and human light chain variable regions (FIGS. 11B and 12B). These data demonstrate that inserted human IGH gene segments (an insertion of at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6) are fully functional in the aspect of rearrangement, BCR signalling and B cell maturation. Functionality is retained also when human light chain VJ gene segments are inserted to provide transgenic light chains, as per the insertion used to create the K2 allele. This insertion is an insertion comprising human gene segments Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5. Greater than 90% of the antibodies expressed by the S1F/HA; K2/KA mice comprised human kappa light chain variable regions and human kappa light chain variable regions. These mice are, therefore, very useful for the selection of antibodies having human variable regions that specifically bind human antigen following immunisation of the mice with such antigen. Following isolation of such an antibody, the skilled person can replace the mouse constant regions with human constant regions using conventional techniques to arrive at totally human antibodies which are useful as drug candidates for administration to humans (optionally following mutation or adaptation to produce a further derivative, eg, with Fc enhancement or inactivation or following conjugation to a toxic payload or reporter or label or other active moiety).

A further experiment was carried out to assess the IgG and IgM levels and relative proportions in transgenic mice of the invention that express antibodies that have human heavy and light (kappa) variable regions (S1F/HA, K2/KA mice; n=15). These were compared against 12 mice expressing only mouse antibody chains (+/HA, +/KA (n=6) and wild-type mice (WT; n=6)). The results are tabulated below (Table 19) and shown in FIG. 14.

It can be seen that the mice of the invention, in which essentially all heavy chain variable regions are human heavy chain variable regions, expressed normal proportions of IgM and IgG subtypes, and also total IgG relative to IgM was normal.

TABLE 19

|  | IgG1 (μg/mL) | IgG2a (μg/mL) | IgG2b (μg/mL) | IgM (μg/mL) | | Total IgG + IgM (μg/mL) | |
| --- | --- | --- | --- | --- | --- | --- | --- |
| KMCB22.1a S1F/HA, K2/KA | 30.5 | 38.3 | 49.9 | 1.7 | 224.4 | 1.8 | 343.1 |
| KMCB 19.1d S1F/HA, K2/KA | 103.6 | 181.2 | 85.6 | 1.9 | 351.7 | 1.10 | 722.1 |
| KMCB 19.1h S1F/HA, K2/KA | 191.4 | 456.6 | 383.3 | 1.11 | 643.2 | 1.12 | 1674.6 |
| KMCB 20.1a S1F/HA, K2/KA | 53.6 | 384.4 | 249.7 | 1.13 | 427.1 | 1.14 | 1114.7 |
| KMCB 20.1c S1F/HA, K2/KA | 87.3 | 167.0 | 125.7 | 1.15 | 422.1 | 1.16 | 802.1 |
| KMCB 20.1f S1F/HA, K2/KA | 55.4 | 177.2 | 95.6 | 1.17 | 295.7 | 1.18 | 623.9 |
| KMCB22.1f S1F/HA, K2/KA | 61.1 | 56.3 | 111.4 | 1.19 | 245.8 | 1.20 | 474.5 |

TABLE 19-continued

| | IgG1 (µg/mL) | IgG2a (µg/mL) | IgG2b (µg/mL) | IgM (µg/mL) | Total IgG + IgM (µg/mL) |
|---|---|---|---|---|---|
| KMCB23.1c S1F/HA, K2/KA | 71.4 | 70.7 | 80.5 | 585.4 | 808.0 |
| KMCB23.1d S1F/HA, K2/KA | 65.4 | 148.7 | 187.4 | 255.4 | 657.0 |
| KMCB24.1f S1F/HA, K2/KA | 60.0 | 56.6 | 150.5 | 294.8 | 561.9 |
| KMCB13.1a S1F/HA, K2/KA | 101.2 | 200.5 | 269.8 | 144.1 | 715.7 |
| KMCB13.1d S1F/HA, K2/KA | 124.5 | 117.5 | 246.6 | 183.2 | 671.9 |
| KMCB17.1f S1F/HA, K2/KA | 58.3 | 174.2 | 116.2 | 218.1 | 566.8 |
| KMCB14.1a S1F/HA, K2/KA | 51.9 | 46.5 | 27.9 | 222.2 | 348.6 |
| KMCB14.1b S1F/HA, K2/KA | 11.5 | 54.2 | 48.5 | 194.4 | 308.6 |
| KMCB19.1e +/HA, +/KA | 233.0 | 6.7 | 465.6 | 420.9 | 1126.3 |
| KMCB19.1f +/HA, +/KA | 154.3 | 4.6 | 610.2 | 435.7 | 1204.8 |
| KMCB19.1l +/HA, +/KA | 113.5 | 1.1 | 246.8 | 374.6 | 736.0 |
| KMCB20.1e +/HA, +/KA | 561.0 | 4.3 | 614.3 | 482.1 | 1661.7 |
| KMCB13.1e +/HA, +/KA | 439.3 | 17.1 | 584.1 | 196.9 | 1237.3 |
| KMCB14.1c +/HA, +/KA | 93.4 | 1.3 | 112.0 | 106.8 | 313.6 |
| KMWT 1.3c WT | 212.9 | 155.2 | 104.6 | 233.7 | 706.4 |
| KMWT 1.3d WT | 297.1 | 203.2 | 144.6 | 248.6 | 893.5 |
| KMWT 1.3e WT | 143.1 | 174.2 | 619.1 | 251.8 | 1188.2 |
| KMWT 1.3f WT | 218.8 | 86.8 | 256.1 | 294.8 | 856.4 |
| KMWT 1.3b WT | 150.2 | 114.2 | 114.7 | 225.6 | 604.7 |
| KMWT 3.1e WT | 125.9 | 335.5 | 174.6 | 248.9 | 884.9 |

Example 4

Assessment of Kappa:Lambda Ratio & Splenic B-Cell Compartments in Transgenic Mice of the Invention Mice comprising the following genomes were obtained.

WT/WT=wild-type;

KA/KA=each endogenous kappa allele has been inactivated; and the endogenous lambda loci are left intact;

K3F/K3F=each endogenous kappa allele has three kappa chain locus DNA insertions between the 3' most endogenous Jκ and the mouse Cκ, providing insertion of human V gene segments Vκ2-40, Vκ1-39, Vκ1-33, Vκ2-30, Vκ2-29, Vκ2-28, Vκ1-27, Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2 and Vκ4-1 and human J gene segments Jκ1, Jκ2, Jκ3, Jκ4 and Jκ5 (the human V gene segments being 5' of the human J gene segments); each endogenous kappa VJ has been inactivated by inversion and movement upstream on the chromosome; and the endogenous lambda loci are left intact;

L2/L2=as described in Example 2 (L2 homozygotes where human lambda variable region DNA has been inserted into the endogenous lambda loci; the endogenous kappa loci are left intact);

L2/L2;KA/KA=as L2/L2 but the endogenous kappa alleles have been inactivated (by insertion of an endogenous interrupting sequence=KA);

L3/L3;KA/KA=as L2/L2;KA/KA but supplemented by a third human lambda variable region DNA insertion 5' of the second lambda DNA insertion in the endogenous lambda loci such that the following human lambda gene segments are inserted between 3' most Jλ and the mouse Cλ: human V gene segments Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 and Vλ3-1, human J and C gene segments Jλ1-Cλ1, Jλ2-Cλ2, Jλ3-Cλ3, Jλ6-Cλ6 and Jλ7-Cλ7 (non-functional segments Jλ4-Cλ4, Jλ5-Cλ5 were also included), thus providing an insertion corresponding to coordinates 22886217 to 23327884 of human chromosome 22 inserted immediately after position 19047551 on mouse chromosome 16;

S3F/HA;KA/KA;L3/L3=first endogenous heavy chain allele has three human heavy chain variable region DNA insertions between the 3' most endogenous $J_H$ and the $E_\mu$, providing insertion of human gene segments $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, D1-1, D2-2, D3-9, D3-10, D4-11, D5-12, D6-13, D1-14, D2-15, D3-16, D4-17, D5-18, D6-19, D1-20, D2-21, D3-22, D4-23, D5-24, D6-25, D1-26, D7-27, $J_H1$, $J_H2$, $J_H3$, $J_H4$, $J_H5$ and $J_H6$ (in the order: human V gene segments, human D gene segments and human J gene segments); the endogenous heavy chain VDJ sequence has been inactivated by inversion and movement upstream on the chromosome; and the endogenous lambda loci are left intact; the second endogenous heavy chain allele has been inactivated by insertion of an endogenous interrupting sequence=HA); the endogenous kappa alleles have been inactivated (=KA/KA); and the endogenous lambda alleles have been modified by insertion of human lambda variable region DNA (=L3/L3);

P2/WT=P2 allele (human lambda variable region DNA as described in Example 1) at one endogenous kappa locus; the other endogenous kappa locus left intact; both endogenous lambda loci left intact;

P2/P2=see Example 14; both endogenous lambda loci left intact;

P2/K2=P2 allele at one endogenous kappa locus; the other endogenous kappa locus having two DNA insertions between the 3' most endogenous Jκ and the mouse Cκ, providing insertion of human V gene segments Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2 and Vκ4-1 and human J gene segments Jκ1, Jκ2, Jκ3, Jκ4 and Jκ5 (the human V gene segments being 5' of the human J gene segments); both endogenous lambda loci left intact;

P3/K3F=as one endogenous kappa locus having an insertion between the following human lambda gene segments are inserted between the 3' most endogenous Jκ and the mouse Cκ, providing insertion of human V gene segments Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 and Vλ3-1, human J and C gene segments Jλ1-Cλ1, Jλ2-Cλ2, Jλ3-Cλ3, Jλ6-Cλ6 and Jλ7-Cλ7 (non functional segments Jλ4-Cλ4, Jλ5-Cλ5 were also included), thus providing an insertion corresponding to coordinates 22886217 to 23327884 of human chromosome 22 inserted immediately after position 70674755 on mouse chromosome 6; the other endogenous kappa locus having the K3F allele described above (human V and J kappa gene segments inserted); both endogenous lambda loci left intact;

P2/P2; L2/WT=As P2/P2 but wherein one endogenous lambda locus has the L2 allele (human lambda V and J gene segments inserted) and the other endogenous lambda locus is wild-type; and P2/P2; L2/L2=homozygous for P2 and L2 alleles at endogenous kappa and lambda loci respectively.

FACS analysis of splenic B-cells (as described above) was carried out and proportions of light chain expression were determined. We also determined the proportions of T1, T2 and mature (M) splenic B-cells and compared with wild-type mice, in order to assess whether or not we obtained normal splenic B-cell compartments in the transgenic mice. The results are shown in Tables 20 and 21. We also assessed the proportion of B220 positive cells as an indication of the proportion of B-cells in the splenic cell samples.

TABLE 20

Comparisons With Mice With Human Lambda Variable Region Inserts At Endogenous Lambda Locus

| Genotype | B220 | | IGL percentage | | | | | Splenic B-cell compartment | | | | |
|---|---|---|---|---|---|---|---|---|---|---|---|---|
| | | 1.62 | mIGκ | 1.63 | mIGλ | 1.64 | hIGλ | | T1 | | T2 | | M |
| WT/WT (n = 2) | 20% | | 90% | | 3.80% | 1.65 | | 1.66 | 16% | 1.67 | 16.5 | 1.68 | 57.50% |
| KA/KA (n = 2) | 13.60% | | 0.28% | | 68.50% | 1.69 | 0% | 1.70 | 33% | 1.71 | 9% | 1.72 | 41% |
| K3F/K3F (n = 2) | 20% | | 83% | | 7% | 1.73 | | 1.74 | 16% | 1.75 | 15.50% | 1.76 | 58% |
| L2/L2 (n = 2) | 17.80% | | 91.60% | | 1.60% | 1.77 | 6.50% | 1.78 | 21.50% | 1.79 | 10% | 1.80 | 50% |
| L2/L2; KA/KA (n = 1) | 9.10% | | 0% | | 5% | 1.81 | 93% | 1.82 | 28% | 1.83 | 7% | 1.84 | 44% |
| L3/L3; KA/KA (n = 2) | 16.90% | | 0.10% | | 4.50% | 1.85 | 93.20% | 1.86 | 17.40% | 1.87 | 13.10% | 1.88 | 53.90% |
| S3F/HA; KA/K; L3/L3 (n = 1) | 19% | | 0.20% | | 3.80% | 1.89 | 98% | 1.90 | 15.50% | 1.91 | 19% | 1.92 | 53.20% |

TABLE 21

Mice With Human Lambda Variable Region Inserts At Endogenous Kappa Locus

| Genotype | B220 | | IGL Percentage | | | | | Splenic B-cell compartment | | | | |
|---|---|---|---|---|---|---|---|---|---|---|---|---|
| | | 1.93 | mIGκ | 1.94 | mIGλ | 1.95 | hIGλ | | T1 | | T2 | | M |
| P2/WT (n = 2) | N.D | | 90% | | 4.20% | 1.96 | 6.55% | 1.97 | 17.30% | 1.98 | 8.90% | 1.99 | 52.50% |
| P2/P2 (n = 2) | 14.80% | | 0.20% | | 15% | 1.100 | 76% | 1.101 | 27.50% | 1.102 | 12% | 1.103 | 42% |
| P2/K2 (n = 2) | 18.20% | | 78.80% | | 7.90% | 1.104 | 15.60% | 1.105 | 19.50% | 1.106 | 12% | 1.107 | 50% |
| P3/K3F (n = 2) | 18.40% | | 64.80% | | 11.60% | 1.108 | 19.40% | 1.109 | 11.80% | 1.110 | 18.40% | 1.111 | 56.10% |
| P2/P2; L2/WT (n = 2) | 20.40% | | 0.05% | | 8.50% | 1.112 | 94% | 1.113 | 13.10% | 1.114 | 16.10% | 1.115 | 59.90% |
| P2/P2; L2/L2 (n = 2) | 12.70% | | 0.07% | | 5.10% | 1.116 | 95.40% | 1.117 | 13.40% | 1.118 | 13.80% | 1.119 | 57.30% |

Conclusions

As demonstrated by L2/L2;KA/KA and L3/L3;KA/KA, the human lambda variable region DNA insertions at the endogenous lambda locus (with an endogenous kappa knockout) displayed predominate expression of light chains bearing human lambda variable regions (indicated by the expression of Cλ-positive chains at around 93%). This surprisingly occurs even though endogenous mouse lambda variable region DNA is still present, indicating that the inserted human lambda variable region DNA can outcompete endogenous IGA rearrangement.

Furthermore, mice having the human V and J gene segments present in the homozygous L3 insertion produce B-cells (B220 positive cells) at a proportion that is similar to wild-type and additionally produce a normal proportion or percentage of mature splenic B-cells (ie, similar to wild-type). This is confirmed not only by the L3/L3;KA/KA mice, but also was observed for S3F/HA;KA/KA;L3/L3, which also comprises a chimaeric (human-mouse) IgH locus.

Also, we observed that mice having the human V and J gene segments present in the homozygous K3F insertion produce B-cells (B220 positive cells) at a proportion that is similar to wild-type and additionally produce a normal proportion or percentage of mature splenic B-cells (ie, similar to wild-type).

Mice having the human V and J gene segments present in the homozygous P2 insertion at the endogenous kappa locus showed high expression of light chains comprising human lambda variable regions (as indicated by an observed proportion of 76%). We could skew to an even higher percentage overall by combining insertion of human lambda V and J gene segments at both the endogenous kappa and lambda loci (see P2/P2; L2/WT at around 94% and P2/P2; L2/L2 at around 95%). Furthermore, mice comprising the human V and J gene segment arrangement of P2/P2; L2/L2 produce a normal proportion or percentage of mature splenic B-cells (ie, similar to wild-type).

When human lambda V and J gene segments were inserted at one endogenous kappa locus and the other endogenous kappa locus comprised an insertion of human kappa V and J gene segments, we obtained mice that could express light chains comprising lambda variable regions and also light chains comprising kappa variable regions. Surprisingly observed that we could raise the proportion of light chains comprising lambda variable regions above that seen in a wild-type mouse where only 5% or less of light chains typically comprise lambda variable regions. We observed a proportion of around 22% for the P2/K2 genotype and around 31% for the P3/K3F genotype. The proportion observed with the latter genotype approximates that seen in a human where typically around 60% of light chains comprise kappa variable regions and around 40% of light chains comprise lambda variable regions. Also in the P2/K2 and P3/K3F cases, the mice produced a normal proportion of B-cells as compared with wild-type mice. Furthermore, mice comprising the human V and J gene segment arrangement of P3/K3F produce a normal proportion or percentage of mature splenic B-cells (ie, similar to wild-type).

Example 5

Mouse were generated that comprised the specific IgH alleles listed in Table 3; and the specific IgL alleles listed in Tables 10 or 11. Mice were immunised with target antigens and antigen-specific antibodies were isolated. Antibodies were assessed for binding specificity, maturation (ie, extent of junctional and somatic mutation versus germline gene segment sequences) and binding kinetics. Corresponding B-cells were also obtained and in some cases hybridomas produced that express the selected antibodies.

Selected antibodies are summarised in Table 22. Binding kinetics of some of these were determined as follows.

Binding Kinetics Determination

An anti-mouse IgG capture surface was created on a GLM Biosensor™ chip by primary amine coupling using GE Healthcare anti-mouse IgG (BR-1008-38). Test antibodies as set out in Table 22 were captured on this surface and the respective antigen was passed over the captured Ab at the concentrations indicated. An injection of buffer (i.e. 0 nM of antigen) was used to double reference the binding curves, and the data was fitted to the 1:1 model inherent to the ProteOn XPR36™ analysis software. Regeneration of the capture surface was carried out using 10 mM glycine, pH1.7. The assay was run at 25° C. and using HBS-EP as running buffer.

Target 1: a multi-subunit human protein
Target 2: a bacterial cytotoxin
Target 3: a different multi-subunit human protein
Target 4: a protein expressed as a transmembrane protein on human cells Target 1 mAb1.1

| Single concentration TARGET 1 (256 nM), anti-mouse capture | | |
| --- | --- | --- |
| ka | kd | KD |
| 3.85E+05 | 3.22E−05 | 83 pM |

(Apparent affinity since multi-subunit target)

Target 2 mAb2.1

| TARGET 2 at 256, 64, 16, 4 and 1 nM; results of 3 experiments:- | | |
| --- | --- | --- |
| ka | kd | KD |
| Experiment 1: | | |
| 1.40E+04 | 1.83E−05 | 1.300 nM |
| Experiment 2: | | |
| 2.76E+04 | 3.23E−05 | 1.170 |
| Experiment 3: | | |
| Couldn't resolve off-rate - indicating extremely tight binding beyond detectable limits. | | |

Target 3 mAb3.1

| TARGET 3 at 256, 64, 16, 4 and 1 nM | | |
| --- | --- | --- |
| ka | kd | KD |
| 4.00E+05 | 2.34E−04 | 0.59 nM |

(Apparent affinity since multi-subunit target)

Target 3 mAb3.2

| TARGET 3 at 256, 64, 16, 4 and 1 nM | | |
| --- | --- | --- |
| ka | kd | KD |
| 3.86E+05 | 2.57E−04 | 0.67 |

(Apparent affinity since multi-subunit target)

Target 3 mAb3.3

| TARGET 3 at 256, 64, 16, 4 and 1 nM | | |
|---|---|---|
| ka | kd | KD |
| Unable to resolve Off-rate, extremely tight binding | | |

(Apparent affinity since multi-subunit target)

In conclusion, the present invention provides for in vivo affinity-matured antibodies with human variable domains that can expressed in in vivo systems, and specifically bind target antigens with very good affinities, on and off-rates. The invention thus provides for antibodies that are useful for human medicine, as well as non-human vertebrates, cells (eg, B-cells and hybridomas) for producing such antibodies.

Example 6

The S (heavy), K (kappa into kappa locus), L (lambda into lambda locus) and P (lambda into kappa locus) lines used to generate the data in the examples used the alleles of Tables 1 to 18 and demonstrated that such collections of alleles can produce the surprising results shown (eg, good B cell compartments, high human lambda V region expression, desirable lambda:kappa ratio in a mouse and normal repertoire of IgH isotypes). The isolated antibodies were all based on the alleles listed in Table 1 to 18 above. All had V domains with mouse AID and TdT pattern mutation.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference,

TABLE 22

Hybridoma Sequences

| | v | d | j | nonGermlineAA[1] | AAMutations[2] | kv | kj | knonGermlineAA[1] | kAAMutations[2] |
|---|---|---|---|---|---|---|---|---|---|
| TARGET 1: | | | | | | | | | |
| mAb1.1 | IGHV7-4-1*01 | IGHD3-16*02 | IGHJ6*02 | 2 | 0 | IGKV2-28*01 | IGK J4*1 | 0 | 0 |
| mAb1.2 | IGHV4-4*02 | IGHD3-10*01 | IGHJ6*02 | 3 | 0 | IGKV1D-13*d01 | IGK J4*1 | 0 | 0 |
| TARGET 2: | | | | | | | | | |
| mAb2.1 | IGHV1-3*01 | IGHD3-10*01 | IGHJ6*02 | 6 | 9 | IGKV1-12*01 | IGK J4*1 | 1 | 0 |
| TARGET 3: | | | | | | | | | |
| mAb3.1 | IGHV3-13*01 | IGHD3-9*01 | IGHJ6*02 | 3 | 5 | IGKV1D-12*02 | IGK J4*1 | 0 | 4 |
| mAb3.2 | IGHV3-13*01 | IGHD3-9*01 | IGHJ6*02 | 3 | 5 | IGKV1D-12*02 | IGK J4*1 | 0 | 4 |
| mAb3.3 | IGHV4-4*02 | IGHD3-10*01 | IGHJ6*02 | 2 | 7 | IGKV1D-13*d01 | IGK J4*1 | 3 | 3 |

BcellTech Sequences
TARGET 1:

| id | v | d | j | nonGermlineAA[1] | AAMutations[2] | kv | kj | knonGermlineAA[1] | kAAMutations[2] |
|---|---|---|---|---|---|---|---|---|---|
| mAb1.3 | IGHV3-13*01 | IGHD3-10*01 | IGHJ6*02 | 5 | 0 | IGKV3-20*01 | IGK J4*1 | 0 | 0 |

TARGET 3:

| id | v | d | j | nonGermlineAA[1] | AAMutations[2] | kv | kj | knonGermlineAA[1] | kAAMutations[2] |
|---|---|---|---|---|---|---|---|---|---|
| mAb3.4 | IGHV3-23*04 | IGHD3-22*01 | IGHJ6*02 | 9 | 8 | IGKV1-17*01 | IGK J4*1 | 1 | 1 |
| mAb3.5 | IGHV3-23*04 | IGHD3-22*01 | IGHJ6*02 | 10 | 5 | IGKV1-17*01 | IGK J4*1 | 1 | 0 |
| mAb3.6 | IGHV3-7*01 | IGHD3-9*01 | IGHJ6*02 | 6 | 2 | IGKV1D-39*01 | IGK J4*1 | 2 | 3 |

TABLE 22-continued

| id | v | d | j | | nonGermlineAA[1] | | AAMutations[2] | | kv | | kj | | knonGermlineAA[1] | | kAAMutations[2] |
|---|---|---|---|---|---|---|---|---|---|---|---|---|---|---|---|
| mAb3.7 | IGHV3-23*04 | IGHD3-22*01 | IGHJ6*02 | 1.198 | 9 | 1.199 | 5 | 1.200 | IGKV1-17*01 | 1.201 | IGK J4*1 | 1.202 | 1 | 1.203 | 1 |
| mAb3.8 | IGHV3-13*01 | IGHD3-10*01 | IGHJ6*02 | 1.204 | 7 | 1.205 | 6 | 1.206 | IGKV1D-39*01 | 1.207 | IGK J4*1 | 1.208 | 2 | 1.209 | 4 |
| mAb3.9 | IGHV3-13*01 | IGHD3-10*01 | IGHJ6*02 | 1.210 | 3 | 1.211 | 3 | 1.212 | IGKV3-11*01 | 1.213 | IGK J4*1 | 1.214 | 0 | 1.215 | 5 |

TARGET 4:

| id | v | d | j | | nonGermlineAA[1] | | AAMutations[2] | | kv | | kj | | knonGermlineAA[1] | | kAAMutations[2] |
|---|---|---|---|---|---|---|---|---|---|---|---|---|---|---|---|
| mAb4.1 | IGHV4-4*02 | IGHD3-9*01 | IGHJ6*02 | 1.222 | 7 | 1.223 | 7 | 1.224 | IGKV1D-16*01 | 1.225 | IGK J4*1 | 1.226 | 1 | 1.227 | 1 |
| mAb4.2 | IGHV3-20*d01 | IGHD3-10*01 | IGHJ6*02 | 1.228 | 6 | 1.229 | 4 | 1.230 | IGKV1-9*d01 | 1.231 | IGK J4*1 | 1.232 | 1 | 1.233 | 1 |

[All gene segments are human]
[1] nonGermlineAA: number of non-germline amino acids introduced into VH-D or D-JH junctions or into VL-JL junctions
[2] AAMutations: number of AA mutations in V and J region (CDRH3 or CDRL3 region excluded)

Sequences for examples of gene segments in accordance with the invention are set out below.

IGLC7*01
ggtcagcccaaggctgcccctcggtcactctgttcccaccctcctctgaggagcttcaa gccaacaaggccacactggtgtgtctcgtaagtgacttctacccgggagccgtgacagtg gcctggaaggcagatggcagcccgtcaaggtgggagtggagaccaccaaaccctccaaa caaagcaacaacaagtatgcggccagcagctacctgagcctgacgcccgagcagtggaag tcccacagaagctacagctgccgggtcacgcatgaagggagcaccgtggagaagacagtg gcccctgcagaatgctct IGLJ7*01
tgagtgttcggaggaggcacccagctgaccgtcctcg IGLC6*01
ggtcagcccaaggctgcccatcggtcactctgttcccgccctcctctgaggagcttcaa gccaacaaggccacactggtgtgcctgatcagtgacttctacccgggagctgtgaaagtg gcctggaaggcagatggcagcccgtcaacacgggagtggagaccaccacaccctccaaa cagagcaacaacaagtacgcggccagcagctacctgagcctgacgcctgagcagtggaag tcccacagaagctacagctgccaggtcacgcatgaagggagcaccgtggagaagacagtg gcccctgcagaatgttca IGLC6*04
gtcagcccaaggctgcccatcggtcactctgttcccgccctcctctgaggagcttcaag ccaacaaggccacactggtgtgcctgatcagtgacttctacccgggagctgtgaaagtgg cctggaaggcagatggcagcccgtcaacacgggagtggagaccaccacaccctccaaac agagcaacaacaagtacgcggccagcagctagctacctgagcctgacgcctgagcagtgg aagtcccacagaagctacagttgccaggtcacgcatgaagggagcaccgtggagaagaca gtggcccctgcagaatgctct IGLJ6*01
taatgtgttcggcagtggcaccaaggtgaccgtcctcg IGLC3*03
ggtcagcccaaggctgcccctcggtcactctgttcccaccctcctctgaggagcttcaa gccaacaaggccacactggtgtgtctcataagtgacttctacccgggagccgtgacagtg gcctggaaggcagatagcagcccgtcaaggcgggagtggagaccaccacaccctccaaa caaagcaacaacaagtacgcggccagcagctacctgagcctgacgcctgagcagtggaag tcccacaaaagctacagctgccaggtcacgcatgaagggagcaccgtggagaagacagtg gcccctacagaatgttca IGLJ3*02
ttgggtgttcggcggagggaccaagctgaccgtcctag IGLC2*02
ggtcagcccaaggctgcccctcggtcactctgttcccgccctcctctgaggagcttcaa gccaacaaggccacactggtgtgtctcataagtgacttctacccgggagccgtgacagtg gcctggaaggcagatagcagccccgtcaaggcgggagtggagaccaccacccctccaaa caaagcaacaacaagtacgcggccagcagctatctgagcctgacgcctgagcagtggaag tcccacagaagctacagctgccaggtcacgcatgaagggagcaccgtggagaagacagtg gcccctacagaatgttca IGLJ2*01
tgtggtattcggcggagggaccaagctgaccgctag IGLC1*02
ggtcagcccaaggccaacccccactgtcactctgttcccgccctcctctgaggagctccaa gccaacaaggccacactagtgtgtctgatcagtgacttctacccgggagctgtgacagtg gcctggaaggcagatggcagccccgtcaaggcgggagtggagaccaccaaaccctccaaa cagagcaacaacaagtacgcggccagcagctacctgagcctgacgcccgagcagtggaag tcccacagaagctacagctgccaggtcacgcatgaagggagcaccgtggagaagacagtg gcccctacagaatgttca IGLJ1*01
ttatgtcttcggaactgggaccaaggtcaccgtcctag IGLV3-1*01
gatccgtggcctcctatgagctgactcagccaccctcagtgtccgtgtcccaggacagacagccagc atcacctgctctggagataaaattgggggataaatatgcttgctggtatcagcagaagcca ggccagtcccctgtgctggtcatctatcaagatagcaagcggccctcagggatccctgag cgattctctggctccaactctgggaacacagccactctgaccatcagcgggacccaggct atggatgaggctgactattactgtcaggcgtgggacagcagcactgca IGLV4-3*01
ctgcctgtgctgactcagccccgtctgcatctgccttgctgggagcctcgatcaagctcacc tgcacccctaagcagtgagcacagcacctacaccatcgaatggtatcaacagagaccaggg aggtcccccagtatataatgaaggttaagagtgatggcagccacagcaaggggacggg atccccgatcgcttcatgggaccagttctggggctgaccgctacctcaccttctccaac ctccagtctgacgatgaggctgagtatcactgtggagagagccacacgattgatggccaa gtcggttgagc IGLV2-8*01
cagtctgccctgactcagcctccctccgcgtccgggtctcctggacagtcagtcaccatctcctgcactgga accagcagtgacgttggtggttataactatgtctcctggtaccaacagcacccaggcaaa gcccccaaactcatgatttatgaggtcagtaagcggccctcaggggtccctgatcgcttc tctggctccaagtctggcaacacggcctccctgaccgtctctgggctccaggctgaggat gaggctgattattactgcagctcatatgcaggcagcaacaatttc IGLV3-9*01
tcctatgagctgactcagccactctcagtgtcagtggccctgggacagacggccaggattacc tgtgggggaaacaacattggaagtaaaaatgtgcactggtaccagcagaagccaggccag -continued

```
gccctgtgctggtcatctatagggatagcaaccggccctctgggatccctgagcgattc tctggctccaactcggggaacacggccaccctgaccatcagcagagcccaagccgggat gaggctgactattactgtcaggtgtgggacagcagcactgca
```

IGLV3-10*01
```
tcctatgagctgacacagccaccctcggtgtcagtgtccccaggacaaacggccaggatcacc tgctctggagatgcattgccaaaaaaatatgcttattggtaccagcagaagtcaggccag gccctgtgctggtcatctatgaggacagcaaacgaccctccgggatccctgagagattc tctggctccagctcagggacaatggccaccttgactatcagtggggcccaggtggaggat gaagagactactactgttactaacagacagcagtggtaatcatag
```

IGLV2-11*01
```
cagtctgccctgactcagcctcgctcagtgtccgggtctcctggacagtcagtcaccatctcc tgcactggaaccagcagtgatgttggtggttataactatgtctcctggtaccaacagcac ccaggcaaagcccccaaactcatgatttatgatgtcagtaagcggccctcaggggtccct gatcgcttactggctccaagtctggcaacacggcctccctgaccatctctgggctccag gctgaggatgaggctgattattactgctgctcatatgcaggcagctacactttc
```

IGLV3-12*02
```
tcctatgagctgactcagccacactcagtgtcagtggccacagcacagatggccaggatcacc tgtggggggaaacaacattggaagtaaagctgtgcactggtaccagcaaaagccaggccag gaccctgtgctggtcatctatagcgatagcaaccggccctcagggatccctgagcgattc tctggctccaacccagggaacaccgccaccctaaccatcagcaggatcgaggctggggat gaggctgactattactgtcaggtgtgggacagtagtagtgatcatcc
```

IGLV2-14*01
```
cagtctgccctgactcagcctgcctccgtgtctgggtctcctggacagtcgatcaccatctcc tgcactggaaccagcagtgacgttggtggttataactatgtctcctggtaccaacagcac ccaggcaaagcccccaaactcatgatttatgaggtcagtaatcggccctcaggggtttct aatcgcttctctggctccaagtctggcaacacggcctccctgaccatctctgggctccag gctgaggacgaggctgattattactgcagctcatatacaagcagcagcactctc
```

IGLV3-16*01
```
tcctatgagctgacacagccaccctcggtgtcagtgtccctaggacagatggccaggatcacc tgctctggagaagcattgccaaaaaaatatgcttattggtaccagcagaagccaggccag ttccctgtgctggtgatatataaagacagcgagaggccctcagggatccctgagcgattc taggctccagctcagggacaatagtcacattgaccatcagtggagtccaggcagaagac gaggctgactattactgtctatcagcagacagcagtggtacttatcc
```

IGLV2-18*01
```
cagtctgccctgactcagcctccctccggtccgggtctccggacagtcagtcaccactcc tgcactggaaccagcagtgacgttggtagttataaccgtgtctcctggaccagcagccc ccaggcacagcccccaaactcatgatttatgaggtcagtaatcggccctcaggggtccct gatcgcttctctgggtccaagtctggcaacacggcctccctgaccatctctgggctccag gctgaggacgaggctgattattactgcagcttatatacaagcagcagcactttc
```

IGLV3-19*01
```
tcttctgagctgactcaggaccctgctgtgtctgtggccttgggacagacagtcaggatcaca tgccaaggagacagcctcagaagctattatgcaagctggtaccagcagaagccaggacag gccctgtacttgtcatctatggtaaaaacaaccggccctcagggatcccagaccgattc tctggctccagctcaggaaacacagcttccttgaccatcactggggctcaggcggaagat
```

-continued gaggctgactattactgtaactcccgggacagcagtggtaaccatct

IGLV3-21*01
tcctatgtgctgactcagccaccctcagtgtcagtggccccaggaaagacggccaggattacc tgtgggggaaacaacattggaagtaaaagtgtgcactggtaccagcagaagccaggccag gcccctgtgctggtcatctattatgatagcgaccggccctcagggatccctgagcgattc tctggctccaactctgggaacacggccaccctgaccatcagcagggtcgaagccggggat gaggccgactattactgtcaggtgtgggacagtagtagtgatcatcc IGLV3-21*d01
tcctatgtgctgactcagccaccctcagtgtcagtggccccaggaaagacggccaggattacc tgtgggggaaacaacattggaagtaaaagtgtgcactggtaccagcagaagccaggccag gcccctgtgctggtcatctattatgatagcgaccggccctcagggatccctgagcgattc tctggctccaactctgggaacacggccaccctgaccatcagcagggtcgaagccggggat gaggccgactattactgtcaggtgtgggatagtagtagtgatcatcc IGLV3-22*d01
tcctatgagctgacacagctaccctcggtgtcagtgtccccaggacagaaagccaggatcacc tgctctggagatgtactggggaaaaattatgctgactggtaccagcagaagccaggccag gtctgatatacgagttggtgatatacgaagatagtgagcggtaccctggaatccctgaac gattctctgggtccacctcagggaacacgaccaccctgaccatcagcagggtcctgaccg aagacgaggctgactattactgtttgtctgggaatgaggacaatcc IGLV3-22*01
tcctatgagctgacacagctaccctcggtgtcagtgtccccaggacagacagccaggatcacc tgctctggagatgtactggggaaaaattatgctgactggtaccagcagaagccaggccag gcccctgagttggtgatatacgaagatagtgagcggtaccctggaatccctgaacgattc tctgggtccacctcagggaacacgaccaccctgaccatcagcagggtcctgaccgaagac gaggctgactattactgtttgtctggggatgaggacaatcc IGLV2-23*d02
cagtctgccctgactcagcctgcctccgtgtctgggtctcctggacagtcgatcaccatctcc tgcactggaaccagcagtgatgttggtggttataactatgtctcctggtaccaacagcac ccaggcaaagcccccaaactcatgatttatgatgtcagtaagcggccctcaggggtttct aatcgcttctctggctccaagtctggcaacacggcctccctgacaatctctgggctccag gctgaggacgaggctgattattactgctgctcatatgcaggtagtagcactttc IGLV2-23*02
cagtctgccctgactcagcctgcctccgtgtctgggtctccggacagtcgatcaccatctcc tgcactggaaccagcagtgatgttgggagttataaccttgtctcctggtaccaacagcac ccaggcaaagcccccaaactcatgatttatgaggtcagtaagcggccctcaggggtttct aatcgcttctctggctccaagtctggcaacacggcctccctgacaatctctgggctccag gctgaggacgaggctgattattactgctgctcatatgcaggtagtagcactttc IGLV3-25*d03
tcctatgagctgacacagccaccctcggtgtcagtgtcc ccaggacagacggccaggatcacctgctctgcagatgcattgccaaagcaatatgcttat tggtaccagcagaagccaggccaggcccctgtgctggtgatatataaagacagtgagagg ccctcagggatccctgagcgattctctggctccagctcagggacaacagtcacgttgacc atcagtggagtccaggcagaagacgaggctgactattactgtcaatcagcagacagcagt ggtacttatcc -continued IGLV3-25*01
tcctatgagctgatgcagccaccctcggtgtcagtgtcc ccaggacagacggccaggatcacctgctctggagatgcattgccaaagcaatatgcttat tggtaccagcagaagccaggccaggcccctgtgctggtgatatataaagacagtgagagg ccctcagggatccctgagcgattctctggctccagctcagggacaacagtcacgttgacc atcagtggagtccaggcagaagatgaggctgactattactgtcaatcagcagacagcagt ggtacttatcc IGLV3-27*01
tcctatgagctgacacagccatcctcagtgtcagtgtctccgggacagacagccaggatcacc tgctcaggagatgtactggcaaaaaaatatgctcggtggttccagcagaagccaggccag gcccctgtgctggtgatttataaagacagtgagcggccctcagggatccctgagcgattc tccggctccagctcagggaccacagtcaccttgaccatcagcggggcccaggttgaggat gaggctgactattactgttactctgcggctgacaacaatct IGLV1-36*01|Homo sapiens
cagtctgtgctgactcagccaccctcggtgtctgaagcccccaggcagagggtcaccatct cctgttctggaagcagctccaacatcggaaataatgctgtaaactggtaccagcagctccc aggaaaggctcccaaactcctcatctattatgatgatctgctgccctcaggggtctctgac cgattctctggctccaagtctggcacctcagcctccctggccatcagtgggctccagtctg aggatgaggctgattattactgtgcagcatgggatgacagcctgaatggtcc IGLV5-37*01|Homo sapiens
cagcctgtgctgactcagccacccttcctcctccgcatctcctggagaatccgccagactca cctgcaccttgcccagtgacatcaatgttggtagctacaacatatactggtaccagcagaa gccagggagccctcccaggtatctcctgtactactactcagactcagataagggccagggc tctggagtccccagccgcttctctggatccaaagatgcttcagccaatacagggattttac tcatctccgggctccagtagaggatgaggctgactattactgtatgatttggccaagcaa tgcttct IGLV5-39*01|Homo sapiens
cagcctgtgctgactcagccaacctccctctcagcatctcctggagcatcagccagattca cctgcaccttgcgcagtggcatcaatgttggtacctacaggatatactggtaccagcagaa gccagggagtcttccccggtatctcctgaggtacaaatcagactcagataagcagcagggc tctggagtccccagccgcttctctggatccaaagatgcttcaaccaatgcaggccttttac tcatctctgggctccagtctgaagatgaggctgactattactgtgccatttggtacagcag cacttct IGLV1-40*01|Homo sapiens
cagtctgtgctgacgcagccgccctcagtgtctggggcccagggcagagggtcaccatct cctgcactgggagcagctccaacatcggggcaggttatgatgtacactggtaccagcagct tccaggaacagcccccaaactcctcatctatggtaacagcaatcggccctcaggggtccct gaccgattctctggctccaagtctggcacctcagcctccctggccatcactgggctccagg ctgaggatgaggctgattattactgccagtcctatgacagcagcctgagtggttc >|IGLV7-43*01|Homo sapiens
cagactgtggtgactcaggagccctcactgactgtgtccccaggagggacagtcactctca cctgtgatccagcactggagcagtcaccagtggttactatccaaactggttccagcagaa acctggacaagcacccagggcactgatttatagtacaagcaacaaacactcctggacccct gcccggttctcaggctccctccttgggggcaaagctgccctgacactgtcaggtgtgcagc -continued
ctgaggacgaggctgagtattactgcctgctctactatggtggtgctcag >|IGLV1-44*01|Homo sapiens
cagtctgtgctgactcagccaccctcagcgtctgggaccccgggcagagggtcaccatct cttgttctggaagcagctccaacatcggaagtaatactgtaaactggtaccagcagctccc aggaacggcccccaaactcctcatctatagtaataatcagcggccctcaggggtccctgac cgattctctggctccaagtctggcacctcagcctccctggccatcagtgggctccagtctg aggatgaggctgattattactgtgcagcatgggatgacagcctgaatggtcc

|IGLV5-45*03|Homo sapiens
caggctgtgctgactcagccgtcttccctctctgcatctcctggagcatcagccagtctca cctgcaccttgcgcagtggcatcaatgttggtacctacaggatatactggtaccagcagaa gccagggagtcctccccagtatctcctgaggtacaaatcagactcagataagcagcagggc tctggagtccccagccgatctctggatccaaagatgcttcggccaatgcagggattttac tcatctctgggctccagtctgaggatgaggctgactattactgtatgatttggcacagcag cgcttct >|IGLV7-46*01|Homo sapiens
caggctgtggtgactcaggagccdcactgactgtgtcccaggagggacagtcactctca cctgtggctccagcactggagctgtcaccagtggtcattatccctactggttccagcagaa gcctggccaagcccccaggacactgatttatgatacaagcaacaaacactcctggacacct gcccggttctcaggctccctccttgggggcaaagctgccctgacccttteggggtgcgcage ctgaggatgaggctgagtattactgcttgctctcctatagtggtgctcgg >|IGLV1-47*01|Homo sapiens
cagtctgtgctgactcagccaccctcagcg tctgggaccccgggcagagggtcaccatctcttgttctggaagcagctccaacatcgga agtaattatgtatactggtaccagcagctcccaggaacggcccccaaactcctcatctat aggaataatcagcggccctcaggggtccctgaccgattctctggctccaagtctggcacc tcagcctccctggccatcagtgggctccggtccgaggatgaggctgattattactgtgca gcatgggatgacagcctgagtggtcc >|IGLV9-49*01
cagcctgtgctgactcagccaccttctgcatcagcctccctgggagcctcggtcacactcacc tgcaccctgagcagcggctacagtaattataaagtggactggtaccagcagagaccaggg aagggccccggtttgtgatgcgagtgggcactggtgggattgtgggatccaagggggat ggcatccctgatcgcttctcagtctgggctcaggcctgaatcggtacctgaccatcaag aacatccaggaagaggatgagagtgactaccactgtggggcagaccatggcagtgggagc aacttcgtgtaacc >|IGLV1-51*01
cagtctgtgttgacgcagccgccctcagtgtctgcggccccaggacagaaggtcaccatctcc tgctctggaagcagctccaacattgggaataattatgtatcctggtaccagcagctccca ggaacagccccaaactcctcatttatgacaataatgcgaccctcagggattcctgac cgattctctggctccaagtctggcacgtcagccaccctgggcatcaccggactccagact ggggacgaggccgattattactgcggaacatgggatagcagcctgagtgctgg >|IGLV5-52*01
cagcctgtgctgactcagccatcttcccattctgcatcttctggagcacagtcagactcacctgcatg ctgagcagtggcttcagtgttggggacttctggataaggtggtaccaacaaaagccaggg aaccctccccggtatctcctgtactaccactcagactccaataagggccaaggctagga -continued gttcccagccgcttctctggatccaacgatgcatcagccaatgcagggattctgcgtatc tctgggctccagcctgaggatgaggctgactattactgtggtacatggcacagcaactct aagactca >|IGLV10-54*02
caggcagggctgactcagccaccctcggtgtccaagggcttgagacagaccgccacactcacc tgcactgggaacagcaacattgttggcaaccaaggagcagcttggctgcagcagcaccag ggccaccctcccaaactcctatcctacaggaataacaaccggccctcagggatctcagag agattctctgcatccaggtcaggaaacacagcctccctgaccattactggactccagcct gaggacgaggctgactattactgctcagcattggacagcagcctcagtgctca >|IGLV6-57*01
aattttatgctgactcagccccactctgtgtcggagctccggggaagacggtaaccatctcc tgcacccgcagcagtggcagcattgccagcaactatgtgcagtggtaccagcagcgcccg ggcagttcccccaccactgtgatctatgaggataaccaaagaccctctggggtccctgat cggttctctggctccatcgacagcctccaactctgcctccctcaccatctctggactg aagactgaggacgaggctgactactactgtcagtcttatgatagcagcaatca >|IGLV4-60*d03
cagcctgtgctgactcaatcatcctctgcctctgcttccctgggatcctcggtca agctcacctgcactctgagcagtgggcacagtagctacatcatcgcatggcatcagcagc agccagggaaggcccctcggtacttgatgaagcttgaaggtagtggaagctacaacaagg ggagcggagttcctgatcgcttctcaggctccagctctgtggctgaccgctacctcacca tctccaacctccagtctgaggatgaggctgattattactgtgagacctgggacagtaaca ctca >other|IGLV4-60*03
cagcctgtgctgactcaatcatcctctgcctctgcttccctgggatcctcggtca agctcacctgcactctgagcagtgggcacagtagctacatcatcgcatggcatcagcagc agccagggaaggcccctcggtacttgatgaagcttgaaggtagtggaagctacaacaagg ggagcggagttcctgatcgcttctcaggctccagctctggggctgaccgctacctcacca tctccaacctccagtctgaggatgaggctgattattactgtgagacctgggacagtaaca ct >|IGLV8-61*01
cagactgtggtgacccaggagccatcgttctcagtgtccctggagggacagtcacactcact tgtggcttgagctctggctcagtctctactagttactaccccagctggtaccagcagacc ccaggccaggctccacgcacgctcatctacagcacaaacactcgctcttctggggtccct gatcgcttctctggctccatccttgggaacaaagctgccctcaccatcacgggggcccag gcagatgatgaatctgattattactgtgctgtatatgggtagtggcatttc >|IGLV4-69*01
cagcttgtgctgactcaatcgccctctgcctctgcctccctgggagcctcggtcaagctc acctgcactctgagcagtgggcacagcagctacgccatcgcatggcatcagcagcagcca gagaagggcccctcggtacttgatgaagcttaacagtgatggcagccacagcaaggggac gggatccagatcgcttctcaggctccagctctggggctgagcgctacctcaccatctcc agcctccagtctgaggatgaggctgactattactgtcagacctggggcactggcattca >|IGHV3-20*d0-1
gaggtgcagctggtggagtctgggggaggtgtggtacggcctggggggtccctgagactccc tgtgcagcctctggattcacctttgatgattatggcatgagctgggtccgccaagctcca

```
gggaaggggaggagtgggtctctggtattaattggaatggtggtagcacaggttatgca gactctgtgaagggccgattcaccatctccagagacaacgccaagaactccctgtatctg caaatgaacagtctgagagccgaggacacggccttgtattactgtgcgagaga
```

>|IGHV1-24*d01
```
caggtccagctggtacagtctggggctgaggtgaagaagcctggggcctcagtgaaggtctcc tgcaaggtttccggatacaccctcactgaattatccatgcactgggtgcgacaggctcct ggaaaagggcttgagtggatgggaggttttgatcctgaagatggtgaaacaatctacgca cagaagttccagggcagagtcaccatgaccgaggacacatctacagacacagcctacatg gacctgagcagcctgagatctgaggacacggccgtgtattactgtgcaacaga
```

>|IGHV2-26*d01
```
caggtcaccttgaaggagtctggtcctgtgctggtgaaacccacagagaccctcacgctgacc tgcaccgtctctgggttctcactcagcaatgctagaatgggtgtgagctggatccatcag cccccagggaaggccctggagtggcttgcacacattttttcgaatgacgaaaaatcctac agcacatctctgaagagcaggctcaccatctccaaggacacctccaaaagccaggtggtc cttaccatgaccaatatggaccctgtggacacagccacatattactgtgcacggatac
```

>|IGKV5-2*d01
```
gaaacgacactcacgcagtctccagcattcatgtcagcgactccaggagacaaagtcaac atctcctgcaaagccagccaagacattgatgatgatatgaactggtaccaacagaaacca ggagaagctgctattttcattattcaagaagctactactctcgttcctggaatctcacct cgattcagtggcagcgggtatggaacagattttaccctcacaattaataacatagaatct gaggatgctgcatattacttctgtctacaacatgataatttccctct
```

>|IGKV1-9*d01
```
gacatccagttgacccagtctccatcatcctgtagcatctgtaggagacaga gtcaccatcacttgctgggccagtcagggcattagcagttatttagcctggtatcagcaa aaaccagggaaagcccctaagctcctgatctatgctgcatccactttgcaaagtggggtc ccatcaaggttcagcggcagtggatctgggacagaattcactctcacaatcagcagcctg cagcctgaagattttgcaacttattactgtcaacagcttaatagttaccctcc
```

>|IGKV1D-8*d01
```
gccatctggatgacccagtctccatccttactctctgcatctacaggagacaga gtcaccatcagttgtcggatgagtcagggcattagcagttatttagcctggtatcagcaa aaaccagggaaagcccctgagctcctgatctatgctgcatccactttgcaaagtggggtc ccatcaaggttcagtggcagtggatctgggacagatttcactctcaccatcagctgcctg cagtctgaagattttgcaacttattactgtcaacagtattatagtttccctcc
```

>|IGKV3D-11*d01
```
gaaattgtgttgacacagtctccagccaccctgtctttgtctccaggggaaagagccacc ctctcctgcagggccagtcagagtgttagcagctacttagcctggtaccagcagaaacct ggccaggctcccaggctcctcatctatgatgcatccaacagggccactggcatcccagcc aggttcagtggcagtgggcctgggacagacttcactctcaccatcagcagcctagagcct gaagattttgcagtttattactgtcagcagcgtagcaactggcatcc
```

>|IGKV1D-13*d01
```
gccatccagttgacccagtctccatcctccctgtctgcatctgtagga gacagagtcaccatcacttgccgggcaagtcagggcattagcagtgctttagcctggtat cagcagaaaccagggaaagctcctaagctcctgatctatgatgcctccagtttggaaagt ggggtcccatcaaggttcagcggcagtggatctgggacagatttcactctcaccatcagc
```

-continued agcctgcagcctgaagattttgcaacttattactgtcaacagtttaatagttaccctca

>|IGKV3D-15*d01
gaaatagtgatgacgcagtctccagccaccctgtctgtgtctccaggggaaagagccaccctctcctgcagggccagtca gagtgttagcagcaacttagcctggtaccagcagaaacctggccaggctcc caggctcctcatctatggtgcatccatcagggccactggcatcccagccaggttcagtgg cagtgggtctgggacagagttcactctcaccatcagcatcctgcagtctgaagattttgc agtttattactgtcagcagtataataactggcctcctcc >|IGKV2D-26*d01
gagattgtgatgacccagactccactctccttgtctatcaccccctggagagcaggcctcc atgtcctgcaggtctagtcagagcctcctgcatagtgatggatacacctatttgtattgg tttctgcagaaagccaggccagtctccacgctcctgatctatgaagtttccaaccggttc tctggagtgccagataggttcagtggcagcgggtcagggacagatttcacactgaaaatc agccgggtggaggctgaggattttggagtttattactgcatgcaagatgcacaagatcct cc >Vκ2D-26*d02 V region sequence:
gagattgtgatgacccagactccactctccttgtctatcaccccctggagagcaggcctccatgtcctgcaggtctagtcagag cctcctgcatagtgatggatacacctatttgtattggtttctgcagaaagccaggcca-
gtctccacgctcctgatctatgaagttt ccaaccggttctctggagtgccagataggttcagtggcagcgggtcagggacagatttcacactgaaaatcagccgggtg gaggctgaggattttggagtttattactgcatgcaagatgcacaagatcctcc >|IGKV2D-28*d01
gatattgtgatgactcagcctccactctccctgcccgtcacccctggagagccggcctcc atctcctgcaggtctagtcagagcctcctgcatagtaatggatacaactatttggattgg tacctgcagaagccagggcagtctccacagctcctgatctatttgggttctaatcgggcc tccggggtccctgacaggttcagtggcagtggatcaggcacagattttacactgaaaatc agcagagtggaggctgaggatgttggggtttattactgcatgcaagctctacaaactcct cc

The invention claimed is:

1. A method of producing an antibody or an antigen binding fragment thereof, the method comprising the steps of
   (i) immunising a mouse with an antigen;
      wherein said mouse has a genome comprising an IgH locus comprising one or more human variable heavy (VH) gene segments, one or more human joining heavy (JH) gene segments and one or more human D gene segments positioned at an endogenous IgH locus upstream of an enhancer and a constant (C) region comprising an endogenous IgH C gene segment, and one or more human JL gene segments and one or more human VL gene segments upstream of a constant gene segment at an endogenous light chain locus,
      wherein said IgH locus comprises in 5' to 3' transcriptional orientation said unrearranged human IgH and said unrearranged human IgH joining (JH) gene segments, a human/mouse chimeric DNA junction, an enhancer, and said C region,
      wherein said one or more unrearranged human IgH joining (JH) gene segments comprises a human JH gene segment closest to said chimeric DNA junction, wherein said closest human JH gene segment is less than 2 kb upstream of said chimeric DNA junction, wherein DNA between said closest human JH gene segment and said chimeric DNA junction comprises human DNA naturally contiguous with said closest human JH gene segment,
      wherein DNA between said chimeric DNA junction and said enhancer comprises mouse DNA of the mouse JC intron, wherein said mouse JC intronic DNA comprises less than the complete mouse JC intron, and said human DNA is contiguous with said mouse DNA at a mouse JC intron internal position,
      wherein said human gene segments in each said Ig locus are unrearranged and operably linked to the constant gene segment thereof so that the mouse is capable of producing an antibody heavy chain generated by recombination of a said one or more human JH gene segments with a said one or more D gene segments and a said one or more VH segments, and an antibody light chain generated by recombination of a said one or more human JL gene segments with a said one or more VL segments,
      wherein said one or more human VH gene segments of the heavy chain locus comprise one or more human VH gene segments selected from the group consisting of VH3-23*04, VH7-4-1*01, VH4-4*02, VH 1-3*01, VH3-13*01, VH3-7*01, VH3-20*d01 and VH3-9*01; and/or
      wherein said one or more human VL gene segments of the light chain locus comprise one or more human VK gene segments selected from the group consisting of VK4-1*01, VK2-28*01, VK1 D-13*d01, VK1-12*01, VK1 D-12*02, VK3-20*01, VK1-17*01, VK1 D-39*01, VK3-11*01, VK1 D-16*01 and VK1-9*d01;
   (ii) recovering from said immunized mouse of step (i) one or more selected from the group consisting of:
      (a) an antibody or antigen binding fragment thereof comprising one or both of said antibody heavy chain and said antibody light chain,
      (b) a cell producing the antibody or antigen binding fragment thereof of step (ii)(a).

2. The method according to claim 1, further comprising the step of modifying the produced antibody or antigen binding fragment thereof of step (ii)(a), so that it comprises human a constant gene regions operably linked to the variable regions of said antibody or antigen binding fragment thereof.

3. The method according to claim 1, wherein said one or more human JH gene segments of the heavy chain locus comprises human JH2*01 and/or human JH6*02.

4. The method according to claim 1, wherein at least one of said one or more human VH gene segments is selected from the group consisting of VH3-23*04, VH7-4-1*01, VH4-4*02, VH 1-3*01, VH3-13*01, VH3-7*01 and VH3-20*d01.

5. The method according to claim 1, wherein the antigen is a multi-subunit human protein, a bacterial cytotoxin or a protein expressed as a transmembrane protein on human cells.

6. The method according to claim 1, wherein the antibody or antigen binding fragment thereof specifically binds a human target selected from: proprotein convertase PC9, proprotein convertase subtilisin kexin-9 (PCSK9), CD126, I L-4, IL-4 receptor, IL-6, IL-6 receptor, I L-13, IL-18 receptor, Erbb3, cell ASIC1, ANG2, GDF-8, angiopoietin ligand-2, delta-like protein ligand 4, immunoglobulin G1, PDGF ligand, PDGF receptor or NGF receptor, toxin A or toxin B of *Clostridium difficile*, relaxin, CD48, Cd20, glucagon receptor, protease activated receptor 2, TNF-Like ligand 1A (TL1A), angiopoietin related-2 (AR-2), angiopoietin-like protein 4, RANKL, angiopoietin-like protein 3 (ANGPTL3), delta-like ligand 4 (DLL4), big endothelin-1 (ET-1), activin A, receptor tyrosine kinases, for example human AR-1 and tyrosine kinase with Ig and EGF homology domains (TI E) and TIE-2 receptor.

7. The method according to claim 1, further comprising isolating an antibody or antigen binding fragment thereof from the cell of step (ii)(b).

8. The method according to claim 7, further comprising the step of modifying the antibody or antigen binding fragment thereof isolated from the cell of step (ii)(b), so that it comprises human constant regions operably linked to the variable regions of said antibody or antigen binding fragment thereof.

9. A method according to of claim 1,
(a) wherein the heavy chain of the isolated antibody is encoded by a VH gene segment selected from the group consisting of human VH3-23*04 and human VH3-9*01,
(b) wherein the heavy chain of the isolated antibody is encoded by a JH gene segment selected from the group consisting of human J H6*02, human J H6*01, J H2*01 and JH3*02,
(c) wherein the light chain of the isolated antibody is encoded by a VK gene segment selected from the group consisting of human VK1 D-12*02, human VK1-12*01, human VK2-28*01 and human VK4-1*01,
(d) wherein the light chain of the isolated antibody is encoded by a JK gene segment selected from the group consisting of human JK2*01 and human JK4*01.

10. The method of claim 7, wherein the cell of step (ii)(b) is a B-cell encoding an antibody that binds said antigen, further comprising
(iii) one or more of the steps selected from the group consisting of:
(a) identifying a nucleotide sequence of the B-cell that encodes a VH domain of the antibody,
(b) copying a nucleotide sequence of the B-cell that encodes a VH domain of the antibody,
(c) identifying nucleotide sequence of the B-cell that encodes a VL domain of the antibody, and
(d) copying nucleotide sequence of the B-cell that encodes a VL domain of the antibody; and
(iv) using the sequence(s) of step (iii) to produce an isolated antibody or antigen binding fragment thereof comprising the VH and/or VL domain of step (iii).

11. The method of claim 10, further comprising the step of modifying the antibody or antigen binding fragment thereof of step (iv), so that it comprises human constant regions operably linked to the variable regions of said antibody or antigen binding fragment thereof of step (iv).

12. The method of claim 1, wherein the antibody or antigen binding fragment thereof of step (ii) is produced by expression from a host cell selected from a CHO, HEK293, Cos or yeast cell.

13. The method of claim 12, wherein the antibody or antigen binding fragment thereof of step (ii) is produced by expression from a CHO cell.

14. The method of claim 1, further comprising formulating the antibody or antigen binding fragment thereof of step (ii) with a pharmaceutically acceptable diluent, carrier, excipient or a drug, thereby producing a pharmaceutical composition.

15. The method of claim 14, further comprising packaging said pharmaceutical composition in a sterile container.

16. The method of claim 15, wherein said sterile container is selected from the group consisting of a vial, a tube, an Intravenous bag and a syringe.

17. The method of claim 15, wherein said packaging comprising a label or instructions comprises a medicament batch number and/or a marketing authorization number, further optionally an EMA or FDA marketing authorization number.

18. The method of claim 1, wherein the antibody or antigen binding fragment thereof produced by said method comprises
(a) a human heavy chain variable domain that is a recombinant of a human VH gene segment selected from the group consisting of VH3-23*04, VH7-4-1*01, VH4-4*02, VH1-3*01, VH3-13*01, VH3-7*01, VH3-20*d01 and VH3-9*01, a human J H gene segment and a human D gene segment; and/or
(b) a human light chain variable domain is a recombinant of a human VL gene segment selected from the group consisting of VK4-1*01, VK2-28*01, VK1 D-13*d01, VK1-12*01, VK1 D-12*02, VK3-20*01, VK1-17*01, VK1 D-39*01, VK3-11*01, VK1 D-16*01 and V 1-9*d01 and a human J gene segment.

19. The method of claim 18, wherein the human JH gene segment of claim 18 (a) is selected from the group consisting of JH2*01, JH6*02, JH6*01 and JH3*02.

20. The method of claim 18, wherein the human JL gene segment of claim 18 (b) is selected from the group consisting of JK4*01 and JK2*01.

21. The method of claim 18, wherein the antibody or antigen binding fragment thereof produced by the method comprises a heavy chain variable domain recombinant of claim 19 and a light chain variable domain recombinant of claim 20.

22. The method of claim 18, wherein the antibody or antigen binding fragment thereof produced by the method comprises a human heavy chain variable domain recombinant of VH3-23*04 and JH2*01 and a human light chain variable domain recombinant of VK4-1*01 and JK2*01.

23. The method of claim 18, wherein the antibody or antigen binding fragment thereof produced by the method comprises a human heavy chain variable domain recombinant of VH3-7*01 and JH6*02 and a human light chain variable domain recombinant of VK2-28*01 and JK4*01.

24. The method of claim 1, said mouse being functional to form rearranged human VH, D and JH gene segments and to express mRNA transcripts encoding chimeric immunoglobulin heavy chain polypeptide comprising a human VH region and a mouse $C\mu$ region, wherein said mouse comprises IgH mRNA transcripts comprising IgH-VDJC$\mu$ transcripts comprising rearranged human heavy chain V, D, and J gene segments and mouse $C\mu$ and encoding chimeric IgH polypeptides, wherein each IgH-VDJC$\mu$ transcript encodes a human variable region comprising a CDR-H3, wherein said IgH-VDJC$\mu$ transcripts comprise transcripts encoding a human variable region comprising a CDR-H3 length of 17 amino acids and transcripts encoding human variable region comprising a CDR-H3 length of 18 amino acids, wherein the mean frequency of the group consisting of said transcripts encoding CDR-H3 lengths of 17 and 18 amino acids present in said IgH-VDJC$\mu$ transcripts of said mouse is between 5% and 10%.

* * * * *

SEQUENCE LISTING

<160> NUMBER OF SEQ ID NOS: 61

<210> SEQ ID NO 1
<211> LENGTH: 318
<212> TYPE: DNA
<213> ORGANISM: Homo sapiens

<400> SEQUENCE: 1
ggtcagccca aggctgcccc ctcggtcact ctgttcccac cctcctctga ggagcttcaa     60
gccaacaagg ccacactggt gtgtctcgta agtgacttct acccgggagc cgtgacagtg    120
gcctggaagg cagatggcag ccccgtcaag gtgggagtgg agaccaccaa accctccaaa    180
caaagcaaca acaagtatgc ggccagcagc tacctgagcc tgacgcccga gcagtggaag    240
tcccacagaa gctacagctg ccgggtcacg catgaaggga gcaccgtgga aagacagtg     300 gcccctgcag aatgctct                                                  318

<210> SEQ ID NO 2
<211> LENGTH: 38
<212> TYPE: DNA
<213> ORGANISM: Homo sapiens

```
<400> SEQUENCE: 2
tgctgtgttc ggaggaggca cccagctgac cgtcctcg                               38

<210> SEQ ID NO 3
<211> LENGTH: 318
<212> TYPE: DNA
<213> ORGANISM: Homo sapiens

<400> SEQUENCE: 3
ggtcagccca aggctgcccc atcggtcact ctgttcccgc cctcctctga ggagcttcaa       60
gccaacaagg ccacactggt gtgcctgatc agtgacttct acccgggagc tgtgaaagtg      120
gcctggaagg cagatggcag cccgtcaac acgggagtgg agaccaccac accctccaaa      180
cagagcaaca caagtacgc ggccagcagc tacctgagcc tgacgcctga gcagtggaag      240
tcccacagaa gctacagctg ccaggtcacg catgaaggga gcaccgtgga aagacagtg      300 gcccctgcag aatgttca                                                   318

<210> SEQ ID NO 4
<211> LENGTH: 321
<212> TYPE: DNA
<213> ORGANISM: Homo sapiens

<400> SEQUENCE: 4
gtcagcccaa ggctgcccca tcggtcactc tgttcccgcc ctcctctgag gagcttcaag       60
ccaacaaggc cacactggtg tgcctgatca gtgacttcta cccgggagct gtgaaagtgg      120
cctggaaggc agatggcagc cccgtcaaca cgggagtgga gaccaccaca ccctccaaac      180
agagcaacaa caagtacgcg gccagcagct agctacctga gcctgacgcc tgagcagtgg      240
aagtcccaca gaagctacag ttgccaggtc acgcatgaag ggagcaccgt ggagaagaca      300
gtggcccctg cagaatgctc t                                               321

<210> SEQ ID NO 5
<211> LENGTH: 38
<212> TYPE: DNA
<213> ORGANISM: Homo sapiens

<400> SEQUENCE: 5
taatgtgttc ggcagtggca ccaaggtgac cgtcctcg                               38

<210> SEQ ID NO 6
<211> LENGTH: 318
<212> TYPE: DNA
<213> ORGANISM: Homo sapiens

<400> SEQUENCE: 6
ggtcagccca aggctgcccc ctcggtcact ctgttcccac cctcctctga ggagcttcaa       60
gccaacaagg ccacactggt gtgtctcata agtgacttct acccgggagc cgtgacagtg      120
gcctggaagg cagatagcag ccccgtcaag gcgggagtgg agaccaccac accctccaaa      180
caaagcaaca caagtacgc ggccagcagc tacctgagcc tgacgcctga gcagtggaag      240
tcccacaaaa gctacagctg ccaggtcacg catgaaggga gcaccgtgga aagacagtg      300 gcccctacag aatgttca                                                   318

<210> SEQ ID NO 7
<211> LENGTH: 38
<212> TYPE: DNA
<213> ORGANISM: Homo sapiens
```

<400> SEQUENCE: 7
ttgggtgttc ggcggaggga ccaagctgac cgtcctag                                38

<210> SEQ ID NO 8
<211> LENGTH: 318
<212> TYPE: DNA
<213> ORGANISM: Homo sapiens

<400> SEQUENCE: 8
ggtcagccca aggctgcccc ctcggtcact ctgttcccgc cctcctctga ggagcttcaa        60
gccaacaagg ccacactggt gtgtctcata agtgacttct acccgggagc cgtgacagtg       120
gcctggaagg cagatagcag ccccgtcaag gcgggagtgg agaccaccac accctccaaa       180
caaagcaaca caagtacgc ggccagcagc tatctgagcc tgacgcctga gcagtggaag        240
tcccacagaa gctacagctg ccaggtcacg catgaaggga gcaccgtgga agacagtg         300 gcccctacag aatgttca                                                     318

<210> SEQ ID NO 9
<211> LENGTH: 38
<212> TYPE: DNA
<213> ORGANISM: Homo sapiens

<400> SEQUENCE: 9
tgtggtattc ggcggaggga ccaagctgac cgtcctag                                38

<210> SEQ ID NO 10
<211> LENGTH: 318
<212> TYPE: DNA
<213> ORGANISM: Homo sapiens

<400> SEQUENCE: 10
ggtcagccca aggccaaccc cactgtcact ctgttcccgc cctcctctga ggagctccaa        60
gccaacaagg ccacactagt gtgtctgatc agtgacttct acccgggagc tgtgacagtg       120
gcctggaagg cagatggcag ccccgtcaag gcgggagtgg agaccaccaa accctccaaa       180
cagagcaaca caagtacgc ggccagcagc tacctgagcc tgacgcccga gcagtggaag        240
tcccacagaa gctacagctg ccaggtcacg catgaaggga gcaccgtgga agacagtg         300 gcccctacag aatgttca                                                     318

<210> SEQ ID NO 11
<211> LENGTH: 38
<212> TYPE: DNA
<213> ORGANISM: Homo sapiens

<400> SEQUENCE: 11
ttatgtcttc ggaactggga ccaaggtcac cgtcctag                                38

<210> SEQ ID NO 12
<211> LENGTH: 296
<212> TYPE: DNA
<213> ORGANISM: Homo sapiens

<400> SEQUENCE: 12
gatccgtggc ctcctatgag ctgactcagc accctcagt gtccgtgtcc ccaggacaga        60
cagccagcat cacctgctct ggagataaat tgggggataa atatgcttgc tggtatcagc       120
agaagccagg ccagtcccct gtgctggtca tctatcaaga tagcaagcgg ccctcaggga       180

```
tccctgagcg attctctggc tccaactctg gaacacagc cactctgacc atcagcggga      240
cccaggctat ggatgaggct gactattact gtcaggcgtg ggacagcagc actgca          296
```

<210> SEQ ID NO 13
<211> LENGTH: 314
<212> TYPE: DNA
<213> ORGANISM: Homo sapiens

<400> SEQUENCE: 13

```
ctgcctgtgc tgactcagcc cccgtctgca tctgccttgc tgggagcctc gatcaagctc       60
acctgcaccc taagcagtga gcacagcacc tacaccatcg aatggtatca acagagacca     120
gggaggtccc cccagtatat aatgaaggtt aagagtgatg gcagccacag caaggggggac    180 gggatccccg atcgcttcat gggctccagt tctggggctg accgctacct caccttctcc      240
aacctccagt ctgacgatga ggctgagtat cactgtggag agagccacac gattgatggc     300
caagtcggtt gagc                                                        314
```

<210> SEQ ID NO 14
<211> LENGTH: 297
<212> TYPE: DNA
<213> ORGANISM: Homo sapiens

<400> SEQUENCE: 14

```
cagtctgccc tgactcagcc tccctccgcg tccgggtctc ctggacagtc agtcaccatc       60
tcctgcactg gaaccagcag tgacgttggt ggttataact atgtctcctg gtaccaacag     120
cacccaggca agcccccaa actcatgatt tatgaggtca gtaagcggcc ctcaggggtc      180
cctgatcgct tctctggctc caagtctggc aacacggcct ccctgaccgt ctctgggctc     240
caggctgagg atgaggctga ttattactgc agctcatatg caggcagcaa caatttc        297
```

<210> SEQ ID NO 15
<211> LENGTH: 285
<212> TYPE: DNA
<213> ORGANISM: Homo sapiens

<400> SEQUENCE: 15

```
tcctatgagc tgactcagcc actctcagtg tcagtggccc tgggacagac ggccaggatt       60
acctgtgggg gaaacaacat tggaagtaaa aatgtgcact ggtaccagca gaagccaggc     120
caggcccctg tgctggtcat ctatagggat agcaaccggc cctctgggat ccctgagcga     180
ttctctggct ccaactcggg gaacacggcc accctgacca tcagcagagc caagccgggg    240
gatgaggctg actattactg tcaggtgtgg gacagcagca ctgca                      285
```

<210> SEQ ID NO 16
<211> LENGTH: 290
<212> TYPE: DNA
<213> ORGANISM: Homo sapiens

<400> SEQUENCE: 16

```
tcctatgagc tgacacagcc accctcggtg tcagtgtccc caggacaaac ggccaggatc       60
acctgctctg gagatgcatt gccaaaaaaa tatgcttatt ggtaccagca gaagtcaggc     120
caggcccctg tgctggtcat ctatgaggac agcaaacgac cctccgggat ccctgagaga     180
ttctctggct ccagctcagg gacaatggcc accttgacta tcagtggggc ccaggtggag    240
gatgaagctg actactactg ttactcaaca gacagcagtg gtaatcatag                 290
```

```
<210> SEQ ID NO 17
<211> LENGTH: 297
<212> TYPE: DNA
<213> ORGANISM: Homo sapiens

<400> SEQUENCE: 17
cagtctgccc tgactcagcc tcgctcagtg tccgggtctc ctggacagtc agtcaccatc      60
tcctgcactg gaaccagcag tgatgttggt ggttataact atgtctcctg gtaccaacag     120
cacccaggca aagcccccaa actcatgatt tatgatgtca gtaagcggcc ctcaggggtc     180
cctgatcgct tctctggctc caagtctggc aacacggcct ccctgaccat ctctgggctc     240
caggctgagg atgaggctga ttattactgc tgctcatatg caggcagcta cactttc       297

<210> SEQ ID NO 18
<211> LENGTH: 290
<212> TYPE: DNA
<213> ORGANISM: Homo sapiens

<400> SEQUENCE: 18
tcctatgagc tgactcagcc acactcagtg tcagtggcca cagcacagat ggccaggatc      60
acctgtgggg gaaacaacat tggaagtaaa gctgtgcact ggtaccagca aaagccaggc     120
caggaccctg tgctggtcat ctatagcgat agcaaccggc cctcagggat ccctgagcga     180
ttctctggct ccaacccagg gaacaccgcc accctaacca tcagcaggat cgaggctggg     240
gatgaggctg actattactg tcaggtgtgg gacagtagta gtgatcatcc               290

<210> SEQ ID NO 19
<211> LENGTH: 297
<212> TYPE: DNA
<213> ORGANISM: Homo sapiens

<400> SEQUENCE: 19
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca aagcccccaa actcatgatt tatgaggtca gtaatcggcc ctcagggggtt    180 tctaatcgct tctctggctc caagtctggc aacacggcct ccctgaccat ctctgggctc     240
caggctgagg acgaggctga ttattactgc agctcatata caagcagcag cactctc       297

<210> SEQ ID NO 20
<211> LENGTH: 290
<212> TYPE: DNA
<213> ORGANISM: Homo sapiens

<400> SEQUENCE: 20
tcctatgagc tgacacagcc accctcggtg tcagtgtccc taggacagat ggccaggatc      60
acctgctctg gagaagcatt gccaaaaaaa tatgcttatt ggtaccagca gaagccaggc     120
cagttccctg tgctggtgat atataaagac agcgagaggc cctcagggat ccctgagcga     180
ttctctggct ccagctcagg gacaatagtc acattgacca tcagtggagt ccaggcagaa     240
gacgaggctg actattactg tctatcagca gacagcagtg gtacttatcc               290

<210> SEQ ID NO 21
<211> LENGTH: 297
<212> TYPE: DNA
<213> ORGANISM: Homo sapiens

<400> SEQUENCE: 21
```

```
cagtctgccc tgactcagcc tccctccgtg tccgggtctc ctggacagtc agtcaccatc    60
tcctgcactg gaaccagcag tgacgttggt agttataacc gtgtctcctg gtaccagcag   120
cccccaggca cagcccccaa actcatgatt tatgaggtca gtaatcggcc ctcaggggtc   180
cctgatcgct tctctgggtc caagtctggc aacacggcct ccctgaccat ctctgggctc   240
caggctgagg acgaggctga ttattactgc agcttatata caagcagcag cactttc     297
```

<210> SEQ ID NO 22
<211> LENGTH: 290
<212> TYPE: DNA
<213> ORGANISM: Homo sapiens

<400> SEQUENCE: 22

```
tcttctgagc tgactcagga ccctgctgtg tctgtggcct tgggacagac agtcaggatc    60
acatgccaag agacagcct cagaagctat atgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactggggc tcaggcggaa   240
gatgaggctg actattactg taactcccgg gacagcagtg gtaaccatct              290
```

<210> SEQ ID NO 23
<211> LENGTH: 290
<212> TYPE: DNA
<213> ORGANISM: Homo sapiens

<400> SEQUENCE: 23

```
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gacagtagta gtgatcatcc              290
```

<210> SEQ ID NO 24
<211> LENGTH: 290
<212> TYPE: DNA
<213> ORGANISM: Homo sapiens

<400> SEQUENCE: 24

```
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatcc              290
```

<210> SEQ ID NO 25
<211> LENGTH: 289
<212> TYPE: DNA
<213> ORGANISM: Homo sapiens

<400> SEQUENCE: 25

```
tcctatgagc tgacacagct accctcggtg tcagtgtccc caggacagaa agccaggatc    60
acctgctctg gagatgtact ggggaaaaat tatgctgact ggtaccagca gaagccaggc   120
caggtctgat atacgagttg gtgatatacg aagatagtga gcggtaccct ggaatccctg   180
aacgattctc tgggtccacc tcagggaaca cgaccaccct gaccatcagc agggtcctga   240
```

```
ccgaagacga ggctgactat tactgtttgt ctgggaatga ggacaatcc          289
```

<210> SEQ ID NO 26
<211> LENGTH: 284
<212> TYPE: DNA
<213> ORGANISM: Homo sapiens

<400> SEQUENCE: 26

```
tcctatgagc tgacacagct accctcggtg tcagtgtccc aggacagac agccaggatc   60 acctgctctg gagatgtact gggggaaaat tatgctgact ggtaccagca gaagccaggc  120
caggcccctg agttggtgat atacgaagat agtgagcgt accctggaat ccctgaacga  180
ttctctgggt ccacctcagg gaacacgacc accctgacca tcagcagggt cctgaccgaa  240
gacgaggctg actattactg tttgtctggg gatgaggaca atcc                   284
```

<210> SEQ ID NO 27
<211> LENGTH: 297
<212> TYPE: DNA
<213> ORGANISM: Homo sapiens

<400> SEQUENCE: 27

```
cagtctgccc tgactcagcc tgcctccgtg tctgggtctc ctggacagtc gatcaccatc   60
tcctgcactg gaaccagcag tgatgttggt ggttataact atgtctcctg gtaccaacag  120
cacccaggca agcccccaa actcatgatt tatgatgtca gtaagcggcc ctcaggggtt  180
tctaatcgct tctctggctc caagtctggc aacacggcct ccctgacaat ctctgggctc  240
caggctgagg acgaggctga ttattactgc tgctcatatg caggtagtag cactttc     297
```

<210> SEQ ID NO 28
<211> LENGTH: 297
<212> TYPE: DNA
<213> ORGANISM: Homo sapiens

<400> SEQUENCE: 28

```
cagtctgccc tgactcagcc tgcctccgtg tctgggtctc ctggacagtc gatcaccatc   60
tcctgcactg gaaccagcag tgatgttggg agttataacc ttgtctcctg gtaccaacag  120
cacccaggca agcccccaa actcatgatt tatgaggtca gtaagcggcc ctcaggggtt  180
tctaatcgct tctctggctc caagtctggc aacacggcct ccctgacaat ctctgggctc  240
caggctgagg acgaggctga ttattactgc tgctcatatg caggtagtag cactttc     297
```

<210> SEQ ID NO 29
<211> LENGTH: 290
<212> TYPE: DNA
<213> ORGANISM: Homo sapiens

<400> SEQUENCE: 29

```
tcctatgagc tgacacagcc accctcggtg tcagtgtccc aggacagac ggccaggatc   60 acctgctctg cagatgcatt gccaaagcaa tatgcttatt ggtaccagca gaagccaggc  120
caggcccctg tgctggtgat atataaagac agtgagaggc cctcagggat ccctgagcga  180
ttctctggct ccagctcagg gacaacatc acgttgacca tcagtggagt ccaggcagaa  240
gacgaggctg actattactg tcaatcagca gacagcagtg gtacttatcc            290
```

<210> SEQ ID NO 30
<211> LENGTH: 290
<212> TYPE: DNA

<210> SEQ ID NO 30
<211> LENGTH: 290
<212> TYPE: DNA
<213> ORGANISM: Homo sapiens

<400> SEQUENCE: 30
tcctatgagc tgatgcagcc accctcggtg tcagtgtccc caggacagac ggccaggatc       60
acctgctctg gagatgcatt gccaaagcaa tatgcttatt ggtaccagca gaagccaggc      120
caggcccctg tgctggtgat atataaagac agtgagaggc cctcagggat ccctgagcga      180
ttctctggct ccagctcagg gacaacagtc acgttgacca tcagtggagt ccaggcagaa      240
gatgaggctg actattactg tcaatcagca gacagcagtg gtacttatcc                 290

<210> SEQ ID NO 31
<211> LENGTH: 284
<212> TYPE: DNA
<213> ORGANISM: Homo sapiens

<400> SEQUENCE: 31
tcctatgagc tgacacagcc atcctcagtg tcagtgtctc cgggacagac agccaggatc       60
acctgctcag gagatgtact ggcaaaaaaa tatgctcggt ggttccagca gaagccaggc      120
caggcccctg tgctggtgat ttataaagac agtgagcggc cctcagggat ccctgagcga      180
ttctccggct ccagctcagg gaccacagtc accttgacca tcagcggggc ccaggttgag      240
gatgaggctg actattactg ttactctgcg gctgacaaca atct                       284

<210> SEQ ID NO 32
<211> LENGTH: 296
<212> TYPE: DNA
<213> ORGANISM: Homo sapiens

<400> SEQUENCE: 32
cagtctgtgc tgactcagcc accctcggtg tctgaagccc ccaggcagag ggtcaccatc       60
tcctgttctg gaagcagctc caacatcgga aataatgctg taaactggta ccagcagctc      120
ccaggaaagg ctcccaaact cctcatctat tatgatgatc tgctgccctc aggggtctct      180
gaccgattct ctggctccaa gtctggcacc tcagcctccc tggccatcag tgggctccag      240
tctgaggatg aggctgatta ttactgtgca gcatgggatg acagcctgaa tggtcc          296

<210> SEQ ID NO 33
<211> LENGTH: 312
<212> TYPE: DNA
<213> ORGANISM: Homo sapiens

<400> SEQUENCE: 33
cagcctgtgc tgactcagcc accttcctcc tccgcatctc ctggagaatc cgccagactc       60
acctgcacct tgcccagtga catcaatgtt ggtagctaca acatatactg gtaccagcag      120
aagccaggga gccctcccag gtatctcctg tactactact cagactcaga taagggccag      180
ggctctggag tccccagccg cttctctgga tccaaagatg cttcagccaa tacagggatt      240
ttactcatct ccgggctcca gtctgaggat gaggctgact attactgtat gatttggcca      300
agcaatgctt ct                                                         312

<210> SEQ ID NO 34
<211> LENGTH: 312
<212> TYPE: DNA
<213> ORGANISM: Homo sapiens

<400> SEQUENCE: 34
cagcctgtgc tgactcagcc aacctccctc tcagcatctc ctggagcatc agccagattc       60

```
acctgcacct tgcgcagtgg catcaatgtt ggtacctaca ggatatactg gtaccagcag    120
aagccaggga gtcttccccg gtatctcctg aggtacaaat cagactcaga taagcagcag    180
ggctctggag tccccagccg cttctctgga tccaaagatg cttcaaccaa tgcaggcctt    240
ttactcatct ctgggctcca gtctgaagat gaggctgact attactgtgc catttggtac    300
agcagcactt ct                                                       312
```

<210> SEQ ID NO 35
<211> LENGTH: 299
<212> TYPE: DNA
<213> ORGANISM: Homo sapiens

<400> SEQUENCE: 35

```
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttc    299
```

<210> SEQ ID NO 36
<211> LENGTH: 294
<212> TYPE: DNA
<213> ORGANISM: Homo sapiens

<400> SEQUENCE: 36

```
cagactgtgg tgactcagga gccctcactg actgtgtccc caggagggac agtcactctc    60
acctgtgctt ccagcactgg agcagtcacc agtggttact atccaaactg gttccagcag   120
aaacctggac aagcacccag gcactgattt atagtacaa gcaacaaaca ctcctggacc   180
cctgcccggt tctcaggctc cctccttggg ggcaaagctg ccctgacact gtcaggtgtg   240
cagcctgagg acgaggctga gtattactgc ctgctctact atggtggtgc tcag         294
```

<210> SEQ ID NO 37
<211> LENGTH: 296
<212> TYPE: DNA
<213> ORGANISM: Homo sapiens

<400> SEQUENCE: 37

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggtccct   180 gaccgattct ctggctccaa gtctggcacc tcagcctccc tggccatcag tgggctccag   240
tctgaggatg aggctgatta ttactgtgca gcatgggatg acagcctgaa tggtcc        296
```

<210> SEQ ID NO 38
<211> LENGTH: 312
<212> TYPE: DNA
<213> ORGANISM: Homo sapiens

<400> SEQUENCE: 38

```
caggctgtgc tgactcagcc gtcttccctc tctgcatctc ctggagcatc agccagtctc    60
acctgcacct tgcgcagtgg catcaatgtt ggtacctaca ggatatactg gtaccagcag   120
aagccaggga gtcctcccca gtatctcctg aggtacaaat cagactcaga taagcagcag   180
```

```
ggctctggag tccccagccg cttctctgga tccaaagatg cttcggccaa tgcagggatt    240
ttactcatct ctgggctcca gtctgaggat gaggctgact attactgtat gatttggcac    300
agcagcgctt ct                                                        312
```

<210> SEQ ID NO 39
<211> LENGTH: 294
<212> TYPE: DNA
<213> ORGANISM: Homo sapiens
<400> SEQUENCE: 39

```
caggctgtgg tgactcagga gccctcactg actgtgtccc caggagggac agtcactctc     60
acctgtggct ccagcactgg agctgtcacc agtggtcatt atccctactg gttccagcag    120
aagcctggcc aagccccag  gacactgatt tatgatacaa gcaacaaaca ctcctggaca    180 cctgcccgt  tctcaggctc cctccttggg ggcaaagctg ccctgaccct ttcgggtgcg    240
cagcctgagg atgaggctga gtattactgc ttgctctcct atagtggtgc tcgg          294
```

<210> SEQ ID NO 40
<211> LENGTH: 296
<212> TYPE: DNA
<213> ORGANISM: Homo sapiens
<400> SEQUENCE: 40

```
cagtctgtgc tgactcagcc accctcagcg tctgggaccc ccgggcagag ggtcaccatc     60
tcttgttctg gaagcagctc caacatcgga agtaattatg tatactggta ccagcagctc    120
ccaggaacgg ccccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tggtcc         296
```

<210> SEQ ID NO 41
<211> LENGTH: 317
<212> TYPE: DNA
<213> ORGANISM: Homo sapiens
<400> SEQUENCE: 41

```
cagcctgtgc tgactcagcc accttctgca tcagcctccc tgggagcctc ggtcacactc     60
acctgcaccc tgagcagcgg ctacagtaat tataaagtgg actggtacca gcagagacca    120
gggaagggcc cccggtttgt gatgcgagtg ggcactggtg ggattgtggg atccaagggg    180
gatggcatcc ctgatcgctt ctcagtcttg ggctcaggcc tgaatcggta cctgaccatc    240
aagaacatcc aggaagagga tgagagtgac taccactgtg gggcagacca tggcagtggg    300
agcaacttcg tgtaacc                                                   317
```

<210> SEQ ID NO 42
<211> LENGTH: 296
<212> TYPE: DNA
<213> ORGANISM: Homo sapiens
<400> SEQUENCE: 42

```
cagtctgtgt tgacgcagcc gccctcagtg tctgcggccc caggacagaa ggtcaccatc     60
tcctgctctg gaagcagctc caacattggg aataattatg tatcctggta ccagcagctc    120
ccaggaacag ccccccaaact cctcatttat gacaataata agcgaccctc agggattcct    180
gaccgattct ctggctccaa gtctggcacg tcagccaccc tggcatcac  cggactccag    240 actgggggacg aggccgatta ttactgcgga acatgggata gcagcctgag tgctgg        296
```

<210> SEQ ID NO 43
<211> LENGTH: 317
<212> TYPE: DNA
<213> ORGANISM: Homo sapiens

<400> SEQUENCE: 43

```
cagcctgtgc tgactcagcc atcttcccat tctgcatctt ctggagcatc agtcagactc        60
acctgcatgc tgagcagtgg cttcagtgtt ggggacttct ggataaggtg gtaccaacaa       120
aagccaggga accctccccg tatctcctg tactaccact cagactccaa taagggccaa       180
ggctctggag ttcccagccg cttctctgga tccaacgatg catcagccaa tgcagggatt       240
ctgcgtatct ctgggctcca gcctgaggat gaggctgact attactgtgg tacatggcac       300
agcaactcta agactca                                                     317
```

<210> SEQ ID NO 44
<211> LENGTH: 296
<212> TYPE: DNA
<213> ORGANISM: Homo sapiens

<400> SEQUENCE: 44

```
caggcagggc tgactcagcc accctcggtg tccaagggct tgagacagac cgccacactc        60
acctgcactg ggaacagcaa cattgttggc aaccaaggag cagcttggct gcagcagcac       120
cagggccacc ctcccaaact cctatcctac aggaataaca accggccctc agggatctca       180
gagagattct ctgcatccag gtcaggaaac acagcctccc tgaccattac tggactccag       240
cctgaggacg aggctgacta ttactgctca gcattggaca gcagcctcag tgctca          296
```

<210> SEQ ID NO 45
<211> LENGTH: 296
<212> TYPE: DNA
<213> ORGANISM: Homo sapiens

<400> SEQUENCE: 45

```
aattttatgc tgactcagcc ccactctgtg tcggagtctc cggggaagac ggtaaccatc        60
tcctgcaccc gcagcagtgg cagcattgcc agcaactatg tgcagtggta ccagcagcgc       120
ccgggcagtt cccccaccac tgtgatctat gaggataacc aaagaccctc tggggtccct       180
gatcggttct ctggctccat cgacagctcc tccaactctg cctccctcac catctctgga       240
ctgaagactg aggacgaggc tgactactac tgtcagtctt atgatagcag caatca          296
```

<210> SEQ ID NO 46
<211> LENGTH: 299
<212> TYPE: DNA
<213> ORGANISM: Homo sapiens

<400> SEQUENCE: 46

```
cagcctgtgc tgactcaatc atcctctgcc tctgcttccc tgggatcctc ggtcaagctc        60
acctgcactc tgagcagtgg gcacagtagc tacatcatcg catggcatca gcagcagcca       120
gggaaggccc ctcggtactt gatgaagctt gaaggtagtg gaagctacaa caaggggagc       180
ggagttcctg atcgcttctc aggctccagc tctgtggctg accgctacct caccatctcc       240
aacctccagt ctgaggatga ggctgattat tactgtgaga cctgggacag taacactca       299
```

<210> SEQ ID NO 47
<211> LENGTH: 297
<212> TYPE: DNA

<213> ORGANISM: Homo sapiens

<400> SEQUENCE: 47

| | |
|---|---|
| cagcctgtgc tgactcaatc atcctctgcc tctgcttccc tgggatcctc ggtcaagctc | 60 |
| acctgcactc tgagcagtgg gcacagtagc tacatcatcg catggcatca gcagcagcca | 120 |
| gggaaggccc ctcggtactt gatgaagctt gaaggtagtg gaagctacaa caaggggagc | 180 |
| ggagttcctg atcgcttctc aggctccagc tctggggctg accgctacct caccatctcc | 240 |
| aacctccagt ctgaggatga ggctgattat tactgtgaga cctgggacag taacact | 297 |

<210> SEQ ID NO 48
<211> LENGTH: 296
<212> TYPE: DNA
<213> ORGANISM: Homo sapiens

<400> SEQUENCE: 48

| | |
|---|---|
| cagactgtgg tgacccagga gccatcgttc tcagtgtccc ctggagggac agtcacactc | 60 |
| acttgtggct tgagctctgg ctcagtctct actagttact accccagctg gtaccagcag | 120 |
| accccaggcc aggctccacg cacgctcatc tacagcacaa acactcgctc ttctggggtc | 180 |
| cctgatcgct tctctggctc catccttggg aacaaagctg ccctcaccat cacggggggcc | 240 |
| caggcagatg atgaatctga ttattactgt gtgctgtata tgggtagtgg catttc | 296 |

<210> SEQ ID NO 49
<211> LENGTH: 299
<212> TYPE: DNA
<213> ORGANISM: Homo sapiens

<400> SEQUENCE: 49

| | |
|---|---|
| cagcttgtgc tgactcaatc gccctctgcc tctgcctccc tgggagcctc ggtcaagctc | 60 |
| acctgcactc tgagcagtgg gcacagcagc tacgccatcg catggcatca gcagcagcca | 120 |
| gagaagggcc ctcggtactt gatgaagctt aacagtgatg gcagccacag caaggggggac | 180 |
| gggatccctg atcgcttctc aggctccagc tctggggctg agcgctacct caccatctcc | 240 |
| agcctccagt ctgaggatga ggctgactat tactgtcaga cctggggcac tggcattca | 299 |

<210> SEQ ID NO 50
<211> LENGTH: 296
<212> TYPE: DNA
<213> ORGANISM: Homo sapiens

<400> SEQUENCE: 50

| | |
|---|---|
| gaggtgcagc tggtggagtc tgggggaggt gtggtacggc ctgggggtgtc cctgagactc | 60 |
| tcctgtgcag cctctggatt cacctttgat gattatggca tgagctgggt ccgccaagct | 120 |
| ccagggaagg ggctggagtg ggtctctggt attaattgga atggtggtag cacaggttat | 180 |
| gcagactctg tgaagggccg attcaccatc tccagagaca acgccaagaa ctccctgtat | 240 |
| ctgcaaatga acagtctgag agccgaggac acggccttgt attactgtgc gagaga | 296 |

<210> SEQ ID NO 51
<211> LENGTH: 296
<212> TYPE: DNA
<213> ORGANISM: Homo sapiens

<400> SEQUENCE: 51

| | |
|---|---|
| caggtccagc tggtacagtc tggggctgag gtgaagaagc ctgggcctc agtgaaggtc | 60 |
| tcctgcaagg tttccggata caccctcact gaattatcca tgcactgggt gcgacaggct | 120 |

```
cctggaaaag ggcttgagtg gatgggaggt tttgatcctg aagatggtga acaatctac      180 gcacagaagt tccagggcag agtcaccatg accgaggaca catctacaga cacagcctac     240
atggacctga gcagcctgag atctgaggac acggccgtgt attactgtgc aacaga         296
```

<210> SEQ ID NO 52
<211> LENGTH: 301
<212> TYPE: DNA
<213> ORGANISM: Homo sapiens

<400> SEQUENCE: 52

```
caggtcacct tgaaggagtc tggtcctgtg ctggtgaaac ccacagagac cctcacgctg     60
acctgcaccg tctctgggtt ctcactcagc aatgctagaa tgggtgtgag ctggatccat    120
cagcccccag ggaaggccct ggagtggctt gcacacattt tttcgaatga cgaaaaatcc    180
tacagcacat ctctgaagag caggctcacc atctccaagg acacctccaa aagccaggtg    240
gtccttacca tgaccaatat ggaccctgtg gacacagcca catattactg tgcacggata    300
c                                                                    301
```

<210> SEQ ID NO 53
<211> LENGTH: 287
<212> TYPE: DNA
<213> ORGANISM: Homo sapiens

<400> SEQUENCE: 53

```
gaaacgacac tcacgcagtc tccagcattc atgtcagcga ctccaggaga caaagtcaac    60
atctcctgca aagccagcca agacattgat gatgatatga actggtacca acagaaacca   120
ggagaagctg ctattttcat tattcaagaa gctactactc tcgttcctgg aatctcacct   180
cgattcagtg gcagcgggta tggaacagat tttaccctca caattaataa catagaatct   240
gaggatgctg catattactt ctgtctacaa catgataatt tccctct                  287
```

<210> SEQ ID NO 54
<211> LENGTH: 287
<212> TYPE: DNA
<213> ORGANISM: Homo sapiens

<400> SEQUENCE: 54

```
gacatccagt tgacccagtc tccatccttc ctgtctgcat ctgtaggaga cagagtcacc    60
atcacttgct gggccagtca gggcattagc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt accctcc                  287
```

<210> SEQ ID NO 55
<211> LENGTH: 287
<212> TYPE: DNA
<213> ORGANISM: Homo sapiens

<400> SEQUENCE: 55

```
gccatctgga tgacccagtc tccatcctta ctctctgcat ctacaggaga cagagtcacc    60
atcagttgtc ggatgagtca gggcattagc agttatttag cctggtatca gcaaaaacca   120
gggaaagccc ctgagctcct gatctatgct gcatccactt tgcaaagtgg ggtcccatca   180
aggttcagtg gcagtggatc tgggacagat ttcactctca ccatcagctg cctgcagtct   240
```

```
gaagattttg caacttatta ctgtcaacag tattatagtt tccctcc            287
```

<210> SEQ ID NO 56
<211> LENGTH: 287
<212> TYPE: DNA
<213> ORGANISM: Homo sapiens

<400> SEQUENCE: 56

```
gaaattgtgt tgacacagtc tccagccacc ctgtctttgt ctccagggga aagagccacc    60
ctctcctgca gggccagtca gagtgttagc agctacttag cctggtacca gcagaaacct   120
ggccaggctc ccaggctcct catctatgat gcatccaaca gggccactgg catcccagcc   180
aggttcagtg gcagtgggcc tgggacagac ttcactctca ccatcagcag cctagagcct   240
gaagattttg cagtttatta ctgtcagcag cgtagcaact ggcatcc              287
```

<210> SEQ ID NO 57
<211> LENGTH: 287
<212> TYPE: DNA
<213> ORGANISM: Homo sapiens

<400> SEQUENCE: 57

```
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accctca              287
```

<210> SEQ ID NO 58
<211> LENGTH: 290
<212> TYPE: DNA
<213> ORGANISM: Homo sapiens

<400> SEQUENCE: 58

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccatca gggccactgg catcccagcc   180
aggttcagtg gcagtgggtc tgggacagag ttcactctca ccatcagcat cctgcagtct   240
gaagattttg cagtttatta ctgtcagcag tataataact ggcctcctcc              290
```

<210> SEQ ID NO 59
<211> LENGTH: 302
<212> TYPE: DNA
<213> ORGANISM: Homo sapiens

<400> SEQUENCE: 59

```
gagattgtga tgacccagac tccactctcc ttgtctatca cccctggaga gcaggcctcc    60
atgtcctgca ggtctagtca gagcctcctg catagtgatg gatacaccta tttgtattgg   120
tttctgcaga aagccaggcc agtctccacg ctcctgatct atgaagtttc caaccggttc   180
tctggagtgc cagataggtt cagtggcagc gggtcaggga cagatttcac actgaaaatc   240
agccgggtgg aggctgagga ttttggagtt tattactgca tgcaagatgc acaagatcct   300
cc                                                                   302
```

<210> SEQ ID NO 60
<211> LENGTH: 302

```
<212> TYPE: DNA
<213> ORGANISM: Homo sapiens

<400> SEQUENCE: 60
gatattgtga tgactcagcc tccactctcc ctgcccgtca ccctggaga gccggcctcc      60 atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cc                                                                    302

<210> SEQ ID NO 61
<211> LENGTH: 302
<212> TYPE: DNA
<213> ORGANISM: Homo sapiens

<400> SEQUENCE: 61
gatattgtga tgactcagcc tccactctcc ctgcccgtca ccctggaga gccggcctcc      60 atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cc                                                                    302
```